(12) United States Patent
Holden et al.

(10) Patent No.: US 6,455,323 B1
(45) Date of Patent: Sep. 24, 2002

(54) ANTI-BACTERIAL METHODS AND MATERIALS

(75) Inventors: David Holden, London (GB); Ji Min Mei, Middlesex (GB)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 08/887,534

(22) Filed: Jul. 3, 1997

(51) Int. Cl.$^7$ ................. G01N 33/543; G01N 33/538; C07H 21/04; C12Q 1/00
(52) U.S. Cl. ............... 436/518; 536/23.5; 536/22.1; 536/23.1; 435/4; 435/6; 436/501; 436/536; 436/541
(58) Field of Search .................. 536/23.5, 22.1, 536/23.1; 435/4, 6; 436/518, 501, 536, 541

(56) References Cited

U.S. PATENT DOCUMENTS

| | | | |
|---|---|---|---|
| 4,877,612 A | 10/1989 | Berger et al. | 424/92 |
| 4,973,554 A | 11/1990 | Luong et al. | 435/213 |
| 5,283,173 A | 2/1994 | Fields et al. | 435/6 |
| 5,284,933 A | 2/1994 | Döbeli et al. | 530/350 |
| 5,310,663 A | 5/1994 | Döbeli et al. | 435/69.7 |
| 5,585,277 A | 12/1996 | Bowie et al. | 436/518 |
| 5,587,288 A | 12/1996 | Cheung et al. | 435/6 |
| 5,783,397 A * | 7/1998 | Hughes et al. | 204/407 |
| 6,326,167 B1 * | 12/2001 | Chalker et al. | 435/193 |

FOREIGN PATENT DOCUMENTS

| | | |
|---|---|---|
| EP | 0 109 942 A2 | 5/1984 |
| EP | 0 180 564 A2 | 5/1986 |
| EP | 0 231 039 A1 | 8/1987 |
| EP | 0 625 575 A | 11/1994 |
| EP | 786 519 A2 | 7/1997 |
| GB | 2 189 141 A | 10/1987 |
| WO | WO 96/03637 | 2/1996 |
| WO | WO 96/10579 A1 | 4/1996 |
| WO | WO 96/17951 A2 | 6/1996 |
| WO | WO 97/11690 A3 | 4/1997 |

OTHER PUBLICATIONS

Alborn et al, Gene, 180:177–181, 1996.*
Berger–Bächi et al, Mol. Gen. Genet. 219: 263–269, 1989.*
Jüngst et al, FEBS Lett. 279/2: 205–209, 1991.*
Arai et al, Biosci. Biotech. Biochem. 58/7:1286–1291, 1994.*
Nystedt et al, JBC 271/25:14910–14915, 1996.*
Kamata et al, JBC 267/30: 21650–21655, 1992.*
Wood et al., Neuro Report, 5:977–980, 1994.*
Hensel et al, Science, 269:400–403, 1995.*
Hensel et al, Microbiology, 142:1049–58, 1996.*
Jungst et al, FEBS Lett. 314/3:308–314, 1992.*
Mei et al, Mol. Microbiol. 26/2:399–407, 1997.*
Hensel et al, Mol. Microbiol. 24/1:155–167, 1997.*
Hensel et al, Mol. Microbiol, 30/1:163–174, 1998.*
Kernodle et al, Infection and Immunity, 1997, 65/1:179–187.*
Bayer et al, J. Bacteriology, 1996, 178/15:4563–4570.*
Balaban et al, Proc. Natl. Acad. Sci., 1995, 92:1619–1623.*
Berger–Bächi, B. et al., "FemA, a host–mediated factor essential for methicillin resistance in *Staphylococcus aureus*: Molecular cloning and characterization," *Mol. Gen. Genet.*, 219:263–269 (1989).
Cheung, A.L. et al., "Insertional Inactivation of a Chromosomal Locus That Modulates Expression of Potential Virulence Determinants in *Staphylococcus aureus*," *J. Bacteriology*, 177(11):3220–3226 (1995).
Fields S., et al., "A novel genetic system to detect protein–protein interactions," *Nature*, 340:245–246 (1989).
Fields, S. et al., "The two–hybrid system: an assay for protein–protein interactions," *Trends in Genetics*, 10(8):286–292 (1994).
Groisman E.A. et al., "How to become a pathogen," *Trends in Microbiology*, 2(8):289–294 (1994).
Grosjean, H. et al., "Preferential codon usage in prokaryotic genes: the optimal codon–anticodon interaction energy and the selective codon usage in efficiently expressed genes," *Gene*, 18:199–209 (1982).
*Harrison's Principles of Internal Medicine*, Thirteenth Edition, Isselbacher, K.J. et al., (eds.), McGraw–Hill, New York, 611–617 (1994).
Hensel, M. et al., "Simultaneous Identification of Bacterial Virulence Genes by Negative Selection," *Science*, 269:400–403 (1995).
Hopp, T.P. et al., "A Short Polypeptide Marker Sequence Useful for Recombinant Protein Identification and Purification," *Biotechnology*, 6:1205–1210 (1988).
Konigsberg, W. et al., "Evidence for use of rare codons in the dnaG Gene and other regulatory genes of *Escherichia coli*," *Proc. Natl. Acad. Sci., USA*, 80:687–691 (1983).
LaVallie, E.R. et al., "A Thioredoxin Gene Fusion Expression System That Circumvents Inclusion Body Formation in the *E. coli* Cytoplasm," *Bio/Technology*, 11:187–193 (1993).
Lei, S–P et al., "Characterization of the *Erwinia carotovora* pelB Gene and Its Product Pectate Lyase," *J. of Bacteriology*, 169(9):4379–4383 (1987).
Mühldorfer, I. et al., "Genetic aspects of *Escherichia coli* virulence," *Microbial Pathogenesis*, 16:171–181 (1994).
Pospiech et al., "A versatile quick–prep of genomic DNA from Gram–positive bacteria," *Trends in Genetics.*, 11(6):217–218 (1995).

(List continued on next page.)

*Primary Examiner*—Nita Minnifield
(74) *Attorney, Agent, or Firm*—Pharmacia & Upjohn Attorney; James D. Darnley, Jr.

(57) ABSTRACT

*Staphylococcus aureus* virulence genes are identified, thereby allowing the identification of novel anti-bacterial agents that target these virulence genes and their products, and the provision of novel *S. aureus* mutants useful in vaccines.

18 Claims, No Drawings

OTHER PUBLICATIONS

Schenk, S. et al., "Improved method for electroporation of *Staphylococcus aureus*," *FEMS Microbiolology Letters*, 94:133–138 (1992).

Schmidt, T.G.M., et al., "The random peptide library–assisted engineering of a C–terminal affinity peptide, useful for the detection and purification of a functional Ig Fv fragment," *Protein Engineering*, 6(1):109–122 (1993).

Smith, D.B. et al., "Single–step purification of polypeptides expressed in *Escherichia coli* as fusions with glutathione S–transferase," *Gene*, 67:31–40 (1988).

Wieboldt, R. et al., "Immunoaffinity Ultrafiltration with Ion Spray HPLC/MS for Screening Small–Molecule Libraries," *Anal. Chem.*, 69:1683–1691 (1997).

Youngman,P., "Plasmid vectors for recovering and exploiting Tn917 transpositions in Bacillus and other Gram–positive bacteria," in *Plasmids: a practical approach*, K. Hard, ed., Oxford: IRL Press, pp. 79–103 (1985).

Albus et al. "Virulence of *Staphylococcus aureus* Mutants Altered in Type 5 Capsule Production", *Infect. Immun.*, 59(3):1008–1014 (1991).

Cheung et al. "Regulation of exoprotein expression in *Staphylococcus aureus* by a locus (sar) distinct from agr", *Proc. Natl. Acad. Sci.*, 89:6462–6466 (1992).

Schwan et al. "Identification and Characterization of the PutP Proline Permease That Contributes to In Vivo of Survival *Staphylococcus aureus* in Animal Models", *Infect. Immun.* 66(2):567–572 (1998).

Ebbole, et al., "Cloning and Characterization of a 12–Gene Cluster from *Bacillus subtilis* Encoding Nine Enzymes for de Novo Purine Nucleotide Synthesis*" *J. Biol. Chem.*, 262:8274–8287 (1987).

Samuelsson, "A Mycoplasma protein homologous to mammalian SRP54 recognizes a highly conserved domain of SRP RNA" *Nucl. Acids. Res.*, 20:5763–5770 (1993).

Kappes, et al., "Three Transport Systems for the Osmoprotectant Glycine Betaine Operate in *Bacillus subtilis*: Characterization of OpuD" *J. Bacteriol.*, 178:5071–5079 (1996).

Rudner, et al., "The spoOK Locus of *Bacillus subtilis* Is Homologous to the Oligopeptide Permease Locus and Is Required for Sporulation and Competence" *J. Bacteriol.*, 173:1388–1398 (1991).

Database Accession No. W28288.

Holden, "Discovering New Targets for Anti–Bacterial Agents by Identification of Genes Essential for Pathogenicity" *Br. J. Pharmacol.*, 123:349P (1998).

Database Accession No. F69884.

* cited by examiner

ANTI-BACTERIAL METHODS AND MATERIALS

The invention relates generally to the identification of genes responsible for the virulence of Staphylococcus bacteria, thereby allowing the identification of new anti-bacterial agents that target these virulence genes and their products and the provision of novel *S. aureus* mutants useful in vaccines.

BACKGROUND OF THE INVENTION

The staphylococci, of which *Staphylococcus aureus* is the most important human pathogen, are hardy, gram-positive bacteria that colonize the skin of most humans. Staphylococcal strains that produce coagulase are designated *S. aureus*; other clinically important coagulase-negative staphylococci are *S. epidermidis* and *S. saprophyticus*. When the skin or mucous membrane barriers are disrupted, staphylococci can cause localized and superficial infections that are commonly harmless and self-limiting. However, when staphylococci invade the lymphatics and the blood, potentially serious complications may result, such as bacteremia, septic shock, and serious metastatic infections, including endocarditis, arthritis, osteomyelitis, pneumonia and abscesses in virtually any organ. Certain strains of *S. aureus* produce toxins that cause skin rashes, food poisoning, or multisystem dysfunction (as in toxic shock syndrome). *S. aureus* and *S. epidermidis* together have become the most common cause of nosocomial non-urinary tract infection in U.S. hospitals. They are the most frequently isolated pathogens in both primary and secondary bacteremias and in cutaneous and surgical wound infections. See generally *Harrison's Principles of Internal Medicine*, 13th ed., Isselbacher et al., eds., McGraw-Hill, New York (1994), particularly pages 611–617.

Transient colonization of the nose by *S. aureus* is seen in 70 to 90 percent of people, of which 20 to 30 percent carry the bacteria for relatively prolonged periods of time. Independent colonization of the perineal area occurs in 5 to 20 percent of people. Higher carriage rates of *S. aureus* have been documented in persons with atopic dermatitis, hospital employees, hospitalized patients, patients whose care requires frequent puncture of the skin, and intravenous drug abusers.

Infection by staphylococci usually results from a combination of bacterial virulence factors and a diminution in host defenses. Important microbial factors include the ability of the staphylococcus to survive under harsh conditions, its cell wall constituents, the production of enzymes and toxins that promote tissue invasion, its capacity to persist intracellularly in certain phagocytes, and its potential to acquire resistance to antimicrobials. Important host factors include an intact mucocutaneous barrier, an adequate number of functional neutrophils, and removal of foreign bodies or dead tissue.

Cell wall components of *S. aureus* include a large peptidoglycan complex that confers rigidity on the organism and enables it to survive under unfavorable osmotic conditions, a unique teichoic acid linked to peptidoglycan, and protein A, which is found both attached to peptidoglycan over the outermost parts of the cell and released in soluble form. Proteins designated femA and femB are involved in the formation of cell wall peptidoglycan pentaglycine cross-bridges and are factors in methicillin resistance. [Berger-Bachi et al., *Mol. Gen. Genet.,* 219:263–269 (1989).] *S. aureus* also has specific receptors for laminin and fibronectin that may mediate the organism's spread through the bloodstream to other tissues. Both peptidoglycan and teichoic acid are capable of activating the complement cascade via the alternative pathway. *S. aureus* also appears to activate tissue factor in the coagulation pathway.

Certain enzymes produced by *S. aureus* may play a role in virulence. Catalase degrades hydrogen peroxide and may protect the organism during phagocytosis. Coagulase is present in both soluble and cell-bound forms and causes plasma to clot by formation of thrombin-like material. The high correlation between coagulase production and virulence suggests that this substance is important in the pathogenesis of staphylococcal infections, but its precise role as a determinant of pathogenicity has not been determined. Many strains also produce hyaluronidase, an enzyme that degrades hyaluronic acid in the connective tissue matrix and that may promote spreading of infection. A trypsin-like protease from some strains enhances influenza virus infection by proteolytic cleavage of the viral precursor hemagglutinin into its active fragments and may contribute to the morbidity of such coinfections.

*S. aureus* produces numerous extracellular exotoxins that have been implicated in disease processes. The exfoliatin toxins A and B, the staphylococcal enterotoxins, and the toxic shock syndrome toxin, TSST-1, belong to the growing family of microbial superantigens that activate T cells and monocytes/macrophages, resulting in the production of cytokines that mediate local or systemic effects depending on the amount of toxin formed, the immune status of the host, and the access of the toxin to the circulation. The exfoliatin toxins mediate the dermatologic manifestations of the staphylococcal scalded-skin syndrome and bullous impetigo. These toxins cause intraepidermal cleavage of the skin at the stratum granulosum, leading to bullae formation and denudation. Seven distinct enterotoxins (A, B, C1, C2, C3, D, and E) have been implicated in food poisoning due to *S. aureus*. These toxins enhance intestinal peristalsis and appear to induce vomiting by a direct effect on the central nervous system. Toxic shock syndrome (TSS) is most commonly mediated by TSST-1, which is present in 5 to 25 percent of clinical isolates of *S. aureus*. TSS is also mediated less frequently by enterotoxin B and, rarely, enterotoxin C1.

*S. aureus* produces other toxins whose role in virulence is incompletely understood. Four different red blood cell hemolysins, which are designated alpha, beta, gamma, and delta toxins, have been identified. Alpha toxin also causes necrosis of the skin when injected subcutaneously into animals, while delta toxin also inhibits water absorption in the intestines and may play a role in the acute watery diarrhea seen in some cases of staphylococcal infection. Leukocidin lyses granulocyte and macrophage membranes by producing membrane pores permeable to cations.

The agr, xpr, sae and sar genes have been identified as being involved in the regulation of staphylococcal exotoxins. See U.S. Pat. No. 5,587,228 and International Patent Publication Nos. WO 96/10579 and WO 97/11690. Of interest is the report in WO 97/11690 of screening for inhibitors of these regulatory systems.

Staphylococci can invade the skin or mucosa through plugged hair follicles and sebaceous glands or areas traumatized by burns, wounds, abrasions, insect bites, or dermatitis. Staphylococci often colonize prosthetic devices and intravenous catheters; *S. aureus* infection of the vascular access site is a major cause of morbidity and death among patients on hemodialysis. Colonization and invasion of the lungs may occur with endotracheal intubation, or when the lungs' clearance mechanisms are depressed, e.g., after viral infections, after aspiration, or in patients with cystic fibrosis. Mucosal damage to the gastrointestinal tract following cytotoxic chemotherapy or radiotherapy predisposes to invasion from that site.

Once the skin or mucosa have been breached, local bacterial multiplication is accompanied by inflammation, neutrophil accumulation, tissue necrosis, thrombosis and fibrin deposition at the site of infection. Later, fibroblasts create a relatively avascular wall about the area. When host mechanisms fail to contain the cutaneous or submucosal infection, staphylococci may enter the lymphatics and the bloodstream. Common sites of metastatic spread include the lungs, kidneys, cardiac valves, myocardium, liver, spleen, bones and brain.

Bacteremia due to *S. aureus* may arise from any local infection, at either extravascular (cutaneous infections, bums, cellulitis, osteomyelitis, arthritis) or intravascular foci (intravenous catheters, dialysis access sites, intravenous drug abuse). Rarely, patients with bacteremia die within 12 to 24 hours with high fever, tachycardia, cyanosis, and vascular collapse. Disseminated intravascular coagulation may produce a disease mimicking meningococcemia. Commonly, the disease progresses more slowly, with hectic fever and metastatic abscess formation.

A major complication of *S. aureus* bacteremia is endocarditis. *S. aureus* is the second most common cause of endocarditis and the most common cause among drug addicts. The disease is typically acute, with high fever, progressive anemia, and frequent embolic and extracardiac septic complications. Valve ring and myocardial abscesses are common. The mortality rate is 20 to 30 percent.

Staphylococcal scalded-skin syndrome (SSSS) is a generalized exfoliative dermatitis that is a complication of infection by exfoliatin toxin-producing strains of *S. aureus*. The disease typically occurs in newborns (Ritter's disease) and in children under the age of five. A scarlatiniform rash begins in the perioral area, becomes generalized over the trunk and extremities, and finally desquamates. The disease may consist of rash alone (staphylococcal scarlet fever), or large, flaccid bullae develop that may be localized (more common in adults) or generalized. The bullae burst, resulting in red, denuded skin resembling a bum. Most adults with SSSS are immunosuppressed or have renal isufficiency. Blood cultures are frequently positive, and mortality is significant.

Toxic shock syndrome (TSS) is a multisystem disease mediated by toxins (generally TSST-1, and less frequently enterotoxins B and C1) produced by certain strains of *S. aureus*. It was first described in children, but in 1980 became epidemic among young women, with onset during menstruation. The diagnosis of TSS is based on clinical criteria that include high fever, a diffuse rash that desquamates on the palms and soles over the subsequent one or two weeks, hypotension that may be orthostatic, and evidence of involvement in three or more organs systems. Such involvement commonly includes gastrointestinal dysfunction (vomiting or diarrhea), renal or hepatic insufficiency, mucous membrane hyperemia, thrombocytopenia, myalgias with elevated creatine phosphokinase (CK) levels, and disorientation with a normal cerebrospinal fluid examination. The mortality rate of TSS is three percent.

*S. aureus* causes approximately three percent of community-acquired bacterial pneumonias. This disease occurs sporadically except during influenza outbreaks, when staphylococcal pneumonia ia relatively more common, although still less frequent than pneumococcal pneumonia. Primary staphylococcal pneumonia in infants and children frequently presents with high fever and cough. Multiple thin-walled abscesses are seen on the chest X-ray, and empyema formation is common. In older children and healthy adults, staphylococcal pneumonia is generally preceded by an influenza-like respiratory infection. Onset of staphylococcal involvement is abrupt, with chills, high fever, progressive dyspnea, cyanosis, cough, pleural pain, and sometimes bloody sputum. Staphylococcal pneumonia is sen more frequently in patients with cystic fibrosis, in intubated patients in intensive care units and in debilitated patients who are prone to aspiration.

*S. aureus* is responsible for the majority of cases of acute osteomyelitis. Although the disease is most common in people under the age of 20, it is becoming increasingly prevalent in adults over 50, particularly with involvement of the spine. A primary portal of entry is frequently not identified, although many patients give a history of preceding trauma to the involved area. Once established, infection spreads through the bone to the periosteum or along thee marrow cavity. Rarely, the joint capsule is penetrated, producing pyogenic arthritis. Osteomyelitis in children may present as an acute process beginning abruptly with chills, high fever, nausea, vomiting, and progressive pain at the site of bony involvement.

*S. aureus* causes 1 to 9 percent of cases of bacterial meningitis and 10 to 15 percent of brain abscesses. Most commonly, the bacteria are spread from a focus outside the central nervous system, typically from infective endocarditis, by extension from a paraspinal or parameningeal abscess, or by nosocomial infection following neurosurgical procedures. Over 50 percent of epidural abscesses are due to *S. aureus*; up to half of these cases may be associated with vertebral osteomyelitis. Patients present with either acute or chronic back pain, usually with low-grade fever and malaise. The onset of radicular pain is an ominous sign that the disease may progress to neurologic dysfunction and ultimate paralysis.

Antimicrobial resistance by staphylococci favors their persistence in the hospital environment. Over 90 percent of both hospital and community strains of *S. aureus* causing infection are resistant to penicillin. This resistance is due to the production of β-lactamases enzymes; the genes for these enzymes are usually carried by plasmids. Infections due to organisms with such acquired resistance can sometimes be treated with penicillinase-resistant β-lactam antimicrobial agents. However, the true penicillinase-resistant *S. aureus* organisms, called methicillin-resistant *S. aureus* (MRSA), are resistant to all the β-lactam antimicrobials as well as the cephalosporins. MRSA resistance is chromosomally mediated and involves production of an altered penicillin-binding protein (PBP 2a or PBP 2') with a low binding affinity for β-lactams. MRSA frequently also have acquired plasmids mediating resistance to erythromycin, tetracycline, chloramphenicol, clindamycin, and aminoglycosides. MRSA have become increasingly common worldwide, particularly in tertiary-care referral hospitals. In the United States, approximately 5 percent of hospital isolates of *S. aureus* are methicillin-resistant.

Thus, there continues to exist a need for new agents useful for treating bacterial infections, particularly those caused by antibiotic-resistant bacteria, and for methods of identifying such new agents. Such methods ideally would identify agents that are unrelated to existing antimicrobials and that target different aspects of staphylococcal invasion of and replication in the host, compared to existing antimicrobials.

SUMMARY OF THE INVENTION

The present invention relates generally to the identification of genes responsible for the virulence of Staphylococcus bacteria, thereby allowing the identification of new anti-bacterial agents that target these virulence genes and their products and the provision of novel *S. aureus* mutants useful in vaccines.

According to one aspect of the present invention, methods are provided for identifying anti-bacterial agents that target the function of staphylococcal virulence genes or gene products. Such methods include assaying potential agents for the ability to interfere with expression of virulence gene products represented by the DNA sequences set forth in any one of SEQ ID NOS: 1 through 94, or assaying potential agents for the ability to interfere with the function of a bacterial protein encoded in whole or in part by a DNA sequence set forth in any one of SEQ ID NOS: 1 through 94 or the complementary strand thereof, followed by identifying agents that are positive in such assays.

The use of a number of different assays is contemplated according to this aspect of the invention. When the function of the virulence gene product is known or predicted by sequence similarity to a known gene product, potential inhibitors can be screened in enzymatic or other types of assays keyed to the function of the gene product. When the virulence gene product is known or predicted by sequence similarity to a known gene product to interact with another protein or nucleic acid, inhibitors of this interaction can be screened directly in binding assays or using the two-hybrid assay. Other assays may be used when a ligand for the virulence gene product is not known, including two-hybrid screening assays that identify gene products that interact with target protein, assays that identify ligands of target protein through measuring of direct binding of test ligand to target protein, and assays that identify ligands of target proteins through affinity ultrafiltration with ion spray mass spectroscopy/HPLC methods or other physical and analytical methods.

In another aspect of this invention, methods are provided for assaying potential agents for the ability to interfere with expression of or function of virulence gene products, wherein the virulence genes encoding these products are obtainable by identification through signature-tagged mutagenesis as defined herein and exemplified in Example 1.

According to a further aspect of this invention, novel anti-bacterial agents identified by the methods described herein are provided, as well as methods for treating a subject suffering from infection with staphylococci involving administration of such novel anti-bacterial agents. In particular, agents that interfere with the expression of virulence gene products include anti-sense polynucleotides that are complementary to the virulence gene sequences. Agents that interfere with the function of virulence gene products include variants of virulence gene products, ligands of these virulence gene products and variants thereof, and enzyme inhibitors (where the product is an enzyme).

Yet a further aspect of this invention provides *Staphylococcus aureus* organisms containing a functional mutation in a gene represented by any one of SEQ ID NOS: 1 through 94, said functional mutation resulting in a reduction in virulence of the organism. Also contemplated are vaccine compositions comprising such mutated *S. aureus* organisms, optionally comprising a suitable adjuvant and a pharmaceutically acceptable diluent or carrier.

Numerous additional aspects and advantages of the invention will become apparent th those skilled in the art upon consideration of the following detailed description of the invention which describes presently prepared embodiments thereof.

DETAILED DESCRIPTION OF THE INVENTION

"Virulence genes", as used herein, are genes whose function or products are required for successful establishment and/or maintenance of bacterial infection in host animal. Thus, virulence genes and/or the proteins encoded thereby are involved in pathogenesis in the host organism, but may not be necessary for growth in vitro. Since antibiotics are typically screened in vitro, identification of these in vivo virulence genes provides a means for discovering new antimicrobials with different targets and mechanisms of action compared to existing antibiotics. There may be 50 to 100 virulence genes in *S. aureus* [see Groisman and Ochman] *Trends Microbiol. Sci.*, 2:289–294 (1984) (discussing Salmonella virulence genes); Muhldorfer and Hacker, *Microb. Pathogenesis*, 16:171–181 (1994) (discussing *E. coli* virulence genes].

"Signature-tagged mutagenesis," as used herein, is a method generally described in International Patent Publication No. WO 96/17951, incorporated herein by reference, and includes, for example, a method for identifying *S. aureus* genes required for virulence in a murine model of bacteremia. In this method, each insertional mutation carries a different DNA signature tag which allows mutants to be differentiated from each other. The tags comprise 40-bp variable central regions flanked by invariant "arms" of 20-bp which allow the central portions to be co-amplified by polymerase chain reaction (PCR). Tagged mutant strains are assembled in microtitre dishes, then combined to form the "inoculum pool" for infection studies. At an appropriate time after inoculation, bacteria are isolated from the animal and pooled to form the "recovered pool." The tags in the recovered pool and the tags in the inoculum pool are separately amplified, labelled, and then used to probe filters arrayed with the different tags representing the mutants in the inoculum. Mutants with attenuated virulence are those with tags that give hybridization signals when probed with tags from the inoculum pool but not when probed with tags from the recovered pool.

Signature-tagged mutagenesis allows a large number of insertional mutant strains to be screened simultaneously in a single animal for loss of virulence. Screening thirteen pools of 96 mutant *S. aureus* strains resulted in the identification of 50 strains with reduced virulence, many of which were confirmed to be attenuated in virulence by subsequent analysis of individual mutants. The nucleotide sequences of the regions flanking the transposon insertion points of these mutants were analyzed by searching DNA and protein sequence databases to identify the genes inactivated by the insertion of the transposon.

On the basis of these searches many of the virulence genes may be grouped into different classes. The first class encodes proteins involved in cell surface metabolism (e.g., P2C73, P11C29, P13C83, P9B65, P10B89). Both femA and femB, which are involved in the formation of cell wall peptidoglycan pentaglycine cross bridges, were identified as virulence genes. Mutant P2C73 contains a transposon insertion in a previously unknown gene that shares significant similarity to femB. Mutant P14C15 contains a transposon insertion in a gene whose product is similar to aspartate semialdehyde dehydrogenase (Asd) from different bacteria, with the highest level of similarity to Asd from *Bacillus subtilis*. Asd is a key enzyme in the biosynthesis of methionine, threonine, isoleucine, lysine and diaminopimelic acid (DAP), which is an important component of cell wall peptidoglycan.

The second class encodes enzymes involved in cellular biosynthetic pathways (e.g., P9B74, P5C4, P9B66, P14C15, P13B26, P7C18, P15C31, P10B18, P6B18, P10B66, P10C34, P12C3). Deduced protein products of two genes (mutants P7C18 and P13B26) show strong similarity to *B. subtilis* LysA and ThrB. These enzymes, like Asd, are involved in aspartate metabolism. LysA is diaminopimelate decarboxylase, which converts diaminopimelate to lysine, and ThrB phosphorylates homoserine before conversion into threonine. Transposon insertions were also obtained in genes homologous to *Methanococcus jannaschii* trpA, *Lactococcus lactis* trpB and *L. lactis* trpD. These genes encode enzymes of the tryptophan biosynthetic pathway: the alpha chain of tryptophan synthetase, the beta chain of tryptophan synthetase, and anthranilate phosphoribosyltransferase, respectively. The gene mutated in P15C31 is a homolog of *L. lactis* purL encoding phosphoribosylformylglycinamidine decarboxylase, an enzyme of the purine biosynthetic pathway. Mutant P9B66 contains an insertion in a gene whose product is similar to peptide methionine sulphoxide reductases.

A third class of genes are those encoding components of the TCA cycle (e.g., mutants P4C27, P4C52, P10B2, P10C20, P12C32). Strains P10B2 and P12C32 carry mutations in genes for a subunit of the oxoglutarate dehydrogenase complex and aconitase, respectively.

The fourth class is composed of genes whose products are similar to a oligopeptide transport proteins of the ATP-binding cassette (ABC) transporter superfamily (e.g., mutants P7C26, P10C15, P5C3, P11C66, P5C34). Oligopeptide transport is important for peptide utilization and the proteolytic system in lactococci. In Group A streptococci, Opp proteins are involved not only in obtaining nutrients but also in adherence, protease production and processing of secreted proteins.

The fifth class of genes are involved in cellular regulatory and repair processes (e.g., mutants P4C15, P13B74, P13C72, P10B30, P6C63, P14B25). Mutant P4C15 and P6C63 contain insertions in *S. aureus* MarR/LuxR-like regulatory proteins. MarR and LuxR belong to a family of transcription regulators and these MarR/LuxR-like proteins likely have a similar function in *S. aureus*. In *Streptococcus pneumoniae, Neisseria gonorrhoeae* and *Escherichia coli* this enzyme helps to maintain surface adhesins in their functional oxidative state. Mutant P10B30 is associated with a transposon insertion in a gene with a product similar to the ATP-dependent Clp protease of *E. coli*. The Clp stress response system for intracellular protein degradation is widely conserved in bacteria and components of the system are important for virulence of Listeria monocytogenes and *S. typhimurium*. Mutants P13B74 and P13C72 have stem-loop termination sequences which possibly function in transcription termination.

The identification of these genes as virulence genes renders them useful in methods of identifying new antibacterial agents according to the present invention. Such methods include assaying potential agents for the ability to interfere with expression of virulence gene products represented by the DNA sequences set forth in any one of SEQ ID NOS: 1 through 94 (i.e., the genes represented by DNA sequences of SEQ ID NOS: 1 through 94 encode the virulence gene product, or the DNA sequences of SEQ ID NOS: 1 through 94 are adjacent to the gene encoding the virulence gene product, or are involved in regulation of expression of the virulence gene product), or assaying potential agents for the ability to interfere with the function of a bacterial protein encoded in whole or in part by a DNA sequence set forth in any one of SEQ ID NOS: 1 through 94 or the complementary strand thereof, followed by identifying agents that are positive in such assays. Polynucleotides and polypeptides useful in these assays include not only the genes and encoded polypeptides as disclosed herein, but also variants thereof that have substantially the same activity as the wild-type genes and polypeptides. "Variants," as used herein, includes polynucleotides or polypeptides which contain one or more deletions, insertions or substitutions, as long as the variant retains substantially the same activity of the wild-type polynucleotide or polypeptide. With regard to polypeptides, deletion variants are contemplated to include fragments lacking portions of the polypeptide not essential for biological activity, and insertion variants are contemplated to include fusion polypeptides in which the wild-type polypeptide or fragment thereof have been fused to another polypeptide.

The virulence genes may be cloned by PCR, using *S. aureus* genomic DNA as the template. For ease of inserting the gene into expression vectors, PCR primers are chosen so that the PCR-amplified gene has a restriction enzyme site at the 5' end preceding the initiation codon ATG, and a restriction enzyme site at the 3' end after the termination codon TAG, TGA or TAA. If desirable, the codons in the gene are changed, without changing the amino acids, according to *E. coli* codon preference described by Grosjean and Fiers, *Gene*, 18:199–209 (1982), and Konigsberg and Godson, *Proc. Natl. Acad. Sci. (USA)*, 80:687–691 (1983). Optimization of codon usage may lead to an increase in the expression of the gene product when produced in *E. coli*. If the gene product is to be produced extracellularly, either in the periplasm of *E. coli* or other bacteria, or into the cell culture medium, the gene is cloned without its initiation codon and placed into an expression vector behind a signal sequence. For example, cloning and expression of the femA gene is described in Example 3 below.

To simplify the protein purification process, a purification tag may be added either at the 5' or 3' end of the gene coding sequence. Commonly used purification tags include a stretch of six histidine residues (U.S. Pat. Nos. 5,284,933 and 5,310,663), a streptavidin-affinity tag described by Schmidt and Skerra, *Protein Engineering*, 6:109–122 (1993), a FLAG peptide [Hopp et al., *Biotechnology*, 6:1205–1210 (1988)], glutathione S-transferase [Smith and Johnson, *Gene*, 67:31–40 (1988)], and thioredoxin [LaVallie et al., *Bio/Technology*, 11:187–193 (1993)]. To remove these peptide or polypeptides, a proteolytic cleavage recognition site may be inserted at the fusion junction. Commonly used proteases are factor Xa, thrombin, and enterokinase.

Proteins are produced in any number of well-known prokaryotic or eukaryotic expression systems using known promoters, vectors, and hosts. Any suitable host cell may be used for expression of the gene product, such as *E. coli*, other bacteria, including Bacillus and *S. aureus*, yeast, including *Pichia pastoris* and *Saccharomyces cerevisiae*, insect cells, or mammalian cells, including CHO cells, utilizing suitable vectors known in the art. Proteins may be produced directly or fused to a peptide or polypeptide, and either intracellularly or extracellularly by secretion into the periplasmic space of a bacterial cell or into the cell culture medium. Secretion of a protein requires a signal peptide (also known as pre-sequence); a number of signal sequences from prokaryotes and eukaryotes are known to function for the secretion of recombinant proteins. During the protein secretion process, the signal peptide is removed by signal peptidase to yield the mature protein.

The virulence gene products produced by the methods described above are used in high throughput assays to screen for inhibitory agents. The sources for potential agents to be screened are chemical compound libraries, fermentation media of Streptomycetes, other bacteria and fungi, and cell extracts of plants and other vegetations. For proteins with known enzymatic activity, assays are established based on the activity, and a large number of potential agents are screened for ability to inhibit the activity. For proteins that interact With another protein or nucleic acid, binding assays are established to measure such interaction directly, and the potential agents are screened for ability to inhibit the binding interaction.

Alternatively, such binding interactions are evaluated indirectly using the yeast two-hybrid system described in Fields and Song, *Nature,* 340:245–246 (1989), and Fields and Sternglanz, *Trends in Genetics,* 10:286–292 (1994), both of which are incorporated herein by reference. The two-hybrid system is a genetic assay for detecting interactions between two proteins or polypeptides. It can be used to identify proteins that bind to a known protein of interest, or to delineate domains or residues critical for an interaction. Variations on this methodology have been developed to clone genes that encode DNA-binding proteins, to identify peptides that bind to a protein, and to screen for drugs. The two-hybrid system exploits the ability of a pair of interacting proteins to bring a transcription activation domain into close proximity with a DNA-binding domain that binds to an upstream activation sequence (UAS) of a reporter gene, and is generally performed in yeast. The assay requires the construction of two hybrid genes encoding (1) a DNA-binding domain that is fused to a protein X, and (2) an activation domain fused to a protein Y. The DNA-binding domain targets the first hybrid protein to the UAS of the reporter gene; however, because most proteins lack an activation domain, this DNA-binding hybrid protein does not activate transcription of the reporter gene. The second hybrid protein, which contains the activation domain, cannot by itself activate expression of the reporter gene because it does not bind the UAS. However, when both hybrid proteins are present, the noncovalent interaction of protein X and protein Y tethers the activation domain to the UAS, activating transcription of the reporter gene. When the virulence gene product (protein X, for example) is already known to interact with another protein or nucleic acid (protein Y, for example), this assay can be used to detect agents that interfere with the interaction of X and Y. Expression of the reporter gene is monitored as different test agents are added to the system; the presence of an inhibitory agent results in lack of a reporter signal.

When the function of the virulence gene product is unknown and no ligands are known to bind the gene product, the yeast two-hybrid assay can also be used to identify proteins that bind to the gene product. In an assay to identify proteins that bind to protein X (the target protein), a large number of hybrid genes each containing a different protein Y are produced and screened in the assay. Typically, Y is encoded by a pool of plasmids in which total cDNA or genomic DNA is ligated to the activation domain. This system is applicable to a wide variety of proteins, and it is not even necessary to know the identity or function of protein Y. The system is highly sensitive and can detect interactions not revealed by other methods; even transient interactions may trigger transcription to produce a stable mRNA that can be repeatedly translated to yield the reporter protein.

Other assays may be used to search for agents that bind to the target protein. One such screening method to identify direct binding of test ligands to a target protein is described in U.S. Pat. No. 5,585,277, incorporated herein by reference. This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method which distinguishes between the folded and unfolded states of the target protein. The function of the target protein need not be known in order for this assay to be performed. Virtually any agent can be assessed by this method as a test ligand, including, but not limited to, metals, polypeptides, proteins, lipids, polysaccharides, polynucleotides and small organic molecules. For example, use of femA in this method of screening for potential ligands is described in Example 3 below.

Another method for identifying ligands for a target protein is described in Wieboldt et al., *Anal. Chem.,* 69:1683–1691 (1997), incorporated herein by reference. This technique screens combinatorial libraries of 20–30 agents at a time in solution phase for binding to the target protein. Agents that bind to the target protein are separated from other library components by centrifugal ultrafiltration. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

The inhibitors/binders identified by the initial screens are evaluated for their effect on virulence in in vivo mouse models of *S. aureus* infections. Models of bacteremia, endocarditis, septic arthritis, soft tissue abscess or pneumonia may be utilized. Inhibitors/binders that interfere with bacterial virulence are capable of preventing the establishment of an infection or reversing the outcome of an infection once it is established.

The identification of *S. aureus* virulence genes also provides for microorganisms exhibiting reduced virulence, which are useful in vaccines. Such microorganisms include the *S. aureus* mutants generated in Example 1 below and other *S. aureus* mutants containing at least one functional mutation in a gene represented by any one of SEQ ID NOS: 1 through 94. The reduced virulence of these organisms and their immunogenicity may be confirmed by administration to a subject. While it is possible for an avirulent microorganism of the invention to be administered alone, one or more of such mutant microorganisms are preferably administered in a vaccine composition containing suitable adjuvant(s) and pharmaceutically acceptable diluent(s) or carrier(s). The carrier(s) must be "acceptable" in the sense of being compatible with the avirulent microorganism of the invention and not deleterious to the subject to be immunized. Typically, the carriers will be water or saline which will be sterile and pyrogen free. The subject to be immunized is a subject needing protection from a disease caused by a virulent form of *S. aureus.*

Any adjuvant known in the art may be used in the vaccine composition, including oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), proteoglycans (e.g., extracted from *Klebsiella pneumoniae*), streptococcal preparations (e.g., OK432), Biostim™ (e.g., 01K2), the "Iscoms" of EP 109 942, EP 180 564 and EP 231 039, aluminum hydroxide, saponin, DEAE-dextran, neutral oils (such as miglyol), vegetable oils (such as arachis oil), liposomes, Pluronic® polyols or the Ribi adjuvant system (see, for example GB-A-2 189 141). Recently, an alternative adjuvant consisting of extracts of Amycolata, a bacterial genus in the order Actinomycetales, has been described in U.S. Pat. No. 4,877,612. Additionally, proprietary adjuvant mixtures are commercially available. The adjuvant used will depend, in part, on the recipient organism. The amount of adjuvant to administer will depend on the type and size of animal. Optimal dosages may be readily determined by routine methods.

The vaccine compositions optionally may include pharmaceutically acceptable (i.e., sterile and non-toxic) liquid, semisolid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma.

The vaccine compositions can be packaged in forms convenient for delivery. The compositions can be enclosed within a capsule, sachet, cachet, gelatin, paper or other container. These delivery forms are preferred when compatible with entry of the immunogenic composition into the recipient organism and, particularly, when the immunogenic composition is being delivered in unit dose form. The dosage units can be packaged, e.g., in tablets, capsules, suppositories or cachets.

The vaccine compositions may be introduced into the subject to be immunized by any conventional method including, e.g., by intravenous, intradermal, intramuscular, intramammary, intraperitoneal, or subcutaneous injection; by oral, sublingual, nasal, anal, vaginal, or transdermal delivery; or by surgical implantation, e.g., embedded under the splenic capsule or in the cornea. The treatment may consist of a single dose or a plurality of doses over a period of time.

It will be appreciated that the vaccine of the invention may be useful in the fields of human medicine and veterinary medicine. Thus, the subject to be immunized may be a human or an animal, for example, cows, sheep, pigs, horses, dogs and cats, and poultry such as chickens, turkeys, ducks and geese.

Other aspects and advantages of the present invention will be understood upon consideration of the following illustrative examples. Example 1 addresses identification of *S. aureus* genes associated with virulence by generating *S. aureus* mutants that contain a chromosomal insertion of a signature-tagged transposon and identifying the mutants with reduced virulence. Example 2 addresses confirmation of the attenuated virulence of individual mutants. Example 3 addresses use of the virulence genes and gene products in assays for screening potential agents for anti-bacterial activity.

EXAMPLE 1

Identification of *S. aureus* Genes Associated with Virulence

*S. aureus* genes associated with virulence were identified by signature-tagged mutagenesis as follows, generally according to International Patent Publication No. WO 96/17951 and Hensel et al., *Science*, 269:400–403 (1995).

A. Construction of Plasmid pID408

A temperature-sensitive shuttle plasmid pID408 was constructed for use in transferring the signature-tagged transposons into *S. aureus*. DNA restriction digestions and ligations were performed as described by Sambrook et al., *Molecular cloning: a laboratory manual*, 2nd ed., Cold Spring Harbor Laboratory Press, Cold Spring Harbor, N.Y. (1989). A 6.5 kb BamHI fragment of pTV32ts [described in Youngman, in *Plasmids: a practical approach*, K. Hard, ed., Oxford: IRL Press, pages 79–103 (1985); obtained from J. Iandolo, Department of Diagnostic Medicine, College of Veterinary Medicine, Manhattan, Kansas] carrying the temperature-sensitive replicon pE194ts and a chloramphenicol (cm) resistance gene ($cm^R$) was inserted into the BamHI site of plasmid pSP72 (Promega), forming pID402. Plasmid pID402 was digested with SmaI and self-ligated to remove a small fragment containing a BamHI site between the SmaI sites, resulting in pID405. A DNA fragment of pBR322 (New England BioLabs) containing the ampicillin resistance gene ($amp^R$)/ori/rop region (corresponding to bases 1904–4359 of pBR322) was prepared by polymerase chain reaction (PCR) amplification using primers pBR1 (5'-GGAGCTCACTAGTCGGAGGCATCAGTGACC-3', SEQ ID NO: 95) and pBR2 (5'-GGGATCCCATGAGAATTCTTGAAGACG-3', SEQ ID NO: 96). Primer pBR1 contains sites for SacI and SpeI, and pBR2 contains sites for BamHI and EcoRI. The PCR product was digested with BamRI and SacI and ligated to the BamHI/SacI-digested fragment of pID405 (carrying replicon pE194ts and $cm^R$) to create pID406, in which the $amp^R$/ori region of pSP72 is replaced with the replicon of pBR322. Finally, a 6.5 kb BamHI-EcoRI fragment from pTV9 [described in Youngman, in *Plasmids: a practical approach*, K. Hard, ed., Oxford: IRL Press, pages 79–103 (1985)], containing transposon Tn917 and its erythromycin (erm) resistance gene ($erm^R$), was ligated with BamHI and EcoRI digested pID406, resulting in plasmid pID408. The origin of replication from pBR322 allows pID408 to replicate in *E. coli*, and the temperature-sensitive replicon pE194ts (from pTV32ts) allows replication in *S. aureus* at 32° C.

B. Cloning and Selection of Signature Tags

DNA signature tags were prepared as described by Hensel et al., *Science*, 269:400–403 (1995) and inserted into the transposon Tn917 carried by pID408 as follows. Oligonucleotides tags in pool RT1 (5'-CTAGGTACCTACAACCTCAAGCTT- [N K]$_{20}$-AAGCTTGGTTAGAATGGGTACCATG-3', SEQ ID NO: 97, where N is A, C, G or T, and K is G or T were synthesized on an oligonucleotide synthesizer (Applied Biosystems). The 80 bp tags from oligonucleotide pool RT1 were PCR-amplified from the using primers P10 (5'-CTAGAATTCTACAACCTCAAGCTT-3', SEQ ID NO: 98) and P11 (5'-AAGCTTGGTTAGAATGGAATTCATG-3', SEQ ID NO: 99). The PCR-amplified tags were digested with EcoRI, gel-purified, and ligated with EcoRI digested, dephosphorylated pID408, to form plasmids containing uniquely signature-tagged Tn917 transposons. The ligated DNA was transformed into *S. aureus* strain RN4220 (a restriction defective strain derived from NCTC 8325-4 and described in Youngman, in *Plasmids: a practical approach*, K. Hard, ed., Oxford: IRL Press, pages 79–103 (1985) by electroporation. Electroporation was performed by the method of Schenk and Laddaga, *FEMS Microbiol. Lett.*, 94:133–138 (1992), with the following modifications: electrotransformed bacteria were plated on non-selective brain-heart infusion (BHI, Difco) agar plates (1.5% agar), grown at 32° C. for 8 to 12 hours and then replicated using an Accutran Replica Plater (Schleicher and Schuell) onto BHI agar plates containing 20 μg/mi erm and 20 μg/ml cm, and grown at 32° C. overnight.

A total of 400 erm$^R$, cm$^R$ transformants were then screened to identify 150 tags that amplified and labelled efficiently. The 150 transformants were each cultured in 10 ml BHI broth containing 20 μg/ml erm and 20 μg/ml cm at 32° C. overnight. Plasmid DNA was extracted from each culture using a Qiagen Plasmid Miniprep Kit according to the manufacturer's protocol except that the bacterial cells were lysed by lysostaphin (Sigma; 200 mg/ml) at 37° C. for 30 min. in the P1 solution of the Qiagen miniprep kit. An aliquot of each plasmid DNA preparation (1 μg) was transferred onto a Hybond N$^+$ membrane (Amersham) by using a Bio-Dot Microfiltration Apparatus according to the manufacturer's protocol (Bio-Rad) to give 75 different plasmids per membrane. The membranes were then transferred to Whatman 3MM paper saturated with denaturing solution (0.5 N NaOH, 1.5 M NaCl), incubated for 5 min. then transferred to another piece of Whatman 3MM paper saturated with neutralizing solution (1.5 M NaOH, 0.5 M Tris-Cl pH 7.4) for 5 min. After neutralization, the membranes were dried at 80° C. for 10 min and the DNA cross-linked by UV light using a Stratalinker (Stratagene). The signature tags from the 150 transformants were also labelled for use as probes. Aliquots of the plasmid preparations were combined to form four pools of 37, 37, 38 and 38 plasmids. The DNA signature tags from these four pools were PCR-amplified with primers P12 (5'-GAATTCCATTCTAAC-3', SEQ ID NO: 100) and P13 (5'-ATTCCATTCTAACCAAGC-3', SEQ ID NO: 101) according to Hensel et al., Science, 269:400–403 (1995). These PCR products were gel-purified, subjected to a digoxygenin (DIG)-labelling PCR using a PCR DIG Probe Synthesis Kit as described by the manufacturer (Boehringer Mannheim). The DIG-labelled PCR products were hybridized separately with the membranes according to the method described in the DIG Probe Synthesis Kit, to identify tags that gave strong hybridization signals, but which did not cross-hybridize with tags in the other pools. From these experiments, a total of 96 plasmids were chosen on the basis of labelling efficiency of tags and lack of cross-hybridization.

C. Generation of the *S. aureus* Mutant Bank

The 96 plasmids containing uniquely signature tagged-transposons were used to generate *S. aureus* mutants with a chromosomal transposon insertion. A series of identical membranes for dot-blot hybridizations were prepared by transferring 1 μg of each of the 96 plasmids onto Hybond N$^+$ membranes using the Bio-Dot Microfiltration Apparatus. The 96 plasmids were separately transformed into *S. aureus* strain RN6390 by electroporation [Schenk and Laddaga, *FEMS Microbiol. Lett.*, 94:133–138 (1992)]. Electrotransformed bacteria were plated directly on BHI agar plates containing 20 μg/ml cm and 20 μg/ml erm at 32° C. overnight. A single colony from each transformation was transferred into each well of a microtitre dish containing 200 μl BHI broth, 20 μg/ml erm and 20 μg/ml cm. The microtitre dish was incubated at 32° C. overnight. Glycerol was added to each well to give a final concentration of 50% and the plates were stored at –80° C. This collection of 96 transformants was designated the master pool and was used for all subsequent mutagenesis.

To generate 96 different Tn917 mutants, bacteria from the master pool were replicated using a microtitre dish replicator (Sigma) into the wells of a new microtitre dish containing 200 μl BHI broth and 20 μg/ml erm. This dish was incubated at 43° C. overnight and then bacteria from each well were streaked on BHI agar containing 20 μg/ml erm and incubated at 43° C. overnight to obtain single colonies. Approximately five different erm$^R$ colonies obtained from each well were transferred onto BHI agar containing 20 μg/ml cm and incubated at 32° C., and onto BHI agar containing 20 μg/ml erm and incubated at 43° C., to screen for cm$^S$ colonies. Erm$^R$, cm$^S$ colonies should lack the plasmid and carry a chromosomal insertion of Tn917. Individual erm$^R$, cm$^S$ colonies from each of the 96 wells were transferred into a new 96 well microtitre dish with BHI broth containing 20 μg/ml erm and grown overnight at 43° C. for use as inoculum. These 96 mutants, taken together, form one "inoculum pool." Mutant pools were also stored at –80° C. in 50% glycerol.

To verify that erm$^R$, cm$^S$ colonies lack the plasmid and carry a single chromosomal insertion of Tn917, chromosomal DNA samples from individual mutant strains and from a pool of 46 colonies that had been cultured separately were digested with EcoRI and subjected to Southern analysis using a fragment of the β-lactamase gene as a probe. For each of 12 separately analyzed mutants, a single hybridizing fragment of different size was observed in each lane. A large number of hybridizing fragments were observed in the lane containing DNA from 46 mutants. These results indicate that the majority of Tn917 insertions occur singly and at different locations in the *S. aureus* chromosome.

D. Infection Studies to Identify Mutants with Reduced Virulence

The "inoculum pool" of 96 *S. aureus* mutants containing chromosomal transposon insertions was evaluated for attenuated virulence in a mouse model of bacteremia. After overnight incubation at 43° C., the 96 different mutants from individual wells of the microtitre dish were pooled together and washed twice with BHI broth by centrifugation at 4000×g for 10 min and resuspended in BHI broth. The OD$_{620}$ was determined using a spectrophotometer (OD$_{620}$ of 1.6×10$^9$ colony forming units (CFU)/m]) [Cheung et al., *J. Bacteriol.*, 177:3220–3226 (1995).]. The bacterial suspension was diluted to approximately 5×10$^6$ CFU/ml and then mixed with an equal volume of pre-autoclaved 4% (w/v) Brewer's yeast (Sigma) in BHI broth. A total of 0.2 ml of this mixture, containing approximately 5×10$^5$ CFU bacteria, was injected intraperitoneally into a CD-1 mouse (approximately 25 g in weight). The number of CFU in the inoculum was verified by viable counts after plating a diluted aliquot of the inoculum to BHI agar. Two to four mice were inoculated with each pool. 48 hours after inoculation, bacteria were recovered from the spleens of the animals as described by Hensel et al., Science, 269:400–403 (1995) and pooled to form the "recovered pool." Each recovered pool was made from at least 10,000 bacterial colonies. The signature tags present in the recovered pools were compared with the signature tags present in the inoculum pools by PCR amplifying the tags using primers P12 and P13 (described in section B above), DIG labelling the tags, and hybridizing the labelled tags to the 96 plasmids which had been transferred to Hybond N$^+$ membranes using the Bio-Dot Microfiltration Apparatus as described above in section C.

E. Virulence Gene Identification and DNA Sequencing

A total of 13 pools, each comprising 96 *S. aureus* Tn917mutants, were screened as described above for loss of virulence in mice. From these, 50 mutants were identified whose tags hybridized strongly to probes from the inoculum pools but weakly to probes from the corresponding recovery pools.

To clone the chromosomal DNA flanking the transposon insertion points of these 50 mutants, 3–5 μg of S. aureus chromosomal DNA from each mutant was isolated as described by Pospiech and Neumann, Trends Genetc., 11:217–218 (1995) and completely digested with HindIII. Half of the digested DNA was then subjected to Southern hybridization analysis using the pBR322 fragment of pID408 as a probe to determine the size of the DNA fragment carrying this part of the transposon. The rest of the DNA was resuspended in 200 μl of ligation buffer (Gibco-BRL) and self-ligated overnight at 16° C. The ligated products were transformed into E. coli DHα (Gibco) and plated onto Luria Bertani (LB) agar containing 50 μg/ml ampicillin, and incubated at 37° C. overnight. A single amp$^R$ colony from each transformation was grown up in LB broth containing 100 μg/ml amp. Plasmid DNA was extracted using a Qiagen plasmid miniprep kit. Chromosomal DNA flanking the transposon was obtained using primer pseq-1 (5'-TGAACTGCCACTGTAGAGAGA-3', SEQ ID NO: 102) based on the erm-proximal end of Tn917, and sequenced (for a stretch of several hundred nucleotides) using a Model 373A Sequencing System (Applied Biosystems). The sequence obtained is indicated in Table 1 below with reference to the corresponding nucleotides of the SEQ ID NO:.

These DNA sequences were analyzed by searching the S. aureus database from Human Genome Sciences and the European Molecular Biology Laboratory and Genbank DNA and Protein Databases using the BLAST and FASTA network service at the Human Genome Mapping Project Recourse Centre, Hinxton, UK. Results of the searches done to date in identifying the virulence genes and their possible function are shown in Table 1. Table 1 below displays the signature tag identification number, the SEQ ID NO: corresponding to each virulence gene (and the nucleotide positions within the SEQ ID NO: that correspond to the actual stretch of DNA that was sequenced), the possible function of the gene, and the $LD_{50}$ of the knockout mutant as determined in Example 2 below.

EXAMPLE 2

Assessment of Virulence of S. aureus Knockout Mutants

The virulence of individual knockout mutants, identified in Example 1 as having reduced virulence when tested. in pools of 96 mutants, was assessed by carrying out an $LD_{50}$ determination for each mutant. Confirmation that a given mutation is in a virulence gene may be obtained by comparing the parent and mutated bacterial strains in terms of whether both strains are equally effective in establishing an infection with the same consequences for the host animal. In practice, this may be done by comparing $LD_{50}$ values (the number of bacteria required to produce a 50% mortality rate in the animals under standardized conditions) between the wild-type strain and the mutant derivative strain. If the $LD_{50}$ values are within standard error of each other then the mutation is not in or does not affect a virulence gene. If significant differences occur between the wild-type and the mutant strain, where the mutant strain is significantly less able to cause lethal infection, then the mutation is in a virulence gene or dramatically affects a virulence gene.

Briefly, $LD_{50}$ determinations were conducted as follows. CF1 female mice weighing between 19 and 22 grams were injected intraperitoneally with a set concentration of either wild-type or mutant S. aureus in 0.2 ml of BHI broth containing 4% (w/v) dried brewer's yeast as an adjuvant for establishment of infection. The amount of brewer's yeast may vary from 0–8% dependent upon the bacteria being utilized in the infection. A single $LD_{50}$ determination utilizes five log-dilutions of bacteria ($10^3$ to $10^7$), with each log-dilution being tested in 10 mice. The actual number of bacteria employed was estimated in each $LD_{50}$ determination by a plate count conducted on the bacterial stock to determine the number of CFU of bacteria. Following infection, the mice were monitored daily for mortality for a period of at least one week. At the end of the observation period the $LD_{50}$ was determined using probit analysis on the mortality data. The $LD_{50}$ value of the wild-type S. aureus strain RN6390 ranges from $1.4 \times 10^4$ to $1.4 \times 10^5$. The $LD_{50}$ values for the virulence gene mutants are shown in Table 1 below.

TABLE 1

VIRULENCE GENE SEQUENCES AND POSSIBLE FUNCTION

| SIGNA-TURE TAG ID | SEQ ID NO: (DNA; amino acid) | Position of DNA sequence obtained in Example1 | IDENTIFICATION OF POSSIBLE FUNCTION OF GENE | $LD_{50}$ of knockout mutant (#CFU)* |
|---|---|---|---|---|
| p2c73 | SEQ ID NO: 1; 2 | 517–756 | FemA/B like with ~40% identity | >6.8 × $10^8$ |
| p2c90 | SEQ ID NO: 3 | 281–431 | Unknown; near Opp operon | |
| p9b74 | SEQ ID NO: 4; 5 | 593–711 | Tryptophan synthase alpha chain TrpA | |
| p11c29 | SEQ ID NO: 6; 7 | 1107–1260 | FemB | |
| p13c83 | SEQ ID NO: 6; 7 | 1107–1260 | FemB | 3.9 × $10^5$ |
| p4c15 | SEQ ID NO: 8; 9 & 10 | 360–654 | MarR/LuxR-like regulatory protein | |
| p6c63 | SEQ ID NO: 8; 9 & 10 | 388–659 | MarR/LuxR-like regulatory protein | >5.4 × $10^8$ |
| p5c4 | SEQ ID NO: 11; 12 | 192–481 | 41% identity to nitrate reductase NirQ | |

TABLE 1-continued

VIRULENCE GENE SEQUENCES AND POSSIBLE FUNCTION

| SIGNA-TURE TAG ID | SEQ ID NO: (DNA; amino acid) | Position of DNA sequence obtained in Example1 | IDENTIFICATION OF POSSIBLE FUNCTION OF GENE | $LD_{50}$ of knockout mutant (#CFU)* |
|---|---|---|---|---|
| p9b66 | SEQ ID NO: 13; 14 | 221–474 | Peptide methionine sulfoxide reductase | $4.0 \times 10^4$ |
| p7c26 | SEQ ID NO: 15; 16 | 44–410 | Oligopeptide transporter OppF | |
| p10c15 | SEQ ID NO: 17 & 19; 18 & 20 | 562–825 | Oligopeptide transporter OppD | $>2.6 \times 10^8$ |
| p13b74 | SEQ ID NO: 21 | all | Possible stem-loop termination sequence; no obvious ORF | $8.8 \times 10^4$ |
| p13c72 | SEQ ID NO: 21 | all | Possible stem-loop termination sequence; no obvious ORF | |
| p14c15 | SEQ ID NO: 22; 23 & 24 | 669–1009 | C-term of aspartokinase 2 alpha subunit and N-term of aspartate semialdeyde dehydrogenase Asd; both involved in homoserine synthesis | |
| p13b26 | SEQ ID NO: 25; 26 | 442–819 | homoserine kinase | $7.7 \times 10^4$ |
| p7c18 | SEQ ID NO: 27; 28 | 667–847 | diaminopimelate decarboxylase LysA; lysine synthesis | |
| p15c31 | SEQ ID NO: 29; 30 | 1594–2018 | phosphoribosylformylglyinamide decarboxylase PurL; purine synthesis | |
| p10b18 | SEQ ID NO: 31; 32 | 3–404 | tryptophan synthase alpha chain trpA | $>5.2 \times 10^8$ |
| p6b18 | SEQ ID NO: 31; 32 | 3–404 | tryptophan synthase alpha chain trpA | |
| p10b66 | SEQ ID NO: 33; 34 | 30–282 | tryptophan synthase beta chain trpB | $>4.2 \times 10^6$ |
| p10c34 | SEQ ID NO: 35; 36 | 609–817 | Anthranilate phosphoribosyl transferase TrpD; tryptophan synthesis | $>4 \times 10^6$ |
| p4c27 | SEQ ID NO: 37; 38 | 1130–1254 | dihydrolipoamide succinyl transferase component(e2) of 2-oxoglutarate dehydrogenase complex in TCA cycle | |
| p4c52 | SEQ ID NO: 39; 40 | 498–738 | dihydrolipoamide succinyl transferase component(e2) of 2-oxoglutarate dehydrogenase complex in TCA cycle | |
| p10b2 | SEQ ID NO: 41; 42 | 880–1159 | dihydrolipoamide succinyl transferase component(e2) of 2-oxoglutarate dehydrogenase complex in TCA cycle | $>2.6 \times 10^8$ |
| p10c20 | SEQ ID NO: 43 | all | Sequence 3' to the dihydrolipoamide succinyl transferase component(e2) of 2-oxoglutarate dehydrogenase complex in TCA cycle; no obvious ORF | $3.7 \times 10^5$ |
| p12c32 | SEQ ID NO: 44; 45 | 188–438 | Alpha-ketoglutarate dehydrogenase (e1) of the 2-oxoglutarate dehydrogenase complex in TCA cycle; acetyl CoA synthase | $>1.0 \times 10^6$ |
| p10b30 | SEQ ID NO: 46; 47 | 2419–2574 | Heat shock protein ClpB | $1.4 \times 10^6$ |
| p13c3 | SEQ ID NO: 48; 49 | 454–765 | 35% identity to hypothetical 45.9 kDa protein from *B. subtilis* ImpB/MucB/SamB family | $1.8 \times 10^4$ |

TABLE 1-continued

VIRULENCE GENE SEQUENCES AND POSSIBLE FUNCTION

| SIGNA- TURE TAG ID | SEQ ID NO: (DNA; amino acid) | Position of DNA sequence obtained in Example1 | IDENTIFICATION OF POSSIBLE FUNCTION OF GENE | $LD_{50}$ of knockout mutant (#CFU)* |
|---|---|---|---|---|
| p4b3 | SEQ ID NO: 50; 51 | 790–1203 | Unknown; homology to hypothetical proteins from *B. subtilis* YAAD and YAAE | |
| p4c63 | SEQ ID NO: 52; 53 | 576–806 | Unknown; metallopeptidase motif | |
| p5c3 | SEQ ID NO: 54; 55 | 1–450 | Unknown; membrane transporter motif | $7.1 \times 10^4$ |
| p8d26 | SEQ ID NO: 56 & 58; 57 & 59 | 32–262 | Unknown; 38% identity to *C. elegans* ORF | |
| p9b65 | SEQ ID NO: 60; 61 | 1–361 | sodium/proton dependent alanine carrier protein | $>9.2 \times 10^8$ |
| p10b32 | SEQ ID NO: 62; 63 | 205–296 | Unknown | |
| p10b85 | SEQ ID NO: 64 | 38–212 | Unknown | |
| p10b89 | SEQ ID NO: 65; 66 | 1–205 | Unknown; prokaryotic membrane lipoprotein lipid attachment motif | $>2.2 \times 10^8$ |
| p10c30 | SEQ ID NO: 67; 68 | 730–1041 | Unknown; sensor-type protein motif | $8.8 \times 10^5$ |
| p10c52 | SEQ ID NO: 69; 70 | 1–262 | Unknown | |
| p10d9 | SEQ ID NO: 71; 72 | 422–639 | Unknown; enterotoxin-like motif | |
| p11c12 | SEQ ID NO: 73; 74 | 1–150 | Unknown; 40% identity to *Mycoplasma mycoides* hypothetical protein in ffh 5' region q01444 | $>4.2 \times 10^6$ |
| p11c66 | SEQ ID NO: 75 & 77; 76 & 78 | 292–529 | Unknown; near Opp operon | |
| p5c34 | SEQ ID NO: 79; 80 | 1180–1236 | glycine betaine transporter; region 55% identity to *B. subtilis* p54417 | |
| p10c18 | SEQ ID NO: 81 | 1–477 | Unknown-potential ORF in 120 bp | |
| p12c3 | SEQ ID NO: 82; 83 | 1–318 | acetyl-CoA synthetase; region 59% identity to *B. subtilis* p39062 | |
| p14b25 | SEQ ID NO: 84; 85 | 1–148 | Unknown; exonuclease-like; 25% identity to *E. coli* p13458; contains ATP binding motif | |
| p14b74 | SEQ ID NO: 86; 87 | 243–624 | Unknown; 51% identity to hypothetical 45.9 kd protein(YQJW) from *B. subtilis* p54560 | |
| p14c13 | SEQ ID NO: 88 | 1–441 | Unknown; near Opp operon | |
| p15b9 | SEQ ID NO: 89; 90 | 654–867 | Unknown; 41% identity to hypothetical 33.7 kd protein (YHCT) from *B. subtilis* p54604 | |
| p15b32 | SEQ ID NO: 91; 92 | 286–370 | Unknown; similar to orf1 5' of acvB of *Agro. tumefaciens* a36922 | |
| p15c4 | SEQ ID NO: 93; 94 | 25–192 | 4-oxalocrotonate tautomerase; 42% identity to *Pseudo. putida* a43397 | |

*The $LD_{50}$ for wild-type *S. aureus* RN6390 is normally $1.4 \times 10^4$ to $1.4 \times 10^5$.

EXAMPLE 3

Use of Virulence Gene Products in Screen for Anti-bacterial Agents

The virulence genes and their gene products are utilized in assays for identifying new anti-bacterial agents against *S. aureus*. The genes are cloned, the proteins encoded by the genes are produced and purified, high throughput assays are established to screen for inhibitors, and the inhibitors identified in the primary screen are evaluated in secondary assays. The cloning and expression of FemA, and its use in screening potential inhibitory agents, is described below.

A. Cloning of FemA Gene

DNA restriction digestions and ligations are performed as described by Sambrook et al., *Molecular cloning: a laboratory manual*, 2nd ed., Cold Spring Harbor Laboratory Press, Cold Spring Harbor, N.Y. (1989). Cloning of the *S. aureus* femA gene [Berger-Bachi et al., *Mol. Gen. Genet.*, 219:263–269 (1989)] for intracellular expression in *E. coli* is carried out as follows. To clone the gene with six histidine residues at the 3'-terminus, the following two oligonucleotides primers, 5'-GGCCATCGATAATGAAATTAATTAACGAGAGACA AATAGG-3', SEQ ID NO: 103, and 5 GGCCGGATCCCTAGTGATGGTGATGGTGAT GAAAAATTCTGTCTTTAACTTTTT-3', SEQ ID NO: 104, are used to PCR amplify the gene from *S. aureus* genomic DNA. The resulting femA gene has a ClaI site at 5'-end and a BamHI site at 3'-end for cloning into *E. coli* expression vectors. For secretion of the femA gene with six histidine residues at the 3'-terminus into the periplasm of *E. coli*, PCR amplification using the following two oligonucleotide primers, 5'-GGCCGGTACCAAATTAATTAACGAGAGACAAAT AGG-3', SEQ ID NO:105 and

5 GGCCGGATCCCTAGTGATGGTGATGGTGAT GAAAAATTCTGTCTTTAACTTTTT-3', SEQ ID NO: 106, results in a fragment with a KpnI site at the 5'-end and a BamHI site at the 3'-end. The approximately 1.3 kb PCR fragment may be sequenced directly, or after cloning into an expression vector, to confirm the sequence of the femA gene and its flanking regions.

B. Recombinant FemA Protein Production and Purification

Expression of femA in *E. coli* is carried out as follows. The *E. coli* expression vector pSRtac-pelB contains the synthetic tac promoter and the signal sequence of PelB [Lei et al., *J. Bact.*, 169:4379–4383 (1987)], with transcription terminators upstream and downstream to minimize transcription read through. For intracellular expression, the femA gene generated by PCR as described above in section A with ClaI and BamHI sites at the termini is cloned into pSRtac-pelB digested with ClaI and BamHI (replacing the PelB signal sequence). For secretion into periplasm, the femA gene generated by PCR as described above in section A with KpnI and BamHI sites at the termini is cloned into pSRtac-pelB digested with KpnI and BamHI, directly downstream from the pelB signal sequence. *E. coli* are transformed with the expression vector containing the femA gene. To induce the tac promoter and optimize expression level, the transformed bacteria are incubated with IPTG (isopropylthio-β-galactoside) at concentrations ranging from $2\times10^{-3}$ M to $1\times10^{-5}$ M, at cell growth temperatures between 27° C. to 42° C. in rich medium or minimal medium.

The recombinant FemA thus produced contains six histidine residues at the C-terminus and can be purified via the affinty of histidine to nickel. Chromatography may be carried out with the metal chelating resin Ni-nitrilotriacetic acid (Ni-NTA) (available from Qiagen, Chatsworth, Calif.) under native or denaturing conditions.

C. High Throughput Assays Using FemA for Screening Potential Inhibitors

The screening method described in U.S. Pat. No. 5,585,277 is used as follows to establish a high throughput assay to identify ligands that bind to FemA. The test ligand and femA are combined under conditions (e.g., temperature, pH, salt concentration, time) appropriate for detecting binding of femA to a ligand. If too little target protein is unfolded, the observed signal will occur at too low a level or rate to be conveniently measured. The conditions are optimized using known methods. Binding of a test ligand to femA is assessed in one of several ways: by determining the extent to which folded femA is present in the test ligand-femA combination, by determining the extent to which unfolded femA is present in the test ligand femA combination, or by determining the ratio of folded femA to unfolded femA in the combination. There are numerous methods to carry out these determinations. For example, proteolysis may be used. A protease which acts preferentially on unfolded femA is combined with the test ligand-femA combination, and after an appropriate period of incubation, the difference between intact or degraded femA in the presence and in the absence of the test ligand is determined. The addition of a test ligand which binds the folded femA, thus stabilizing it in the protease-resistant form, changes the rate of proteolysis. A wide variety of known proteases, such as trypsin, chymotrypsin, V8 protease, elastase, carboxypeptidase, proteinase K, thermolysin and subtilisin, can be used. As another example, the binding of the test ligand to the femA is assessed through the use of antibodies that specifically bind to the protein only in the unfolded state. There are numerous methods known in the art for producing antibodies to a particular protein.

D. In Vivo Assays to Evaluate Inhibitors

The inhibitors/binders identified by the initial screens such as the one described in section C above are evaluated for their effect on virulence in mouse models of *S. aureus* infection. Mice are infected with 100 $LD_{50}$'s of the wild-type bacteria and treated with varying doses of the test inhibitory agent. The $ED_{50}$ of the test inhibitory agent (the amount in milligrams of drug per kilogram of body weight required to cure 50% of infected animals) is determined. Each trial contains two control groups, a negative control group given an $LD_{50}$ dose of bacteria and no test inhibitory agent (which ensures that the infecting dose is operationally close to 100 $LD_{50}$'s), and a positive control group given a 100 $LD_{50}$ dose of bacteria and an $ED_{50}$ dose of a known and effective antibiotic for that bacterial infection (which confirms that the infection can be cured under appropriate conditions).

Five dosage levels of test inhibitory agent, utilizing serial two-fold dilutions, are employed. An exemplary dosage scheme begins with a minimum of 6.25 mg of drug per kg of body weight per dose, and ranges up to a maximum dose of 100 mg/kg. Each dosage level is tested in six mice and deaths following infection and treatment are monitored for at least 6 days. At the end of the test period, probit analysis is employed to determine the $ED_{50}$ value of the inhibitor or the amount of drug in milligrams of drug per kilogram of body weight required to reverse virulence so as to result in only 50% mortality of infected animals in the test. In tests designed to detect the prevention of infection by interference with virulence factors, the first dose of the inhibitor is given one hour prior to infection, and then four and eight hours post infection. In tests designed to detect virulence inhibitors which reverse the outcome of infection, the inhibitor is administered one and four hours post infection on the first day of infection and once in the morning and afternoon (separated by 6–8 hours) on the second and third days following infection. Inhibitory agents that successfully prevent the establishment of an infection or reverse the outcome of an infection once established are identified.

Numerous modifications and variations of the above-described invention are expected to occur to those of skill in the art. Accordingly, only such limitations as appear in the appended claims should be placed thereon.

What is claimed is:

1. A method of screening for a anti-bacterial agent comprising the steps of:
   (a) contacting a bacterial virulence protein encoded by a DNA sequence set forth in any one of SEQ ID NOS: 8, 17, 19, 29, 73, and 79 (corresponding to signature tag identification numbers p4c15, p6c63, p10c15, p15c31, p11c12 and p5c34) with a chemical compound, and
   (b) identifying said chemical compound as an agent that interferes with the function of said bacterial virulence protein when said chemical compound binds to or interacts with said bacterial virulence protein.

2. A method of screening for an anti-bacterial agent comprising the steps of:
   (a) contacting a bacterial virulence protein represented by any one of SEQ ID NOS: 9, 10, 18, 20, 30, 74, and 80 (corresponding to signature tag identification numbers p4c15, p6c63, p10c15, p15c31, p11c12 and p5c34) with a chemical compound, and
   (b) identifying said chemical compound as an agent that interferes with the function of said bacterial virulence protein when said chemical compound binds to or interacts with said bacterial virulence protein.

3. The method of any one of claims 1 and 2 wherein said bacterial virulence protein is an enzyme and in step (b) binding or interaction of said chemical compound with said bacterial virulence protein inhibits enzymatic activity of said bacterial virulence protein.

4. The method of any one of claims 1 and 2 wherein said chemical compound is a polypeptide and step (b) comprises a two-hybrid screening assay detecting expression of a reporter gene in a host cell that comprises
   (a) said bacterial virulence protein fused to a DNA-binding domain that interacts with an upstream activation sequence (UAS),
   (b) said chemical compound fused to a transcription activation domain, and
   (c) said UAS operatively linked to said reporter gene, and wherein expression of said reporter gene occurs upon interaction of said bacterial virulence protein with said chemical compound.

5. The method of any one of claims 1 and 2 wherein step (b) comprises a binding assay wherein unfolding of said bacterial virulence protein is measured in the presence and absence of said chemical compound.

6. The method of any one of claims 1 and 2 wherein step (h) comprises an affinity ultrafiltration assay wherein ultrafiltration is used to separate chemical compounds that bind to said bacterial virulence protein from chemical compounds that do not bind to said bacterial virulence protein.

7. The method of any one of claims 1 and 2 wherein said chemical compound is a polypeptide and step (b) comprises a two-hybrid screening assay detecting expression of a reporter gene in a host cell that comprises
   (a) said chemical compound fused to a DNA-binding domain that interacts with an upstream activation sequences (UAS),
   (b) said bacterial protein fused to a transcription activation domain, and
   (c) said UAS operatively linked to said reporter gene, and wherein expression of said reporter gene occurs upon interaction of said bacterial protein with said chemical compound.

8. The method of any one of claims 1 and 2 further comprising the step of measuring effect of said identified potential agent on bacterial replication.

9. The method of any one of claims 1 and 2 further comprising the step of measuring effect of said identified potential agent on bacterial infection in an animal.

10. A method of screening for an anti-bacterial agent comprising the steps of:
    (a) contacting a bacterial virulence protein encoded by a DNA sequence set forth in SEQ ID NO:1, (corresponding to signature tag identification number p2c73) with a chemical compound, wherein said chemical compound is a candidate anti-virulence agent, and
    (b) identifying said chemical compound as an agent that interferes with the function of said bacterial virulence protein when said chemical compound binds to or interacts with said bacterial virulence protein.

11. A method of screening for an anti-bacterial agent comprising the steps of:
    (a) contacting a bacterial virulence protein represented by any one of SEQ ID NO: 2, (corresponding to signature tag identification numbers p2c73) with a chemical compound, wherein said chemical compound is a candidate anti-virulence agent, and
    (b) identifying said chemical compound as an agent that interferes with the function of said bacterial virulence protein when said chemical compound binds to or interacts with said bacterial virulence protein.

12. The method of any one of claims 10 and 11 wherein said bacterial virulence protein is an enzyme and in step (b) binding or interaction of said chemical compound with said bacterial virulence protein inhibits enzymatic activity of said bacterial virulence protein.

13. The method of any one of claims 10 and 11 wherein said chemical compound is a polypeptide and step (b) comprises a two-hybrid screening assay detecting expression of a reporter gene in a host cell that comprises (a) said bacterial virulence protein fused to a DNA-binding domain that interacts with an upstream activation sequence (UAS), (b) said chemical compound fused to a transcription activation domain, and (c) said UAS operatively linked to said reporter gene, and wherein expression of said reporter gene occurs upon interaction of said bacterial virulence protein with said chemical compound.

14. The method of any one of claims 10 and 11 wherein step (b) comprises a binding assay wherein unfolding of said bacterial virulence protein is measured in the presence and absence of said chemical compound.

15. The method of any one of claims 10 and 11 wherein step (b) comprises an affinity ultrafiltration assay wherein ultrafiltration is used to separate chemical compounds that bind to said bacterial virulence protein from chemical compounds that do not bind to said bacterial virulence protein.

16. The method of any one of claims 10 and 11 wherein said chemical compound is a polypeptide and step (b) comprises a two-hybrid screening assay detecting expression of a reporter gene in a host cell that comprises (a) said chemical compound fused to a DNA-binding domain that interacts with an upstream activation sequence (UAS), (b) said bacterial virulence protein fused to a transcription activation domain, and (c) said UAS operatively linked to said reporter gene, and wherein expression of said reporter gene occurs upon interaction of said bacterial virulence protein with said chemical compound.

17. The method of any one of claims 10 and 11 further comprising the step of measuring effect of said identified agent on bacterial replication.

18. The method of any one of claims 10 and 11 further comprising the step of measuring effect of said identified agent on bacterial infection in an animal.

* * * * *

UNITED STATES PATENT AND TRADEMARK OFFICE
CERTIFICATE OF CORRECTION

PATENT NO. : 6,455,323 B1
DATED : September 24, 2002
INVENTOR(S) : David W. Holden It is certified that error appears in the above-identified patent and that said Letters Patent is hereby corrected as shown below:

<u>Column 242,</u>
Line 24, replace "step (h) comprises" with -- step (b) comprises --.

Signed and Sealed this

Third Day of February, 2004

JON W. DUDAS
*Acting Director of the United States Patent and Trademark Office*

SEQUENCE LISTING (1) GENERAL INFORMATION:

(iii) NUMBER OF SEQUENCES: 106

(2) INFORMATION FOR SEQ ID NO:1:

(i) SEQUENCE CHARACTERISTICS:
        (A) LENGTH: 1260 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p2c73)"

(ix) FEATURE:
        (A) NAME/KEY: CDS
        (B) LOCATION: 1..1257

(xi) SEQUENCE DESCRIPTION: SEQ ID NO:1:

```
ATG AAA TTT ACA GAG TTA ACT GTT ACC GAA TTT GAC AAC TTT GTA CAA        48
Met Lys Phe Thr Glu Leu Thr Val Thr Glu Phe Asp Asn Phe Val Gln
 1               5                  10                  15

AAT CCA TCA TTG GAA AGT CAT TAT TTC CAA GTA AAA GAA AAT ATA GTT        96
Asn Pro Ser Leu Glu Ser His Tyr Phe Gln Val Lys Glu Asn Ile Val
                20                  25                  30

ACC CGT GAG AAT GAT GGC TTT GAA GTA GTT TTA TTA GGT ATT AAA GAC       144
Thr Arg Glu Asn Asp Gly Phe Glu Val Val Leu Leu Gly Ile Lys Asp
         35                  40                  45

GAC AAT AAC AAA GTA ATT GCA GCA AGC CTT TTC TCT AAA ATT CCT ACT       192
Asp Asn Asn Lys Val Ile Ala Ala Ser Leu Phe Ser Lys Ile Pro Thr
     50                  55                  60

ATG GGA AGT TAT GTT TAC TAT TCG AAT CGT GGT CCA GTA ATG GAT TTT       240
Met Gly Ser Tyr Val Tyr Tyr Ser Asn Arg Gly Pro Val Met Asp Phe
 65                  70                  75                  80

TCA GAT TTA GGA TTA GTT GAT TAT TAT TTA AAA GAG TTA GAT AAA TAT       288
Ser Asp Leu Gly Leu Val Asp Tyr Tyr Leu Lys Glu Leu Asp Lys Tyr
                 85                  90                  95

TTA CAG CAA CAT CAA TGT TTA TAT GTT AAA TTA GAT CCG TAT TGG TTA       336
Leu Gln Gln His Gln Cys Leu Tyr Val Lys Leu Asp Pro Tyr Trp Leu
                100                 105                 110

TAT CAT CTA TAT GAT AAA GAT ATC GTG CCA TTT GAA GGT CGC GAG AAA       384
Tyr His Leu Tyr Asp Lys Asp Ile Val Pro Phe Glu Gly Arg Glu Lys
            115                 120                 125

AAT GAT GCC CTA GTA AAC TTG TTT AAA TCA CAT GGT TAC GAG CAT CAT       432
Asn Asp Ala Leu Val Asn Leu Phe Lys Ser His Gly Tyr Glu His His
        130                 135                 140

GGC TTT ACA ACT GAG TAT GAT ACA TCG AGC CAA GTA CGA TGG ATG GGC       480
Gly Phe Thr Thr Glu Tyr Asp Thr Ser Ser Gln Val Arg Trp Met Gly
145                 150                 155                 160

GTA TTA AAC CTT GAA GGT AAA ACA CCC GAA ACA TTG AAA AAG ACA TTT       528
Val Leu Asn Leu Glu Gly Lys Thr Pro Glu Thr Leu Lys Lys Thr Phe
                165                 170                 175

GAT AGT CAA CGT AAA CGT AAT ATT AAT AAA GCG ATA AAC TAT GGT GTT       576
```

```
Asp Ser Gln Arg Lys Arg Asn Ile Asn Lys Ala Ile Asn Tyr Gly Val
            180                 185                 190

AAA GTC AGA TTC CTT GAA CGT GAT GAG TTC AAT CTT TTC TTA GAT TTA      624
Lys Val Arg Phe Leu Glu Arg Asp Glu Phe Asn Leu Phe Leu Asp Leu
            195                 200                 205

TAT CGT GAA ACT GAA GAG CGT GCT GGA TTT GTA TCA AAA ACA GAT GAT      672
Tyr Arg Glu Thr Glu Glu Arg Ala Gly Phe Val Ser Lys Thr Asp Asp
210                 215                 220

TAT TTT TAT AAC TTT ATT GAC ACA TAT GGA GAT AAA GTA TTA GTA CCA      720
Tyr Phe Tyr Asn Phe Ile Asp Thr Tyr Gly Asp Lys Val Leu Val Pro
225                 230                 235                 240

TTA GCA TAT ATT GAC CTT GAT GAA TAT GTG TTA AAG TTG CAA CAG GAA      768
Leu Ala Tyr Ile Asp Leu Asp Glu Tyr Val Leu Lys Leu Gln Gln Glu
            245                 250                 255

TTG AAT GAC AAA GAA AAT CGT CGT GAT CAA ATG ATG GCG AAA GAA AAC      816
Leu Asn Asp Lys Glu Asn Arg Arg Asp Gln Met Met Ala Lys Glu Asn
            260                 265                 270

AAA TCA GAT AAG CAA ATG AAG AAA ATT GCA GAA TTA GAT AAG CAA ATT      864
Lys Ser Asp Lys Gln Met Lys Lys Ile Ala Glu Leu Asp Lys Gln Ile
            275                 280                 285

GAT CAT GAT CAG CAT GAA TTA TTG AAT GCA AGT GAA TTG AGC AAA ACG      912
Asp His Asp Gln His Glu Leu Leu Asn Ala Ser Glu Leu Ser Lys Thr
            290                 295                 300

GAC GGC CCA ATT CTA AAC CTT GCT TCT GGC GTT TAT TTT GCA AAT GCA      960
Asp Gly Pro Ile Leu Asn Leu Ala Ser Gly Val Tyr Phe Ala Asn Ala
305                 310                 315                 320

TAT GAA GTG AAT TAT TTC TCT GGT GGT TCA TCA GAA AAA TAT AAT CAA     1008
Tyr Glu Val Asn Tyr Phe Ser Gly Gly Ser Ser Glu Lys Tyr Asn Gln
            325                 330                 335

TTT ATG GGA CCA TAC ATG ATG CAT TGG TTT ATG ATT AAC TAT TGC TTC     1056
Phe Met Gly Pro Tyr Met Met His Trp Phe Met Ile Asn Tyr Cys Phe
            340                 345                 350

GAT AAT GGC TAT GAT CGT TAT AAT TTC TAT GGT TTA TCA GGT GAT TTT     1104
Asp Asn Gly Tyr Asp Arg Tyr Asn Phe Tyr Gly Leu Ser Gly Asp Phe
            355                 360                 365

ACG GAA AAC AGT GAA GAT TAT GGC GTA TAC CGC TTT AAA CGT GGA TTT     1152
Thr Glu Asn Ser Glu Asp Tyr Gly Val Tyr Arg Phe Lys Arg Gly Phe
            370                 375                 380

AAT GTA CAA ATC GAA GAA TTA ATA GGG GAT TTC TAT AAA CCA ATT CAT     1200
Asn Val Gln Ile Glu Glu Leu Ile Gly Asp Phe Tyr Lys Pro Ile His
385                 390                 395                 400

AAA GTG AAA TAT TGG TTG TTC ACA ACA TTG GAT AAA TTA CGT AAA AAA     1248
Lys Val Lys Tyr Trp Leu Phe Thr Thr Leu Asp Lys Leu Arg Lys Lys
            405                 410                 415

TTA AAG AAA TAG                                                     1260
Leu Lys Lys
```

(2) INFORMATION FOR SEQ ID NO:2:

(i) SEQUENCE CHARACTERISTICS:
        (A) LENGTH: 419 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Phe Thr Glu Leu Thr Val Thr Glu Phe Asp Asn Phe Val Gln
1               5                   10                  15

Asn Pro Ser Leu Glu Ser His Tyr Phe Gln Val Lys Glu Asn Ile Val
            20                  25                  30
```

```
Thr Arg Glu Asn Asp Gly Phe Glu Val Val Leu Leu Gly Ile Lys Asp
        35                  40                  45

Asp Asn Asn Lys Val Ile Ala Ala Ser Leu Phe Ser Lys Ile Pro Thr
    50                  55                  60

Met Gly Ser Tyr Val Tyr Tyr Ser Asn Arg Gly Pro Val Met Asp Phe
 65              70                  75                      80

Ser Asp Leu Gly Leu Val Asp Tyr Tyr Leu Lys Glu Leu Asp Lys Tyr
                85                  90                  95

Leu Gln Gln His Gln Cys Leu Tyr Val Lys Leu Asp Pro Tyr Trp Leu
            100                 105                 110

Tyr His Leu Tyr Asp Lys Asp Ile Val Pro Phe Glu Gly Arg Glu Lys
        115                 120                 125

Asn Asp Ala Leu Val Asn Leu Phe Lys Ser His Gly Tyr Glu His His
    130                 135                 140

Gly Phe Thr Thr Glu Tyr Asp Thr Ser Ser Gln Val Arg Trp Met Gly
145                 150                 155                 160

Val Leu Asn Leu Glu Gly Lys Thr Pro Glu Thr Leu Lys Lys Thr Phe
                165                 170                 175

Asp Ser Gln Arg Lys Arg Asn Ile Asn Lys Ala Ile Asn Tyr Gly Val
            180                 185                 190

Lys Val Arg Phe Leu Glu Arg Asp Glu Phe Asn Leu Phe Leu Asp Leu
        195                 200                 205

Tyr Arg Glu Thr Glu Glu Arg Ala Gly Phe Val Ser Lys Thr Asp Asp
        210                 215                 220

Tyr Phe Tyr Asn Phe Ile Asp Thr Tyr Gly Asp Lys Val Leu Val Pro
225                 230                 235                 240

Leu Ala Tyr Ile Asp Leu Asp Glu Tyr Val Leu Lys Leu Gln Gln Glu
                245                 250                 255

Leu Asn Asp Lys Glu Asn Arg Arg Asp Gln Met Met Ala Lys Glu Asn
            260                 265                 270

Lys Ser Asp Lys Gln Met Lys Lys Ile Ala Glu Leu Asp Lys Gln Ile
        275                 280                 285

Asp His Asp Gln His Glu Leu Leu Asn Ala Ser Glu Leu Ser Lys Thr
    290                 295                 300

Asp Gly Pro Ile Leu Asn Leu Ala Ser Gly Val Tyr Phe Ala Asn Ala
305                 310                 315                 320

Tyr Glu Val Asn Tyr Phe Ser Gly Gly Ser Glu Lys Tyr Asn Gln
                325                 330                 335

Phe Met Gly Pro Tyr Met Met His Trp Phe Met Ile Asn Tyr Cys Phe
            340                 345                 350

Asp Asn Gly Tyr Asp Arg Tyr Asn Phe Tyr Gly Leu Ser Gly Asp Phe
        355                 360                 365

Thr Glu Asn Ser Glu Asp Tyr Gly Val Tyr Arg Phe Lys Arg Gly Phe
    370                 375                 380

Asn Val Gln Ile Glu Glu Leu Ile Gly Asp Phe Tyr Lys Pro Ile His
385                 390                 395                 400

Lys Val Lys Tyr Trp Leu Phe Thr Thr Leu Asp Lys Leu Arg Lys Lys
                405                 410                 415

Leu Lys Lys
```

(2) INFORMATION FOR SEQ ID NO:3:

(i) SEQUENCE CHARACTERISTICS:

(A) LENGTH: 431 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p2c90)"

(xi) SEQUENCE DESCRIPTION: SEQ ID NO:3:

```
GACGTGCTGA TGCAAATATA AGTNCATGAC CATCATGTTG TAATTGTNAC AATGTATCAA    60

TAATAGTCTG GTCAATTAAT CGGCCGTCAA AACAAAGCGT ACCATCAATA TCANAGACAA   120

ATCTCATCAN ATCACTCCAA ACAATATAAT ACCATGATTA TAGCATAAGT NAGTCATGTN   180

ACGATATTAG ATAATGATTA TNATGTAGGG TACCTTTTGC CTTACACACA TATNACTTCC   240

TATNATATAT ATTATGTCAA CNNGAATGTN AAATTCCATA AGGGGACTTA TATAACTGTN   300

TGTCTGTNTA GTGTTTATGT CAGTCAGCTA AATTNACATT CATGTTATGT CTCATTAAAC   360

CAATTACTCA CGTNTTGGTG CATATCNCAT CTTTCATATC GTCATACATC TATCCTCATT   420

CTCNTGNCTG A                                                        431
```

(2) INFORMATION FOR SEQ ID NO:4:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p9b74)"

(ix) FEATURE:
        (A) NAME/KEY: CDS
        (B) LOCATION: 1..726

(xi) SEQUENCE DESCRIPTION: SEQ ID NO:4:

```
ATG ACT AAA TTA TTT ATA CCT TAT ATT ATG GGC AAT AAA GAT TTG ATT        48
Met Thr Lys Leu Phe Ile Pro Tyr Ile Met Gly Asn Lys Asp Leu Ile
1               5                   10                  15

GAA AAT GCA ACA TTG TTG AGT GAA AAT GGT GCA GAT ATA ATT GAA ATT        96
Glu Asn Ala Thr Leu Leu Ser Glu Asn Gly Ala Asp Ile Ile Glu Ile
                20                  25                  30

GGA GTA CCT TTC TCT GAT CCG GTT GCT GAT GGT CCA GTT ATC ATG GAA       144
Gly Val Pro Phe Ser Asp Pro Val Ala Asp Gly Pro Val Ile Met Glu
            35                  40                  45

GCA GGT CAA CAA GCG ATT AAA CAA GGC ATC ACG ATA GAT TAT ATT TTC       192
Ala Gly Gln Gln Ala Ile Lys Gln Gly Ile Thr Ile Asp Tyr Ile Phe
        50                  55                  60

AAT CAA TTA GAA AAA CAT GGT GAT CAA ATT AAG TGT AAC TAT GTA TTA       240
Asn Gln Leu Glu Lys His Gly Asp Gln Ile Lys Cys Asn Tyr Val Leu
65                  70                  75                  80

ATG ACG TAT TAT AAT ATT ATT TGT CAT TAT GGA GAA CAA GCG TTT TTT       288
Met Thr Tyr Tyr Asn Ile Ile Cys His Tyr Gly Glu Gln Ala Phe Phe
                85                  90                  95

GAA AAA TGT CGA GAT ACT GGT GTC TAC GGC TTA ATT ATT CCT GAT TTA       336
Glu Lys Cys Arg Asp Thr Gly Val Tyr Gly Leu Ile Ile Pro Asp Leu
                100                 105                 110

CCA TAT GAA TTA TCG CAG CGT TTA AAA CAA CAA TTT AGT CAC TAT GGC       384
Pro Tyr Glu Leu Ser Gln Arg Leu Lys Gln Gln Phe Ser His Tyr Gly
            115                 120                 125

GTC AAA ATC ATA TCG TTA GTT GCG ATG ACT ACT GAT GAC AAA CGT ATA       432
Val Lys Ile Ile Ser Leu Val Ala Met Thr Thr Asp Asp Lys Arg Ile
        130                 135                 140
```

| | | | | | | | | | | | | | |
|---|---|---|---|---|---|---|---|---|---|---|---|---|---|
| AAA | GAT | ATC | GTA | TCC | CAT | GCG | GAA | GGC | TTT | ATT | TAT | ACT | GTG | ACG | ATG | 480 |
| Lys | Asp | Ile | Val | Ser | His | Ala | Glu | Gly | Phe | Ile | Tyr | Thr | Val | Thr | Met | |
| 145 | | | | | 150 | | | | | 155 | | | | | 160 | |
| AAT | GCG | ACA | ACA | GGG | CAA | AAC | GGT | GCG | TTT | CAT | CCA | GAA | TTA | AAA | CGA | 528 |
| Asn | Ala | Thr | Thr | Gly | Gln | Asn | Gly | Ala | Phe | His | Pro | Glu | Leu | Lys | Arg | |
| | | | | 165 | | | | | 170 | | | | | 175 | | |
| AAA | ATT | GAG | TCA | ATT | AAA | GCG | ATA | GCC | AAT | GTG | CCA | GTT | GTC | GCA | GGA | 576 |
| Lys | Ile | Glu | Ser | Ile | Lys | Ala | Ile | Ala | Asn | Val | Pro | Val | Val | Ala | Gly | |
| | | | 180 | | | | | 185 | | | | | 190 | | | |
| TTT | GGT | ATA | AGA | ACA | CCA | CAA | CAT | GTT | GCA | GAT | ATA | AAA | GAG | GTT | GCA | 624 |
| Phe | Gly | Ile | Arg | Thr | Pro | Gln | His | Val | Ala | Asp | Ile | Lys | Glu | Val | Ala | |
| | | | 195 | | | | | 200 | | | | | 205 | | | |
| GAT | GGC | ATT | GTC | ATT | GGT | AGC | GAA | ATC | GTT | AAG | CGA | TTT | AAA | TCT | AAC | 672 |
| Asp | Gly | Ile | Val | Ile | Gly | Ser | Glu | Ile | Val | Lys | Arg | Phe | Lys | Ser | Asn | |
| 210 | | | | | 215 | | | | | 220 | | | | | | |
| ACG | CGT | GAG | GAA | ATC | ATT | AAA | TAT | TTA | CAA | TCT | ATC | CAA | CAA | ACA | TTG | 720 |
| Thr | Arg | Glu | Glu | Ile | Ile | Lys | Tyr | Leu | Gln | Ser | Ile | Gln | Gln | Thr | Leu | |
| 225 | | | | | 230 | | | | | 235 | | | | | 240 | |
| AAT | AAT | TAA | | | | | | | | | | | | | | 729 |
| Asn | Asn | | | | | | | | | | | | | | | |

(2) INFORMATION FOR SEQ ID NO:5:

(i) SEQUENCE CHARACTERISTICS:
        (A) LENGTH: 242 amino acids
        (B) TYPE: amino acid
        (D) TOPOLOGY: linear (ii) MOLECULE TYPE: protein (xi) SEQUENCE DESCRIPTION: SEQ ID NO:5:

| | | | | | | | | | | | | | |
|---|---|---|---|---|---|---|---|---|---|---|---|---|---|
| Met | Thr | Lys | Leu | Phe | Ile | Pro | Tyr | Ile | Met | Gly | Asn | Lys | Asp | Leu | Ile |
| 1 | | | | 5 | | | | | 10 | | | | | 15 | |
| Glu | Asn | Ala | Thr | Leu | Leu | Ser | Glu | Asn | Gly | Ala | Asp | Ile | Ile | Glu | Ile |
| | | | 20 | | | | | 25 | | | | | 30 | | |
| Gly | Val | Pro | Phe | Ser | Asp | Pro | Val | Ala | Asp | Gly | Pro | Val | Ile | Met | Glu |
| | | | 35 | | | | | 40 | | | | | 45 | | |
| Ala | Gly | Gln | Gln | Ala | Ile | Lys | Gln | Gly | Ile | Thr | Ile | Asp | Tyr | Ile | Phe |
| | 50 | | | | | 55 | | | | | 60 | | | | |
| Asn | Gln | Leu | Glu | Lys | His | Gly | Asp | Gln | Ile | Lys | Cys | Asn | Tyr | Val | Leu |
| 65 | | | | | 70 | | | | | 75 | | | | | 80 |
| Met | Thr | Tyr | Tyr | Asn | Ile | Ile | Cys | His | Tyr | Gly | Glu | Gln | Ala | Phe | Phe |
| | | | | 85 | | | | | 90 | | | | | 95 | |
| Glu | Lys | Cys | Arg | Asp | Thr | Gly | Val | Tyr | Gly | Leu | Ile | Ile | Pro | Asp | Leu |
| | | | 100 | | | | | 105 | | | | | 110 | | |
| Pro | Tyr | Glu | Leu | Ser | Gln | Arg | Leu | Lys | Gln | Gln | Phe | Ser | His | Tyr | Gly |
| | | | 115 | | | | | 120 | | | | | 125 | | |
| Val | Lys | Ile | Ile | Ser | Leu | Val | Ala | Met | Thr | Thr | Asp | Asp | Lys | Arg | Ile |
| | | 130 | | | | | 135 | | | | | 140 | | | |
| Lys | Asp | Ile | Val | Ser | His | Ala | Glu | Gly | Phe | Ile | Tyr | Thr | Val | Thr | Met |
| 145 | | | | | 150 | | | | | 155 | | | | | 160 |
| Asn | Ala | Thr | Thr | Gly | Gln | Asn | Gly | Ala | Phe | His | Pro | Glu | Leu | Lys | Arg |
| | | | | 165 | | | | | 170 | | | | | 175 | |
| Lys | Ile | Glu | Ser | Ile | Lys | Ala | Ile | Ala | Asn | Val | Pro | Val | Val | Ala | Gly |
| | | | 180 | | | | | 185 | | | | | 190 | | |
| Phe | Gly | Ile | Arg | Thr | Pro | Gln | His | Val | Ala | Asp | Ile | Lys | Glu | Val | Ala |
| | | | 195 | | | | | 200 | | | | | 205 | | |

```
Asp Gly Ile Val Ile Gly Ser Glu Ile Val Lys Arg Phe Lys Ser Asn
    210                 215                 220
Thr Arg Glu Glu Ile Ile Lys Tyr Leu Gln Ser Ile Gln Gln Thr Leu
225                 230                 235                 240
Asn Asn
```

(2) INFORMATION FOR SEQ ID NO:6:

(i) SEQUENCE CHARACTERISTICS:
        (A) LENGTH: 1260 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p11c29/p13c83)"

(ix) FEATURE:
        (A) NAME/KEY: CDS
        (B) LOCATION: 1..1257

(xi) SEQUENCE DESCRIPTION: SEQ ID NO:6:

```
ATG AAA TTT ACA GAG TTA ACT GTT ACC GAA TTT GAC AAC TTT GTA CAA        48
Met Lys Phe Thr Glu Leu Thr Val Thr Glu Phe Asp Asn Phe Val Gln
 1               5                  10                  15

AAT CCA TCA TTG GAA AGT CAT TAT TTC CAA GTA AAA GAA AAT ATA GTT        96
Asn Pro Ser Leu Glu Ser His Tyr Phe Gln Val Lys Glu Asn Ile Val
                20                  25                  30

ACC CGT GAG AAT GAT GGC TTT GAA GTA GTT TTA TTA GGT ATT AAA GAC       144
Thr Arg Glu Asn Asp Gly Phe Glu Val Val Leu Leu Gly Ile Lys Asp
            35                  40                  45

GAC AAT AAC AAA GTA ATT GCA GCA AGC CTT TTC TCT AAA ATT CCT ACT       192
Asp Asn Asn Lys Val Ile Ala Ala Ser Leu Phe Ser Lys Ile Pro Thr
 50                  55                  60

ATG GGA AGT TAT GTT TAC TAT TCG AAT CGT GGT CCA GTA ATG GAT TTT       240
Met Gly Ser Tyr Val Tyr Tyr Ser Asn Arg Gly Pro Val Met Asp Phe
 65                  70                  75                  80

TCA GAT TTA GGA TTA GTT GAT TAT TAT TTA AAA GAG TTA GAT AAA TAT       288
Ser Asp Leu Gly Leu Val Asp Tyr Tyr Leu Lys Glu Leu Asp Lys Tyr
                85                  90                  95

TTA CAG CAA CAT CAA TGT TTA TAT GTT AAA TTA GAT CCG TAT TGG TTA       336
Leu Gln Gln His Gln Cys Leu Tyr Val Lys Leu Asp Pro Tyr Trp Leu
            100                 105                 110

TAT CAT CTA TAT GAT AAA GAT ATC GTG CCA TTT GAA GGT CGC GAG AAA       384
Tyr His Leu Tyr Asp Lys Asp Ile Val Pro Phe Glu Gly Arg Glu Lys
        115                 120                 125

AAT GAT GCC CTA GTA AAC TTG TTT AAA TCA CAT GGT TAC GAG CAT CAT       432
Asn Asp Ala Leu Val Asn Leu Phe Lys Ser His Gly Tyr Glu His His
130                 135                 140

GGC TTT ACA ACT GAG TAT GAT ACA TCG AGC CAA GTA CGA TGG ATG GGC       480
Gly Phe Thr Thr Glu Tyr Asp Thr Ser Ser Gln Val Arg Trp Met Gly
145                 150                 155                 160

GTA TTA AAC CTT GAA GGT AAA ACA CCC GAA ACA TTG AAA AAG ACA TTT       528
Val Leu Asn Leu Glu Gly Lys Thr Pro Glu Thr Leu Lys Lys Thr Phe
                165                 170                 175

GAT AGT CAA CGT AAA CGT AAT ATT AAT AAA GCG ATA AAC TAT GGT GTT       576
Asp Ser Gln Arg Lys Arg Asn Ile Asn Lys Ala Ile Asn Tyr Gly Val
            180                 185                 190

AAA GTC AGA TTC CTT GAA CGT GAT GAG TTC AAT CTT TTC TTA GAT TTA       624
Lys Val Arg Phe Leu Glu Arg Asp Glu Phe Asn Leu Phe Leu Asp Leu
        195                 200                 205

TAT CGT GAA ACT GAA GAG CGT GCT GGA TTT GTA TCA AAA ACA GAT GAT       672
```

```
                                                            -continued

Tyr Arg Glu Thr Glu Arg Ala Gly Phe Val Ser Lys Thr Asp Asp
    210                 215                 220

TAT TTT TAT AAC TTT ATT GAC ACA TAT GGA GAT AAA GTA TTA GTA CCA        720
Tyr Phe Tyr Asn Phe Ile Asp Thr Tyr Gly Asp Lys Val Leu Val Pro
225                 230                 235                 240

TTA GCA TAT ATT GAC CTT GAT GAA TAT GTG TTA AAG TTG CAA CAG GAA        768
Leu Ala Tyr Ile Asp Leu Asp Glu Tyr Val Leu Lys Leu Gln Gln Glu
                245                 250                 255

TTG AAT GAC AAA GAA AAT CGT CGT GAT CAA ATG ATG GCG AAA GAA AAC        816
Leu Asn Asp Lys Glu Asn Arg Arg Asp Gln Met Met Ala Lys Glu Asn
            260                 265                 270

AAA TCA GAT AAG CAA ATG AAG AAA ATT GCA GAA TTA GAT AAG CAA ATT        864
Lys Ser Asp Lys Gln Met Lys Lys Ile Ala Glu Leu Asp Lys Gln Ile
        275                 280                 285

GAT CAT GAT CAG CAT GAA TTA TTG AAT GCA AGT GAA TTG AGC AAA ACG        912
Asp His Asp Gln His Glu Leu Leu Asn Ala Ser Glu Leu Ser Lys Thr
    290                 295                 300

GAC GGC CCA ATT CTA AAC CTT GCT TCT GGC GTT TAT TTT GCA AAT GCA        960
Asp Gly Pro Ile Leu Asn Leu Ala Ser Gly Val Tyr Phe Ala Asn Ala
305                 310                 315                 320

TAT GAA GTG AAT TAT TTC TCT GGT GGT TCA TCA GAA AAA TAT AAT CAA       1008
Tyr Glu Val Asn Tyr Phe Ser Gly Gly Ser Ser Glu Lys Tyr Asn Gln
                325                 330                 335

TTT ATG GGA CCA TAC ATG ATG CAT TGG TTT ATG ATT AAC TAT TGC TTC       1056
Phe Met Gly Pro Tyr Met Met His Trp Phe Met Ile Asn Tyr Cys Phe
            340                 345                 350

GAT AAT GGC TAT GAT CGT TAT AAT TTC TAT GGT TTA TCA GGT GAT TTT       1104
Asp Asn Gly Tyr Asp Arg Tyr Asn Phe Tyr Gly Leu Ser Gly Asp Phe
        355                 360                 365

ACG GAA AAC AGT GAA GAT TAT GGC GTA TAC CGC TTT AAA CGT GGA TTT       1152
Thr Glu Asn Ser Glu Asp Tyr Gly Val Tyr Arg Phe Lys Arg Gly Phe
    370                 375                 380

AAT GTA CAA ATC GAA GAA TTA ATA GGG GAT TTC TAT AAA CCA ATT CAT       1200
Asn Val Gln Ile Glu Glu Leu Ile Gly Asp Phe Tyr Lys Pro Ile His
385                 390                 395                 400

AAA GTG AAA TAT TGG TTG TTC ACA ACA TTG GAT AAA TTA CGT AAA AAA       1248
Lys Val Lys Tyr Trp Leu Phe Thr Thr Leu Asp Lys Leu Arg Lys Lys
                405                 410                 415

TTA AAG AAA TAG                                                       1260
Leu Lys Lys (2) INFORMATION FOR SEQ ID NO:7:

(i) SEQUENCE CHARACTERISTICS:
        (A) LENGTH: 419 amino acids
        (B) TYPE: amino acid
        (D) TOPOLOGY: linear (ii) MOLECULE TYPE: protein (xi) SEQUENCE DESCRIPTION: SEQ ID NO:7:

Met Lys Phe Thr Glu Leu Thr Val Thr Glu Phe Asp Asn Phe Val Gln
1               5                   10                  15

Asn Pro Ser Leu Glu Ser His Tyr Phe Gln Val Lys Glu Asn Ile Val
                20                  25                  30

Thr Arg Glu Asn Asp Gly Phe Glu Val Val Leu Leu Gly Ile Lys Asp
            35                  40                  45

Asp Asn Asn Lys Val Ile Ala Ala Ser Leu Phe Ser Lys Ile Pro Thr
        50                  55                  60

Met Gly Ser Tyr Val Tyr Tyr Ser Asn Arg Gly Pro Val Met Asp Phe
```

```
                65                  70                  75                  80
Ser Asp Leu Gly Leu Val Asp Tyr Tyr Leu Lys Glu Leu Asp Lys Tyr
                        85                  90                  95

Leu Gln Gln His Gln Cys Leu Tyr Val Lys Leu Asp Pro Tyr Trp Leu
                100                 105                 110

Tyr His Leu Tyr Asp Lys Asp Ile Val Pro Phe Glu Gly Arg Glu Lys
                115                 120                 125

Asn Asp Ala Leu Val Asn Leu Phe Lys Ser His Gly Tyr Glu His His
            130                 135                 140

Gly Phe Thr Thr Glu Tyr Asp Thr Ser Ser Gln Val Arg Trp Met Gly
145                 150                 155                 160

Val Leu Asn Leu Glu Gly Lys Thr Pro Glu Thr Leu Lys Lys Thr Phe
                165                 170                 175

Asp Ser Gln Arg Lys Arg Asn Ile Asn Lys Ala Ile Asn Tyr Gly Val
                180                 185                 190

Lys Val Arg Phe Leu Glu Arg Asp Glu Phe Asn Leu Phe Leu Asp Leu
                195                 200                 205

Tyr Arg Glu Thr Glu Arg Ala Gly Phe Val Ser Lys Thr Asp Asp
            210                 215                 220

Tyr Phe Tyr Asn Phe Ile Asp Thr Tyr Gly Asp Lys Val Leu Val Pro
225                 230                 235                 240

Leu Ala Tyr Ile Asp Leu Asp Glu Tyr Val Leu Lys Leu Gln Gln Glu
                245                 250                 255

Leu Asn Asp Lys Glu Asn Arg Arg Asp Gln Met Met Ala Lys Glu Asn
                260                 265                 270

Lys Ser Asp Lys Gln Met Lys Lys Ile Ala Glu Leu Asp Lys Gln Ile
                275                 280                 285

Asp His Asp Gln His Glu Leu Leu Asn Ala Ser Glu Leu Ser Lys Thr
            290                 295                 300

Asp Gly Pro Ile Leu Asn Leu Ala Ser Gly Val Tyr Phe Ala Asn Ala
305                 310                 315                 320

Tyr Glu Val Asn Tyr Phe Ser Gly Gly Ser Ser Glu Lys Tyr Asn Gln
                325                 330                 335

Phe Met Gly Pro Tyr Met Met His Trp Phe Met Ile Asn Tyr Cys Phe
                340                 345                 350

Asp Asn Gly Tyr Asp Arg Tyr Asn Phe Tyr Gly Leu Ser Gly Asp Phe
                355                 360                 365

Thr Glu Asn Ser Glu Asp Tyr Gly Val Tyr Arg Phe Lys Arg Gly Phe
            370                 375                 380

Asn Val Gln Ile Glu Glu Leu Ile Gly Asp Phe Tyr Lys Pro Ile His
385                 390                 395                 400

Lys Val Lys Tyr Trp Leu Phe Thr Thr Leu Asp Lys Leu Arg Lys Lys
                405                 410                 415

Leu Lys Lys
```

(2) INFORMATION FOR SEQ ID NO:8:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic)
           (p4c15/p6c63); Unknown = Xaa"

(ix) FEATURE:
    (A) NAME/KEY: CDS
    (B) LOCATION: 1..417

(ix) FEATURE:
    (A) NAME/KEY: CDS
    (B) LOCATION: 524..730

(xi) SEQUENCE DESCRIPTION: SEQ ID NO:8:

```
ATG GAA TTC ACT TAT TCG TAT TTA TTT AGA ATG ATT AGT CAT GAG ATG        48
Met Glu Phe Thr Tyr Ser Tyr Leu Phe Arg Met Ile Ser His Glu Met
 1               5                  10                  15

AAA CAA AAG GCT GAT CAA AAG TTA GAG CAA TTT GAT ATT ACA AAT GAG        96
Lys Gln Lys Ala Asp Gln Lys Leu Glu Gln Phe Asp Ile Thr Asn Glu
             20                  25                  30

CAA GGT CAT ACG TTA GGT TAT CTT TAT GCA CAT CAA CAA GAT GGA CTG       144
Gln Gly His Thr Leu Gly Tyr Leu Tyr Ala His Gln Gln Asp Gly Leu
         35                  40                  45

ACA CAA AAT GAT ATT GCT AAA GCA TTA CAA CGA ACA GGT CCA ACT GTC       192
Thr Gln Asn Asp Ile Ala Lys Ala Leu Gln Arg Thr Gly Pro Thr Val
     50                  55                  60

AGT AAT TTA TTA AGG AAC CTT GAA CGT AAA AAG CTG ATC TAT CGC TAT       240
Ser Asn Leu Leu Arg Asn Leu Glu Arg Lys Lys Leu Ile Tyr Arg Tyr
 65                  70                  75                  80

GTC GAT GCA CAA GAT ACG AGA AGA AAG AAT ATA GGG CTG ACT ACC TCT       288
Val Asp Ala Gln Asp Thr Arg Arg Lys Asn Ile Gly Leu Thr Thr Ser
                 85                  90                  95

GGG ATT AAA CTC GTA GAA GCA TTC ACT TCG ATA TTT GAT GAA ATG GAA       336
Gly Ile Lys Leu Val Glu Ala Phe Thr Ser Ile Phe Asp Glu Met Glu
            100                 105                 110

CAA ACA CTC GTA TCG CAG TTA TCT GAA GAA GAA AAT GAA CAA ATG AAA       384
Gln Thr Leu Val Ser Gln Leu Ser Glu Glu Glu Asn Glu Gln Met Lys
        115                 120                 125

GCA AAC TTA ACT AAA ATG TTA TCT AGT TTA CAA TAAATGATAA GTGTGACTGG     437
Ala Asn Leu Thr Lys Met Leu Ser Ser Leu Gln
    130                 135

TAGAAATCAG TCACTTTGTC TTTAATATTA TAGTTAGATA TCTAATTGTT AGTAAGCTAA     497

TTATTGGAAA AGACAAGGAG TATTGA ACA ATG AAA GAC GAA CAA TTA TAT TAT      550
                             Thr Met Lys Asp Glu Gln Leu Tyr Tyr
                              1               5

TTT GAG AAA TCG CCA GTA TTT AAA GCG ATG ATG CAT TTC TCA TTG CCA       598
Phe Glu Lys Ser Pro Val Phe Lys Ala Met Met His Phe Ser Leu Pro
 10              15                  20                  25

ATG ATG ATA GGG ACT TTA TTA AGC GTT ATT TAT GGC ATA TTA AAT ATT       646
Met Met Ile Gly Thr Leu Leu Ser Val Ile Tyr Gly Ile Leu Asn Ile
                 30                  35                  40

TAC TTT ATA GGA TTT TYA GAM GAY AGC CAC ATG ATT TCT GCT AAT CTC       694
Tyr Phe Ile Gly Phe Xaa Xaa Asp Ser His Met Ile Ser Ala Asn Leu
             45                  50                  55

TCT AAC ACT GCC AGT ATT TGC TAT CTT AAT GGG GTT A                     731
Ser Asn Thr Ala Ser Ile Cys Tyr Leu Asn Gly Val
         60                  65
```

(2) INFORMATION FOR SEQ ID NO:9:

(i) SEQUENCE CHARACTERISTICS:
       (A) LENGTH: 139 amino acids
       (B) TYPE: amino acid
       (D) TOPOLOGY: linear (ii) MOLECULE TYPE: protein (xi) SEQUENCE DESCRIPTION: SEQ ID NO:9:

```
Met Glu Phe Thr Tyr Ser Tyr Leu Phe Arg Met Ile Ser His Glu Met
 1               5                  10                  15

Lys Gln Lys Ala Asp Gln Lys Leu Glu Gln Phe Asp Ile Thr Asn Glu
                20                  25                  30

Gln Gly His Thr Leu Gly Tyr Leu Tyr Ala His Gln Gln Asp Gly Leu
            35                  40                  45

Thr Gln Asn Asp Ile Ala Lys Ala Leu Gln Arg Thr Gly Pro Thr Val
        50                  55                  60

Ser Asn Leu Leu Arg Asn Leu Glu Arg Lys Lys Leu Ile Tyr Arg Tyr
 65                  70                  75                  80

Val Asp Ala Gln Asp Thr Arg Arg Lys Asn Ile Gly Leu Thr Thr Ser
                85                  90                  95

Gly Ile Lys Leu Val Glu Ala Phe Thr Ser Ile Phe Asp Glu Met Glu
            100                 105                 110

Gln Thr Leu Val Ser Gln Leu Ser Glu Glu Asn Glu Gln Met Lys
        115                 120                 125

Ala Asn Leu Thr Lys Met Leu Ser Ser Leu Gln
        130                 135
```

(2) INFORMATION FOR SEQ ID NO:10:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO:10:

```
Thr Met Lys Asp Glu Gln Leu Tyr Tyr Phe Glu Lys Ser Pro Val Phe
 1               5                  10                  15

Lys Ala Met Met His Phe Ser Leu Pro Met Met Ile Gly Thr Leu Leu
                20                  25                  30

Ser Val Ile Tyr Gly Ile Leu Asn Ile Tyr Phe Ile Gly Phe Xaa Xaa
            35                  40                  45

Asp Ser His Met Ile Ser Ala Asn Leu Ser Asn Thr Ala Ser Ile Cys
     50                  55                  60

Tyr Leu Asn Gly Val
 65
```

(2) INFORMATION FOR SEQ ID NO:11:

(i) SEQUENCE CHARACTERISTICS:
        (A) LENGTH: 828 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p5c4)"

(ix) FEATURE:
        (A) NAME/KEY: CDS
        (B) LOCATION: 1..825

(xi) SEQUENCE DESCRIPTION: SEQ ID NO:11:

```
GTG AGG TAC TTG CCT GTG AAT GCG ATT GAA ATC CCG ACT ACC GCC GGC      48
Val Arg Tyr Leu Pro Val Asn Ala Ile Glu Ile Pro Thr Thr Ala Gly
 1               5                  10                  15

ACG CCT GAC GCG CCC TTC TAC CAA CCG TTG GGC AAT GAA GAG CAG CTG      96
```

```
Thr Pro Asp Ala Pro Phe Tyr Gln Pro Leu Gly Asn Glu Glu Gln Leu
             20                  25                  30

TTC CAG CAG GCC TGG CAG CAC GGC ATG CCC GTG CTT ATC AAG GGC CCG      144
Phe Gln Gln Ala Trp Gln His Gly Met Pro Val Leu Ile Lys Gly Pro
         35                  40                  45

ACC GGC TGC GGC AAG ACC CGT TTC GTA CAG CAC ATG GCG CAT CGC CTG      192
Thr Gly Cys Gly Lys Thr Arg Phe Val Gln His Met Ala His Arg Leu
 50                  55                  60

AAT CTG CCG CTG TAC ACC GTG GCC TGC CAT GAC GAC CTG TCG GCG GCC      240
Asn Leu Pro Leu Tyr Thr Val Ala Cys His Asp Asp Leu Ser Ala Ala
 65                  70                  75                  80

GAC CTG GTC GGC CGA CAC CTG ATC GGC GCA CAG GGC ACC TGG TGG CAG      288
Asp Leu Val Gly Arg His Leu Ile Gly Ala Gln Gly Thr Trp Trp Gln
                 85                  90                  95

GAC GGT CCG CTG ACC CGC GCG GTC CGC GAA GGA GGC ATC TGC TAC CTG      336
Asp Gly Pro Leu Thr Arg Ala Val Arg Glu Gly Gly Ile Cys Tyr Leu
            100                 105                 110

GAC GAA GTG GTG GAA GCA CGG CAG GAC ACC GCC GTG GTA CTG CAC CCG      384
Asp Glu Val Val Glu Ala Arg Gln Asp Thr Ala Val Val Leu His Pro
            115                 120                 125

CTG GCC GAT GAT CGC CGC GAA CTG TTC ATC GAG CGC ACC GGC GAG GCG      432
Leu Ala Asp Asp Arg Arg Glu Leu Phe Ile Glu Arg Thr Gly Glu Ala
130                 135                 140

CTC AAG GCG CCG CCG GGC TTC ATG CTG GTG GTG TCC TAC AAC CCC GGT      480
Leu Lys Ala Pro Pro Gly Phe Met Leu Val Val Ser Tyr Asn Pro Gly
145                 150                 155                 160

TAC CAA AAC CTG CTC AAG GGC ATG AAG CCC AGC ACC CGC CAG CGC TTC      528
Tyr Gln Asn Leu Leu Lys Gly Met Lys Pro Ser Thr Arg Gln Arg Phe
                165                 170                 175

GTG GCG ATG CGC TTC GAC TAT CCG CCG ACC GCC GAG GAA GAG CGC ATC      576
Val Ala Met Arg Phe Asp Tyr Pro Pro Thr Ala Glu Glu Glu Arg Ile
            180                 185                 190

GTC GCC AAC GAG GCG CAG GTC GAT GCC GCG CTC GCC GCC CAG GTG GTC      624
Val Ala Asn Glu Ala Gln Val Asp Ala Ala Leu Ala Ala Gln Val Val
            195                 200                 205

AAG CTT GGC CAG GCA CTG CGT CGG CTG GAA CAG CAC GAT CTG GAG GAA      672
Lys Leu Gly Gln Ala Leu Arg Arg Leu Glu Gln His Asp Leu Glu Glu
            210                 215                 220

GTC GCC TCG ACC CGC CTG CTG ATC TTC ACC GCA CGC ATG ATC CGC TCC      720
Val Ala Ser Thr Arg Leu Leu Ile Phe Thr Ala Arg Met Ile Arg Ser
225                 230                 235                 240

GGC ATG ACG CCG CGG CAG GCC TGC CTG GCC TGC CTC GCC GAA CCG CTG      768
Gly Met Thr Pro Arg Gln Ala Cys Leu Ala Cys Leu Ala Glu Pro Leu
                245                 250                 255

TCG GAT GAT CCG CAG ACC GTT GCC GCG CTG ATG GAT GTG GTC TAT GTC      816
Ser Asp Asp Pro Gln Thr Val Ala Ala Leu Met Asp Val Val Tyr Val
            260                 265                 270

CAC TTC GGC TGA                                                      828
His Phe Gly
        275

(2) INFORMATION FOR SEQ ID NO:12:

(i) SEQUENCE CHARACTERISTICS:
        (A) LENGTH: 275 amino acids
        (B) TYPE: amino acid
        (D) TOPOLOGY: linear (ii) MOLECULE TYPE: protein (xi) SEQUENCE DESCRIPTION: SEQ ID NO:12:
```

```
Val Arg Tyr Leu Pro Val Asn Ala Ile Glu Ile Pro Thr Thr Ala Gly
 1               5                  10                  15

Thr Pro Asp Ala Pro Phe Tyr Gln Pro Leu Gly Asn Glu Glu Gln Leu
             20                  25                  30

Phe Gln Gln Ala Trp Gln His Gly Met Pro Val Leu Ile Lys Gly Pro
         35                  40                  45

Thr Gly Cys Gly Lys Thr Arg Phe Val Gln His Met Ala His Arg Leu
     50                  55                  60

Asn Leu Pro Leu Tyr Thr Val Ala Cys His Asp Asp Leu Ser Ala Ala
 65                  70                  75                  80

Asp Leu Val Gly Arg His Leu Ile Gly Ala Gln Gly Thr Trp Trp Gln
                 85                  90                  95

Asp Gly Pro Leu Thr Arg Ala Val Arg Glu Gly Gly Ile Cys Tyr Leu
             100                 105                 110

Asp Glu Val Val Glu Ala Arg Gln Asp Thr Ala Val Val Leu His Pro
         115                 120                 125

Leu Ala Asp Asp Arg Arg Glu Leu Phe Ile Glu Arg Thr Gly Glu Ala
     130                 135                 140

Leu Lys Ala Pro Pro Gly Phe Met Leu Val Val Ser Tyr Asn Pro Gly
145                 150                 155                 160

Tyr Gln Asn Leu Leu Lys Gly Met Lys Pro Ser Thr Arg Gln Arg Phe
                 165                 170                 175

Val Ala Met Arg Phe Asp Tyr Pro Pro Thr Ala Glu Glu Arg Ile
             180                 185                 190

Val Ala Asn Glu Ala Gln Val Asp Ala Ala Leu Ala Ala Gln Val Val
         195                 200                 205

Lys Leu Gly Gln Ala Leu Arg Arg Leu Glu Gln His Asp Leu Glu Glu
    210                 215                 220

Val Ala Ser Thr Arg Leu Leu Ile Phe Thr Ala Arg Met Ile Arg Ser
225                 230                 235                 240

Gly Met Thr Pro Arg Gln Ala Cys Leu Ala Cys Leu Ala Glu Pro Leu
                245                 250                 255

Ser Asp Asp Pro Gln Thr Val Ala Ala Leu Met Asp Val Val Tyr Val
            260                 265                 270

His Phe Gly
        275

(2) INFORMATION FOR SEQ ID NO:13:

(i) SEQUENCE CHARACTERISTICS:
        (A) LENGTH: 528 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA (genomic) (p9b66)"
             Unknown = Xaa (ix) FEATURE:
         (A) NAME/KEY: CDS
         (B) LOCATION: 1..525

(xi) SEQUENCE DESCRIPTION: SEQ ID NO:13:

ATG GAA AGG ATG TCA AAA ATG AAT ATT AAT ACA GCT TAT TTT GCC GGA      48
Met Glu Arg Met Ser Lys Met Asn Ile Asn Thr Ala Tyr Phe Ala Gly
 1               5                  10                  15

GGT TGC TTT TGG TGT ATG ACG AAA CCA TTT GAC ACC TTT GAC GGC ATA      96
Gly Cys Phe Trp Cys Met Thr Lys Pro Phe Asp Thr Phe Asp Gly Ile
```

```
            20                  25                  30
GAA AAA GTA ACT TCT GGA TAT ATG GGC GGA CAT ATT GAA AAT CCT ACT    144
Glu Lys Val Thr Ser Gly Tyr Met Gly Gly His Ile Glu Asn Pro Thr
            35                  40                  45

TAC GAA CAA GTA AAA TCA GGT ACG AGT GGT CAT TTA GAA ACT GTT GAA    192
Tyr Glu Gln Val Lys Ser Gly Thr Ser Gly His Leu Glu Thr Val Glu
        50                  55                  60

ATT CAA TAT GAT GTT GCA TTA TTC TCA TAC AAT AAG TTA TTA GAA ATA    240
Ile Gln Tyr Asp Val Ala Leu Phe Ser Tyr Asn Lys Leu Leu Glu Ile
65                  70                  75                  80

TTT TTC TCA GTC ATT GAC CCA TTA GAT ACA GGT GGT CAA TAT CAA GAC    288
Phe Phe Ser Val Ile Asp Pro Leu Asp Thr Gly Gly Gln Tyr Gln Asp
                85                  90                  95

CGT GGT CCT CAA TAT nAA ACA GCT ATT TTC TAC ACT AAT GAT CAT CAA    336
Arg Gly Pro Gln Tyr Xaa Thr Ala Ile Phe Tyr Thr Asn Asp His Gln
            100                 105                 110

AAA GAA CTC GCT GAG ACT TAT ATC GAG CAG CTT AAA AAT ACG ATT AAT    384
Lys Glu Leu Ala Glu Thr Tyr Ile Glu Gln Leu Lys Asn Thr Ile Asn
            115                 120                 125

GCT GAT AAG GCA ATT GCA ACA AAA ATA yTA CCA GCG TCA CAA TTT TAC    432
Ala Asp Lys Ala Ile Ala Thr Lys Ile Leu Pro Ala Ser Gln Phe Tyr
        130                 135                 140

AAA GCC GAA GAC TAT CAC CAA GAT TTT TAT AAG AAA AAT CCA GAG CGC    480
Lys Ala Glu Asp Tyr His Gln Asp Phe Tyr Lys Lys Asn Pro Glu Arg
145                 150                 155                 160

TAT GCA GAA GAA CAA AAA ATA CGC CAA GAA TAC AAA AAT AAG CAA        525
Tyr Ala Glu Glu Gln Lys Ile Arg Gln Glu Tyr Lys Asn Lys Gln
                165                 170                 175

TAA                                                                528
```

(2) INFORMATION FOR SEQ ID NO:14:

(i) SEQUENCE CHARACTERISTICS:
        (A) LENGTH: 175 amino acids
        (B) TYPE: amino acid
        (D) TOPOLOGY: linear (ii) MOLECULE TYPE: protein (xi) SEQUENCE DESCRIPTION: SEQ ID NO:14:

```
Met Glu Arg Met Ser Lys Met Asn Ile Asn Thr Ala Tyr Phe Ala Gly
1               5                   10                  15

Gly Cys Phe Trp Cys Met Thr Lys Pro Phe Asp Thr Phe Asp Gly Ile
            20                  25                  30

Glu Lys Val Thr Ser Gly Tyr Met Gly Gly His Ile Glu Asn Pro Thr
            35                  40                  45

Tyr Glu Gln Val Lys Ser Gly Thr Ser Gly His Leu Glu Thr Val Glu
        50                  55                  60

Ile Gln Tyr Asp Val Ala Leu Phe Ser Tyr Asn Lys Leu Leu Glu Ile
65                  70                  75                  80

Phe Phe Ser Val Ile Asp Pro Leu Asp Thr Gly Gly Gln Tyr Gln Asp
                85                  90                  95

Arg Gly Pro Gln Tyr Xaa Thr Ala Ile Phe Tyr Thr Asn Asp His Gln
            100                 105                 110

Lys Glu Leu Ala Glu Thr Tyr Ile Glu Gln Leu Lys Asn Thr Ile Asn
            115                 120                 125

Ala Asp Lys Ala Ile Ala Thr Lys Ile Leu Pro Ala Ser Gln Phe Tyr
        130                 135                 140
```

```
Lys Ala Glu Asp Tyr His Gln Asp Phe Tyr Lys Lys Asn Pro Glu Arg
145                 150                 155                 160

Tyr Ala Glu Glu Gln Lys Ile Arg Gln Glu Tyr Lys Asn Lys Gln
                165                 170                 175

(2) INFORMATION FOR SEQ ID NO:15:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p7c26)"

(ix) FEATURE:
        (A) NAME/KEY: CDS
        (B) LOCATION: 1..699

(xi) SEQUENCE DESCRIPTION: SEQ ID NO:15:

ATG ATT GAG TTA AAA CAT GTG ACT TTT GGT TAT AAT AAA AAG CAG ATG      48
Met Ile Glu Leu Lys His Val Thr Phe Gly Tyr Asn Lys Lys Gln Met
 1               5                  10                  15

GTG CTA CAA GAT ATC AAT ATT ACT ATA CCT GAT GGA GAA AAT GTT GGT      96
Val Leu Gln Asp Ile Asn Ile Thr Ile Pro Asp Gly Glu Asn Val Gly
                20                  25                  30

ATT TTA GGC GAA AGT GGC TGT GGT AAA AGT ACG CTC GCT TCA TTG GTT     144
Ile Leu Gly Glu Ser Gly Cys Gly Lys Ser Thr Leu Ala Ser Leu Val
            35                  40                  45

CTT GGC TTG TTT AAA CCT GTT AAA GGA GAG ATT TAC TTA AGT GAC AAT     192
Leu Gly Leu Phe Lys Pro Val Lys Gly Glu Ile Tyr Leu Ser Asp Asn
 50                  55                  60

GCT GTG TTA CCG ATT TTC CAA CAC CCT TTA ACT AGC TTT AAC CCT GAT     240
Ala Val Leu Pro Ile Phe Gln His Pro Leu Thr Ser Phe Asn Pro Asp
 65                  70                  75                  80

TGG ACG ATT GAG ACC TCA TTA AAA GAA GCG TTA TAT TAT TAC AGA GGT     288
Trp Thr Ile Glu Thr Ser Leu Lys Glu Ala Leu Tyr Tyr Tyr Arg Gly
                85                  90                  95

CTA ACT GAT AAT ACT GCT CAG GAT CAA TTA TTA TTA CAA CAT TTA TCT     336
Leu Thr Asp Asn Thr Ala Gln Asp Gln Leu Leu Leu Gln His Leu Ser
            100                 105                 110

ACT TTT GAG TTA AAC GCG CAA TTA TTG ACT AAA TTA CCA AGC GAA GTG     384
Thr Phe Glu Leu Asn Ala Gln Leu Leu Thr Lys Leu Pro Ser Glu Val
        115                 120                 125

AGT GGC GGA CAA TTA CAA AGA TTT AAT GTC ATG CGT TCG TTA TTA GCA     432
Ser Gly Gly Gln Leu Gln Arg Phe Asn Val Met Arg Ser Leu Leu Ala
130                 135                 140

CAG CCT CGC GTT TTA ATA TGT GAT GAG ATA ACT TCA AAT TTA GAT GTT     480
Gln Pro Arg Val Leu Ile Cys Asp Glu Ile Thr Ser Asn Leu Asp Val
145                 150                 155                 160

ATA GCT GAA CAA AAT GTA ATC AAT ATA TTA AAA GCG CAA ACG ATT ACG     528
Ile Ala Glu Gln Asn Val Ile Asn Ile Leu Lys Ala Gln Thr Ile Thr
                165                 170                 175

AAC TTA AAT CAT TTT ATC GTT ATT TCT CAT GAT TTA TCC GTG TTA CAA     576
Asn Leu Asn His Phe Ile Val Ile Ser His Asp Leu Ser Val Leu Gln
            180                 185                 190

CGC TTA GTT AAT AGA ATT ATC GTT CTT AAG GAT GGC ATG ATA GTC GAT     624
Arg Leu Val Asn Arg Ile Ile Val Leu Lys Asp Gly Met Ile Val Asp
        195                 200                 205

GAT TTT GCA ATA GAG GAA TTA TTT AAT GTT GAT AGA CAC CCT TAT ACA     672
Asp Phe Ala Ile Glu Glu Leu Phe Asn Val Asp Arg His Pro Tyr Thr
210                 215                 220
```

```
AAA GAA TTA GTG CAA GCA TTT TCA TAT TAG                                          702
Lys Glu Leu Val Gln Ala Phe Ser Tyr
225             230
```

(2) INFORMATION FOR SEQ ID NO:16:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO:16:

```
Met Ile Glu Leu Lys His Val Thr Phe Gly Tyr Asn Lys Lys Gln Met
 1               5                  10                  15

Val Leu Gln Asp Ile Asn Ile Thr Ile Pro Asp Gly Glu Asn Val Gly
             20                  25                  30

Ile Leu Gly Glu Ser Gly Cys Gly Lys Ser Thr Leu Ala Ser Leu Val
         35                  40                  45

Leu Gly Leu Phe Lys Pro Val Lys Gly Glu Ile Tyr Leu Ser Asp Asn
     50                  55                  60

Ala Val Leu Pro Ile Phe Gln His Pro Leu Thr Ser Phe Asn Pro Asp
65                  70                  75                  80

Trp Thr Ile Glu Thr Ser Leu Lys Glu Ala Leu Tyr Tyr Tyr Arg Gly
                 85                  90                  95

Leu Thr Asp Asn Thr Ala Gln Asp Gln Leu Leu Leu Gln His Leu Ser
            100                 105                 110

Thr Phe Glu Leu Asn Ala Gln Leu Leu Thr Lys Leu Pro Ser Glu Val
        115                 120                 125

Ser Gly Gly Gln Leu Gln Arg Phe Asn Val Met Arg Ser Leu Leu Ala
    130                 135                 140

Gln Pro Arg Val Leu Ile Cys Asp Glu Ile Thr Ser Asn Leu Asp Val
145                 150                 155                 160

Ile Ala Glu Gln Asn Val Ile Asn Ile Leu Lys Ala Gln Thr Ile Thr
                165                 170                 175

Asn Leu Asn His Phe Ile Val Ile Ser His Asp Leu Ser Val Leu Gln
            180                 185                 190

Arg Leu Val Asn Arg Ile Ile Val Leu Lys Asp Gly Met Ile Val Asp
        195                 200                 205

Asp Phe Ala Ile Glu Glu Leu Phe Asn Val Asp Arg His Pro Tyr Thr
    210                 215                 220

Lys Glu Leu Val Gln Ala Phe Ser Tyr
225                 230
```

(2) INFORMATION FOR SEQ ID NO:17:

(i) SEQUENCE CHARACTERISTICS:
        (A) LENGTH: 1471 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p10c15)"

(ix) FEATURE:
        (A) NAME/KEY: CDS
        (B) LOCATION: 1..774

(xi) SEQUENCE DESCRIPTION: SEQ ID NO:17:

```
ATG ATG AGT CTC ATT GAT ATA CAA AAT TTA ACA ATA AAG AAT ACT AGT         48
Met Met Ser Leu Ile Asp Ile Gln Asn Leu Thr Ile Lys Asn Thr Ser
 1               5                  10                  15

GAG AAA TCT CTT ATT AAA GGG ATT GAT TTG AAA ATT TTT AGT CAA CAG         96
Glu Lys Ser Leu Ile Lys Gly Ile Asp Leu Lys Ile Phe Ser Gln Gln
             20                  25                  30

ATT AAT GCC TTG ATT GGA GAG AGC GGC GCT GGA AAA AGT TTG ATT GCT        144
Ile Asn Ala Leu Ile Gly Glu Ser Gly Ala Gly Lys Ser Leu Ile Ala
         35                  40                  45

AAA GCT TTA CTT GAA TAT TTA CCA TTT GAT TTA AGC TGC ACG TAT GAT        192
Lys Ala Leu Leu Glu Tyr Leu Pro Phe Asp Leu Ser Cys Thr Tyr Asp
     50                  55                  60

TCG TAC CAA TTT GAT GGG GAA AAT GTT AGT AGA TTG AGT CAA TAT TAT        240
Ser Tyr Gln Phe Asp Gly Glu Asn Val Ser Arg Leu Ser Gln Tyr Tyr
 65                  70                  75                  80

GGT CAT ACA ATT GGC TAT ATT TCT CAA AAT TAT GCA GAA AGT TTT AAC        288
Gly His Thr Ile Gly Tyr Ile Ser Gln Asn Tyr Ala Glu Ser Phe Asn
                 85                  90                  95

GAC CAT ACT AAA TTA GGT AAA CAG TTA ACT GCG ATT TAT CGT AAG CAT        336
Asp His Thr Lys Leu Gly Lys Gln Leu Thr Ala Ile Tyr Arg Lys His
             100                 105                 110

TAT AAA GGT AGT AAA GAA GAG GCT TTG TCC AAA GTT GAT AAG GCT TTG        384
Tyr Lys Gly Ser Lys Glu Glu Ala Leu Ser Lys Val Asp Lys Ala Leu
         115                 120                 125

TCG TGG GTT AAT TTA CAA AGC AAA GAT ATA TTA AAT AAA TAT AGT TTC        432
Ser Trp Val Asn Leu Gln Ser Lys Asp Ile Leu Asn Lys Tyr Ser Phe
     130                 135                 140

CAA CTT TCT GGG GGC CAA CTT GAA CGC GTA TAC ATA GCA AGC GTT CTC        480
Gln Leu Ser Gly Gly Gln Leu Glu Arg Val Tyr Ile Ala Ser Val Leu
145                 150                 155                 160

ATG TTG GAG CCT AAA TTA ATC ATT GCA GAC GAA CCA GTT GCA TCA TTG        528
Met Leu Glu Pro Lys Leu Ile Ile Ala Asp Glu Pro Val Ala Ser Leu
                 165                 170                 175

GAT GCT TTG AAC GGT AAT CAA GTG ATG GAT TTA TTA CAG CAT ATT GTA        576
Asp Ala Leu Asn Gly Asn Gln Val Met Asp Leu Leu Gln His Ile Val
             180                 185                 190

TTA GAA CAT GGT CAA ACA TTA TTT ATT ATC ACA CAT AAC TTA AGT CAT        624
Leu Glu His Gly Gln Thr Leu Phe Ile Ile Thr His Asn Leu Ser His
         195                 200                 205

GTA TTG AAA TAT TGT CAG TAC ATT TAT GTT TTA AAA GAA GGT CAA ATC        672
Val Leu Lys Tyr Cys Gln Tyr Ile Tyr Val Leu Lys Glu Gly Gln Ile
     210                 215                 220

ATT GAA CGA GGT AAT ATT AAT CAT TTC AAG TAT GAG CAT TTG CAT CCG        720
Ile Glu Arg Gly Asn Ile Asn His Phe Lys Tyr Glu His Leu His Pro
225                 230                 235                 240

TAT ACT GAA CGT CTA ATT AAA TAT AGA ACA CAA TTA AAG AGG GAT TAC        768
Tyr Thr Glu Arg Leu Ile Lys Tyr Arg Thr Gln Leu Lys Arg Asp Tyr
                 245                 250                 255

TAT GAT TGAGTTAAAA CATGTGACTT TGGTTATAA TAAAAAGCAG ATGGTGCTAC          824
Tyr Asp

AAGATATCAA TATTACTATA CCTGATGGAG AAAATGTTGG TATTTTAGGC GAAAGTGGCT      884

GTGGTAAAAG TACGCTCGCT TCATTGGTTC TTGGCTTGTT TAAACCTGTT AAAGGAGAGA      944

TTTACTTAAG TGACAATGCT GTGTTACCGA TTTTCCAACA CCCTTTAACT AGCTTTAACC     1004

CTGATTGGAC GATTGAGACC TCATTAAAAG AAGCGTTATA TTATTACAGA GGTCTAACTG     1064

ATAATACTGC TCAGGATCAA TTATTATTAC AACATTTATC TACTTTTGAG TTAAACGCGC     1124

AATTATTGAC TAAATTACCA AGCGAAGTGA GTGGCGGACA ATTACAAAGA TTTAATGTCA     1184
```

```
TGCGTTCGTT ATTAGCACAG CCTCGCGTTT TAATATGTGA TGAGATAACT TCAAATTTAG    1244

ATGTTATAGC TGAACAAAAT GTAATCAATA TATTAAAAGC GCAAACGATT ACGAACTTAA    1304

ATCATTTTAT CGTTATTTCT CATGATTTAT CCGTGTTACA ACGCTTAGTT AATAGAATTA    1364

TCGTTCTTAA GGATGGCATG ATAGTCGATG ATTTTGCAAT AGAGGAATTA TTTAATGTTG    1424

ATAGACACCC TTATACAAAA GAATTAGTGC AAGCATTTTC ATATTAG                  1471
```

(2) INFORMATION FOR SEQ ID NO:18:

(i) SEQUENCE CHARACTERISTICS:
        (A) LENGTH: 258 amino acids
        (B) TYPE: amino acid
        (D) TOPOLOGY: linear (ii) MOLECULE TYPE: protein (xi) SEQUENCE DESCRIPTION: SEQ ID NO:18:

```
Met Met Ser Leu Ile Asp Ile Gln Asn Leu Thr Ile Lys Asn Thr Ser
 1               5                  10                  15

Glu Lys Ser Leu Ile Lys Gly Ile Asp Leu Lys Ile Phe Ser Gln Gln
            20                  25                  30

Ile Asn Ala Leu Ile Gly Glu Ser Gly Ala Gly Lys Ser Leu Ile Ala
        35                  40                  45

Lys Ala Leu Leu Glu Tyr Leu Pro Phe Asp Leu Ser Cys Thr Tyr Asp
    50                  55                  60

Ser Tyr Gln Phe Asp Gly Glu Asn Val Ser Arg Leu Ser Gln Tyr Tyr
65                  70                  75                  80

Gly His Thr Ile Gly Tyr Ile Ser Gln Asn Tyr Ala Glu Ser Phe Asn
                85                  90                  95

Asp His Thr Lys Leu Gly Lys Gln Leu Thr Ala Ile Tyr Arg Lys His
            100                 105                 110

Tyr Lys Gly Ser Lys Glu Glu Ala Leu Ser Lys Val Asp Lys Ala Leu
        115                 120                 125

Ser Trp Val Asn Leu Gln Ser Lys Asp Ile Leu Asn Lys Tyr Ser Phe
    130                 135                 140

Gln Leu Ser Gly Gly Gln Leu Glu Arg Val Tyr Ile Ala Ser Val Leu
145                 150                 155                 160

Met Leu Glu Pro Lys Leu Ile Ile Ala Asp Glu Pro Val Ala Ser Leu
                165                 170                 175

Asp Ala Leu Asn Gly Asn Gln Val Met Asp Leu Leu Gln His Ile Val
            180                 185                 190

Leu Glu His Gly Gln Thr Leu Phe Ile Ile Thr His Asn Leu Ser His
        195                 200                 205

Val Leu Lys Tyr Cys Gln Tyr Ile Tyr Val Leu Lys Glu Gly Gln Ile
    210                 215                 220

Ile Glu Arg Gly Asn Ile Asn His Phe Lys Tyr Glu His Leu His Pro
225                 230                 235                 240

Tyr Thr Glu Arg Leu Ile Lys Tyr Arg Thr Gln Leu Lys Arg Asp Tyr
                245                 250                 255

Tyr Asp
```

(2) INFORMATION FOR SEQ ID NO:19:

(i) SEQUENCE CHARACTERISTICS:
        (A) LENGTH: 1471 base pairs
        (B) TYPE: nucleic acid (C) STRANDEDNESS: single
(D) TOPOLOGY: linear (ii) MOLECULE TYPE: other nucleic acid
  (A) DESCRIPTION: /desc = "DNA (genomic) (p10c15)"

(ix) FEATURE:
  (A) NAME/KEY: CDS
  (B) LOCATION: 770..1468

(xi) SEQUENCE DESCRIPTION: SEQ ID NO:19:

```
ATGATGAGTC TCATTGATAT ACAAAATTTA ACAATAAAGA ATACTAGTGA GAAATCTCTT      60

ATTAAAGGGA TTGATTTGAA AATTTTTAGT CAACAGATTA ATGCCTTGAT TGGAGAGAGC     120

GGCGCTGGAA AAAGTTTGAT TGCTAAAGCT TTACTTGAAT ATTTACCATT TGATTTAAGC     180

TGCACGTATG ATTCGTACCA ATTTGATGGG GAAAATGTTA GTAGATTGAG TCAATATTAT     240

GGTCATACAA TTGGCTATAT TTCTCAAAAT TATGCAGAAA GTTTTAACGA CCATACTAAA     300

TTAGGTAAAC AGTTAACTGC GATTTATCGT AAGCATTATA AAGGTAGTAA AGAAGAGGCT     360

TTGTCCAAAG TTGATAAGGC TTTGTCGTGG GTTAATTTAC AAAGCAAAGA TATATTAAAT     420

AAATATAGTT CCAACTTTC TGGGGGCCAA CTTGAACGCG TATACATAGC AAGCGTTCTC      480

ATGTTGGAGC CTAAATTAAT CATTGCAGAC GAACCAGTTG CATCATTGGA TGCTTTGAAC     540

GGTAATCAAG TGATGGATTT ATTACAGCAT ATTGTATTAG AACATGGTCA AACATTATTT     600

ATTATCACAC ATAACTTAAG TCATGTATTG AAATATTGTC AGTACATTTA TGTTTTAAAA     660

GAAGGTCAAA TCATTGAACG AGGTAATATT AATCATTTCA AGTATGAGCA TTTGCATCCG     720

TATACTGAAC GTCTAATTAA ATATAGAACA CAATTAAAGA GGGATTACT ATG ATT         775
                                                        Met Ile
                                                         1

GAG TTA AAA CAT GTG ACT TTT GGT TAT AAT AAA AAG CAG ATG GTG CTA      823
Glu Leu Lys His Val Thr Phe Gly Tyr Asn Lys Lys Gln Met Val Leu
    5              10                  15

CAA GAT ATC AAT ATT ACT ATA CCT GAT GGA GAA AAT GTT GGT ATT TTA      871
Gln Asp Ile Asn Ile Thr Ile Pro Asp Gly Glu Asn Val Gly Ile Leu
20                  25                  30

GGC GAA AGT GGC TGT GGT AAA AGT ACG CTC GCT TCA TTG GTT CTT GGC      919
Gly Glu Ser Gly Cys Gly Lys Ser Thr Leu Ala Ser Leu Val Leu Gly
35                  40                  45                  50

TTG TTT AAA CCT GTT AAA GGA GAG ATT TAC TTA AGT GAC AAT GCT GTG      967
Leu Phe Lys Pro Val Lys Gly Glu Ile Tyr Leu Ser Asp Asn Ala Val
                55                  60                  65

TTA CCG ATT TTC CAA CAC CCT TTA ACT AGC TTT AAC CCT GAT TGG ACG     1015
Leu Pro Ile Phe Gln His Pro Leu Thr Ser Phe Asn Pro Asp Trp Thr
            70                  75                  80

ATT GAG ACC TCA TTA AAA GAA GCG TTA TAT TAT TAC AGA GGT CTA ACT     1063
Ile Glu Thr Ser Leu Lys Glu Ala Leu Tyr Tyr Tyr Arg Gly Leu Thr
        85                  90                  95

GAT AAT ACT GCT CAG GAT CAA TTA TTA TTA CAA CAT TTA TCT ACT TTT     1111
Asp Asn Thr Ala Gln Asp Gln Leu Leu Leu Gln His Leu Ser Thr Phe
    100                 105                 110

GAG TTA AAC GCG CAA TTA TTG ACT AAA TTA CCA AGC GAA GTG AGT GGC     1159
Glu Leu Asn Ala Gln Leu Leu Thr Lys Leu Pro Ser Glu Val Ser Gly
115                 120                 125                 130

GGA CAA TTA CAA AGA TTT AAT GTC ATG CGT TCG TTA TTA GCA CAG CCT     1207
Gly Gln Leu Gln Arg Phe Asn Val Met Arg Ser Leu Leu Ala Gln Pro
                135                 140                 145

CGC GTT TTA ATA TGT GAT GAG ATA ACT TCA AAT TTA GAT GTT ATA GCT     1255
Arg Val Leu Ile Cys Asp Glu Ile Thr Ser Asn Leu Asp Val Ile Ala
            150                 155                 160
```

```
GAA CAA AAT GTA ATC AAT ATA TTA AAA GCG CAA ACG ATT ACG AAC TTA    1303
Glu Gln Asn Val Ile Asn Ile Leu Lys Ala Gln Thr Ile Thr Asn Leu
            165                 170                 175

AAT CAT TTT ATC GTT ATT TCT CAT GAT TTA TCC GTG TTA CAA CGC TTA    1351
Asn His Phe Ile Val Ile Ser His Asp Leu Ser Val Leu Gln Arg Leu
        180                 185                 190

GTT AAT AGA ATT ATC GTT CTT AAG GAT GGC ATG ATA GTC GAT GAT TTT    1399
Val Asn Arg Ile Ile Val Leu Lys Asp Gly Met Ile Val Asp Asp Phe
195                 200                 205                 210

GCA ATA GAG GAA TTA TTT AAT GTT GAT AGA CAC CCT TAT ACA AAA GAA    1447
Ala Ile Glu Glu Leu Phe Asn Val Asp Arg His Pro Tyr Thr Lys Glu
                215                 220                 225

TTA GTG CAA GCA TTT TCA TAT TAG                                    1471
Leu Val Gln Ala Phe Ser Tyr
            230
```

(2) INFORMATION FOR SEQ ID NO:20:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO:20:

```
Met Ile Glu Leu Lys His Val Thr Phe Gly Tyr Asn Lys Lys Gln Met
 1               5                  10                  15

Val Leu Gln Asp Ile Asn Ile Thr Ile Pro Asp Gly Glu Asn Val Gly
            20                  25                  30

Ile Leu Gly Glu Ser Gly Cys Gly Lys Ser Thr Leu Ala Ser Leu Val
        35                  40                  45

Leu Gly Leu Phe Lys Pro Val Lys Gly Glu Ile Tyr Leu Ser Asp Asn
    50                  55                  60

Ala Val Leu Pro Ile Phe Gln His Pro Leu Thr Ser Phe Asn Pro Asp
65                  70                  75                  80

Trp Thr Ile Glu Thr Ser Leu Lys Glu Ala Leu Tyr Tyr Arg Gly
                85                  90                  95

Leu Thr Asp Asn Thr Ala Gln Asp Gln Leu Leu Leu Gln His Leu Ser
            100                 105                 110

Thr Phe Glu Leu Asn Ala Gln Leu Leu Thr Lys Leu Pro Ser Glu Val
        115                 120                 125

Ser Gly Gly Gln Leu Gln Arg Phe Asn Val Met Arg Ser Leu Leu Ala
    130                 135                 140

Gln Pro Arg Val Leu Ile Cys Asp Glu Ile Thr Ser Asn Leu Asp Val
145                 150                 155                 160

Ile Ala Glu Gln Asn Val Ile Asn Ile Leu Lys Ala Gln Thr Ile Thr
                165                 170                 175

Asn Leu Asn His Phe Ile Val Ile Ser His Asp Leu Ser Val Leu Gln
            180                 185                 190

Arg Leu Val Asn Arg Ile Ile Val Leu Lys Asp Gly Met Ile Val Asp
        195                 200                 205

Asp Phe Ala Ile Glu Glu Leu Phe Asn Val Asp Arg His Pro Tyr Thr
    210                 215                 220

Lys Glu Leu Val Gln Ala Phe Ser Tyr
225                 230
```

(2) INFORMATION FOR SEQ ID NO:21:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p13b74)"

(xi) SEQUENCE DESCRIPTION: SEQ ID NO:21:

```
AATCATAAAT TACGAATTAG ATATAACAAA AAAGAGCTTG GGACATTAAG TCCTTAAAGT      60

CTTAGGCAAT GTAAAAAGC TGATTTCTAT TATTTATTTG ATAGAAATCA GCTTTTTTGA      120

TATGTATTTT ATAATGTACA GCTCGTTGAG CTGCTATTTT CCTTATATTA AGTGCCATTA     180

ATACAAAACC TAGCTCTCGT TTAACTTTAT TTATTCCCGA ACTGACATTC GAGTGAAACC     240

CAAAATAGCC TTCTAATCCA AAACAGGCT CTACTCAATT TTCCTTTTGA CTAATAGATT      300

TTTTCGTTTC TGGTTCCAAA GCCTTGAGGT TGTAGAATTC TTGAAGACGA AAAGGGCCCC     360

GTGATACGCC CTATTTTTAA AGGTTAATGT TCTGAA                              396
```

(2) INFORMATION FOR SEQ ID NO:22:

(i) SEQUENCE CHARACTERISTICS:
        (A) LENGTH: 1845 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p14c15)"

(ix) FEATURE:
        (A) NAME/KEY: CDS
        (B) LOCATION: 3..788

(ix) FEATURE:
        (A) NAME/KEY: CDS
        (B) LOCATION: 856..1842

(xi) SEQUENCE DESCRIPTION: SEQ ID NO:22:

```
GC ATC AAT GAA CAT CAG GAA TTA ACA ACT TTA GGC AGA GGT GGT TCT          47
   Ile Asn Glu His Gln Glu Leu Thr Thr Leu Gly Arg Gly Gly Ser
    1               5                  10                  15

GAT ACG ACC GCT GTG GCA CTT GCT GTT AGT AAT CAA ATA CCT TGT GAA         95
Asp Thr Thr Ala Val Ala Leu Ala Val Ser Asn Gln Ile Pro Cys Glu
            20                  25                  30

ATT TAT ACC GAC GTT GAT GGT GTG TAT GCC ACT GAC CCA AGA CTT TTA        143
Ile Tyr Thr Asp Val Asp Gly Val Tyr Ala Thr Asp Pro Arg Leu Leu
        35                  40                  45

CCA AAG GCT AAA CGA CTA GAC ATC GTC TCA TAT GAA GAA ATG ATG GAA        191
Pro Lys Ala Lys Arg Leu Asp Ile Val Ser Tyr Glu Glu Met Met Glu
    50                  55                  60

ATG AGC GCT TTA GGT GCT GGT GTA CTT GAA ACA AGA AGT GTT GAA TTA        239
Met Ser Ala Leu Gly Ala Gly Val Leu Glu Thr Arg Ser Val Glu Leu
65                  70                  75

GCT AAA AAC TAT AAT ATC CCT TTA TAT TTA GGA AAA ACT TTA TCG AAC        287
Ala Lys Asn Tyr Asn Ile Pro Leu Tyr Leu Gly Lys Thr Leu Ser Asn
80                  85                  90                  95

GTG AAA GGA ACA TGG ATT ATG TCA AAT GAA GAA ATA TTA GAG AAA AAA        335
Val Lys Gly Thr Trp Ile Met Ser Asn Glu Glu Ile Leu Glu Lys Lys
                100                 105                 110

GCA GTT ACT GGT GTG GCT TTG GAT AAA CAT ATG ATG CAT GTA ACA ATT        383
Ala Val Thr Gly Val Ala Leu Asp Lys His Met Met His Val Thr Ile
```

-continued

```
                115                 120                 125
AGT TAT CCC CTA CCT GAC AAT CAG CTA CTT ACC CAA CTA TTT ACG GAA      431
Ser Tyr Pro Leu Pro Asp Asn Gln Leu Leu Thr Gln Leu Phe Thr Glu
        130                 135                 140

CTT GAA GAA GGT GCT GTA AAT GTT GAT ATG ATT TCA CAA ATC GTC AAC      479
Leu Glu Glu Gly Ala Val Asn Val Asp Met Ile Ser Gln Ile Val Asn
145                 150                 155

TTG GAT GGG CTA CAA CTA TCC TTC ACG ATT AAA GAT AGT GAT TTT CAT      527
Leu Asp Gly Leu Gln Leu Ser Phe Thr Ile Lys Asp Ser Asp Phe His
160                 165                 170                 175

CAA ATT TCT ATG ATT CTT GAA ACA TTA AAG AAT CAA TAT GAA GCA TTA      575
Gln Ile Ser Met Ile Leu Glu Thr Leu Lys Asn Gln Tyr Glu Ala Leu
            180                 185                 190

GCT TAT AAA ATC AAT GAG CAT TAT GTC AAA ATT TCA TTA ATT GGC TCA      623
Ala Tyr Lys Ile Asn Glu His Tyr Val Lys Ile Ser Leu Ile Gly Ser
        195                 200                 205

GGC ATG CGT GAT ATG TCA GGT GTG GCA TCA AAA GCA TTT TTG ACA TTA      671
Gly Met Arg Asp Met Ser Gly Val Ala Ser Lys Ala Phe Leu Thr Leu
    210                 215                 220

ATT GAA AAT AAT ATA CCT TTC TAC CAA ACA ACA ACA TCT GAA ATA AGT      719
Ile Glu Asn Asn Ile Pro Phe Tyr Gln Thr Thr Thr Ser Glu Ile Ser
225                 230                 235                 240

ATT TCA TAC GTC ATT GAT GAT TTT AAT GGG CAA CAA GCG GTA GAA AAA      767
Ile Ser Tyr Val Ile Asp Asp Phe Asn Gly Gln Gln Ala Val Glu Lys
                245                 250                 255

CTA TAT GAC GCA TTT AAC ATT TAATGGTAAA ATGATTGTTA AAATATTCTA         818
Leu Tyr Asp Ala Phe Asn Ile
            260

AAAATTGGGA AATTATTATA AAATGGAGTG ACAAGTT ATG ACA AAG TTA GCA GTT     873
                                        Met Thr Lys Leu Ala Val
                                          1               5

GTG GGT GCA ACA GGA TTA GTA GGT ACA AAA ATG TTG GAG ACA TTA AAT      921
Val Gly Ala Thr Gly Leu Val Gly Thr Lys Met Leu Glu Thr Leu Asn
            10                  15                  20

CGT AAA AAT ATT CCT TTC GAT GAA TTA GTA TTA TTT TCA TCA GCA CGT      969
Arg Lys Asn Ile Pro Phe Asp Glu Leu Val Leu Phe Ser Ser Ala Arg
        25                  30                  35

TCT GCA GGG CAA GAA GTT GAA TTT CAA GGA AAA ACA TAT ACA GTT CAA     1017
Ser Ala Gly Gln Glu Val Glu Phe Gln Gly Lys Thr Tyr Thr Val Gln
    40                  45                  50

GAA TTA ACT GAT GCT CGT GCA AGT GAA CAT TTC GAT TAT GTA TTA ATG     1065
Glu Leu Thr Asp Ala Arg Ala Ser Glu His Phe Asp Tyr Val Leu Met
55                  60                  65                  70

AGT GCT GGT GGC GGT ACA AGC GAA CAC TTT GCC CCA CTT TTT GAA AAA     1113
Ser Ala Gly Gly Gly Thr Ser Glu His Phe Ala Pro Leu Phe Glu Lys
                75                  80                  85

GCT GGT GCA ATC GTT ATA GAC AAT TCA AGT CAA TGG CGT ATG GCA GAA     1161
Ala Gly Ala Ile Val Ile Asp Asn Ser Ser Gln Trp Arg Met Ala Glu
            90                  95                  100

GAT ATT GAT TTA ATC GTT CCG GAA GTC AAT GAA CCT ACA TTT ACA AGA     1209
Asp Ile Asp Leu Ile Val Pro Glu Val Asn Glu Pro Thr Phe Thr Arg
        105                 110                 115

GGT ATC ATT GCC AAT CCA AAC TGC TCT ACG ATT CAA TCT GTT GTA CCT     1257
Gly Ile Ile Ala Asn Pro Asn Cys Ser Thr Ile Gln Ser Val Val Pro
    120                 125                 130

CTA AAA GTA TTG CAA GAT GCT TAT GGT TTA AAA CGA GTG GCA TAT ACA     1305
Leu Lys Val Leu Gln Asp Ala Tyr Gly Leu Lys Arg Val Ala Tyr Thr
135                 140                 145                 150

ACA TAT CAA GCT GTA TCA GGT TCA GGG ATG AAA GGT AAG AAA GAT TTA     1353
```

```
Thr Tyr Gln Ala Val Ser Gly Ser Gly Met Lys Gly Lys Lys Asp Leu
                155                 160                 165

GCT GAA GGT GTA AAT GGT AAA GCA CCA GAA GCA TAT CCA CAT CCA ATT      1401
Ala Glu Gly Val Asn Gly Lys Ala Pro Glu Ala Tyr Pro His Pro Ile
            170                 175                 180

TAT AAT AAT GTG TTA CCG CAT ATT GAT GTG TTT TTA GAA AAC GGA TAT      1449
Tyr Asn Asn Val Leu Pro His Ile Asp Val Phe Leu Glu Asn Gly Tyr
                185                 190                 195

ACA AAA GAA GAA CAA AAA ATG ATT GAT GAG ACG AGA AAA ATT TTA AAT      1497
Thr Lys Glu Glu Gln Lys Met Ile Asp Glu Thr Arg Lys Ile Leu Asn
        200                 205                 210

GCG CCA GAC TTA AAA GTA ACA GCA ACA TGC GCA CGT GTG CCT GTT CAA      1545
Ala Pro Asp Leu Lys Val Thr Ala Thr Cys Ala Arg Val Pro Val Gln
215                 220                 225                 230

GAT AGT CAT AGT GTT GAA ATT GAT GTA ACG CTT GAC AAA GAA ACA ACA      1593
Asp Ser His Ser Val Glu Ile Asp Val Thr Leu Asp Lys Glu Thr Thr
                235                 240                 245

GCA GAA GAT ATT AAA GCG TTA TTT GAT CAA GAT GAC CGC GTT GTT TTA      1641
Ala Glu Asp Ile Lys Ala Leu Phe Asp Gln Asp Asp Arg Val Val Leu
            250                 255                 260

GTA GAC AAT CCA GAG AAC AAT GAA TAT CCA ATG GCA ATC AAT TCT ACT      1689
Val Asp Asn Pro Glu Asn Asn Glu Tyr Pro Met Ala Ile Asn Ser Thr
                265                 270                 275

AAT AAA GAT GAA GTG TTT GTT GGC CGT ATA CGT AGA GAT GAT TCA TTA      1737
Asn Lys Asp Glu Val Phe Val Gly Arg Ile Arg Arg Asp Asp Ser Leu
        280                 285                 290

GAA AAT ACT TTC CAT GTA TGG TGT ACA TCA GAC AAT TTA TTA AAA GGT      1785
Glu Asn Thr Phe His Val Trp Cys Thr Ser Asp Asn Leu Leu Lys Gly
295                 300                 305                 310

GCT GCA TTA AAT GCT GTA CAA GTA TTG GAA CAA GTT ATG CGT TTA AAA      1833
Ala Ala Leu Asn Ala Val Gln Val Leu Glu Gln Val Met Arg Leu Lys
                315                 320                 325

GGA GCG AAT TAA                                                      1845
Gly Ala Asn (2) INFORMATION FOR SEQ ID NO:23:

(i) SEQUENCE CHARACTERISTICS:
        (A) LENGTH: 262 amino acids
        (B) TYPE: amino acid
        (D) TOPOLOGY: linear (ii) MOLECULE TYPE: protein (xi) SEQUENCE DESCRIPTION: SEQ ID NO:23:

Ile Asn Glu His Gln Glu Leu Thr Thr Leu Gly Arg Gly Gly Ser Asp
1               5                   10                  15

Thr Thr Ala Val Ala Leu Ala Val Ser Asn Gln Ile Pro Cys Glu Ile
                20                  25                  30

Tyr Thr Asp Val Asp Gly Val Tyr Ala Thr Asp Pro Arg Leu Leu Pro
            35                  40                  45

Lys Ala Lys Arg Leu Asp Ile Val Ser Tyr Glu Glu Met Met Glu Met
        50                  55                  60

Ser Ala Leu Gly Ala Gly Val Leu Glu Thr Arg Ser Val Glu Leu Ala
65                  70                  75                  80

Lys Asn Tyr Asn Ile Pro Leu Tyr Leu Gly Lys Thr Leu Ser Asn Val
                85                  90                  95

Lys Gly Thr Trp Ile Met Ser Asn Glu Glu Ile Leu Glu Lys Lys Ala
            100                 105                 110
```

-continued

```
Val Thr Gly Val Ala Leu Asp Lys His Met Met His Val Thr Ile Ser
        115                 120                 125

Tyr Pro Leu Pro Asp Asn Gln Leu Leu Thr Gln Leu Phe Thr Glu Leu
130                 135                 140

Glu Glu Gly Ala Val Asn Val Asp Met Ile Ser Gln Ile Val Asn Leu
145                 150                 155                 160

Asp Gly Leu Gln Leu Ser Phe Thr Ile Lys Asp Ser Asp Phe His Gln
                165                 170                 175

Ile Ser Met Ile Leu Glu Thr Leu Lys Asn Gln Tyr Glu Ala Leu Ala
                180                 185                 190

Tyr Lys Ile Asn Glu His Tyr Val Lys Ile Ser Leu Ile Gly Ser Gly
                195                 200                 205

Met Arg Asp Met Ser Gly Val Ala Ser Lys Ala Phe Leu Thr Leu Ile
                210                 215                 220

Glu Asn Asn Ile Pro Phe Tyr Gln Thr Thr Ser Glu Ile Ser Ile
225                 230                 235                 240

Ser Tyr Val Ile Asp Asp Phe Asn Gly Gln Gln Ala Val Glu Lys Leu
                245                 250                 255

Tyr Asp Ala Phe Asn Ile
                260

(2) INFORMATION FOR SEQ ID NO:24:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:24:

Met Thr Lys Leu Ala Val Val Gly Ala Thr Gly Leu Val Gly Thr Lys
  1               5                  10                  15

Met Leu Glu Thr Leu Asn Arg Lys Asn Ile Pro Phe Asp Glu Leu Val
                 20                  25                  30

Leu Phe Ser Ser Ala Arg Ser Ala Gly Gln Glu Val Glu Phe Gln Gly
                 35                  40                  45

Lys Thr Tyr Thr Val Gln Glu Leu Thr Asp Ala Arg Ala Ser Glu His
             50                  55                  60

Phe Asp Tyr Val Leu Met Ser Ala Gly Gly Thr Ser Glu His Phe
 65                  70                  75                  80

Ala Pro Leu Phe Glu Lys Ala Gly Ala Ile Val Ile Asp Asn Ser Ser
                 85                  90                  95

Gln Trp Arg Met Ala Glu Asp Ile Asp Leu Ile Val Pro Glu Val Asn
                100                 105                 110

Glu Pro Thr Phe Thr Arg Gly Ile Ile Ala Asn Pro Asn Cys Ser Thr
                115                 120                 125

Ile Gln Ser Val Val Pro Leu Lys Val Leu Gln Asp Ala Tyr Gly Leu
            130                 135                 140

Lys Arg Val Ala Tyr Thr Thr Tyr Gln Ala Val Ser Gly Ser Gly Met
145                 150                 155                 160

Lys Gly Lys Lys Asp Leu Ala Glu Gly Val Asn Gly Lys Ala Pro Glu
                165                 170                 175

Ala Tyr Pro His Pro Ile Tyr Asn Asn Val Leu Pro His Ile Asp Val
                180                 185                 190

Phe Leu Glu Asn Gly Tyr Thr Lys Glu Glu Gln Lys Met Ile Asp Glu
```

```
                195                 200                 205
Thr Arg Lys Ile Leu Asn Ala Pro Asp Leu Lys Val Thr Ala Thr Cys
    210                 215                 220

Ala Arg Val Pro Val Gln Asp Ser His Ser Val Glu Ile Asp Val Thr
225                 230                 235                 240

Leu Asp Lys Glu Thr Thr Ala Glu Asp Ile Lys Ala Leu Phe Asp Gln
                245                 250                 255

Asp Asp Arg Val Val Leu Val Asp Asn Pro Glu Asn Asn Glu Tyr Pro
            260                 265                 270

Met Ala Ile Asn Ser Thr Asn Lys Asp Glu Val Phe Val Gly Arg Ile
            275                 280                 285

Arg Arg Asp Asp Ser Leu Glu Asn Thr Phe His Val Trp Cys Thr Ser
    290                 295                 300

Asp Asn Leu Leu Lys Gly Ala Ala Leu Asn Ala Val Gln Val Leu Glu
305                 310                 315                 320

Gln Val Met Arg Leu Lys Gly Ala Asn
                325
```

(2) INFORMATION FOR SEQ ID NO:25:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p13b26)"

(ix) FEATURE:
        (A) NAME/KEY: CDS
        (B) LOCATION: 1..924

(xi) SEQUENCE DESCRIPTION: SEQ ID NO:25:

```
ATG AAC GAA GCC GAC ATG CTG TTC TCT GTC ACT GTT CCC GGA AGC ACA        48
Met Asn Glu Ala Asp Met Leu Phe Ser Val Thr Val Pro Gly Ser Thr
  1               5                  10                  15

GCT AAC CTA GGC CCC GGC TTT GAT TCA GTC GGA ATG GCG CTC AGC AGA        96
Ala Asn Leu Gly Pro Gly Phe Asp Ser Val Gly Met Ala Leu Ser Arg
             20                  25                  30

TAT TTG AAG CTG ACC GTC TTT GAA AGC GAC AAA TGG TCT TTT GAG GCT       144
Tyr Leu Lys Leu Thr Val Phe Glu Ser Asp Lys Trp Ser Phe Glu Ala
         35                  40                  45

GAA ACA GAA ACA GTC GCC GGA ATT CGC GGT ACA GAT AAC CTG ATC TAC       192
Glu Thr Glu Thr Val Ala Gly Ile Arg Gly Thr Asp Asn Leu Ile Tyr
     50                  55                  60

CAA GTG GCT AAA CGG ACC GCA GAT TTG TAC GGA AAA GAA ATG CCT CCT       240
Gln Val Ala Lys Arg Thr Ala Asp Leu Tyr Gly Lys Glu Met Pro Pro
 65                  70                  75                  80

GTC CAT GTG AAG GTG TGG AGC GAC ATC CCG CTT GCA CGC GGC CTT GGC       288
Val His Val Lys Val Trp Ser Asp Ile Pro Leu Ala Arg Gly Leu Gly
                 85                  90                  95

AGC AGC GCC GCA GCG ATT GTA GCG GCC ATT GAA CTG GCT GAT GAA TTA       336
Ser Ser Ala Ala Ala Ile Val Ala Ala Ile Glu Leu Ala Asp Glu Leu
            100                 105                 110

TGC GGC TTA AAG CTG TCT GAA GCG GAC AAG CTG CAT TTA GCG AGT CTA       384
Cys Gly Leu Lys Leu Ser Glu Ala Asp Lys Leu His Leu Ala Ser Leu
        115                 120                 125

GAA GAA GGA CAC CCG GAC AAT GCT GGC GCT TCT CTC GTC GGC GGA CTT       432
Glu Glu Gly His Pro Asp Asn Ala Gly Ala Ser Leu Val Gly Gly Leu
    130                 135                 140
```

```
GTG ATC GGC CTG CAT GAG GAT GAC GAG ACC CAA ATG ATC CGC GTC CCG        480
Val Ile Gly Leu His Glu Asp Asp Glu Thr Gln Met Ile Arg Val Pro
145                 150                 155                 160

AAT GCT GAC ATT GAC GTA GTC GTT GTC ATT CCT TTT TAT GAA GTG CTG        528
Asn Ala Asp Ile Asp Val Val Val Val Ile Pro Phe Tyr Glu Val Leu
                165                 170                 175

ACA AGA GAC GCG AGA GAC GTG CTT CCG AAG GAG TTT CCA TAT GCC GAT        576
Thr Arg Asp Ala Arg Asp Val Leu Pro Lys Glu Phe Pro Tyr Ala Asp
            180                 185                 190

GCC GTA AAA GCA AGT GCT GTC AGC AAT ATC CTC ATT GCT GCG ATC ATG        624
Ala Val Lys Ala Ser Ala Val Ser Asn Ile Leu Ile Ala Ala Ile Met
        195                 200                 205

TCC AAG GAT TGG CCG CTT GTC GGG AAA ATC ATG AAG AAG GAT ATG TTC        672
Ser Lys Asp Trp Pro Leu Val Gly Lys Ile Met Lys Lys Asp Met Phe
    210                 215                 220

CAT CAG CCG TAC CGG GCG ATG CTT GTG CCT GAG CTG TCA AAA GTA GAG        720
His Gln Pro Tyr Arg Ala Met Leu Val Pro Glu Leu Ser Lys Val Glu
225                 230                 235                 240

CAC GTC GCC GAG ATG AAG GGC GCA TAT GGA ACG GCT CTC AGC GGA GCA        768
His Val Ala Glu Met Lys Gly Ala Tyr Gly Thr Ala Leu Ser Gly Ala
                245                 250                 255

GGC CCA ACG ATT CTC GTC ATG ACC GAA AAA GGA AAG GGA GAA GAG CTA        816
Gly Pro Thr Ile Leu Val Met Thr Glu Lys Gly Lys Gly Glu Glu Leu
            260                 265                 270

AAA GAA CAG CTC GCG CTT CAT TTC CCT CAT TGT GAA GTA GAC GCT TTG        864
Lys Glu Gln Leu Ala Leu His Phe Pro His Cys Glu Val Asp Ala Leu
        275                 280                 285

ACC GTT CCG AAA GAG GGA AGT ATA ATA GAG CGA AAT CCT TTA TAT CAA        912
Thr Val Pro Lys Glu Gly Ser Ile Ile Glu Arg Asn Pro Leu Tyr Gln
    290                 295                 300

GTA AAA AGT GTA TAG                                                    927
Val Lys Ser Val
305
```

(2) INFORMATION FOR SEQ ID NO:26:

(i) SEQUENCE CHARACTERISTICS:
        (A) LENGTH: 308 amino acids
        (B) TYPE: amino acid
        (D) TOPOLOGY: linear (ii) MOLECULE TYPE: protein (xi) SEQUENCE DESCRIPTION: SEQ ID NO:26:

```
Met Asn Glu Ala Asp Met Leu Phe Ser Val Thr Val Pro Gly Ser Thr
1               5                   10                  15

Ala Asn Leu Gly Pro Gly Phe Asp Ser Val Gly Met Ala Leu Ser Arg
            20                  25                  30

Tyr Leu Lys Leu Thr Val Phe Glu Ser Asp Lys Trp Ser Phe Glu Ala
        35                  40                  45

Glu Thr Glu Thr Val Ala Gly Ile Arg Gly Thr Asp Asn Leu Ile Tyr
    50                  55                  60

Gln Val Ala Lys Arg Thr Ala Asp Leu Tyr Gly Lys Glu Met Pro Pro
65                  70                  75                  80

Val His Val Lys Val Trp Ser Asp Ile Pro Leu Ala Arg Gly Leu Gly
                85                  90                  95

Ser Ser Ala Ala Ala Ile Val Ala Ala Ile Glu Leu Ala Asp Glu Leu
            100                 105                 110

Cys Gly Leu Lys Leu Ser Glu Ala Asp Lys Leu His Leu Ala Ser Leu
```

-continued

```
            115                 120                 125
Glu Glu Gly His Pro Asp Asn Ala Gly Ala Ser Leu Val Gly Gly Leu
            130                 135                 140

Val Ile Gly Leu His Glu Asp Asp Glu Thr Gln Met Ile Arg Val Pro
145                 150                 155                 160

Asn Ala Asp Ile Asp Val Val Val Ile Pro Phe Tyr Glu Val Leu
                165                 170                 175

Thr Arg Asp Ala Arg Asp Val Leu Pro Lys Glu Phe Pro Tyr Ala Asp
                180                 185                 190

Ala Val Lys Ala Ser Ala Val Ser Asn Ile Leu Ile Ala Ala Ile Met
            195                 200                 205

Ser Lys Asp Trp Pro Leu Val Gly Lys Ile Met Lys Lys Asp Met Phe
210                 215                 220

His Gln Pro Tyr Arg Ala Met Leu Val Pro Glu Leu Ser Lys Val Glu
225                 230                 235                 240

His Val Ala Glu Met Lys Gly Ala Tyr Gly Thr Ala Leu Ser Gly Ala
                245                 250                 255

Gly Pro Thr Ile Leu Val Met Thr Glu Lys Gly Lys Gly Glu Glu Leu
                260                 265                 270

Lys Glu Gln Leu Ala Leu His Phe Pro His Cys Glu Val Asp Ala Leu
            275                 280                 285

Thr Val Pro Lys Glu Gly Ser Ile Ile Glu Arg Asn Pro Leu Tyr Gln
            290                 295                 300

Val Lys Ser Val
305
```

(2) INFORMATION FOR SEQ ID NO:27:

(i) SEQUENCE CHARACTERISTICS:
        (A) LENGTH: 1320 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p7c18)"

(ix) FEATURE:
        (A) NAME/KEY: CDS
        (B) LOCATION: 1..1317

(xi) SEQUENCE DESCRIPTION: SEQ ID NO:27:

```
TTG TTC TTA CAC GGC ACA AGC AGA CAA AAT CAA CAT GGT CAT TTA GAA      48
Leu Phe Leu His Gly Thr Ser Arg Gln Asn Gln His Gly His Leu Glu
 1               5                  10                  15

ATC GGA GGT GTG GAT GCT CTC TAT TTA GCG GAG AAA TAT GGT ACA CCT      96
Ile Gly Gly Val Asp Ala Leu Tyr Leu Ala Glu Lys Tyr Gly Thr Pro
                20                  25                  30

CTT TAC GTA TAT GAT GTG GCT TTA ATA CGT GAG CGT GCT AAA AGC TTT     144
Leu Tyr Val Tyr Asp Val Ala Leu Ile Arg Glu Arg Ala Lys Ser Phe
            35                  40                  45

AAG CAG GCG TTT ATT TCT GCA GGG CTG AAA GCA CAG GTG GCA TAT GCG     192
Lys Gln Ala Phe Ile Ser Ala Gly Leu Lys Ala Gln Val Ala Tyr Ala
        50                  55                  60

AGC AAA GCA TTC TCA TCA GTC GCA ATG ATT CAG CTC GCT GAG GAA GAG     240
Ser Lys Ala Phe Ser Ser Val Ala Met Ile Gln Leu Ala Glu Glu Glu
65                  70                  75                  80

GGA CTT TCT TTA GAT GTC GTA TCC GGA GGA GAG CTA TAT ACG GCT GTT     288
Gly Leu Ser Leu Asp Val Val Ser Gly Gly Glu Leu Tyr Thr Ala Val
                85                  90                  95
```

```
GCA GCA GGC TTT CCG GCA GAA CGC ATC CAC TTT CAT GGA AAC AAT AAG      336
Ala Ala Gly Phe Pro Ala Glu Arg Ile His Phe His Gly Asn Asn Lys
            100                 105                 110

AGC AGG GAA GAA CTG CGG ATG GCG CTT GAG CAC CGC ATC GGC TGC ATT      384
Ser Arg Glu Glu Leu Arg Met Ala Leu Glu His Arg Ile Gly Cys Ile
            115                 120                 125

GTG GTG GAT AAT TTC TAT GAA ATC GCG CTT CTT GAA GAC CTA TGT AAA      432
Val Val Asp Asn Phe Tyr Glu Ile Ala Leu Leu Glu Asp Leu Cys Lys
130                 135                 140

GAA ACG GGT CAC TCC ATC GAT GTT CTT CTT CGG ATC ACG CCC GGA GTA      480
Glu Thr Gly His Ser Ile Asp Val Leu Leu Arg Ile Thr Pro Gly Val
145                 150                 155                 160

GAA GCG CAT ACG CAT GAC TAC ATT ACA ACG GGC CAG GAA GAT TCA AAG      528
Glu Ala His Thr His Asp Tyr Ile Thr Thr Gly Gln Glu Asp Ser Lys
                165                 170                 175

TTT GGT TTC GAT CTT CAT AAC GGA CAA ACT GAA CGG GCC ATT GAA CAA      576
Phe Gly Phe Asp Leu His Asn Gly Gln Thr Glu Arg Ala Ile Glu Gln
            180                 185                 190

GTA TTA CAA TCG GAA CAC ATT CAG CTG CTG GGT GTC CAT TGC CAT ATC      624
Val Leu Gln Ser Glu His Ile Gln Leu Leu Gly Val His Cys His Ile
            195                 200                 205

GGC TCG CAA ATC TTT GAT ACG GCC GGT TTT GTG TTA GCA GCG GAA AAA      672
Gly Ser Gln Ile Phe Asp Thr Ala Gly Phe Val Leu Ala Ala Glu Lys
210                 215                 220

ATC TTC AAA AAA CTA GAC GAA TGG AGA GAT TCA TAT TCA TTT GTA TCC      720
Ile Phe Lys Lys Leu Asp Glu Trp Arg Asp Ser Tyr Ser Phe Val Ser
225                 230                 235                 240

AAG GTG CTG AAT CTT GGA GGA GGT TTC GGC ATT CGT TAT ACG GAA GAT      768
Lys Val Leu Asn Leu Gly Gly Gly Phe Gly Ile Arg Tyr Thr Glu Asp
                245                 250                 255

GAT GAA CCG CTT CAT GCC ACT GAA TAC GTT GAA AAA ATT ATC GAA GCT      816
Asp Glu Pro Leu His Ala Thr Glu Tyr Val Glu Lys Ile Ile Glu Ala
            260                 265                 270

GTG AAA GAA AAT GCT TCC CGT TAC GGT TTT GAC ATT CCG GAA ATT TGG      864
Val Lys Glu Asn Ala Ser Arg Tyr Gly Phe Asp Ile Pro Glu Ile Trp
            275                 280                 285

ATC GAA CCG GGC CGT TCT CTC GTG GGA GAC GCA GGC ACA ACT CTT TAT      912
Ile Glu Pro Gly Arg Ser Leu Val Gly Asp Ala Gly Thr Thr Leu Tyr
290                 295                 300

ACG GTT GGC TCT CAA AAA GAA GTG CCG GGT GTC CGC CAA TAT GTG GCT      960
Thr Val Gly Ser Gln Lys Glu Val Pro Gly Val Arg Gln Tyr Val Ala
305                 310                 315                 320

GTA GAC GGA GGC ATG AAC GAC AAT ATT CGT CCT GCG CTT TAC CAA GCT     1008
Val Asp Gly Gly Met Asn Asp Asn Ile Arg Pro Ala Leu Tyr Gln Ala
                325                 330                 335

AAA TAT GAA GCT GCG GCA GCC AAC AGG ATC GGA GAA GCG CAT GAC AAA     1056
Lys Tyr Glu Ala Ala Ala Ala Asn Arg Ile Gly Glu Ala His Asp Lys
            340                 345                 350

ACG GTA TCA ATT GCC GGA AAG TGC TGT GAA AGC GGA GAT ATG CTG ATT     1104
Thr Val Ser Ile Ala Gly Lys Cys Cys Glu Ser Gly Asp Met Leu Ile
            355                 360                 365

TGG GAT ATT GAC CTG CCG GAA GTA AAA GAA GGC GAT CTT CTT GCC GTT     1152
Trp Asp Ile Asp Leu Pro Glu Val Lys Glu Gly Asp Leu Leu Ala Val
370                 375                 380

TTT TGT ACA GGC GCT TAT GGA TAC AGC ATG GCC AAC AAT TAT AAC CGT     1200
Phe Cys Thr Gly Ala Tyr Gly Tyr Ser Met Ala Asn Asn Tyr Asn Arg
385                 390                 395                 400

ATT CCG AGA CCC GCC GTT GTA TTT GTC GAA AAC GGT GAG GCT CAT TTA     1248
Ile Pro Arg Pro Ala Val Val Phe Val Glu Asn Gly Glu Ala His Leu
```

```
                        405                 410                 415
GTC GTG AAG CGA GAA ACA TAC GAA GAT ATT GTA AAA CTT GAT CTG CCA              1296
Val Val Lys Arg Glu Thr Tyr Glu Asp Ile Val Lys Leu Asp Leu Pro
            420                 425                 430

TTT AAA ACG GGT GTA AAG CAA TAA                                              1320
Phe Lys Thr Gly Val Lys Gln
        435
```

(2) INFORMATION FOR SEQ ID NO:28:

(i) SEQUENCE CHARACTERISTICS:
      (A) LENGTH: 439 amino acids
      (B) TYPE: amino acid
      (D) TOPOLOGY: linear (ii) MOLECULE TYPE: protein (xi) SEQUENCE DESCRIPTION: SEQ ID NO:28:

```
Leu Phe Leu His Gly Thr Ser Arg Gln Asn Gln His Gly His Leu Glu
 1               5                  10                  15

Ile Gly Gly Val Asp Ala Leu Tyr Leu Ala Glu Lys Tyr Gly Thr Pro
            20                  25                  30

Leu Tyr Val Tyr Asp Val Ala Leu Ile Arg Glu Arg Ala Lys Ser Phe
        35                  40                  45

Lys Gln Ala Phe Ile Ser Ala Gly Leu Lys Ala Gln Val Ala Tyr Ala
    50                  55                  60

Ser Lys Ala Phe Ser Ser Val Ala Met Ile Gln Leu Ala Glu Glu Glu
65                  70                  75                  80

Gly Leu Ser Leu Asp Val Val Ser Gly Gly Glu Leu Tyr Thr Ala Val
                85                  90                  95

Ala Ala Gly Phe Pro Ala Glu Arg Ile His Phe His Gly Asn Asn Lys
            100                 105                 110

Ser Arg Glu Glu Leu Arg Met Ala Leu Glu His Arg Ile Gly Cys Ile
        115                 120                 125

Val Val Asp Asn Phe Tyr Glu Ile Ala Leu Leu Glu Asp Leu Cys Lys
    130                 135                 140

Glu Thr Gly His Ser Ile Asp Val Leu Leu Arg Ile Thr Pro Gly Val
145                 150                 155                 160

Glu Ala His Thr His Asp Tyr Ile Thr Thr Gly Gln Glu Asp Ser Lys
                165                 170                 175

Phe Gly Phe Asp Leu His Asn Gly Gln Thr Glu Arg Ala Ile Glu Gln
            180                 185                 190

Val Leu Gln Ser Glu His Ile Gln Leu Leu Gly Val His Cys His Ile
        195                 200                 205

Gly Ser Gln Ile Phe Asp Thr Ala Gly Phe Val Leu Ala Ala Glu Lys
    210                 215                 220

Ile Phe Lys Lys Leu Asp Glu Trp Arg Asp Ser Tyr Ser Phe Val Ser
225                 230                 235                 240

Lys Val Leu Asn Leu Gly Gly Gly Phe Gly Ile Arg Tyr Thr Glu Asp
                245                 250                 255

Asp Glu Pro Leu His Ala Thr Glu Tyr Val Glu Lys Ile Ile Glu Ala
            260                 265                 270

Val Lys Glu Asn Ala Ser Arg Tyr Gly Phe Asp Ile Pro Glu Ile Trp
        275                 280                 285

Ile Glu Pro Gly Arg Ser Leu Val Gly Asp Ala Gly Thr Thr Leu Tyr
    290                 295                 300
```

```
Thr Val Gly Ser Gln Lys Glu Val Pro Gly Val Arg Gln Tyr Val Ala
305                 310                 315                 320

Val Asp Gly Gly Met Asn Asp Asn Ile Arg Pro Ala Leu Tyr Gln Ala
                325                 330                 335

Lys Tyr Glu Ala Ala Ala Ala Asn Arg Ile Gly Glu Ala His Asp Lys
            340                 345                 350

Thr Val Ser Ile Ala Gly Lys Cys Cys Glu Ser Gly Asp Met Leu Ile
        355                 360                 365

Trp Asp Ile Asp Leu Pro Glu Val Lys Glu Gly Asp Leu Leu Ala Val
    370                 375                 380

Phe Cys Thr Gly Ala Tyr Gly Tyr Ser Met Ala Asn Asn Tyr Asn Arg
385                 390                 395                 400

Ile Pro Arg Pro Ala Val Val Phe Val Glu Asn Gly Glu Ala His Leu
                405                 410                 415

Val Val Lys Arg Glu Thr Tyr Glu Asp Ile Val Lys Leu Asp Leu Pro
                420                 425                 430

Phe Lys Thr Gly Val Lys Gln
            435

(2) INFORMATION FOR SEQ ID NO:29:

(i) SEQUENCE CHARACTERISTICS:
        (A) LENGTH: 2190 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p15c31)"
            Unknown = Xaa (ix) FEATURE:
        (A) NAME/KEY: CDS
        (B) LOCATION: 1..2187

(xi) SEQUENCE DESCRIPTION: SEQ ID NO:29:

ATG TCT AAA TTT ATC GAA CCA AGC GTT GAA GAA ATT AAA CTT GAA AAA        48
Met Ser Lys Phe Ile Glu Pro Ser Val Glu Glu Ile Lys Leu Glu Lys
 1               5                  10                  15

GTA TAT CAA GAT ATG GGA TTA AGT GAT CAA GAA TAT GAA AAA GTT TGC        96
Val Tyr Gln Asp Met Gly Leu Ser Asp Gln Glu Tyr Glu Lys Val Cys
                20                  25                  30

GAT ATT TTA GGC AGA CAA CCT AAC TTT ACA GAA ACA GGT ATC TTT TCT       144
Asp Ile Leu Gly Arg Gln Pro Asn Phe Thr Glu Thr Gly Ile Phe Ser
            35                  40                  45

GTT ATG TGG AGT GAA CAT TGC TCT TAT AAA CAT TCT AAA CCG TTT TTA       192
Val Met Trp Ser Glu His Cys Ser Tyr Lys His Ser Lys Pro Phe Leu
    50                  55                  60

AAG CAA TTT CCT ACG TCA GGT GAC CAT GTG CTT ATG GGG CCT GGT GAA       240
Lys Gln Phe Pro Thr Ser Gly Asp His Val Leu Met Gly Pro Gly Glu
65                  70                  75                  80

GGT GCA GGG GTA GTC GAT ATA GGT GAT AAT CAA GCC GTA GTA TTT AAA       288
Gly Ala Gly Val Val Asp Ile Gly Asp Asn Gln Ala Val Val Phe Lys
                85                  90                  95

GTA GAG TCT CAC AAT CAT CCA TCA GCA ATT GAA CCA TAT CAA GGG GCT       336
Val Glu Ser His Asn His Pro Ser Ala Ile Glu Pro Tyr Gln Gly Ala
            100                 105                 110

GCT ACA GGC GTT GGT GGA ATC ATT CGT GAC ATT GTC TCT ATT GGG GCT       384
Ala Thr Gly Val Gly Gly Ile Ile Arg Asp Ile Val Ser Ile Gly Ala
        115                 120                 125

AGA CCT ATT AAT TTG TTA AAC AGT CTT AGA TTT GGA GAA TTA GAT AAT       432
```

```
Arg Pro Ile Asn Leu Leu Asn Ser Leu Arg Phe Gly Glu Leu Asp Asn
    130                 135                 140

AAA CAA AAC CAA AGA TTA CTT AAA GGT GTT GTA AAG GGT ATC GGA GGT        480
Lys Gln Asn Gln Arg Leu Leu Lys Gly Val Val Lys Gly Ile Gly Gly
145                 150                 155                 160

TAT GGT AAC TGC ATT GGT ATT CCA ACA ACT GCT GGT GAA ATC GAA TTT        528
Tyr Gly Asn Cys Ile Gly Ile Pro Thr Thr Ala Gly Glu Ile Glu Phe
                165                 170                 175

GAT GAA CGT TAT GAT GGC AAT CCA CTT GTT AAT GCA ATG TGT GTT GGT        576
Asp Glu Arg Tyr Asp Gly Asn Pro Leu Val Asn Ala Met Cys Val Gly
            180                 185                 190

GTT ATC AAT CAC GAC ATG ATT CAA AAA GGC ACA GCA AAA GGT GTA GGT        624
Val Ile Asn His Asp Met Ile Gln Lys Gly Thr Ala Lys Gly Val Gly
        195                 200                 205

AAT TCG GTC ATT TAT GTT GGT TTG AAA ACT GGT CGA GAT GGT ATT CAT        672
Asn Ser Val Ile Tyr Val Gly Leu Lys Thr Gly Arg Asp Gly Ile His
    210                 215                 220

GGT GCT ACT TTT GCA TCT GAA GAA TTG ACG GAA GAA AGC GAA AGT AAA        720
Gly Ala Thr Phe Ala Ser Glu Glu Leu Thr Glu Glu Ser Glu Ser Lys
225                 230                 235                 240

CGA CCT TCT GTA CAA ATC GGT GAT CCA TTT GTA GGT AAA AAA TTA ATG        768
Arg Pro Ser Val Gln Ile Gly Asp Pro Phe Val Gly Lys Lys Leu Met
                245                 250                 255

GAA GCA ACA CTT GAA GCA ATT ACA TTT GAT GAA TTA GTT GGT ATT CAA        816
Glu Ala Thr Leu Glu Ala Ile Thr Phe Asp Glu Leu Val Gly Ile Gln
            260                 265                 270

GAT ATG GGT GCT GCT GGT TTA ACA TCT TCA TCG TCT GAA ATG GCG GCA        864
Asp Met Gly Ala Ala Gly Leu Thr Ser Ser Ser Ser Glu Met Ala Ala
        275                 280                 285

AAA GGT GGT AGT GGG TTA CAT TTG AGA TTA GAA CAA GTG CCA ACA CGT        912
Lys Gly Gly Ser Gly Leu His Leu Arg Leu Glu Gln Val Pro Thr Arg
    290                 295                 300

GAG CCA GGT ATT TCT CCT TAT GAA ATG ATG CTT TCA GAA ACT CAA GAA        960
Glu Pro Gly Ile Ser Pro Tyr Glu Met Met Leu Ser Glu Thr Gln Glu
305                 310                 315                 320

CGT ATG TTA CTA GTT GTT GAA AAA GGT ACT GAA CAA AAA TTC TTA GAT       1008
Arg Met Leu Leu Val Val Glu Lys Gly Thr Glu Gln Lys Phe Leu Asp
                325                 330                 335

TTA TTT GAT AAG CAC GAA TTG GAT AGT GCT GTT ATA GGT GAA GTT ACA       1056
Leu Phe Asp Lys His Glu Leu Asp Ser Ala Val Ile Gly Glu Val Thr
            340                 345                 350

GAT ACA AAT CGT TTT GTT TTA ACA TAT GAT GAC GAA GTT TAT GCT GAC       1104
Asp Thr Asn Arg Phe Val Leu Thr Tyr Asp Asp Glu Val Tyr Ala Asp
        355                 360                 365

ATT CCA GTT GAA CCA CTA GCT GAT GAA GCA CCT GTA TAT ATT TTA GAA       1152
Ile Pro Val Glu Pro Leu Ala Asp Glu Ala Pro Val Tyr Ile Leu Glu
    370                 375                 380

GGA GAA GAA AAA GAT TAT AAT ACT TCT AAA AAT GAT TAT ACA CAC ATC       1200
Gly Glu Glu Lys Asp Tyr Asn Thr Ser Lys Asn Asp Tyr Thr His Ile
385                 390                 395                 400

GAT GTT AAA GAT ACT TTC TTT AAA TTA CTT AAG CAT CCG ACT ATA GCA       1248
Asp Val Lys Asp Thr Phe Phe Lys Leu Leu Lys His Pro Thr Ile Ala
                405                 410                 415

TCT AAA CAC TAT TTA TAT GAT CAA TAC GAC CAA CAA GTT GGT GCC AAT       1296
Ser Lys His Tyr Leu Tyr Asp Gln Tyr Asp Gln Gln Val Gly Ala Asn
            420                 425                 430

ACG ATA ATT AAG CCA GGA CTT CAA GCA TCG GTA GTA CGT GTG GAA GGC       1344
Thr Ile Ile Lys Pro Gly Leu Gln Ala Ser Val Val Arg Val Glu Gly
        435                 440                 445
```

```
ACA AAT AAG GCA ATT GCT TCA ACA ATT GAT GGT GAA GCG CGT TAT GTA    1392
Thr Asn Lys Ala Ile Ala Ser Thr Ile Asp Gly Glu Ala Arg Tyr Val
    450                 455                 460

TAT AAC AAT CCA TAT GAA GGT GGA AAG ATG GTA GTA GCT GAA GCT TAT    1440
Tyr Asn Asn Pro Tyr Glu Gly Gly Lys Met Val Val Ala Glu Ala Tyr
465                 470                 475                 480

CGA AAT TTA ATT GCC GTG GGT GCA ACA CCA TTA GCA ATG ACA GAT TGT    1488
Arg Asn Leu Ile Ala Val Gly Ala Thr Pro Leu Ala Met Thr Asp Cys
                485                 490                 495

TTA AAT TAT GGT TCT CCT GAA AAG AAA GAA ATC TAT CAA CAG TTG ATA    1536
Leu Asn Tyr Gly Ser Pro Glu Lys Lys Glu Ile Tyr Gln Gln Leu Ile
                500                 505                 510

GAT TCA ACG AAA GGT ATG GCA GAA GCA TGC GAC ATT CTT AAG ACA CCA    1584
Asp Ser Thr Lys Gly Met Ala Glu Ala Cys Asp Ile Leu Lys Thr Pro
            515                 520                 525

GTA GTT TCT GGT AAT GTA TCT TTA TAT AAC GAA ACG AAA GGT ACT TCT    1632
Val Val Ser Gly Asn Val Ser Leu Tyr Asn Glu Thr Lys Gly Thr Ser
        530                 535                 540

ATT TTC CCA ACA CCA GTT GTT GGA ATG GTA GGT TTG ATT GAA AAT GTA    1680
Ile Phe Pro Thr Pro Val Val Gly Met Val Gly Leu Ile Glu Asn Val
545                 550                 555                 560

AAT TAT TTA AAT GAT TTT GAA CCT CAA GTT GGA GAT AAA TTA TAT TTA    1728
Asn Tyr Leu Asn Asp Phe Glu Pro Gln Val Gly Asp Lys Leu Tyr Leu
                565                 570                 575

ATC GGT GAT ACT AAG GAC GAC TTT GGT GGT AGT CAA CTT GAA AAG TTA    1776
Ile Gly Asp Thr Lys Asp Asp Phe Gly Gly Ser Gln Leu Glu Lys Leu
                580                 585                 590

ATT TAT GGC AAA GTT AAT CAT GAA TTT GAG TCA TTA GAT TTG AGT TCA    1824
Ile Tyr Gly Lys Val Asn His Glu Phe Glu Ser Leu Asp Leu Ser Ser
            595                 600                 605

GAA GTT GAA AAA GGT GAA TCA ATC AAG ACC GCT ATT CGT GAA GGA CTA    1872
Glu Val Glu Lys Gly Glu Ser Ile Lys Thr Ala Ile Arg Glu Gly Leu
        610                 615                 620

TTA TCA CAT GTT CAA ACA GTT GGT AAA GGT GGC TTA CTG ATT ACC TTA    1920
Leu Ser His Val Gln Thr Val Gly Lys Gly Gly Leu Leu Ile Thr Leu
625                 630                 635                 640

GCT AAA CTA AGT GCG CAT TAC GGT TTA GGA TTA AAA TCT TCA ATA GAT    1968
Ala Lys Leu Ser Ala His Tyr Gly Leu Gly Leu Lys Ser Ser Ile Asp
                645                 650                 655

ATA ACA AAT GCA CAA TTG TTT AGT GAG ACG CAA GGC CGA TAT GTT GTT    2016
Ile Thr Asn Ala Gln Leu Phe Ser Glu Thr Gln Gly Arg Tyr Val Val
                660                 665                 670

TCT GTT AAA TCA GGT AAA ACT TTA AAT ATT GAT AAT GCA ATA GAA ATT    2064
Ser Val Lys Ser Gly Lys Thr Leu Asn Ile Asp Asn Ala Ile Glu Ile
            675                 680                 685

GGA CTT TTA ACA GAT AGT GAT AAT TyC AAG GTA ACA ACA CCA TAT ACA    2112
Gly Leu Leu Thr Asp Ser Asp Asn Xaa Lys Val Thr Thr Pro Tyr Thr
        690                 695                 700

GAG ATT AGT GAA AAT GTT TCA GAT ATT AAA CAA ATA TGG GAA GGG GCA    2160
Glu Ile Ser Glu Asn Val Ser Asp Ile Lys Gln Ile Trp Glu Gly Ala
705                 710                 715                 720

ATT GCT CAA TGT TTA ACT ACT CAG GAT TAA                            2190
Ile Ala Gln Cys Leu Thr Thr Gln Asp
                725

(2) INFORMATION FOR SEQ ID NO:30:

(i) SEQUENCE CHARACTERISTICS:
        (A) LENGTH: 729 amino acids
        (B) TYPE: amino acid
        (D) TOPOLOGY: linear
```

(ii) MOLECULE TYPE: protein (xi) SEQUENCE DESCRIPTION: SEQ ID NO:30:

```
Met Ser Lys Phe Ile Glu Pro Ser Val Glu Glu Ile Lys Leu Glu Lys
 1               5                  10                  15

Val Tyr Gln Asp Met Gly Leu Ser Asp Gln Glu Tyr Glu Lys Val Cys
                20                  25                  30

Asp Ile Leu Gly Arg Gln Pro Asn Phe Thr Glu Thr Gly Ile Phe Ser
            35                  40                  45

Val Met Trp Ser Glu His Cys Ser Tyr Lys His Ser Lys Pro Phe Leu
        50                  55                  60

Lys Gln Phe Pro Thr Ser Gly Asp His Val Leu Met Gly Pro Gly Glu
 65                  70                  75                  80

Gly Ala Gly Val Val Asp Ile Gly Asp Asn Gln Ala Val Val Phe Lys
                85                  90                  95

Val Glu Ser His Asn His Pro Ser Ala Ile Glu Pro Tyr Gln Gly Ala
                100                 105                 110

Ala Thr Gly Val Gly Gly Ile Ile Arg Asp Ile Val Ser Ile Gly Ala
            115                 120                 125

Arg Pro Ile Asn Leu Leu Asn Ser Leu Arg Phe Gly Glu Leu Asp Asn
130                 135                 140

Lys Gln Asn Gln Arg Leu Leu Lys Gly Val Val Lys Gly Ile Gly Gly
145                 150                 155                 160

Tyr Gly Asn Cys Ile Gly Ile Pro Thr Thr Ala Gly Glu Ile Glu Phe
                165                 170                 175

Asp Glu Arg Tyr Asp Gly Asn Pro Leu Val Asn Ala Met Cys Val Gly
            180                 185                 190

Val Ile Asn His Asp Met Ile Gln Lys Gly Thr Ala Lys Gly Val Gly
        195                 200                 205

Asn Ser Val Ile Tyr Val Gly Leu Lys Thr Gly Arg Asp Gly Ile His
    210                 215                 220

Gly Ala Thr Phe Ala Ser Glu Glu Leu Thr Glu Ser Glu Ser Lys
225                 230                 235                 240

Arg Pro Ser Val Gln Ile Gly Asp Pro Phe Val Gly Lys Lys Leu Met
                245                 250                 255

Glu Ala Thr Leu Glu Ala Ile Thr Phe Asp Glu Leu Val Gly Ile Gln
            260                 265                 270

Asp Met Gly Ala Ala Gly Leu Thr Ser Ser Ser Glu Met Ala Ala
        275                 280                 285

Lys Gly Gly Ser Gly Leu His Leu Arg Leu Glu Gln Val Pro Thr Arg
290                 295                 300

Glu Pro Gly Ile Ser Pro Tyr Glu Met Met Leu Ser Glu Thr Gln Glu
305                 310                 315                 320

Arg Met Leu Leu Val Val Glu Lys Gly Thr Glu Gln Lys Phe Leu Asp
                325                 330                 335

Leu Phe Asp Lys His Glu Leu Asp Ser Ala Val Ile Gly Glu Val Thr
            340                 345                 350

Asp Thr Asn Arg Phe Val Leu Thr Tyr Asp Asp Glu Val Tyr Ala Asp
        355                 360                 365

Ile Pro Val Glu Pro Leu Ala Asp Glu Ala Pro Val Tyr Ile Leu Glu
    370                 375                 380

Gly Glu Glu Lys Asp Tyr Asn Thr Ser Lys Asn Asp Tyr Thr His Ile
385                 390                 395                 400
```

```
Asp Val Lys Asp Thr Phe Phe Lys Leu Leu Lys His Pro Thr Ile Ala
                405                 410                 415

Ser Lys His Tyr Leu Tyr Asp Gln Tyr Asp Gln Gln Val Gly Ala Asn
            420                 425                 430

Thr Ile Ile Lys Pro Gly Leu Gln Ala Ser Val Val Arg Val Glu Gly
            435                 440                 445

Thr Asn Lys Ala Ile Ala Ser Thr Ile Asp Gly Glu Ala Arg Tyr Val
        450                 455                 460

Tyr Asn Asn Pro Tyr Glu Gly Gly Lys Met Val Val Ala Glu Ala Tyr
465                 470                 475                 480

Arg Asn Leu Ile Ala Val Gly Ala Thr Pro Leu Ala Met Thr Asp Cys
                485                 490                 495

Leu Asn Tyr Gly Ser Pro Glu Lys Lys Glu Ile Tyr Gln Gln Leu Ile
            500                 505                 510

Asp Ser Thr Lys Gly Met Ala Glu Ala Cys Asp Ile Leu Lys Thr Pro
            515                 520                 525

Val Val Ser Gly Asn Val Ser Leu Tyr Asn Glu Thr Lys Gly Thr Ser
        530                 535                 540

Ile Phe Pro Thr Pro Val Val Gly Met Val Gly Leu Ile Glu Asn Val
545                 550                 555                 560

Asn Tyr Leu Asn Asp Phe Glu Pro Gln Val Gly Asp Lys Leu Tyr Leu
                565                 570                 575

Ile Gly Asp Thr Lys Asp Asp Phe Gly Gly Ser Gln Leu Glu Lys Leu
            580                 585                 590

Ile Tyr Gly Lys Val Asn His Glu Phe Glu Ser Leu Asp Leu Ser Ser
        595                 600                 605

Glu Val Glu Lys Gly Glu Ser Ile Lys Thr Ala Ile Arg Glu Gly Leu
610                 615                 620

Leu Ser His Val Gln Thr Val Gly Lys Gly Gly Leu Leu Ile Thr Leu
625                 630                 635                 640

Ala Lys Leu Ser Ala His Tyr Gly Leu Gly Leu Lys Ser Ser Ile Asp
                645                 650                 655

Ile Thr Asn Ala Gln Leu Phe Ser Glu Thr Gln Gly Arg Tyr Val Val
            660                 665                 670

Ser Val Lys Ser Gly Lys Thr Leu Asn Ile Asp Asn Ala Ile Glu Ile
            675                 680                 685

Gly Leu Leu Thr Asp Ser Asp Asn Xaa Lys Val Thr Thr Pro Tyr Thr
        690                 695                 700

Glu Ile Ser Glu Asn Val Ser Asp Ile Lys Gln Ile Trp Glu Gly Ala
705                 710                 715                 720

Ile Ala Gln Cys Leu Thr Thr Gln Asp
                725

(2) INFORMATION FOR SEQ ID NO:31:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p10b18/p6b18)"

(ix) FEATURE:
        (A) NAME/KEY: CDS
        (B) LOCATION: 1..726
```

(xi) SEQUENCE DESCRIPTION: SEQ ID NO:31:

```
ATG ACT AAA TTA TTT ATA CCT TAT ATT ATG GGC AAT AAA GAT TTG ATT     48
Met Thr Lys Leu Phe Ile Pro Tyr Ile Met Gly Asn Lys Asp Leu Ile
 1               5                  10                  15

GAA AAT GCA ACA TTG TTG AGT GAA AAT GGT GCA GAT ATA ATT GAA ATT     96
Glu Asn Ala Thr Leu Leu Ser Glu Asn Gly Ala Asp Ile Ile Glu Ile
             20                  25                  30

GGA GTA CCT TTC TCT GAT CCG GTT GCT GAT GGT CCA GTT ATC ATG GAA    144
Gly Val Pro Phe Ser Asp Pro Val Ala Asp Gly Pro Val Ile Met Glu
         35                  40                  45

GCA GGT CAA CAA GCG ATT AAA CAA GGC ATC ACG ATA GAT TAT ATT TTC    192
Ala Gly Gln Gln Ala Ile Lys Gln Gly Ile Thr Ile Asp Tyr Ile Phe
     50                  55                  60

AAT CAA TTA GAA AAA CAT GGT GAT CAA ATT AAG TGT AAC TAT GTA TTA    240
Asn Gln Leu Glu Lys His Gly Asp Gln Ile Lys Cys Asn Tyr Val Leu
 65                  70                  75                  80

ATG ACG TAT TAT AAT ATT ATT TGT CAT TAT GGA GAA CAA GCG TTT TTT    288
Met Thr Tyr Tyr Asn Ile Ile Cys His Tyr Gly Glu Gln Ala Phe Phe
                 85                  90                  95

GAA AAA TGT CGA GAT ACT GGT GTC TAC GGC TTA ATT ATT CCT GAT TTA    336
Glu Lys Cys Arg Asp Thr Gly Val Tyr Gly Leu Ile Ile Pro Asp Leu
            100                 105                 110

CCA TAT GAA TTA TCG CAG CGT TTA AAA CAA CAA TTT AGT CAC TAT GGC    384
Pro Tyr Glu Leu Ser Gln Arg Leu Lys Gln Gln Phe Ser His Tyr Gly
        115                 120                 125

GTC AAA ATC ATA TCG TTA GTT GCG ATG ACT ACT GAT GAC AAA CGT ATA    432
Val Lys Ile Ile Ser Leu Val Ala Met Thr Thr Asp Asp Lys Arg Ile
    130                 135                 140

AAA GAT ATC GTA TCC CAT GCG GAA GGC TTT ATT TAT ACT GTG ACG ATG    480
Lys Asp Ile Val Ser His Ala Glu Gly Phe Ile Tyr Thr Val Thr Met
145                 150                 155                 160

AAT GCG ACA ACA GGG CAA AAC GGT GCG TTT CAT CCA GAA TTA AAA CGA    528
Asn Ala Thr Thr Gly Gln Asn Gly Ala Phe His Pro Glu Leu Lys Arg
                165                 170                 175

AAA ATT GAG TCA ATT AAA GCG ATA GCC AAT GTG CCA GTT GTC GCA GGA    576
Lys Ile Glu Ser Ile Lys Ala Ile Ala Asn Val Pro Val Val Ala Gly
            180                 185                 190

TTT GGT ATA AGA ACA CCA CAA CAT GTT GCA GAT ATA AAA GAG GTT GCA    624
Phe Gly Ile Arg Thr Pro Gln His Val Ala Asp Ile Lys Glu Val Ala
        195                 200                 205

GAT GGC ATT GTC ATT GGT AGC GAA ATC GTT AAG CGA TTT AAA TCT AAC    672
Asp Gly Ile Val Ile Gly Ser Glu Ile Val Lys Arg Phe Lys Ser Asn
    210                 215                 220

ACG CGT GAG GAA ATC ATT AAA TAT TTA CAA TCT ATC CAA CAA ACA TTG    720
Thr Arg Glu Glu Ile Ile Lys Tyr Leu Gln Ser Ile Gln Gln Thr Leu
225                 230                 235                 240

AAT AAT TAA                                                        729
Asn Asn
```

(2) INFORMATION FOR SEQ ID NO:32:

(i) SEQUENCE CHARACTERISTICS:
        (A) LENGTH: 242 amino acids
        (B) TYPE: amino acid
        (D) TOPOLOGY: linear (ii) MOLECULE TYPE: protein (xi) SEQUENCE DESCRIPTION: SEQ ID NO:32:

Met Thr Lys Leu Phe Ile Pro Tyr Ile Met Gly Asn Lys Asp Leu Ile

```
  1               5                   10                  15
Glu Asn Ala Thr Leu Leu Ser Glu Asn Gly Ala Asp Ile Ile Glu Ile
                20                  25                  30

Gly Val Pro Phe Ser Asp Pro Val Ala Asp Gly Pro Val Ile Met Glu
            35                  40                  45

Ala Gly Gln Gln Ala Ile Lys Gln Gly Ile Thr Ile Asp Tyr Ile Phe
        50                  55                  60

Asn Gln Leu Glu Lys His Gly Asp Gln Ile Lys Cys Asn Tyr Val Leu
 65                 70                  75                  80

Met Thr Tyr Tyr Asn Ile Ile Cys His Tyr Gly Glu Gln Ala Phe Phe
                85                  90                  95

Glu Lys Cys Arg Asp Thr Gly Val Tyr Gly Leu Ile Ile Pro Asp Leu
            100                 105                 110

Pro Tyr Glu Leu Ser Gln Arg Leu Lys Gln Gln Phe Ser His Tyr Gly
        115                 120                 125

Val Lys Ile Ile Ser Leu Val Ala Met Thr Thr Asp Asp Lys Arg Ile
        130                 135                 140

Lys Asp Ile Val Ser His Ala Glu Gly Phe Ile Tyr Thr Val Thr Met
145                 150                 155                 160

Asn Ala Thr Thr Gly Gln Asn Gly Ala Phe His Pro Glu Leu Lys Arg
                165                 170                 175

Lys Ile Glu Ser Ile Lys Ala Ile Ala Asn Val Pro Val Val Ala Gly
                180                 185                 190

Phe Gly Ile Arg Thr Pro Gln His Val Ala Asp Ile Lys Glu Val Ala
            195                 200                 205

Asp Gly Ile Val Ile Gly Ser Glu Ile Val Lys Arg Phe Lys Ser Asn
        210                 215                 220

Thr Arg Glu Glu Ile Ile Lys Tyr Leu Gln Ser Ile Gln Gln Thr Leu
225                 230                 235                 240

Asn Asn (2) INFORMATION FOR SEQ ID NO:33:

(i) SEQUENCE CHARACTERISTICS:
        (A) LENGTH: 1215 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p10b66)"

(ix) FEATURE:
        (A) NAME/KEY: CDS
        (B) LOCATION: 1..1212

(xi) SEQUENCE DESCRIPTION: SEQ ID NO:33:

ATG AAT AAA CAA ATA CAA ACA GAA GCA GAT GAA TTA GGT TTC TTT GGT      48
Met Asn Lys Gln Ile Gln Thr Glu Ala Asp Glu Leu Gly Phe Phe Gly
 1               5                   10                  15

GAA TAT GGA GGG CAA TAT GTT CCA GAA ACA TTA ATG CCA GCA ATT ATT      96
Glu Tyr Gly Gly Gln Tyr Val Pro Glu Thr Leu Met Pro Ala Ile Ile
            20                  25                  30

GAG TTG AAA AAA GCT TAT AAA GAG GCA AAA GCA GAC CCA GAG TTT CAA     144
Glu Leu Lys Lys Ala Tyr Lys Glu Ala Lys Ala Asp Pro Glu Phe Gln
        35                  40                  45

AGA GAA CTG GAA TAC TAT TTA TCA GAG TAT GTA GGA CGC GCG ACA CCA     192
Arg Glu Leu Glu Tyr Tyr Leu Ser Glu Tyr Val Gly Arg Ala Thr Pro
 50                 55                  60
```

```
CTT ACA TAT GCT GCA TCA TAT ACT GAA AGC CTA GGT GGC GCT AAA ATA         240
Leu Thr Tyr Ala Ala Ser Tyr Thr Glu Ser Leu Gly Gly Ala Lys Ile
 65                  70                  75                  80

TAT TTG AAA CGA GAG GAT CTA AAT CAT ACA GGC GCC CAT AAA ATT AAT         288
Tyr Leu Lys Arg Glu Asp Leu Asn His Thr Gly Ala His Lys Ile Asn
                 85                  90                  95

AAT GCG TTA GGT CAA GCG TTG CTT GCT AAA AGA ATG GGC AAG AAG AAG         336
Asn Ala Leu Gly Gln Ala Leu Leu Ala Lys Arg Met Gly Lys Lys Lys
            100                 105                 110

CTT GTT GCT GAA ACT GGT GCG GGT CAA CAT GGT GTA GCT AGT GCT ACG         384
Leu Val Ala Glu Thr Gly Ala Gly Gln His Gly Val Ala Ser Ala Thr
            115                 120                 125

GTT GCT GCA TTA TTT GAT ATG GAA CTT GTT GTC TTT ATG GGA AGT GAA         432
Val Ala Ala Leu Phe Asp Met Glu Leu Val Val Phe Met Gly Ser Glu
        130                 135                 140

GAT ATT AAA AGA CAA CAA CTT AAT GTA TTT AGA ATG GAA TTA CTT GGT         480
Asp Ile Lys Arg Gln Gln Leu Asn Val Phe Arg Met Glu Leu Leu Gly
145                 150                 155                 160

GCA AAG GTT GTG GCA GTT GAA GAT GGT CAA GGG ACT TTA TCG GAT GCA         528
Ala Lys Val Val Ala Val Glu Asp Gly Gln Gly Thr Leu Ser Asp Ala
                165                 170                 175

GTT AAT AAA GCA TTG CAA TAT TGG GTA AGT CAT GTA GAT GAT ACA CAT         576
Val Asn Lys Ala Leu Gln Tyr Trp Val Ser His Val Asp Asp Thr His
            180                 185                 190

TAT TTA TTA GGT TCT GCA TTA GGT CCA GAC CCG TTC CCA ACG ATT GTT         624
Tyr Leu Leu Gly Ser Ala Leu Gly Pro Asp Pro Phe Pro Thr Ile Val
            195                 200                 205

AGA GAT TTT CAG AGT GTG ATT GGT AAA GAA ATA AAA TCA CAG ATA TTG         672
Arg Asp Phe Gln Ser Val Ile Gly Lys Glu Ile Lys Ser Gln Ile Leu
        210                 215                 220

AAG AAA GAA GGT CGA CTT CCG GAT GCA ATT GTA GCA TGT ATC GGT GGT         720
Lys Lys Glu Gly Arg Leu Pro Asp Ala Ile Val Ala Cys Ile Gly Gly
225                 230                 235                 240

GGC TCA AAT GCA ATC GGT ACA TTT TAT CCA TTT ATT AAA GAT GAT GTT         768
Gly Ser Asn Ala Ile Gly Thr Phe Tyr Pro Phe Ile Lys Asp Asp Val
                245                 250                 255

GCA TTA TAC GGT GTT GAA GCC GCA GGT CAA GGC GAT GAT ACT GAT AAA         816
Ala Leu Tyr Gly Val Glu Ala Ala Gly Gln Gly Asp Asp Thr Asp Lys
            260                 265                 270

CAT GCA CTT GCA ATT GGC AAA GGA TCA CCT GGC GTA TTA CAT GGT ACT         864
His Ala Leu Ala Ile Gly Lys Gly Ser Pro Gly Val Leu His Gly Thr
        275                 280                 285

AAA ATG TAT TTA ATT CAA GAT GAA GAT GGG CAA GTG CAA CTA GCA CAT         912
Lys Met Tyr Leu Ile Gln Asp Glu Asp Gly Gln Val Gln Leu Ala His
        290                 295                 300

TCT ATT TCA GCA GGA CTT GAT TAT CCT GGT ATT GGA CCA GAA CAT TCT         960
Ser Ile Ser Ala Gly Leu Asp Tyr Pro Gly Ile Gly Pro Glu His Ser
305                 310                 315                 320

TAT TAC CAC GAC ATT GGT AGA GTA ACT TTT GAA AAT GCT AGT GAT ACA        1008
Tyr Tyr His Asp Ile Gly Arg Val Thr Phe Glu Asn Ala Ser Asp Thr
                325                 330                 335

CAA GCA ATG AAT GCT TTA ATC AAC TTT ACA AAA CAT GAA GGT ATT ATA        1056
Gln Ala Met Asn Ala Leu Ile Asn Phe Thr Lys His Glu Gly Ile Ile
            340                 345                 350

CCT GCA ATT GAA AGT GCA CAT GCA CTG AGT TAT GTT GAA AGA CTA GCG        1104
Pro Ala Ile Glu Ser Ala His Ala Leu Ser Tyr Val Glu Arg Leu Ala
        355                 360                 365

CCT ACG ATG TCG AAA GAA GAT ATT ATT GTA GTA ACT ATT TCT GGA CGT        1152
Pro Thr Met Ser Lys Glu Asp Ile Ile Val Val Thr Ile Ser Gly Arg
```

```
                    370                 375                 380
GGC GAT AAA GAT ATG GAA ACA ATT AGA CAA TAT ATG GTA GAG CGA GGT    1200
Gly Asp Lys Asp Met Glu Thr Ile Arg Gln Tyr Met Val Glu Arg Gly
385                 390                 395                 400

CTT GCA AAT GAC TAA                                                 1215
Leu Ala Asn Asp
```

(2) INFORMATION FOR SEQ ID NO:34:

(i) SEQUENCE CHARACTERISTICS:
        (A) LENGTH: 404 amino acids
        (B) TYPE: amino acid
        (D) TOPOLOGY: linear (ii) MOLECULE TYPE: protein (xi) SEQUENCE DESCRIPTION: SEQ ID NO:34:

```
Met Asn Lys Gln Ile Gln Thr Glu Ala Asp Glu Leu Gly Phe Phe Gly
 1               5                  10                  15

Glu Tyr Gly Gly Gln Tyr Val Pro Glu Thr Leu Met Pro Ala Ile Ile
                20                  25                  30

Glu Leu Lys Lys Ala Tyr Lys Glu Ala Lys Ala Asp Pro Glu Phe Gln
             35                  40                  45

Arg Glu Leu Glu Tyr Tyr Leu Ser Glu Tyr Val Gly Arg Ala Thr Pro
         50                  55                  60

Leu Thr Tyr Ala Ala Ser Tyr Thr Glu Ser Leu Gly Ala Lys Ile
 65                  70                  75                  80

Tyr Leu Lys Arg Glu Asp Leu Asn His Thr Gly Ala His Lys Ile Asn
                 85                  90                  95

Asn Ala Leu Gly Gln Ala Leu Leu Ala Lys Arg Met Gly Lys Lys Lys
                100                 105                 110

Leu Val Ala Glu Thr Gly Ala Gly Gln His Gly Val Ala Ser Ala Thr
             115                 120                 125

Val Ala Ala Leu Phe Asp Met Glu Leu Val Val Phe Met Gly Ser Glu
130                 135                 140

Asp Ile Lys Arg Gln Gln Leu Asn Val Phe Arg Met Glu Leu Leu Gly
145                 150                 155                 160

Ala Lys Val Val Ala Val Glu Asp Gly Gln Gly Thr Leu Ser Asp Ala
                165                 170                 175

Val Asn Lys Ala Leu Gln Tyr Trp Val Ser His Val Asp Asp Thr His
                180                 185                 190

Tyr Leu Leu Gly Ser Ala Leu Gly Pro Asp Pro Phe Pro Thr Ile Val
             195                 200                 205

Arg Asp Phe Gln Ser Val Ile Gly Lys Glu Ile Lys Ser Gln Ile Leu
210                 215                 220

Lys Lys Glu Gly Arg Leu Pro Asp Ala Ile Val Ala Cys Ile Gly Gly
225                 230                 235                 240

Gly Ser Asn Ala Ile Gly Thr Phe Tyr Pro Phe Ile Lys Asp Asp Val
                245                 250                 255

Ala Leu Tyr Gly Val Glu Ala Ala Gly Gln Gly Asp Asp Thr Asp Lys
                260                 265                 270

His Ala Leu Ala Ile Gly Lys Gly Ser Pro Gly Val Leu His Gly Thr
             275                 280                 285

Lys Met Tyr Leu Ile Gln Asp Glu Asp Gly Gln Val Gln Leu Ala His
         290                 295                 300

Ser Ile Ser Ala Gly Leu Asp Tyr Pro Gly Ile Gly Pro Glu His Ser
```

-continued

```
        305                 310                 315                 320
    Tyr Tyr His Asp Ile Gly Arg Val Thr Phe Glu Asn Ala Ser Asp Thr
                    325                 330                 335

Gln Ala Met Asn Ala Leu Ile Asn Phe Thr Lys His Glu Gly Ile Ile
                    340                 345                 350

Pro Ala Ile Glu Ser Ala His Ala Leu Ser Tyr Val Glu Arg Leu Ala
                    355                 360                 365

Pro Thr Met Ser Lys Glu Asp Ile Ile Val Val Thr Ile Ser Gly Arg
                    370                 375                 380

Gly Asp Lys Asp Met Glu Thr Ile Arg Gln Tyr Met Val Glu Arg Gly
    385                 390                 395                 400

Leu Ala Asn Asp (2) INFORMATION FOR SEQ ID NO:35:

(i) SEQUENCE CHARACTERISTICS:
           (A) LENGTH: 1008 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "DNA (genomic) (p10c34)"
               Unknown = Xaa (ix) FEATURE:
           (A) NAME/KEY: CDS
           (B) LOCATION: 1..1005

(xi) SEQUENCE DESCRIPTION: SEQ ID NO:35:

ATG AAA ACC ATG ACA TTA CTA ACA AGA ATA AAA ACT GAA ACT ATA TTA        48
Met Lys Thr Met Thr Leu Leu Thr Arg Ile Lys Thr Glu Thr Ile Leu
 1               5                  10                  15

CTT GAA AGC GAC ATT AAA GAG CTA ATC GAT ATA CTT ATT TCT CCT AGT        96
Leu Glu Ser Asp Ile Lys Glu Leu Ile Asp Ile Leu Ile Ser Pro Ser
                20                  25                  30

ATT GGA ACT GAT ATT AAA TAT GAA TTA CTT AGT TCC TAT TCG GAG CGA       144
Ile Gly Thr Asp Ile Lys Tyr Glu Leu Leu Ser Ser Tyr Ser Glu Arg
            35                  40                  45

GAA ATC CAA CAA CAA GAA TTA ACA TAT ATT GTA CGT AGC TTA ATT AAT       192
Glu Ile Gln Gln Gln Glu Leu Thr Tyr Ile Val Arg Ser Leu Ile Asn
    50                  55                  60

ACA ATG TAT CCA CAT CAA CCA TGT TAT GAA GGG GCT ATG TGT GTG TGC       240
Thr Met Tyr Pro His Gln Pro Cys Tyr Glu Gly Ala Met Cys Val Cys
65                  70                  75                  80

GGC ACA GGT GGT GAC AAG TCA AAT AGT TTC AAC ATT TCA ACG ACT GTT       288
Gly Thr Gly Gly Asp Lys Ser Asn Ser Phe Asn Ile Ser Thr Thr Val
                85                  90                  95

GCT TTT GTT GTA GCA AGT GCT GGC GTA AAA GTT ATA AAA CAT GGT AAT       336
Ala Phe Val Val Ala Ser Ala Gly Val Lys Val Ile Lys His Gly Asn
                100                 105                 110

AAA AGT ATT ACC TCA AAT TCA GGT AGT ACG GAT TTG TTA AAT CAA ATG       384
Lys Ser Ile Thr Ser Asn Ser Gly Ser Thr Asp Leu Leu Asn Gln Met
            115                 120                 125

AAC ATA CAA ACA ACA ACT GTT GAT GAT ACA CCT AAC CAA TTA AAT GAn       432
Asn Ile Gln Thr Thr Thr Val Asp Asp Thr Pro Asn Gln Leu Asn Xaa
        130                 135                 140

AAA GAC CTT GTA TTC ATT GGT GCA ACT GAA TCA TAT CCA ATC ATG AAG       480
Lys Asp Leu Val Phe Ile Gly Ala Thr Glu Ser Tyr Pro Ile Met Lys
145                 150                 155                 160

TAT ATG CAA CCA GTT AGA AAA ATG ATT GGA AAG CCT ACA ATA TTA AAC       528
```

```
                Tyr Met Gln Pro Val Arg Lys Met Ile Gly Lys Pro Thr Ile Leu Asn
                                165                 170                 175

CTT GTG GGT CCA TTA ATT AAT CCA TAT CAC TTA ACG TAT CAA ATG GTA           576
Leu Val Gly Pro Leu Ile Asn Pro Tyr His Leu Thr Tyr Gln Met Val
            180                 185                 190

GGC GTC TTT GAT CCT ACA AAG TTA AAG TTA GTT GCT AAA ACG ATT AAA           624
Gly Val Phe Asp Pro Thr Lys Leu Lys Leu Val Ala Lys Thr Ile Lys
        195                 200                 205

GAT TTA GGT AGA AAA CGT GCA ATC GTT TTA CAT GGT GCA AAT GGT ATG           672
Asp Leu Gly Arg Lys Arg Ala Ile Val Leu His Gly Ala Asn Gly Met
    210                 215                 220

GAT GAA GCA ACA CTA TCT GGT GAT AAT TTG ATA TAT GAA TTG ACT GAA           720
Asp Glu Ala Thr Leu Ser Gly Asp Asn Leu Ile Tyr Glu Leu Thr Glu
225                 230                 235                 240

GAT GGA GAA ATC AAA AAT TAC ACA TTA AAT GCG ACT GAT TAT GGT TTG           768
Asp Gly Glu Ile Lys Asn Tyr Thr Leu Asn Ala Thr Asp Tyr Gly Leu
                245                 250                 255

AAA CAT GCG CCG AAT AGT GAT TTT AAA GGC GGT TCA CCT GAA GAA AAT           816
Lys His Ala Pro Asn Ser Asp Phe Lys Gly Gly Ser Pro Glu Glu Asn
            260                 265                 270

TTA GCA ATC TCC CTT AAT ATC TTG AAT GGT AAA GAT CAG TCA rGT CGA           864
Leu Ala Ile Ser Leu Asn Ile Leu Asn Gly Lys Asp Gln Ser Xaa Arg
        275                 280                 285

CGT GAT GTT GTC TTA CTA AAT GCG GGT TTA AGC CTT TAT GTT GCA GAG           912
Arg Asp Val Val Leu Leu Asn Ala Gly Leu Ser Leu Tyr Val Ala Glu
    290                 295                 300

AAA rTG GAT ACC ATC GCA GAA GGC ATA GAA CTT GCA ACT ACA TTG ATT           960
Lys Xaa Asp Thr Ile Ala Glu Gly Ile Glu Leu Ala Thr Thr Leu Ile
305                 310                 315                 320

GAT AAT GGT GAA GCA TTG GAA AAA TAC CAT CAA ATG AGA GGT GAA              1005
Asp Asn Gly Glu Ala Leu Glu Lys Tyr His Gln Met Arg Gly Glu
                325                 330                 335

TAA                                                                      1008

(2) INFORMATION FOR SEQ ID NO:36:

(i) SEQUENCE CHARACTERISTICS:
        (A) LENGTH: 335 amino acids
        (B) TYPE: amino acid
        (D) TOPOLOGY: linear (ii) MOLECULE TYPE: protein (xi) SEQUENCE DESCRIPTION: SEQ ID NO:36:

Met Lys Thr Met Thr Leu Leu Thr Arg Ile Lys Thr Glu Thr Ile Leu
 1               5                  10                  15

Leu Glu Ser Asp Ile Lys Glu Leu Ile Asp Ile Leu Ile Ser Pro Ser
                20                  25                  30

Ile Gly Thr Asp Ile Lys Tyr Glu Leu Leu Ser Ser Tyr Ser Glu Arg
            35                  40                  45

Glu Ile Gln Gln Gln Glu Leu Thr Tyr Ile Val Arg Ser Leu Ile Asn
        50                  55                  60

Thr Met Tyr Pro His Gln Pro Cys Tyr Glu Gly Ala Met Cys Val Cys
65                  70                  75                  80

Gly Thr Gly Gly Asp Lys Ser Asn Ser Phe Asn Ile Ser Thr Thr Val
                85                  90                  95

Ala Phe Val Val Ala Ser Ala Gly Val Lys Val Ile Lys His Gly Asn
            100                 105                 110

Lys Ser Ile Thr Ser Asn Ser Gly Ser Thr Asp Leu Leu Asn Gln Met
```

```
                115                 120                   125
Asn Ile Gln Thr Thr Val Asp Asp Thr Pro Asn Gln Leu Asn Xaa
        130                 135                 140

Lys Asp Leu Val Phe Ile Gly Ala Thr Glu Ser Tyr Pro Ile Met Lys
145                 150                 155                 160

Tyr Met Gln Pro Val Arg Lys Met Ile Gly Lys Pro Thr Ile Leu Asn
                165                 170                 175

Leu Val Gly Pro Leu Ile Asn Pro Tyr His Leu Thr Tyr Gln Met Val
            180                 185                 190

Gly Val Phe Asp Pro Thr Lys Leu Lys Leu Val Ala Lys Thr Ile Lys
        195                 200                 205

Asp Leu Gly Arg Lys Arg Ala Ile Val Leu His Gly Ala Asn Gly Met
210                 215                 220

Asp Glu Ala Thr Leu Ser Gly Asp Asn Leu Ile Tyr Glu Leu Thr Glu
225                 230                 235                 240

Asp Gly Glu Ile Lys Asn Tyr Thr Leu Asn Ala Thr Asp Tyr Gly Leu
                245                 250                 255

Lys His Ala Pro Asn Ser Asp Phe Lys Gly Gly Ser Pro Glu Glu Asn
            260                 265                 270

Leu Ala Ile Ser Leu Asn Ile Leu Asn Gly Lys Asp Gln Ser Xaa Arg
        275                 280                 285

Arg Asp Val Val Leu Leu Asn Ala Gly Leu Ser Leu Tyr Val Ala Glu
290                 295                 300

Lys Xaa Asp Thr Ile Ala Glu Gly Ile Glu Leu Ala Thr Thr Leu Ile
305                 310                 315                 320

Asp Asn Gly Glu Ala Leu Glu Lys Tyr His Gln Met Arg Gly Glu
                325                 330                 335

(2) INFORMATION FOR SEQ ID NO:37:

(i) SEQUENCE CHARACTERISTICS:
        (A) LENGTH: 1254 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p4c27)"

(ix) FEATURE:
        (A) NAME/KEY: CDS
        (B) LOCATION: 1..1251

(xi) SEQUENCE DESCRIPTION: SEQ ID NO:37:

ATG GCG GAA ATT AAG GTA CCT GAA TTA GCA GAA TCA ATC TCA GAA GGA        48
Met Ala Glu Ile Lys Val Pro Glu Leu Ala Glu Ser Ile Ser Glu Gly
 1               5                  10                  15

ACA ATA GCC CAA TGG TTA AAG CAG CCT GGT GAC TAT GTA GAA CAG GGT        96
Thr Ile Ala Gln Trp Leu Lys Gln Pro Gly Asp Tyr Val Glu Gln Gly
                20                  25                  30

GAA TAT CTG CTT GAA CTA GAA ACG GAT AAA GTG AAT GTT GAA TTG ACA       144
Glu Tyr Leu Leu Glu Leu Glu Thr Asp Lys Val Asn Val Glu Leu Thr
            35                  40                  45

GCA GAA GAA TCG GGT GTA CTT CAA GAG GTA TTG AAA GAT TCG GGT GAT       192
Ala Glu Glu Ser Gly Val Leu Gln Glu Val Leu Lys Asp Ser Gly Asp
        50                  55                  60

ACC GTC CAG GTC GGA GAA ATT ATC GGT ACG ATT TCA GAA GGC GCG GGT       240
Thr Val Gln Val Gly Glu Ile Ile Gly Thr Ile Ser Glu Gly Ala Gly
65                  70                  75                  80
```

```
GAA AGT TCT GCC CCT GCT CCT ACA GAG AAA ACA GAA AGC AAG GAA AGC      288
Glu Ser Ser Ala Pro Ala Pro Thr Glu Lys Thr Glu Ser Lys Glu Ser
                85                  90                  95

GTA AAA GAA GAG AAA CAG GCT GAA CCA GCT GCA CAA GAG GTG AGC GAG      336
Val Lys Glu Glu Lys Gln Ala Glu Pro Ala Ala Gln Glu Val Ser Glu
            100                 105                 110

GAA GCA CAA TCT GAA GCA AAA TCA AGA ACG ATC GCT TCT CCG TCG GCC      384
Glu Ala Gln Ser Glu Ala Lys Ser Arg Thr Ile Ala Ser Pro Ser Ala
            115                 120                 125

CGT AAG CTT GCG AGA GAA AAA GGA ATT GAC CTG TCT CAA GTT CCA ACT      432
Arg Lys Leu Ala Arg Glu Lys Gly Ile Asp Leu Ser Gln Val Pro Thr
    130                 135                 140

GGA GAT CCG CTT GGA AGA GTG CGC AAG CAG GAT GTC GAA GCG TAC GAA      480
Gly Asp Pro Leu Gly Arg Val Arg Lys Gln Asp Val Glu Ala Tyr Glu
145                 150                 155                 160

AAA CCG GCA TCA AAA CCG GCT CCT CAG CAA AAG CAG CAG CCT CAG GCT      528
Lys Pro Ala Ser Lys Pro Ala Pro Gln Gln Lys Gln Gln Pro Gln Ala
                165                 170                 175

CAA AAA GCA CAG CAA AGC TTT GAC AAA CCT GTT GAA GTG CAA AAA ATG      576
Gln Lys Ala Gln Gln Ser Phe Asp Lys Pro Val Glu Val Gln Lys Met
            180                 185                 190

TCA CGC CGC AGA CAA ACG ATT GCA AAA CGC CTT GTA GAG GTA CAG CAA      624
Ser Arg Arg Arg Gln Thr Ile Ala Lys Arg Leu Val Glu Val Gln Gln
            195                 200                 205

ACA TCA GCG ATG CTG ACT ACA TTT AAT GAA GTG GAC ATG ACG GCT GTC      672
Thr Ser Ala Met Leu Thr Thr Phe Asn Glu Val Asp Met Thr Ala Val
    210                 215                 220

ATG AAT CTC AGA AAA CGC CGC AAA GAT CAA TTT TTT GAG CAA AAT GAA      720
Met Asn Leu Arg Lys Arg Arg Lys Asp Gln Phe Phe Glu Gln Asn Glu
225                 230                 235                 240

GTG AAG CTC GGC TTT ATG TCT TTC TTC ACG AAA GCG GTC GTG GCT GCA      768
Val Lys Leu Gly Phe Met Ser Phe Phe Thr Lys Ala Val Val Ala Ala
                245                 250                 255

TTG AAA AAA TAT CCG CTG TTG AAT GCA GAA ATT CAA GGC GAT GAG TTG      816
Leu Lys Lys Tyr Pro Leu Leu Asn Ala Glu Ile Gln Gly Asp Glu Leu
            260                 265                 270

ATC GTT AAA AAA TTC TAC GAT ATC GGA ATC GCT GTT GCT GCT GTA GAA      864
Ile Val Lys Lys Phe Tyr Asp Ile Gly Ile Ala Val Ala Ala Val Glu
            275                 280                 285

GGT CTT GTC GTT CCG GTT GTA CGG GAT GCG GAT CGC CTG ACA TTT GCA      912
Gly Leu Val Val Pro Val Val Arg Asp Ala Asp Arg Leu Thr Phe Ala
    290                 295                 300

GGA ATC GAA AAA GAG ATC GGC GAG CTT GCG AAA AAA GCA AGA AAC AAT      960
Gly Ile Glu Lys Glu Ile Gly Glu Leu Ala Lys Lys Ala Arg Asn Asn
305                 310                 315                 320

AAA TTA ACC CTT AGC GAG CTT GAG GGA GGC TCC TTC ACG ATT ACA AAC     1008
Lys Leu Thr Leu Ser Glu Leu Glu Gly Gly Ser Phe Thr Ile Thr Asn
                325                 330                 335

GGA GGG ACT TTC GGT TCA TTG ATG TCA ACT CCA ATT TTA AAC AGC CCG     1056
Gly Gly Thr Phe Gly Ser Leu Met Ser Thr Pro Ile Leu Asn Ser Pro
            340                 345                 350

CAA GTC GGT ATA CTG GGC ATG CAT AAG ATT CAG CTG CGC CCT GTA GCC     1104
Gln Val Gly Ile Leu Gly Met His Lys Ile Gln Leu Arg Pro Val Ala
            355                 360                 365

ATT GAT GAA GAG CGT TTC GAA AAC CGT CCG ATG ATG TAT ATC GCT TTA     1152
Ile Asp Glu Glu Arg Phe Glu Asn Arg Pro Met Met Tyr Ile Ala Leu
    370                 375                 380

TCT TAT GAT CAC CGA ATT GTA GAC GGT AAA GAA GCG GTT GGT TTC CTC     1200
Ser Tyr Asp His Arg Ile Val Asp Gly Lys Glu Ala Val Gly Phe Leu
385                 390                 395                 400
```

```
GTG ACA ATC AAA AAT TTA CTG GAA GAT CCT GAA CAG CTT TTA TTA GAA    1248
Val Thr Ile Lys Asn Leu Leu Glu Asp Pro Glu Gln Leu Leu Leu Glu
            405                 410                 415

GGA TAA                                                              1254
Gly
```

(2) INFORMATION FOR SEQ ID NO:38:

(i) SEQUENCE CHARACTERISTICS:
        (A) LENGTH: 417 amino acids
        (B) TYPE: amino acid
        (D) TOPOLOGY: linear (ii) MOLECULE TYPE: protein (xi) SEQUENCE DESCRIPTION: SEQ ID NO:38:

```
Met Ala Glu Ile Lys Val Pro Glu Leu Ala Glu Ser Ile Ser Glu Gly
 1               5                  10                  15

Thr Ile Ala Gln Trp Leu Lys Gln Pro Gly Asp Tyr Val Glu Gln Gly
            20                  25                  30

Glu Tyr Leu Leu Glu Leu Glu Thr Asp Lys Val Asn Val Glu Leu Thr
        35                  40                  45

Ala Glu Glu Ser Gly Val Leu Gln Glu Val Leu Lys Asp Ser Gly Asp
    50                  55                  60

Thr Val Gln Val Gly Glu Ile Gly Thr Ile Ser Glu Gly Ala Gly
 65                  70                  75                  80

Glu Ser Ser Ala Pro Ala Pro Thr Glu Lys Thr Glu Ser Lys Glu Ser
                85                  90                  95

Val Lys Glu Glu Lys Gln Ala Glu Pro Ala Ala Gln Glu Val Ser Glu
            100                 105                 110

Glu Ala Gln Ser Glu Ala Lys Ser Arg Thr Ile Ala Ser Pro Ser Ala
        115                 120                 125

Arg Lys Leu Ala Arg Glu Lys Gly Ile Asp Leu Ser Gln Val Pro Thr
    130                 135                 140

Gly Asp Pro Leu Gly Arg Val Arg Lys Gln Asp Val Glu Ala Tyr Glu
145                 150                 155                 160

Lys Pro Ala Ser Lys Pro Ala Pro Gln Gln Lys Gln Pro Gln Ala
                165                 170                 175

Gln Lys Ala Gln Gln Ser Phe Asp Lys Pro Val Glu Val Gln Lys Met
            180                 185                 190

Ser Arg Arg Arg Gln Thr Ile Ala Lys Arg Leu Val Glu Val Gln Gln
        195                 200                 205

Thr Ser Ala Met Leu Thr Thr Phe Asn Glu Val Asp Met Thr Ala Val
    210                 215                 220

Met Asn Leu Arg Lys Arg Lys Asp Gln Phe Phe Glu Gln Asn Glu
225                 230                 235                 240

Val Lys Leu Gly Phe Met Ser Phe Phe Thr Lys Ala Val Val Ala Ala
                245                 250                 255

Leu Lys Lys Tyr Pro Leu Leu Asn Ala Glu Ile Gln Gly Asp Glu Leu
            260                 265                 270

Ile Val Lys Lys Phe Tyr Asp Ile Gly Ile Ala Val Ala Ala Val Glu
        275                 280                 285

Gly Leu Val Val Pro Val Val Arg Asp Ala Asp Arg Leu Thr Phe Ala
    290                 295                 300

Gly Ile Glu Lys Glu Ile Gly Glu Leu Ala Lys Lys Ala Arg Asn Asn
305                 310                 315                 320
```

```
Lys Leu Thr Leu Ser Glu Leu Glu Gly Gly Ser Phe Thr Ile Thr Asn
            325                 330                 335

Gly Gly Thr Phe Gly Ser Leu Met Ser Thr Pro Ile Leu Asn Ser Pro
            340                 345                 350

Gln Val Gly Ile Leu Gly Met His Lys Ile Gln Leu Arg Pro Val Ala
            355                 360                 365

Ile Asp Glu Glu Arg Phe Glu Asn Arg Pro Met Met Tyr Ile Ala Leu
            370                 375                 380

Ser Tyr Asp His Arg Ile Val Asp Gly Lys Glu Ala Val Gly Phe Leu
385                 390                 395                 400

Val Thr Ile Lys Asn Leu Leu Glu Asp Pro Glu Gln Leu Leu Leu Glu
            405                 410                 415

Gly (2) INFORMATION FOR SEQ ID NO:39:

(i) SEQUENCE CHARACTERISTICS:
        (A) LENGTH: 1254 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p4c52)"

(ix) FEATURE:
        (A) NAME/KEY: CDS
        (B) LOCATION: 1..1251

(xi) SEQUENCE DESCRIPTION: SEQ ID NO:39:

ATG GCG GAA ATT AAG GTA CCT GAA TTA GCA GAA TCA ATC TCA GAA GGA        48
Met Ala Glu Ile Lys Val Pro Glu Leu Ala Glu Ser Ile Ser Glu Gly
 1               5                  10                  15

ACA ATA GCC CAA TGG TTA AAG CAG CCT GGT GAC TAT GTA GAA CAG GGT        96
Thr Ile Ala Gln Trp Leu Lys Gln Pro Gly Asp Tyr Val Glu Gln Gly
            20                  25                  30

GAA TAT CTG CTT GAA CTA GAA ACG GAT AAA GTG AAT GTT GAA TTG ACA       144
Glu Tyr Leu Leu Glu Leu Glu Thr Asp Lys Val Asn Val Glu Leu Thr
        35                  40                  45

GCA GAA GAA TCG GGT GTA CTT CAA GAG GTA TTG AAA GAT TCG GGT GAT       192
Ala Glu Glu Ser Gly Val Leu Gln Glu Val Leu Lys Asp Ser Gly Asp
 50                  55                  60

ACC GTC CAG GTC GGA GAA ATT ATC GGT ACG ATT TCA GAA GGC GCG GGT       240
Thr Val Gln Val Gly Glu Ile Ile Gly Thr Ile Ser Glu Gly Ala Gly
 65                  70                  75                  80

GAA AGT TCT GCC CCT GCT CCT ACA GAG AAA ACA GAA AGC AAG GAA AGC       288
Glu Ser Ser Ala Pro Ala Pro Thr Glu Lys Thr Glu Ser Lys Glu Ser
            85                  90                  95

GTA AAA GAA GAG AAA CAG GCT GAA CCA GCT GCA CAA GAG GTG AGC GAG       336
Val Lys Glu Glu Lys Gln Ala Glu Pro Ala Ala Gln Glu Val Ser Glu
            100                 105                 110

GAA GCA CAA TCT GAA GCA AAA TCA AGA ACG ATC GCT TCT CCG TCG GCC       384
Glu Ala Gln Ser Glu Ala Lys Ser Arg Thr Ile Ala Ser Pro Ser Ala
            115                 120                 125

CGT AAG CTT GCG AGA GAA AAA GGA ATT GAC CTG TCT CAA GTT CCA ACT       432
Arg Lys Leu Ala Arg Glu Lys Gly Ile Asp Leu Ser Gln Val Pro Thr
            130                 135                 140

GGA GAT CCG CTT GGA AGA GTG CGC AAG CAG GAT GTC GAA GCG TAC GAA       480
Gly Asp Pro Leu Gly Arg Val Arg Lys Gln Asp Val Glu Ala Tyr Glu
145                 150                 155                 160
```

```
AAA CCG GCA TCA AAA CCG GCT CCT CAG CAA AAG CAG CAG CCT CAG GCT         528
Lys Pro Ala Ser Lys Pro Ala Pro Gln Gln Lys Gln Gln Pro Gln Ala
            165                 170                 175

CAA AAA GCA CAG CAA AGC TTT GAC AAA CCT GTT GAA GTG CAA AAA ATG         576
Gln Lys Ala Gln Gln Ser Phe Asp Lys Pro Val Glu Val Gln Lys Met
            180                 185                 190

TCA CGC CGC AGA CAA ACG ATT GCA AAA CGC CTT GTA GAG GTA CAG CAA         624
Ser Arg Arg Arg Gln Thr Ile Ala Lys Arg Leu Val Glu Val Gln Gln
            195                 200                 205

ACA TCA GCG ATG CTG ACT ACA TTT AAT GAA GTG GAC ATG ACG GCT GTC         672
Thr Ser Ala Met Leu Thr Thr Phe Asn Glu Val Asp Met Thr Ala Val
    210                 215                 220

ATG AAT CTC AGA AAA CGC CGC AAA GAT CAA TTT TTT GAG CAA AAT GAA         720
Met Asn Leu Arg Lys Arg Arg Lys Asp Gln Phe Phe Glu Gln Asn Glu
225                 230                 235                 240

GTG AAG CTC GGC TTT ATG TCT TTC TTC ACG AAA GCG GTC GTG GCT GCA         768
Val Lys Leu Gly Phe Met Ser Phe Phe Thr Lys Ala Val Val Ala Ala
            245                 250                 255

TTG AAA AAA TAT CCG CTG TTG AAT GCA GAA ATT CAA GGC GAT GAG TTG         816
Leu Lys Lys Tyr Pro Leu Leu Asn Ala Glu Ile Gln Gly Asp Glu Leu
            260                 265                 270

ATC GTT AAA AAA TTC TAC GAT ATC GGA ATC GCT GTT GCT GCT GTA GAA         864
Ile Val Lys Lys Phe Tyr Asp Ile Gly Ile Ala Val Ala Ala Val Glu
            275                 280                 285

GGT CTT GTC GTT CCG GTT GTA CGG GAT GCG GAT CGC CTG ACA TTT GCA         912
Gly Leu Val Val Pro Val Val Arg Asp Ala Asp Arg Leu Thr Phe Ala
    290                 295                 300

GGA ATC GAA AAA GAG ATC GGC GAG CTT GCG AAA AAA GCA AGA AAC AAT         960
Gly Ile Glu Lys Glu Ile Gly Glu Leu Ala Lys Lys Ala Arg Asn Asn
305                 310                 315                 320

AAA TTA ACC CTT AGC GAG CTT GAG GGA GGC TCC TTC ACG ATT ACA AAC        1008
Lys Leu Thr Leu Ser Glu Leu Glu Gly Gly Ser Phe Thr Ile Thr Asn
            325                 330                 335

GGA GGG ACT TTC GGT TCA TTG ATG TCA ACT CCA ATT TTA AAC AGC CCG        1056
Gly Gly Thr Phe Gly Ser Leu Met Ser Thr Pro Ile Leu Asn Ser Pro
            340                 345                 350

CAA GTC GGT ATA CTG GGC ATG CAT AAG ATT CAG CTG CGC CCT GTA GCC        1104
Gln Val Gly Ile Leu Gly Met His Lys Ile Gln Leu Arg Pro Val Ala
            355                 360                 365

ATT GAT GAA GAG CGT TTC GAA AAC CGT CCG ATG ATG TAT ATC GCT TTA        1152
Ile Asp Glu Glu Arg Phe Glu Asn Arg Pro Met Met Tyr Ile Ala Leu
    370                 375                 380

TCT TAT GAT CAC CGA ATT GTA GAC GGT AAA GAA GCG GTT GGT TTC CTC        1200
Ser Tyr Asp His Arg Ile Val Asp Gly Lys Glu Ala Val Gly Phe Leu
385                 390                 395                 400

GTG ACA ATC AAA AAT TTA CTG GAA GAT CCT GAA CAG CTT TTA TTA GAA        1248
Val Thr Ile Lys Asn Leu Leu Glu Asp Pro Glu Gln Leu Leu Leu Glu
            405                 410                 415

GGA TAA                                                                1254
Gly
```

(2) INFORMATION FOR SEQ ID NO:40:

(i) SEQUENCE CHARACTERISTICS:
        (A) LENGTH: 417 amino acids
        (B) TYPE: amino acid
        (D) TOPOLOGY: linear (ii) MOLECULE TYPE: protein (xi) SEQUENCE DESCRIPTION: SEQ ID NO:40:

-continued

```
Met Ala Glu Ile Lys Val Pro Glu Leu Ala Glu Ser Ile Ser Glu Gly
 1               5                  10                  15

Thr Ile Ala Gln Trp Leu Lys Gln Pro Gly Asp Tyr Val Glu Gln Gly
             20                  25                  30

Glu Tyr Leu Leu Glu Leu Glu Thr Asp Lys Val Asn Val Glu Leu Thr
         35                  40                  45

Ala Glu Glu Ser Gly Val Leu Gln Glu Val Leu Lys Asp Ser Gly Asp
     50                  55                  60

Thr Val Gln Val Gly Glu Ile Gly Thr Ile Ser Glu Gly Ala Gly
 65                  70                  75                  80

Glu Ser Ser Ala Pro Ala Pro Thr Glu Lys Thr Glu Ser Lys Glu Ser
                 85                  90                  95

Val Lys Glu Glu Lys Gln Ala Glu Pro Ala Ala Gln Glu Val Ser Glu
                100                 105                 110

Glu Ala Gln Ser Glu Ala Lys Ser Arg Thr Ile Ala Ser Pro Ser Ala
             115                 120                 125

Arg Lys Leu Ala Arg Glu Lys Gly Ile Asp Leu Ser Gln Val Pro Thr
         130                 135                 140

Gly Asp Pro Leu Gly Arg Val Arg Lys Gln Asp Val Glu Ala Tyr Glu
145                 150                 155                 160

Lys Pro Ala Ser Lys Pro Ala Pro Gln Gln Lys Gln Gln Pro Gln Ala
                165                 170                 175

Gln Lys Ala Gln Gln Ser Phe Asp Lys Pro Val Glu Val Gln Lys Met
             180                 185                 190

Ser Arg Arg Arg Gln Thr Ile Ala Lys Arg Leu Val Glu Val Gln Gln
         195                 200                 205

Thr Ser Ala Met Leu Thr Thr Phe Asn Glu Val Asp Met Thr Ala Val
         210                 215                 220

Met Asn Leu Arg Lys Arg Arg Lys Asp Gln Phe Phe Glu Gln Asn Glu
225                 230                 235                 240

Val Lys Leu Gly Phe Met Ser Phe Phe Thr Lys Ala Val Val Ala Ala
                245                 250                 255

Leu Lys Lys Tyr Pro Leu Leu Asn Ala Glu Ile Gln Gly Asp Glu Leu
                260                 265                 270

Ile Val Lys Lys Phe Tyr Asp Ile Gly Ile Ala Val Ala Ala Val Glu
             275                 280                 285

Gly Leu Val Val Pro Val Val Arg Asp Ala Asp Arg Leu Thr Phe Ala
290                 295                 300

Gly Ile Glu Lys Glu Ile Gly Glu Leu Ala Lys Lys Ala Arg Asn Asn
305                 310                 315                 320

Lys Leu Thr Leu Ser Glu Leu Glu Gly Gly Ser Phe Thr Ile Thr Asn
                325                 330                 335

Gly Gly Thr Phe Gly Ser Leu Met Ser Thr Pro Ile Leu Asn Ser Pro
             340                 345                 350

Gln Val Gly Ile Leu Gly Met His Lys Ile Gln Leu Arg Pro Val Ala
             355                 360                 365

Ile Asp Glu Glu Arg Phe Glu Asn Arg Pro Met Met Tyr Ile Ala Leu
         370                 375                 380

Ser Tyr Asp His Arg Ile Val Asp Gly Lys Glu Ala Val Gly Phe Leu
385                 390                 395                 400

Val Thr Ile Lys Asn Leu Leu Glu Asp Pro Glu Gln Leu Leu Leu Glu
                405                 410                 415

Gly
```

(2) INFORMATION FOR SEQ ID NO:41:

(i) SEQUENCE CHARACTERISTICS:
        (A) LENGTH: 1254 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p10b2)"

(ix) FEATURE:
        (A) NAME/KEY: CDS
        (B) LOCATION: 1..1251

(xi) SEQUENCE DESCRIPTION: SEQ ID NO:41:

```
ATG GCG GAA ATT AAG GTA CCT GAA TTA GCA GAA TCA ATC TCA GAA GGA        48
Met Ala Glu Ile Lys Val Pro Glu Leu Ala Glu Ser Ile Ser Glu Gly
 1               5                  10                  15

ACA ATA GCC CAA TGG TTA AAG CAG CCT GGT GAC TAT GTA GAA CAG GGT        96
Thr Ile Ala Gln Trp Leu Lys Gln Pro Gly Asp Tyr Val Glu Gln Gly
                20                  25                  30

GAA TAT CTG CTT GAA CTA GAA ACG GAT AAA GTG AAT GTT GAA TTG ACA       144
Glu Tyr Leu Leu Glu Leu Glu Thr Asp Lys Val Asn Val Glu Leu Thr
            35                  40                  45

GCA GAA GAA TCG GGT GTA CTT CAA GAG GTA TTG AAA GAT TCG GGT GAT       192
Ala Glu Glu Ser Gly Val Leu Gln Glu Val Leu Lys Asp Ser Gly Asp
        50                  55                  60

ACC GTC CAG GTC GGA GAA ATT ATC GGT ACG ATT TCA GAA GGC GCG GGT       240
Thr Val Gln Val Gly Glu Ile Ile Gly Thr Ile Ser Glu Gly Ala Gly
 65                  70                  75                  80

GAA AGT TCT GCC CCT GCT CCT ACA GAG AAA ACA GAA AGC AAG GAA AGC       288
Glu Ser Ser Ala Pro Ala Pro Thr Glu Lys Thr Glu Ser Lys Glu Ser
                85                  90                  95

GTA AAA GAA GAG AAA CAG GCT GAA CCA GCT GCA CAA GAG GTG AGC GAG       336
Val Lys Glu Glu Lys Gln Ala Glu Pro Ala Ala Gln Glu Val Ser Glu
                100                 105                 110

GAA GCA CAA TCT GAA GCA AAA TCA AGA ACG ATC GCT TCT CCG TCG GCC       384
Glu Ala Gln Ser Glu Ala Lys Ser Arg Thr Ile Ala Ser Pro Ser Ala
            115                 120                 125

CGT AAG CTT GCG AGA GAA AAA GGA ATT GAC CTG TCT CAA GTT CCA ACT       432
Arg Lys Leu Ala Arg Glu Lys Gly Ile Asp Leu Ser Gln Val Pro Thr
        130                 135                 140

GGA GAT CCG CTT GGA AGA GTG CGC AAG CAG GAT GTC GAA GCG TAC GAA       480
Gly Asp Pro Leu Gly Arg Val Arg Lys Gln Asp Val Glu Ala Tyr Glu
145                 150                 155                 160

AAA CCG GCA TCA AAA CCG GCT CCT CAG CAA AAG CAG CAG CCT CAG GCT       528
Lys Pro Ala Ser Lys Pro Ala Pro Gln Gln Lys Gln Gln Pro Gln Ala
                165                 170                 175

CAA AAA GCA CAG CAA AGC TTT GAC AAA CCT GTT GAA GTG CAA AAA ATG       576
Gln Lys Ala Gln Gln Ser Phe Asp Lys Pro Val Glu Val Gln Lys Met
                180                 185                 190

TCA CGC CGC AGA CAA ACG ATT GCA AAA CGC CTT GTA GAG GTA CAG CAA       624
Ser Arg Arg Arg Gln Thr Ile Ala Lys Arg Leu Val Glu Val Gln Gln
            195                 200                 205

ACA TCA GCG ATG CTG ACT ACA TTT AAT GAA GTG GAC ATG ACG GCT GTC       672
Thr Ser Ala Met Leu Thr Thr Phe Asn Glu Val Asp Met Thr Ala Val
        210                 215                 220

ATG AAT CTC AGA AAA CGC CGC AAA GAT CAA TTT TTT GAG CAA AAT GAA       720
Met Asn Leu Arg Lys Arg Arg Lys Asp Gln Phe Phe Glu Gln Asn Glu
225                 230                 235                 240
```

```
GTG AAG CTC GGC TTT ATG TCT TTC TTC ACG AAA GCG GTC GTG GCT GCA      768
Val Lys Leu Gly Phe Met Ser Phe Phe Thr Lys Ala Val Val Ala Ala
                245                 250                 255

TTG AAA AAA TAT CCG CTG TTG AAT GCA GAA ATT CAA GGC GAT GAG TTG      816
Leu Lys Lys Tyr Pro Leu Leu Asn Ala Glu Ile Gln Gly Asp Glu Leu
            260                 265                 270

ATC GTT AAA AAA TTC TAC GAT ATC GGA ATC GCT GTT GCT GCT GTA GAA      864
Ile Val Lys Lys Phe Tyr Asp Ile Gly Ile Ala Val Ala Ala Val Glu
        275                 280                 285

GGT CTT GTC GTT CCG GTT GTA CGG GAT GCG GAT CGC CTG ACA TTT GCA      912
Gly Leu Val Val Pro Val Val Arg Asp Ala Asp Arg Leu Thr Phe Ala
    290                 295                 300

GGA ATC GAA AAA GAG ATC GGC GAG CTT GCG AAA AAA GCA AGA AAC AAT      960
Gly Ile Glu Lys Glu Ile Gly Glu Leu Ala Lys Lys Ala Arg Asn Asn
305                 310                 315                 320

AAA TTA ACC CTT AGC GAG CTT GAG GGA GGC TCC TTC ACG ATT ACA AAC     1008
Lys Leu Thr Leu Ser Glu Leu Glu Gly Gly Ser Phe Thr Ile Thr Asn
                325                 330                 335

GGA GGG ACT TTC GGT TCA TTG ATG TCA ACT CCA ATT TTA AAC AGC CCG     1056
Gly Gly Thr Phe Gly Ser Leu Met Ser Thr Pro Ile Leu Asn Ser Pro
            340                 345                 350

CAA GTC GGT ATA CTG GGC ATG CAT AAG ATT CAG CTG CGC CCT GTA GCC     1104
Gln Val Gly Ile Leu Gly Met His Lys Ile Gln Leu Arg Pro Val Ala
        355                 360                 365

ATT GAT GAA GAG CGT TTC GAA AAC CGT CCG ATG ATG TAT ATC GCT TTA     1152
Ile Asp Glu Glu Arg Phe Glu Asn Arg Pro Met Met Tyr Ile Ala Leu
    370                 375                 380

TCT TAT GAT CAC CGA ATT GTA GAC GGT AAA GAA GCG GTT GGT TTC CTC     1200
Ser Tyr Asp His Arg Ile Val Asp Gly Lys Glu Ala Val Gly Phe Leu
385                 390                 395                 400

GTG ACA ATC AAA AAT TTA CTG GAA GAT CCT GAA CAG CTT TTA TTA GAA     1248
Val Thr Ile Lys Asn Leu Leu Glu Asp Pro Glu Gln Leu Leu Leu Glu
                405                 410                 415

GGA TAA                                                              1254
Gly (2) INFORMATION FOR SEQ ID NO:42:

(i) SEQUENCE CHARACTERISTICS:
        (A) LENGTH: 417 amino acids
        (B) TYPE: amino acid
        (D) TOPOLOGY: linear (ii) MOLECULE TYPE: protein (xi) SEQUENCE DESCRIPTION: SEQ ID NO:42:

Met Ala Glu Ile Lys Val Pro Glu Leu Ala Glu Ser Ile Ser Glu Gly
 1               5                  10                  15

Thr Ile Ala Gln Trp Leu Lys Gln Pro Gly Asp Tyr Val Glu Gln Gly
                20                  25                  30

Glu Tyr Leu Leu Glu Leu Glu Thr Asp Lys Val Asn Val Glu Leu Thr
            35                  40                  45

Ala Glu Glu Ser Gly Val Leu Gln Glu Val Leu Lys Asp Ser Gly Asp
        50                  55                  60

Thr Val Gln Val Gly Glu Ile Ile Gly Thr Ile Ser Glu Gly Ala Gly
65                  70                  75                  80

Glu Ser Ser Ala Pro Ala Pro Thr Glu Lys Thr Glu Ser Lys Glu Ser
                85                  90                  95

Val Lys Glu Glu Lys Gln Ala Glu Pro Ala Ala Gln Glu Val Ser Glu
                100                 105                 110
```

```
Glu Ala Gln Ser Glu Ala Lys Ser Arg Thr Ile Ala Ser Pro Ser Ala
            115                 120                 125

Arg Lys Leu Ala Arg Glu Lys Gly Ile Asp Leu Ser Gln Val Pro Thr
        130                 135                 140

Gly Asp Pro Leu Gly Arg Val Arg Lys Gln Asp Val Glu Ala Tyr Glu
145                 150                 155                 160

Lys Pro Ala Ser Lys Pro Ala Pro Gln Gln Lys Gln Pro Gln Ala
                165                 170                 175

Gln Lys Ala Gln Gln Ser Phe Asp Lys Pro Val Glu Val Gln Lys Met
            180                 185                 190

Ser Arg Arg Gln Thr Ile Ala Lys Arg Leu Val Glu Val Gln Gln
        195                 200                 205

Thr Ser Ala Met Leu Thr Thr Phe Asn Glu Val Asp Met Thr Ala Val
210                 215                 220

Met Asn Leu Arg Lys Arg Arg Lys Asp Gln Phe Phe Glu Gln Asn Glu
225                 230                 235                 240

Val Lys Leu Gly Phe Met Ser Phe Phe Thr Lys Ala Val Ala Ala
            245                 250                 255

Leu Lys Lys Tyr Pro Leu Leu Asn Ala Glu Ile Gln Gly Asp Glu Leu
        260                 265                 270

Ile Val Lys Lys Phe Tyr Asp Ile Gly Ile Ala Val Ala Ala Val Glu
        275                 280                 285

Gly Leu Val Val Pro Val Val Arg Asp Ala Asp Arg Leu Thr Phe Ala
        290                 295                 300

Gly Ile Glu Lys Glu Ile Gly Glu Leu Ala Lys Lys Ala Arg Asn Asn
305                 310                 315                 320

Lys Leu Thr Leu Ser Glu Leu Glu Gly Gly Ser Phe Thr Ile Thr Asn
                325                 330                 335

Gly Gly Thr Phe Gly Ser Leu Met Ser Thr Pro Ile Leu Asn Ser Pro
            340                 345                 350

Gln Val Gly Ile Leu Gly Met His Lys Ile Gln Leu Arg Pro Val Ala
        355                 360                 365

Ile Asp Glu Glu Arg Phe Glu Asn Arg Pro Met Met Tyr Ile Ala Leu
370                 375                 380

Ser Tyr Asp His Arg Ile Val Asp Gly Lys Glu Ala Val Gly Phe Leu
385                 390                 395                 400

Val Thr Ile Lys Asn Leu Leu Glu Asp Pro Glu Gln Leu Leu Leu Glu
                405                 410                 415

Gly
```

(2) INFORMATION FOR SEQ ID NO:43:

(i) SEQUENCE CHARACTERISTICS:
       (A) LENGTH: 524 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA (genomic) (p10c20)"

(xi) SEQUENCE DESCRIPTION: SEQ ID NO:43:

```
TTTCGAAGAT CGGCTCTTAC AATATTGACG GTAAAGAACA GTTGGATTCT TAAAAACAAT      60

TAAAGAATTA ATTGAAAACC CAAAGACTTA TTATAGAATC TTAATCCACA ACACAAAATA     120

GTTTACTATT CCTAAAAGCG GGATTAAATC AATAACAAAC AGCATAAGAT TATTTCCTAG     180
```

```
TCGAAATATC TTACTGCTGT ACTTTATTTT TATAATGATC TTTAATGTGG GTTTAATTTT      240

GACTACTTAA AAATATATCA TTTCTATTGA AATAGACTCA CAATACAAAT ATAGTAGAAT      300

GCGTGTTTCA ATATGCTAAT GAATGCATTT TAGATATAAC AAACGAGAAA TATATGAATT      360

CTATAAGCGC CTTTAGTTAA TTTAAATCTC TGAACATGAT GTAATTCGCT TTATGGACAC      420

CACATTATAT GTTTTCATGT CCTACAACAC AACACATATT CAATTGTATA TACAGATATT      480

CTTAATGACA CACTCATAGC CCCATAACAA TATATGTTAC CTAT                      524
```

(2) INFORMATION FOR SEQ ID NO:44:

(i) SEQUENCE CHARACTERISTICS:
        (A) LENGTH: 2799 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p12c32)"

(ix) FEATURE:
        (A) NAME/KEY: CDS
        (B) LOCATION: 1..2796

(xi) SEQUENCE DESCRIPTION: SEQ ID NO:44:

```
ATG ACT AAC GAA AGA AAA GAA GTT TCA GAG GCT CCT GTA AAC TTC GGT         48
Met Thr Asn Glu Arg Lys Glu Val Ser Glu Ala Pro Val Asn Phe Gly
 1               5                  10                  15

GCG AAT TTA GGT CTA ATG TTA GAT CTA TAT GAT GAC TTT TTA CAA GAT         96
Ala Asn Leu Gly Leu Met Leu Asp Leu Tyr Asp Asp Phe Leu Gln Asp
                 20                  25                  30

CCA TCA TCT GTA CCA GAA GAT TTA CAA GTC TTA TTC AGC ACA ATT AAG        144
Pro Ser Ser Val Pro Glu Asp Leu Gln Val Leu Phe Ser Thr Ile Lys
             35                  40                  45

AAT GAT GAC TCA ATT GTA CCA GCT TTA AAA AGT ACA AGT AGT CAA AAT        192
Asn Asp Asp Ser Ile Val Pro Ala Leu Lys Ser Thr Ser Ser Gln Asn
 50                  55                  60

AGC GAC GGC ACA ATT AAG CGT GTC ATG CGT TTA ATT GAT AAT ATT CGC        240
Ser Asp Gly Thr Ile Lys Arg Val Met Arg Leu Ile Asp Asn Ile Arg
 65                  70                  75                  80

CAA TAC GGG CAT CTT AAA GCC GAT ATT TAT CCT GTA AAT CCT CCA AAA        288
Gln Tyr Gly His Leu Lys Ala Asp Ile Tyr Pro Val Asn Pro Pro Lys
                 85                  90                  95

AGG AAA CAT GTA CCT AAA TTA GAG ATT GAA GAC TTT GAT TTA GAT CAA        336
Arg Lys His Val Pro Lys Leu Glu Ile Glu Asp Phe Asp Leu Asp Gln
                100                 105                 110

CAG ACT TTG GAA GGT ATA TCA GCA GGA ATT GTT TCA GAT CAC TTT GCC        384
Gln Thr Leu Glu Gly Ile Ser Ala Gly Ile Val Ser Asp His Phe Ala
            115                 120                 125

GAC ATT TAT GAT AAT GCT TAT GAA GCA ATT TTA AGA ATG GAA AAA CGT        432
Asp Ile Tyr Asp Asn Ala Tyr Glu Ala Ile Leu Arg Met Glu Lys Arg
        130                 135                 140

TAC AAA GGA CCA ATT GCA TTT GAG TAT ACA CAT ATT AAT AAC AAT ACC        480
Tyr Lys Gly Pro Ile Ala Phe Glu Tyr Thr His Ile Asn Asn Asn Thr
145                 150                 155                 160

GAA CGT GGT TGG TTA AAA AGA AGA ATT GAA ACG CCA TAT AAA GTA ACG        528
Glu Arg Gly Trp Leu Lys Arg Arg Ile Glu Thr Pro Tyr Lys Val Thr
                165                 170                 175

TTA AAT AAT AAC GAA AAA AGG GCA CTA TTC AAA CAA TTA GCG TAT GTT        576
Leu Asn Asn Asn Glu Lys Arg Ala Leu Phe Lys Gln Leu Ala Tyr Val
                180                 185                 190
```

-continued

| | |
|---|---|
| GAA GGG TTT GAA AAA TAT CTT CAT AAA AAC TTC GTT GGT GCA AAG CGT<br>Glu Gly Phe Glu Lys Tyr Leu His Lys Asn Phe Val Gly Ala Lys Arg<br>195     200     205 | 624 |
| TTT TCA ATT GAA GGG GTA GAC GCA CTT GTA CCG ATG TTA CAA CGT ACT<br>Phe Ser Ile Glu Gly Val Asp Ala Leu Val Pro Met Leu Gln Arg Thr<br> 210     215     220 | 672 |
| ATT ACG ATT GCT GCG AAA GAA GGT ATT AAA AAT ATA CAA ATA GGC ATG<br>Ile Thr Ile Ala Ala Lys Glu Gly Ile Lys Asn Ile Gln Ile Gly Met<br>225     230     235     240 | 720 |
| GCT CAC CGT GGA CGT TTA AAC GTT TTA ACG CAT GTC TTA GAA AAA CCG<br>Ala His Arg Gly Arg Leu Asn Val Leu Thr His Val Leu Glu Lys Pro<br>    245     250     255 | 768 |
| TAC GAA ATG ATG ATT TCA GAA TTT ATG CAT ACA GAT CCA ATG AAA TTC<br>Tyr Glu Met Met Ile Ser Glu Phe Met His Thr Asp Pro Met Lys Phe<br>   260     265     270 | 816 |
| TTA CCT GAA GAT GGT AGC TTG CAG TTA ACT GCT GGA TGG ACT GGT GAT<br>Leu Pro Glu Asp Gly Ser Leu Gln Leu Thr Ala Gly Trp Thr Gly Asp<br>275     280     285 | 864 |
| GTG AAA TAT CAC CTT GGT GGC ATT AAA ACT ACT GAT TCA TAC GGT ACA<br>Val Lys Tyr His Leu Gly Gly Ile Lys Thr Thr Asp Ser Tyr Gly Thr<br> 290     295     300 | 912 |
| ATG CAG CGT ATT GCA CTG GCT AAC AAT CCA AGT CAC TTG GAA ATT GTT<br>Met Gln Arg Ile Ala Leu Ala Asn Asn Pro Ser His Leu Glu Ile Val<br>305     310     315     320 | 960 |
| GCA CCT GTT GTT GAG GGG CGT ACG AGA GCA GCA CAA GAT GAT ACA CAA<br>Ala Pro Val Val Glu Gly Arg Thr Arg Ala Ala Gln Asp Asp Thr Gln<br>    325     330     335 | 1008 |
| CGA GCT GGG GCT CCG ACG ACT GAT CAT CAT AAA GCA ATG CCA ATT ATT<br>Arg Ala Gly Ala Pro Thr Thr Asp His His Lys Ala Met Pro Ile Ile<br>   340     345     350 | 1056 |
| ATA CAT GGC GAT GCT GCT TAT CCT GGT CAA GGA ATT AAC TTC GAA ACA<br>Ile His Gly Asp Ala Ala Tyr Pro Gly Gln Gly Ile Asn Phe Glu Thr<br>355     360     365 | 1104 |
| ATG AAC TTA GGA AAC TTG AAA GGC TAT TCT ACG GGT GGT TCA TTG CAT<br>Met Asn Leu Gly Asn Leu Lys Gly Tyr Ser Thr Gly Gly Ser Leu His<br>370     375     380 | 1152 |
| ATT ATT ACT AAC AAT AGA ATT GGA TTT ACA ACA GAA CCA ATT GAT GCA<br>Ile Ile Thr Asn Asn Arg Ile Gly Phe Thr Thr Glu Pro Ile Asp Ala<br>385     390     395     400 | 1200 |
| CGT TCA ACA ACT TAT TCT ACA GAT GTG GCC AAA GGT TAT GAT GTG CCA<br>Arg Ser Thr Thr Tyr Ser Thr Asp Val Ala Lys Gly Tyr Asp Val Pro<br>    405     410     415 | 1248 |
| ATA TTC CAT GTC AAT GCA GAT GAC GTT GAA GCT ACT ATT GAA GCA ATT<br>Ile Phe His Val Asn Ala Asp Asp Val Glu Ala Thr Ile Glu Ala Ile<br>   420     425     430 | 1296 |
| GAT ATT GCA ATG GAA TTT AGA AAA GAG TTT CAT AAA GAC GTC GTT ATT<br>Asp Ile Ala Met Glu Phe Arg Lys Glu Phe His Lys Asp Val Val Ile<br> 435     440     445 | 1344 |
| GAT TTA GTA GGT TAT CGT CGT TTC GGA CAT AAC GAA ATG GAT GAA CCA<br>Asp Leu Val Gly Tyr Arg Arg Phe Gly His Asn Glu Met Asp Glu Pro<br>450     455     460 | 1392 |
| TCA ATT ACT AAT CCA GTT CCT TAT CAG AAT ATT CGC AAA CAT GAC TCT<br>Ser Ile Thr Asn Pro Val Pro Tyr Gln Asn Ile Arg Lys His Asp Ser<br>465     470     475     480 | 1440 |
| GTT GAA TAT GTG TTT GGT AAA AAG CTT GTT AAT GAA GGT GTC ATT TCA<br>Val Glu Tyr Val Phe Gly Lys Lys Leu Val Asn Glu Gly Val Ile Ser<br>    485     490     495 | 1488 |
| GAA GAT GAA ATG CAT TCA TTT ATA GAA CAA GTC CAA AAG GAA CTA AGA<br>Glu Asp Glu Met His Ser Phe Ile Glu Gln Val Gln Lys Glu Leu Arg<br>   500     505     510 | 1536 |

```
CAA GCT CAT GAT AAA ATT AAT AAA GCT GAT AAA ATG GAT AAT CCA GAT    1584
Gln Ala His Asp Lys Ile Asn Lys Ala Asp Lys Met Asp Asn Pro Asp
        515                 520                 525

ATG GAA AAG CCT GCA GAT CTT GCA TTA CCG TTA CAA GCA GAC GAA CAA    1632
Met Glu Lys Pro Ala Asp Leu Ala Leu Pro Leu Gln Ala Asp Glu Gln
    530                 535                 540

TCA TTT ACT TTT GAT CAC TTG AAA GAA ATA AAT GAT GCA TTG TTA ACA    1680
Ser Phe Thr Phe Asp His Leu Lys Glu Ile Asn Asp Ala Leu Leu Thr
545                 550                 555                 560

TAT CCG GAT GGC TTT AAC ATT TTG AAA AAG TTA AAC AAA GTT CTT GAG    1728
Tyr Pro Asp Gly Phe Asn Ile Leu Lys Lys Leu Asn Lys Val Leu Glu
                565                 570                 575

AAG CGT CAT GAG CCG TTT AAT AAA GAA GAT GGT TTA GTT GAT TGG GCA    1776
Lys Arg His Glu Pro Phe Asn Lys Glu Asp Gly Leu Val Asp Trp Ala
            580                 585                 590

CAA GCA GAA CAA CTT GCA TTT GCG ACA ATT TTA CAA GAT GGT ACA CCG    1824
Gln Ala Glu Gln Leu Ala Phe Ala Thr Ile Leu Gln Asp Gly Thr Pro
        595                 600                 605

ATT CGC TTA ACT GGT CAA GAT AGT GAA CGT GGT ACA TTC AGT CAT AGG    1872
Ile Arg Leu Thr Gly Gln Asp Ser Glu Arg Gly Thr Phe Ser His Arg
    610                 615                 620

CAT GCC GTG TTA CAT GAT GAG CAA ACA GGT GAA ACA TAT ACA CCT TTA    1920
His Ala Val Leu His Asp Glu Gln Thr Gly Glu Thr Tyr Thr Pro Leu
625                 630                 635                 640

CAT CAT GTT CCT GAT CAA AAA GCG ACA TTT GAT ATA CAC AAT TCT CCG    1968
His His Val Pro Asp Gln Lys Ala Thr Phe Asp Ile His Asn Ser Pro
                645                 650                 655

CTT TCA GAA GCA GCA GTA GTT GGT TTT GAA TAC GGC TAT AAT GTG GAA    2016
Leu Ser Glu Ala Ala Val Val Gly Phe Glu Tyr Gly Tyr Asn Val Glu
                660                 665                 670

AAC AAA AAA AGC TTC AAT ATT TGG GAA GCA CAA TAT GGT GAT TTT GCA    2064
Asn Lys Lys Ser Phe Asn Ile Trp Glu Ala Gln Tyr Gly Asp Phe Ala
            675                 680                 685

AAT ATG TCA CAA ATG ATT TTT GAC AAC TTC TTA TTC AGT TCT CGC TCA    2112
Asn Met Ser Gln Met Ile Phe Asp Asn Phe Leu Phe Ser Ser Arg Ser
        690                 695                 700

AAA TGG GGA GAA CGT TCA GGA TTA ACA TTA TTC TTA CCT CAT GCA TAT    2160
Lys Trp Gly Glu Arg Ser Gly Leu Thr Leu Phe Leu Pro His Ala Tyr
705                 710                 715                 720

GAG GGT CAA GGG CCT GAA CAT TCA TCA GCA AGA TTA GAG CGA TTT TTA    2208
Glu Gly Gln Gly Pro Glu His Ser Ser Ala Arg Leu Glu Arg Phe Leu
                725                 730                 735

CAA TTA GCT GCT GAA AAT AAT TGC ACA GTT GTC AAC TTA TCT AGT TCA    2256
Gln Leu Ala Ala Glu Asn Asn Cys Thr Val Val Asn Leu Ser Ser Ser
                740                 745                 750

AGT AAT TAT TTC CAC TTA TTG CGT GCA CAA GCG GCT AGT TTA GAT TCT    2304
Ser Asn Tyr Phe His Leu Leu Arg Ala Gln Ala Ala Ser Leu Asp Ser
            755                 760                 765

GAA CAA ATG CGA CCA TTG GTT GTT ATG TCA CCA AAA AGC TTA CTG AGA    2352
Glu Gln Met Arg Pro Leu Val Val Met Ser Pro Lys Ser Leu Leu Arg
        770                 775                 780

AAT AAA ACA GTT GCA AAA CCA ATT GAT GAA TTT ACT TCT GGT GGA TTT    2400
Asn Lys Thr Val Ala Lys Pro Ile Asp Glu Phe Thr Ser Gly Gly Phe
785                 790                 795                 800

GAG CCA ATT TTG ACA GAA TCA TAT CAA GCG GAT AAG GTT ACA AAA GTT    2448
Glu Pro Ile Leu Thr Glu Ser Tyr Gln Ala Asp Lys Val Thr Lys Val
                805                 810                 815

ATT TTG GCA ACT GGT AAA ATG TTC ATT GAT TTA AAA GAA GCA TTA GCT    2496
Ile Leu Ala Thr Gly Lys Met Phe Ile Asp Leu Lys Glu Ala Leu Ala
```

-continued

```
                      820                 825                 830
AAA AAT CCA GAC GAA TCA GTA TTA CTC GTT GCG ATT GAA AGA TTG TAT          2544
Lys Asn Pro Asp Glu Ser Val Leu Leu Val Ala Ile Glu Arg Leu Tyr
            835                 840                 845

CCA TTC CCA GAG GAA GAG ATT GAA GCA TTA CTA GCA CAA TTG CCA AAC          2592
Pro Phe Pro Glu Glu Glu Ile Glu Ala Leu Leu Ala Gln Leu Pro Asn
        850                 855                 860

CTT GAA GAA GTG TCA TGG GTA CAA GAA GAA CCT AAA AAT CAA GGT GCA          2640
Leu Glu Glu Val Ser Trp Val Gln Glu Glu Pro Lys Asn Gln Gly Ala
865                 870                 875                 880

TGG TTA TAT GTC TAT CCA TAT GTT AAA GTG CTA GTT GCA GAT AAA TAT          2688
Trp Leu Tyr Val Tyr Pro Tyr Val Lys Val Leu Val Ala Asp Lys Tyr
                885                 890                 895

GAT TTA AGT TAT CAT GGC AGA ATT CAA AGG GCT GCT CCA GCT GAA GGC          2736
Asp Leu Ser Tyr His Gly Arg Ile Gln Arg Ala Ala Pro Ala Glu Gly
            900                 905                 910

GAT GGA GAA ATT CAT AAA CTT GTT CAA AAT AAA ATT ATA GAA AAT GCA          2784
Asp Gly Glu Ile His Lys Leu Val Gln Asn Lys Ile Ile Glu Asn Ala
        915                 920                 925

TTA AAA AAT AAC TAG                                                      2799
Leu Lys Asn Asn
    930
```

(2) INFORMATION FOR SEQ ID NO:45:

(i) SEQUENCE CHARACTERISTICS:
        (A) LENGTH: 932 amino acids
        (B) TYPE: amino acid
        (D) TOPOLOGY: linear (ii) MOLECULE TYPE: protein (xi) SEQUENCE DESCRIPTION: SEQ ID NO:45:

```
Met Thr Asn Glu Arg Lys Glu Val Ser Glu Ala Pro Val Asn Phe Gly
  1               5                  10                  15

Ala Asn Leu Gly Leu Met Leu Asp Leu Tyr Asp Asp Phe Leu Gln Asp
             20                  25                  30

Pro Ser Ser Val Pro Glu Asp Leu Gln Val Leu Phe Ser Thr Ile Lys
         35                  40                  45

Asn Asp Asp Ser Ile Val Pro Ala Leu Lys Ser Thr Ser Ser Gln Asn
     50                  55                  60

Ser Asp Gly Thr Ile Lys Arg Val Met Arg Leu Ile Asp Asn Ile Arg
 65                  70                  75                  80

Gln Tyr Gly His Leu Lys Ala Asp Ile Tyr Pro Val Asn Pro Pro Lys
                 85                  90                  95

Arg Lys His Val Pro Lys Leu Glu Ile Glu Asp Phe Asp Leu Asp Gln
            100                 105                 110

Gln Thr Leu Glu Gly Ile Ser Ala Gly Ile Val Ser Asp His Phe Ala
        115                 120                 125

Asp Ile Tyr Asp Asn Ala Tyr Glu Ala Ile Leu Arg Met Glu Lys Arg
    130                 135                 140

Tyr Lys Gly Pro Ile Ala Phe Glu Tyr Thr His Ile Asn Asn Asn Thr
145                 150                 155                 160

Glu Arg Gly Trp Leu Lys Arg Arg Ile Glu Thr Pro Tyr Lys Val Thr
                165                 170                 175

Leu Asn Asn Asn Glu Lys Arg Ala Leu Phe Lys Gln Leu Ala Tyr Val
            180                 185                 190

Glu Gly Phe Glu Lys Tyr Leu His Lys Asn Phe Val Gly Ala Lys Arg
```

-continued

```
            195                 200                 205
Phe Ser Ile Glu Gly Val Asp Ala Leu Val Pro Met Leu Gln Arg Thr
    210                 215                 220

Ile Thr Ile Ala Ala Lys Glu Gly Ile Lys Asn Ile Gln Ile Gly Met
225                 230                 235                 240

Ala His Arg Gly Arg Leu Asn Val Leu Thr His Val Leu Glu Lys Pro
                245                 250                 255

Tyr Glu Met Met Ile Ser Glu Phe Met His Thr Asp Pro Met Lys Phe
                260                 265                 270

Leu Pro Glu Asp Gly Ser Leu Gln Leu Thr Ala Gly Trp Thr Gly Asp
            275                 280                 285

Val Lys Tyr His Leu Gly Gly Ile Lys Thr Thr Asp Ser Tyr Gly Thr
    290                 295                 300

Met Gln Arg Ile Ala Leu Ala Asn Asn Pro Ser His Leu Glu Ile Val
305                 310                 315                 320

Ala Pro Val Val Glu Gly Arg Thr Arg Ala Ala Gln Asp Asp Thr Gln
                325                 330                 335

Arg Ala Gly Ala Pro Thr Thr Asp His His Lys Ala Met Pro Ile Ile
                340                 345                 350

Ile His Gly Asp Ala Ala Tyr Pro Gly Gln Gly Ile Asn Phe Glu Thr
            355                 360                 365

Met Asn Leu Gly Asn Leu Lys Gly Tyr Ser Thr Gly Gly Ser Leu His
    370                 375                 380

Ile Ile Thr Asn Asn Arg Ile Gly Phe Thr Thr Glu Pro Ile Asp Ala
385                 390                 395                 400

Arg Ser Thr Thr Tyr Ser Thr Asp Val Ala Lys Gly Tyr Asp Val Pro
                405                 410                 415

Ile Phe His Val Asn Ala Asp Asp Val Glu Ala Thr Ile Glu Ala Ile
                420                 425                 430

Asp Ile Ala Met Glu Phe Arg Lys Glu Phe His Lys Asp Val Val Ile
            435                 440                 445

Asp Leu Val Gly Tyr Arg Arg Phe Gly His Asn Glu Met Asp Glu Pro
    450                 455                 460

Ser Ile Thr Asn Pro Val Pro Tyr Gln Asn Ile Arg Lys His Asp Ser
465                 470                 475                 480

Val Glu Tyr Val Phe Gly Lys Lys Leu Val Asn Glu Gly Val Ile Ser
                485                 490                 495

Glu Asp Glu Met His Ser Phe Ile Glu Gln Val Gln Lys Glu Leu Arg
                500                 505                 510

Gln Ala His Asp Lys Ile Asn Lys Ala Asp Lys Met Asp Asn Pro Asp
            515                 520                 525

Met Glu Lys Pro Ala Asp Leu Ala Leu Pro Leu Gln Ala Asp Glu Gln
    530                 535                 540

Ser Phe Thr Phe Asp His Leu Lys Glu Ile Asn Asp Ala Leu Leu Thr
545                 550                 555                 560

Tyr Pro Asp Gly Phe Asn Ile Leu Lys Lys Leu Asn Lys Val Leu Glu
                565                 570                 575

Lys Arg His Glu Pro Phe Asn Lys Glu Asp Gly Leu Val Asp Trp Ala
                580                 585                 590

Gln Ala Glu Gln Leu Ala Phe Ala Thr Ile Leu Gln Asp Gly Thr Pro
            595                 600                 605

Ile Arg Leu Thr Gly Gln Asp Ser Glu Arg Gly Thr Phe Ser His Arg
    610                 615                 620
```

```
His Ala Val Leu His Asp Glu Gln Thr Gly Glu Thr Tyr Thr Pro Leu
625                 630                 635                 640

His His Val Pro Asp Gln Lys Ala Thr Phe Asp Ile His Asn Ser Pro
            645                 650                 655

Leu Ser Glu Ala Ala Val Val Gly Phe Glu Tyr Gly Tyr Asn Val Glu
        660                 665                 670

Asn Lys Lys Ser Phe Asn Ile Trp Glu Ala Gln Tyr Gly Asp Phe Ala
    675                 680                 685

Asn Met Ser Gln Met Ile Phe Asp Asn Phe Leu Phe Ser Ser Arg Ser
690                 695                 700

Lys Trp Gly Glu Arg Ser Gly Leu Thr Leu Phe Leu Pro His Ala Tyr
705                 710                 715                 720

Glu Gly Gln Gly Pro Glu His Ser Ser Ala Arg Leu Glu Arg Phe Leu
                725                 730                 735

Gln Leu Ala Ala Glu Asn Asn Cys Thr Val Val Asn Leu Ser Ser Ser
            740                 745                 750

Ser Asn Tyr Phe His Leu Leu Arg Ala Gln Ala Ala Ser Leu Asp Ser
        755                 760                 765

Glu Gln Met Arg Pro Leu Val Val Met Ser Pro Lys Ser Leu Leu Arg
770                 775                 780

Asn Lys Thr Val Ala Lys Pro Ile Asp Glu Phe Thr Ser Gly Gly Phe
785                 790                 795                 800

Glu Pro Ile Leu Thr Glu Ser Tyr Gln Ala Asp Lys Val Thr Lys Val
                805                 810                 815

Ile Leu Ala Thr Gly Lys Met Phe Ile Asp Leu Lys Glu Ala Leu Ala
            820                 825                 830

Lys Asn Pro Asp Glu Ser Val Leu Leu Val Ala Ile Glu Arg Leu Tyr
        835                 840                 845

Pro Phe Pro Glu Glu Glu Ile Glu Ala Leu Leu Ala Gln Leu Pro Asn
850                 855                 860

Leu Glu Glu Val Ser Trp Val Gln Glu Glu Pro Lys Asn Gln Gly Ala
865                 870                 875                 880

Trp Leu Tyr Val Tyr Pro Tyr Val Lys Val Leu Val Ala Asp Lys Tyr
                885                 890                 895

Asp Leu Ser Tyr His Gly Arg Ile Gln Arg Ala Ala Pro Ala Glu Gly
            900                 905                 910

Asp Gly Glu Ile His Lys Leu Val Gln Asn Lys Ile Ile Glu Asn Ala
        915                 920                 925

Leu Lys Asn Asn
930

(2) INFORMATION FOR SEQ ID NO:46:

(i) SEQUENCE CHARACTERISTICS:
        (A) LENGTH: 2574 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p10b30)"

(ix) FEATURE:
        (A) NAME/KEY: CDS
        (B) LOCATION: 1..2571

(xi) SEQUENCE DESCRIPTION: SEQ ID NO:46:
```

-continued

```
ATG CGT CTG GAT CGT CTT ACT AAT AAA TTC CAG CTT GCT CTT GCC GAT    48
Met Arg Leu Asp Arg Leu Thr Asn Lys Phe Gln Leu Ala Leu Ala Asp
 1               5                  10                  15

GCC CAA TCA CTT GCA CTC GGG CAC GAC AAC CAA TTT ATC GAA CCA CTT    96
Ala Gln Ser Leu Ala Leu Gly His Asp Asn Gln Phe Ile Glu Pro Leu
             20                  25                  30

CAT TTA ATG AGC GCC CTG CTG AAT CAG GAA GGG GGT TCG GTT AGT CCT   144
His Leu Met Ser Ala Leu Leu Asn Gln Glu Gly Gly Ser Val Ser Pro
         35                  40                  45

TTA TTA ACA TCC GCT GGC ATA AAT GCT GGC CAG TTG CGC ACA GAT ATC   192
Leu Leu Thr Ser Ala Gly Ile Asn Ala Gly Gln Leu Arg Thr Asp Ile
     50                  55                  60

AAT CAG GCA TTA AAT CGT TTA CCG CAG GTT GAA GGT ACT GGT GGT GAT   240
Asn Gln Ala Leu Asn Arg Leu Pro Gln Val Glu Gly Thr Gly Gly Asp
 65                  70                  75                  80

GTC CAG CCA TCA CAG GAT CTG GTG CGC GTT CTT AAT CTT TGC GAC AAC   288
Val Gln Pro Ser Gln Asp Leu Val Arg Val Leu Asn Leu Cys Asp Asn
                 85                  90                  95

GTG GCG CAA AAA CGT GGT GAT AAC TTT ATC TCG TCA GAA CTG TTC GTT   336
Val Ala Gln Lys Arg Gly Asp Asn Phe Ile Ser Ser Glu Leu Phe Val
            100                 105                 110

CTG GCG GCA CTT GAG TCT CGC GGC ACC GTG GCC GAC ATC CTG AAA GCA   384
Leu Ala Ala Leu Glu Ser Arg Gly Thr Val Ala Asp Ile Leu Lys Ala
        115                 120                 125

GCA GGG GCG ACC ACC GCC AAC ATT ACT CAA GCG ATT GAA CAA ATG CGT   432
Ala Gly Ala Thr Thr Ala Asn Ile Thr Gln Ala Ile Glu Gln Met Arg
    130                 135                 140

GGA GGT GAA AGC GTG AAC GAT CAA GGT GCT GAA GAC CAA CGT CAG GCT   480
Gly Gly Glu Ser Val Asn Asp Gln Gly Ala Glu Asp Gln Arg Gln Ala
145                 150                 155                 160

TTG AAA AAA TAT ACC ATC GAC CTT ACC GAA CGA GCC GAA CAG GGC AAA   528
Leu Lys Lys Tyr Thr Ile Asp Leu Thr Glu Arg Ala Glu Gln Gly Lys
                165                 170                 175

CTC GAT CCG GTG ATT GGT CGT GAT GAA GAA ATT CGC CGT ACC ATT CAG   576
Leu Asp Pro Val Ile Gly Arg Asp Glu Glu Ile Arg Arg Thr Ile Gln
            180                 185                 190

GTG CTG CAA CGT CGT ACT AAA AAT AAC CCG GTA CTG ATT GGT GAA CCC   624
Val Leu Gln Arg Arg Thr Lys Asn Asn Pro Val Leu Ile Gly Glu Pro
        195                 200                 205

GGC GTC GGT AAA ACT GCC ATC GTT GAA GGT CTG GCG CAG CGT ATT ATC   672
Gly Val Gly Lys Thr Ala Ile Val Glu Gly Leu Ala Gln Arg Ile Ile
    210                 215                 220

AAC GGC GAA GTG CCG GAA GGG TTG AAA GGC CGC CGG GTA CTG GCG CTG   720
Asn Gly Glu Val Pro Glu Gly Leu Lys Gly Arg Arg Val Leu Ala Leu
225                 230                 235                 240

GAT ATG GGC GCG CTG GTG GCT GGG GCG AAA TAT CGC GGT GAG TTT GAA   768
Asp Met Gly Ala Leu Val Ala Gly Ala Lys Tyr Arg Gly Glu Phe Glu
                245                 250                 255

GAA CGT TTA AAA GGC GTG CTT AAC GAT CTT GCC AAA CAG GAA GGC AAC   816
Glu Arg Leu Lys Gly Val Leu Asn Asp Leu Ala Lys Gln Glu Gly Asn
            260                 265                 270

GTC ATC CTA TTT ATC GAC GAA TTA CAT ACC ATG GTC GGC GCG GGT AAA   864
Val Ile Leu Phe Ile Asp Glu Leu His Thr Met Val Gly Ala Gly Lys
        275                 280                 285

GCC GAT GGC GCA ATG GAC GCC GGA AAC ATG CTG AAA CCG GCG CTG GCG   912
Ala Asp Gly Ala Met Asp Ala Gly Asn Met Leu Lys Pro Ala Leu Ala
    290                 295                 300

CGT GGT GAA TTG CAC TGC GTA GGT GCC ACG ACG CTT GAC GAA TAT CGC   960
Arg Gly Glu Leu His Cys Val Gly Ala Thr Thr Leu Asp Glu Tyr Arg
305                 310                 315                 320
```

-continued

```
CAG TAC ATT GAA AAA GAT GCT GCG CTG GAA CGT CGT TTC CAG AAA GTG      1008
Gln Tyr Ile Glu Lys Asp Ala Ala Leu Glu Arg Arg Phe Gln Lys Val
            325                 330                 335

TTT GTT GCC GAG CCT TCT GTT GAA GAT ACC ATT GCG ATT CTG CGT GGC      1056
Phe Val Ala Glu Pro Ser Val Glu Asp Thr Ile Ala Ile Leu Arg Gly
        340                 345                 350

CTG AAA GAA CGT TAC GAA TTG CAC CAC CAT GTG CAA ATT ACT GAC CCG      1104
Leu Lys Glu Arg Tyr Glu Leu His His His Val Gln Ile Thr Asp Pro
    355                 360                 365

GCA ATT GTT GCA GCG GCG ACG TTG TCT CAT CGC TAC ATT GCT GAC CGT      1152
Ala Ile Val Ala Ala Ala Thr Leu Ser His Arg Tyr Ile Ala Asp Arg
370                 375                 380

CAG CTG CCG GAT AAA GCC ATC GAC CTG ATC GAT GAA GCA GCA TCC AGC      1200
Gln Leu Pro Asp Lys Ala Ile Asp Leu Ile Asp Glu Ala Ala Ser Ser
385                 390                 395                 400

ATT CGT ATG CAG ATT GAC TCA AAA CCA GAA GAA CTC GAC CGA CTC GAT      1248
Ile Arg Met Gln Ile Asp Ser Lys Pro Glu Glu Leu Asp Arg Leu Asp
            405                 410                 415

CGT CGT ATC ATC CAG CTC AAA CTG GAA CAA CAG GCG TTA ATG AAA GAG      1296
Arg Arg Ile Ile Gln Leu Lys Leu Glu Gln Gln Ala Leu Met Lys Glu
        420                 425                 430

TCT GAT GAA GCC AGT AAA AAA CGT CTG GAT ATG CTC AAC GAA GAA CTG      1344
Ser Asp Glu Ala Ser Lys Lys Arg Leu Asp Met Leu Asn Glu Glu Leu
    435                 440                 445

AGC GAC AAA GAA CGT CAG TAC TCC GAG TTA GAA GAA GAG TGG AAA GCA      1392
Ser Asp Lys Glu Arg Gln Tyr Ser Glu Leu Glu Glu Glu Trp Lys Ala
450                 455                 460

GAG AAG GCA TCG CTT TCT GGT ACG CAG ACC ATT AAA GCG GAA CTG GAA      1440
Glu Lys Ala Ser Leu Ser Gly Thr Gln Thr Ile Lys Ala Glu Leu Glu
465                 470                 475                 480

CAG GCG AAA ATC GCT ATT GAA CAG GCT CGC CGT GTG GGG GAC CTG GCG      1488
Gln Ala Lys Ile Ala Ile Glu Gln Ala Arg Arg Val Gly Asp Leu Ala
            485                 490                 495

CGG ATG TCT GAA CTG CAA TAC GGC AAA ATC CCG GAA CTG GAA AAG CAA      1536
Arg Met Ser Glu Leu Gln Tyr Gly Lys Ile Pro Glu Leu Glu Lys Gln
        500                 505                 510

CTG GAA GCC GCA ACG CAG CTC GAA GGC AAA ACT ATG CGT CTG TTG CGT      1584
Leu Glu Ala Ala Thr Gln Leu Glu Gly Lys Thr Met Arg Leu Leu Arg
    515                 520                 525

AAT AAA GTG ACC GAC GCC GAA ATT GCT GAA GTG CTG GCG CGT TGG ACG      1632
Asn Lys Val Thr Asp Ala Glu Ile Ala Glu Val Leu Ala Arg Trp Thr
530                 535                 540

GGG ATT CCG GTT TCT CGC ATG ATG GAA AGC GAG CGC GAA AAA CTG CTG      1680
Gly Ile Pro Val Ser Arg Met Met Glu Ser Glu Arg Glu Lys Leu Leu
545                 550                 555                 560

CGT ATG GAG CAA GAA CTG CAC CAT CGC GTA ATT GGT CAG AAC GAA GCG      1728
Arg Met Glu Gln Glu Leu His His Arg Val Ile Gly Gln Asn Glu Ala
            565                 570                 575

GTT GAT GCG GTA TCT AAC GCT ATT CGT CGT AGC CGT GCG GGG CTG GCG      1776
Val Asp Ala Val Ser Asn Ala Ile Arg Arg Ser Arg Ala Gly Leu Ala
        580                 585                 590

GAT CCA AAT CGC CCG ATT GGT TCA TTC CTG TTC CTC GGC CCA ACT GGT      1824
Asp Pro Asn Arg Pro Ile Gly Ser Phe Leu Phe Leu Gly Pro Thr Gly
    595                 600                 605

GTG GGG AAA ACA GAG CTT TGT AAG GCG CTG GCG AAC TTT ATG TTT GAT      1872
Val Gly Lys Thr Glu Leu Cys Lys Ala Leu Ala Asn Phe Met Phe Asp
610                 615                 620

AGC GAC GAG GCG ATG GTC CGT ATC GAT ATG TCC GAG TTT ATG GAG AAA      1920
Ser Asp Glu Ala Met Val Arg Ile Asp Met Ser Glu Phe Met Glu Lys
```

```
                625             630             635             640
CAC TCG GTG TCT CGT TTG GTT GGT GCG CCT CCG GGA TAT GTC GGT TAT    1968
His Ser Val Ser Arg Leu Val Gly Ala Pro Pro Gly Tyr Val Gly Tyr
                645             650             655

GAA GAA GGT GGC TAC CTG ACC GAA GCG GTG CGT CGT CGT CCG TAT TCC    2016
Glu Glu Gly Gly Tyr Leu Thr Glu Ala Val Arg Arg Arg Pro Tyr Ser
                660             665             670

GTC ATC CTG CTG GAT GAA GTG GAA AAA GCG CAT CCG GAT GTC TTC AAC    2064
Val Ile Leu Leu Asp Glu Val Glu Lys Ala His Pro Asp Val Phe Asn
                675             680             685

ATT CTG TTG CAG GTA CTG GAT GAT GGG CGT CTG ACT GAC GGG CAA GGG    2112
Ile Leu Leu Gln Val Leu Asp Asp Gly Arg Leu Thr Asp Gly Gln Gly
                690             695             700

AGA ACG GTC GAC TTC CGT AAT ACG GTC GTC ATT ATG ACC TCT AAC CTC    2160
Arg Thr Val Asp Phe Arg Asn Thr Val Val Ile Met Thr Ser Asn Leu
705             710             715             720

GGT TCC GAT CTG ATT CAG GAA CGC TTC GGT GAA CTG GAT TAT GCG CAC    2208
Gly Ser Asp Leu Ile Gln Glu Arg Phe Gly Glu Leu Asp Tyr Ala His
                725             730             735

ATG AAA GAG CTG GTG CTC GGT GTG GTA AGC CAT AAC TTC CGT CCG GAA    2256
Met Lys Glu Leu Val Leu Gly Val Val Ser His Asn Phe Arg Pro Glu
                740             745             750

TTC ATT AAC CGT ATC GAT GAA GTG GTG GTC TTC CAT CCG CTG GGT GAA    2304
Phe Ile Asn Arg Ile Asp Glu Val Val Val Phe His Pro Leu Gly Glu
                755             760             765

CAG CAC ATT GCC TCG ATT GCG CAG ATT CAG TTG AAA CGT CTG TAC AAA    2352
Gln His Ile Ala Ser Ile Ala Gln Ile Gln Leu Lys Arg Leu Tyr Lys
                770             775             780

CGT CTG GAA GAA CGT GGT TAT GAA ATC CAC ATT TCT GAC GAG GCG CTG    2400
Arg Leu Glu Glu Arg Gly Tyr Glu Ile His Ile Ser Asp Glu Ala Leu
785             790             795             800

AAA CTG CTG AGC GAG AAC GGT TAC GAT CCG GTC TAT GGT GCA CGT CCT    2448
Lys Leu Leu Ser Glu Asn Gly Tyr Asp Pro Val Tyr Gly Ala Arg Pro
                805             810             815

CTG AAA CGT GCA ATT CAG CAG CAG ATC GAA AAC CCG CTG GCA CAG CAA    2496
Leu Lys Arg Ala Ile Gln Gln Gln Ile Glu Asn Pro Leu Ala Gln Gln
                820             825             830

ATA CTG TCT GGT GAA TTG GTT CCG GGT AAA GTG ATT CGC CTG GAA GTT    2544
Ile Leu Ser Gly Glu Leu Val Pro Gly Lys Val Ile Arg Leu Glu Val
                835             840             845

AAT GAA GAC CGG ATT GTC GCC GTC CAG TAA                            2574
Asn Glu Asp Arg Ile Val Ala Val Gln
                850             855
```

(2) INFORMATION FOR SEQ ID NO:47:

(i) SEQUENCE CHARACTERISTICS:
        (A) LENGTH: 857 amino acids
        (B) TYPE: amino acid
        (D) TOPOLOGY: linear (ii) MOLECULE TYPE: protein (xi) SEQUENCE DESCRIPTION: SEQ ID NO:47:

```
Met Arg Leu Asp Arg Leu Thr Asn Lys Phe Gln Leu Ala Leu Ala Asp
1               5                   10                  15

Ala Gln Ser Leu Ala Leu Gly His Asp Asn Gln Phe Ile Glu Pro Leu
                20                  25                  30

His Leu Met Ser Ala Leu Leu Asn Gln Glu Gly Gly Ser Val Ser Pro
                35                  40                  45
```

-continued

```
Leu Leu Thr Ser Ala Gly Ile Asn Ala Gly Gln Leu Arg Thr Asp Ile
     50                  55                  60

Asn Gln Ala Leu Asn Arg Leu Pro Gln Val Glu Gly Thr Gly Gly Asp
 65                  70                  75                  80

Val Gln Pro Ser Gln Asp Leu Val Arg Val Leu Asn Leu Cys Asp Asn
                 85                  90                  95

Val Ala Gln Lys Arg Gly Asp Asn Phe Ile Ser Ser Glu Leu Phe Val
                100                 105                 110

Leu Ala Ala Leu Glu Ser Arg Gly Thr Val Ala Asp Ile Leu Lys Ala
                115                 120                 125

Ala Gly Ala Thr Thr Ala Asn Ile Thr Gln Ala Ile Glu Gln Met Arg
            130                 135                 140

Gly Gly Glu Ser Val Asn Asp Gln Gly Ala Glu Asp Gln Arg Gln Ala
145                 150                 155                 160

Leu Lys Lys Tyr Thr Ile Asp Leu Thr Glu Arg Ala Glu Gln Gly Lys
                165                 170                 175

Leu Asp Pro Val Ile Gly Arg Asp Glu Glu Ile Arg Arg Thr Ile Gln
            180                 185                 190

Val Leu Gln Arg Arg Thr Lys Asn Asn Pro Val Leu Ile Gly Glu Pro
        195                 200                 205

Gly Val Gly Lys Thr Ala Ile Val Glu Gly Leu Ala Gln Arg Ile Ile
    210                 215                 220

Asn Gly Glu Val Pro Glu Gly Leu Lys Gly Arg Arg Val Leu Ala Leu
225                 230                 235                 240

Asp Met Gly Ala Leu Val Ala Gly Ala Lys Tyr Arg Gly Glu Phe Glu
                245                 250                 255

Glu Arg Leu Lys Gly Val Leu Asn Asp Leu Ala Lys Gln Glu Gly Asn
                260                 265                 270

Val Ile Leu Phe Ile Asp Glu Leu His Thr Met Val Gly Ala Gly Lys
            275                 280                 285

Ala Asp Gly Ala Met Asp Ala Gly Asn Met Leu Lys Pro Ala Leu Ala
        290                 295                 300

Arg Gly Glu Leu His Cys Val Gly Ala Thr Thr Leu Asp Glu Tyr Arg
305                 310                 315                 320

Gln Tyr Ile Glu Lys Asp Ala Ala Leu Glu Arg Arg Phe Gln Lys Val
                325                 330                 335

Phe Val Ala Glu Pro Ser Val Glu Asp Thr Ile Ala Ile Leu Arg Gly
                340                 345                 350

Leu Lys Glu Arg Tyr Glu Leu His His His Val Gln Ile Thr Asp Pro
            355                 360                 365

Ala Ile Val Ala Ala Thr Leu Ser His Arg Tyr Ile Ala Asp Arg
        370                 375                 380

Gln Leu Pro Asp Lys Ala Ile Asp Leu Ile Asp Glu Ala Ala Ser Ser
385                 390                 395                 400

Ile Arg Met Gln Ile Asp Ser Lys Pro Glu Glu Leu Asp Arg Leu Asp
                405                 410                 415

Arg Arg Ile Ile Gln Leu Lys Leu Glu Gln Gln Ala Leu Met Lys Glu
                420                 425                 430

Ser Asp Glu Ala Ser Lys Lys Arg Leu Asp Met Leu Asn Glu Glu Leu
            435                 440                 445

Ser Asp Lys Glu Arg Gln Tyr Ser Glu Leu Glu Glu Trp Lys Ala
450                 455                 460

Glu Lys Ala Ser Leu Ser Gly Thr Gln Thr Ile Lys Ala Glu Leu Glu
```

-continued

```
465                 470                 475                 480
Gln Ala Lys Ile Ala Ile Glu Gln Ala Arg Arg Val Gly Asp Leu Ala
                485                 490                 495
Arg Met Ser Glu Leu Gln Tyr Gly Lys Ile Pro Glu Leu Glu Lys Gln
                500                 505                 510
Leu Glu Ala Ala Thr Gln Leu Glu Gly Lys Thr Met Arg Leu Leu Arg
                515                 520                 525
Asn Lys Val Thr Asp Ala Glu Ile Ala Glu Val Leu Ala Arg Trp Thr
                530                 535                 540
Gly Ile Pro Val Ser Arg Met Met Glu Ser Glu Arg Glu Lys Leu Leu
545                 550                 555                 560
Arg Met Glu Gln Glu Leu His His Arg Val Ile Gly Gln Asn Glu Ala
                565                 570                 575
Val Asp Ala Val Ser Asn Ala Ile Arg Arg Ser Arg Ala Gly Leu Ala
                580                 585                 590
Asp Pro Asn Arg Pro Ile Gly Ser Phe Leu Phe Leu Gly Pro Thr Gly
                595                 600                 605
Val Gly Lys Thr Glu Leu Cys Lys Ala Leu Ala Asn Phe Met Phe Asp
                610                 615                 620
Ser Asp Glu Ala Met Val Arg Ile Asp Met Ser Glu Phe Met Glu Lys
625                 630                 635                 640
His Ser Val Ser Arg Leu Val Gly Ala Pro Pro Gly Tyr Val Gly Tyr
                645                 650                 655
Glu Glu Gly Gly Tyr Leu Thr Glu Ala Val Arg Arg Pro Tyr Ser
                660                 665                 670
Val Ile Leu Leu Asp Glu Val Glu Lys Ala His Pro Asp Val Phe Asn
                675                 680                 685
Ile Leu Leu Gln Val Leu Asp Asp Gly Arg Leu Thr Asp Gly Gln Gly
                690                 695                 700
Arg Thr Val Asp Phe Arg Asn Thr Val Val Ile Met Thr Ser Asn Leu
705                 710                 715                 720
Gly Ser Asp Leu Ile Gln Glu Arg Phe Gly Glu Leu Asp Tyr Ala His
                725                 730                 735
Met Lys Glu Leu Val Leu Gly Val Val Ser His Asn Phe Arg Pro Glu
                740                 745                 750
Phe Ile Asn Arg Ile Asp Glu Val Val Phe His Pro Leu Gly Glu
                755                 760                 765
Gln His Ile Ala Ser Ile Ala Gln Ile Gln Leu Lys Arg Leu Tyr Lys
                770                 775                 780
Arg Leu Glu Glu Arg Gly Tyr Glu Ile His Ile Ser Asp Glu Ala Leu
785                 790                 795                 800
Lys Leu Leu Ser Glu Asn Gly Tyr Asp Pro Val Tyr Gly Ala Arg Pro
                805                 810                 815
Leu Lys Arg Ala Ile Gln Gln Ile Glu Asn Pro Leu Ala Gln Gln
                820                 825                 830
Ile Leu Ser Gly Glu Leu Val Pro Gly Lys Val Ile Arg Leu Glu Val
                835                 840                 845
Asn Glu Asp Arg Ile Val Ala Val Gln
                850                 855
```

(2) INFORMATION FOR SEQ ID NO:48:

(i) SEQUENCE CHARACTERISTICS:
        (A) LENGTH: 1239 base pairs

-continued

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p13c3)"

(ix) FEATURE:
        (A) NAME/KEY: CDS
        (B) LOCATION: 1..1236

(xi) SEQUENCE DESCRIPTION: SEQ ID NO:48:

ATG ATG AAA GAA AAA GTG ATT TTT CTC GTT GAC ATG CAA TCG TTT TAT      48
Met Met Lys Glu Lys Val Ile Phe Leu Val Asp Met Gln Ser Phe Tyr
 1               5                  10                  15

GCA TCT GTA GAG AAA GCG GAA AAT CCA CAT TTG AAA AAT AGG CCC GTC      96
Ala Ser Val Glu Lys Ala Glu Asn Pro His Leu Lys Asn Arg Pro Val
             20                  25                  30

ATT GTT TCG GGT GAC CCT GAA AAA AGG GGC GGA GTC GTA TTG GCT GCC     144
Ile Val Ser Gly Asp Pro Glu Lys Arg Gly Gly Val Val Leu Ala Ala
         35                  40                  45

TGC CCG CTG GCA AAA CAA AAG GGT GTG GTG AAT GCT TCA CGG CTG TGG     192
Cys Pro Leu Ala Lys Gln Lys Gly Val Val Asn Ala Ser Arg Leu Trp
 50                  55                  60

GAG GCG CAG GAA AAG TGT CCT GAG GCT GTT GTG CTC CGG CCG CGT ATG     240
Glu Ala Gln Glu Lys Cys Pro Glu Ala Val Val Leu Arg Pro Arg Met
 65                  70                  75                  80

CAG CGG TAT ATT GAT GTA TCA CTG CAA ATT ACG GCC ATT CTC GAG GAG     288
Gln Arg Tyr Ile Asp Val Ser Leu Gln Ile Thr Ala Ile Leu Glu Glu
                 85                  90                  95

TAT ACA GAC CTT GTG GAG CCG TAT TCC ATC GAT GAA CAG TTC ATG GAC     336
Tyr Thr Asp Leu Val Glu Pro Tyr Ser Ile Asp Glu Gln Phe Met Asp
            100                 105                 110

ATT ACA GGC AGC CAG AAG CTG TTT GGG ACG CCG ATG GAG ATC GCG AAA     384
Ile Thr Gly Ser Gln Lys Leu Phe Gly Thr Pro Met Glu Ile Ala Lys
        115                 120                 125

AGC ATT CAG GGC AGA ATC ATG CGG GAG ATC GGC GTT TAT GCA CGG GTC     432
Ser Ile Gln Gly Arg Ile Met Arg Glu Ile Gly Val Tyr Ala Arg Val
    130                 135                 140

GGA ATC GGC CCT AAC AAA GCG CTG GCC AAA ATT GCG TGT GAC AAT TTT     480
Gly Ile Gly Pro Asn Lys Ala Leu Ala Lys Ile Ala Cys Asp Asn Phe
145                 150                 155                 160

GCC AAA AAG AAT AAG AAC GGT ATT TTT ACC TTA ACG AAA GAA AAT ATG     528
Ala Lys Lys Asn Lys Asn Gly Ile Phe Thr Leu Thr Lys Glu Asn Met
                165                 170                 175

AAA ACC GAA ATG TGG CCG CTC CCG GTG GGC AGC ATG TTT GGC GTC GGG     576
Lys Thr Glu Met Trp Pro Leu Pro Val Gly Ser Met Phe Gly Val Gly
            180                 185                 190

AGC CGC ATG AAG CAT CAT TTA AAT CGA ATG GGC ATC AGC ACG ATC GGC     624
Ser Arg Met Lys His His Leu Asn Arg Met Gly Ile Ser Thr Ile Gly
        195                 200                 205

GGG CTC GCG GCT TTT CCG CTC GAT CTT TTA AAA AAG AAA TGG GGC ATT     672
Gly Leu Ala Ala Phe Pro Leu Asp Leu Leu Lys Lys Lys Trp Gly Ile
    210                 215                 220

AAC GGC CAC GTG CTG TGG ATG ACG GCA AAC GGA ATC GAC TAT TCC CCT     720
Asn Gly His Val Leu Trp Met Thr Ala Asn Gly Ile Asp Tyr Ser Pro
225                 230                 235                 240

GTG TCA ACT TCG TCT CTG GAC GGG CAA AAG GCG ATA GGT CAT GGA ATG     768
Val Ser Thr Ser Ser Leu Asp Gly Gln Lys Ala Ile Gly His Gly Met
                245                 250                 255

ACT CTC CCG AGA GAC TAC GAA CAC TTT GAC AAA GAA ATC AAG GTC GTA     816
Thr Leu Pro Arg Asp Tyr Glu His Phe Asp Lys Glu Ile Lys Val Val
```

-continued

```
              260                 265                 270
TTG CTT GAG CTG AGT GAA GAG GTG TGC AGG CGA AGC CGA AAC GCC GGG          864
Leu Leu Glu Leu Ser Glu Glu Val Cys Arg Arg Ser Arg Asn Ala Gly
            275                 280                 285

GTC ATG GGG CAG ACA GTG TCA GTG AGC TGC CGG GGT GCT GAT TTT GAT          912
Val Met Gly Gln Thr Val Ser Val Ser Cys Arg Gly Ala Asp Phe Asp
        290                 295                 300

TGG CCG ACG GGC TTC AAC CGG CAA GTG AAG CTG GCA GAG CCG ACT AAT          960
Trp Pro Thr Gly Phe Asn Arg Gln Val Lys Leu Ala Glu Pro Thr Asn
305                 310                 315                 320

TCT ACG CAG GAT GTA TAT GAG GCT GTA CGA CGG CTG TTT CTT ACA TTT         1008
Ser Thr Gln Asp Val Tyr Glu Ala Val Arg Arg Leu Phe Leu Thr Phe
                325                 330                 335

TGG GAC GGG AAA CCC GTC CGC CGC CTC GGT GTC AAT CTG TCT CAG CTC         1056
Trp Asp Gly Lys Pro Val Arg Arg Leu Gly Val Asn Leu Ser Gln Leu
            340                 345                 350

TCA TCT GAT GAC ATA TGG CAG CTC AAT TTA TTT CAG GAT TAT GCA AAG         1104
Ser Ser Asp Asp Ile Trp Gln Leu Asn Leu Phe Gln Asp Tyr Ala Lys
        355                 360                 365

AAA ATG AGC CTA GGC TAT GTG ATG GAT GGC ATT AAA AAT CGA TTC GGC         1152
Lys Met Ser Leu Gly Tyr Val Met Asp Gly Ile Lys Asn Arg Phe Gly
370                 375                 380

GAT ACA GCA ATC ATC AGG GCG GCG TCA CTG ACA GCG GCA GGC CAG GCA         1200
Asp Thr Ala Ile Ile Arg Ala Ala Ser Leu Thr Ala Ala Gly Gln Ala
385                 390                 395                 400

TTT GAA CGT GCG GCT AAA ATA GGG GGG CAT TAT AAA TGA                     1239
Phe Glu Arg Ala Ala Lys Ile Gly Gly His Tyr Lys
                405                 410
```

(2) INFORMATION FOR SEQ ID NO:49:

(i) SEQUENCE CHARACTERISTICS:
        (A) LENGTH: 412 amino acids
        (B) TYPE: amino acid
        (D) TOPOLOGY: linear (ii) MOLECULE TYPE: protein (xi) SEQUENCE DESCRIPTION: SEQ ID NO:49:

```
Met Met Lys Glu Lys Val Ile Phe Leu Val Asp Met Gln Ser Phe Tyr
1               5                   10                  15

Ala Ser Val Glu Lys Ala Glu Asn Pro His Leu Lys Asn Arg Pro Val
            20                  25                  30

Ile Val Ser Gly Asp Pro Glu Lys Arg Gly Gly Val Val Leu Ala Ala
        35                  40                  45

Cys Pro Leu Ala Lys Gln Lys Gly Val Val Asn Ala Ser Arg Leu Trp
    50                  55                  60

Glu Ala Gln Glu Lys Cys Pro Glu Ala Val Val Leu Arg Pro Arg Met
65                  70                  75                  80

Gln Arg Tyr Ile Asp Val Ser Leu Gln Ile Thr Ala Ile Leu Glu Glu
                85                  90                  95

Tyr Thr Asp Leu Val Glu Pro Tyr Ser Ile Asp Glu Gln Phe Met Asp
            100                 105                 110

Ile Thr Gly Ser Gln Lys Leu Phe Gly Thr Pro Met Glu Ile Ala Lys
        115                 120                 125

Ser Ile Gln Gly Arg Ile Met Arg Glu Ile Gly Val Tyr Ala Arg Val
    130                 135                 140

Gly Ile Gly Pro Asn Lys Ala Leu Ala Lys Ile Ala Cys Asp Asn Phe
145                 150                 155                 160
```

```
Ala Lys Lys Asn Lys Asn Gly Ile Phe Thr Leu Thr Lys Glu Asn Met
            165                 170                 175

Lys Thr Glu Met Trp Pro Leu Pro Val Gly Ser Met Phe Gly Val Gly
        180                 185                 190

Ser Arg Met Lys His His Leu Asn Arg Met Gly Ile Ser Thr Ile Gly
        195                 200                 205

Gly Leu Ala Ala Phe Pro Leu Asp Leu Leu Lys Lys Lys Trp Gly Ile
        210                 215                 220

Asn Gly His Val Leu Trp Met Thr Ala Asn Gly Ile Asp Tyr Ser Pro
225                 230                 235                 240

Val Ser Thr Ser Ser Leu Asp Gly Gln Lys Ala Ile Gly His Gly Met
                245                 250                 255

Thr Leu Pro Arg Asp Tyr Glu His Phe Asp Lys Glu Ile Lys Val Val
            260                 265                 270

Leu Leu Glu Leu Ser Glu Val Cys Arg Arg Ser Arg Asn Ala Gly
            275                 280                 285

Val Met Gly Gln Thr Val Ser Val Ser Cys Arg Gly Ala Asp Phe Asp
        290                 295                 300

Trp Pro Thr Gly Phe Asn Arg Gln Val Lys Leu Ala Glu Pro Thr Asn
305                 310                 315                 320

Ser Thr Gln Asp Val Tyr Glu Ala Val Arg Arg Leu Phe Leu Thr Phe
                325                 330                 335

Trp Asp Gly Lys Pro Val Arg Arg Leu Gly Val Asn Leu Ser Gln Leu
            340                 345                 350

Ser Ser Asp Asp Ile Trp Gln Leu Asn Leu Phe Gln Asp Tyr Ala Lys
            355                 360                 365

Lys Met Ser Leu Gly Tyr Val Met Asp Gly Ile Lys Asn Arg Phe Gly
        370                 375                 380

Asp Thr Ala Ile Ile Arg Ala Ala Ser Leu Thr Ala Ala Gly Gln Ala
385                 390                 395                 400

Phe Glu Arg Ala Ala Lys Ile Gly Gly His Tyr Lys
                405                 410
```

(2) INFORMATION FOR SEQ ID NO:50:

(i) SEQUENCE CHARACTERISTICS:
        (A) LENGTH: 1452 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p4b3)"
            Unknown = Xaa
            Unknown for codon no. 296 = TAA (stop codon)

(ix) FEATURE:
        (A) NAME/KEY: CDS
        (B) LOCATION: 1..1449

(xi) SEQUENCE DESCRIPTION: SEQ ID NO:50:

```
ATG AGT AAA ATT ATT GGA TCA GAC AGA GTC AAA AGA GGT ATG GCT GAA      48
Met Ser Lys Ile Ile Gly Ser Asp Arg Val Lys Arg Gly Met Ala Glu
 1               5                  10                  15

ATG CAA AAA GGC GGC GTT ATT ATG GAT GTC GTT AAT GCT GAG CAA GCA      96
Met Gln Lys Gly Gly Val Ile Met Asp Val Val Asn Ala Glu Gln Ala
             20                  25                  30

AGA ATT GCA GAA GAA GCT GGC GCG GTA GCA GTT ATG GCA TTA GAA CGA     144
Arg Ile Ala Glu Glu Ala Gly Ala Val Ala Val Met Ala Leu Glu Arg
```

-continued

```
           35                  40                  45
GTA CCT TCT GAT ATT AGA GCT GCT GGT GGT GTT GCA CGT ATG GCA AAC     192
Val Pro Ser Asp Ile Arg Ala Ala Gly Gly Val Ala Arg Met Ala Asn
         50                  55                  60

CCT AAA ATT GTA GAA GAA GTA ATG AAT GCT GTT TCT ATT CCA GTC ATG     240
Pro Lys Ile Val Glu Glu Val Met Asn Ala Val Ser Ile Pro Val Met
 65                  70                  75                  80

GCT AAA GCA CGT ATT GGT CAT ATC ACT GAA GCA AGA GTA TTA GAG GCG     288
Ala Lys Ala Arg Ile Gly His Ile Thr Glu Ala Arg Val Leu Glu Ala
                 85                  90                  95

ATG GGT GTT GAC TAT ATT GAT GAA TCA GAA GTG TTA ACA CCA GCA GAT     336
Met Gly Val Asp Tyr Ile Asp Glu Ser Glu Val Leu Thr Pro Ala Asp
             100                 105                 110

GAG GAA TAT CAC TTA AGA AAA GAT CAA TTT ACA GTA CCA TTT GTA TGT     384
Glu Glu Tyr His Leu Arg Lys Asp Gln Phe Thr Val Pro Phe Val Cys
         115                 120                 125

GGA TGT CGT AAT TTA GGT GAA GmT GCG CGT AGA ATT GGT GAA GGT GCT     432
Gly Cys Arg Asn Leu Gly Glu Xaa Ala Arg Arg Ile Gly Glu Gly Ala
     130                 135                 140

GCT ATG TTA CGT ACT AAA GGT GAA CCA GGT ACA GGT AAT ATT GTT GAA     480
Ala Met Leu Arg Thr Lys Gly Glu Pro Gly Thr Gly Asn Ile Val Glu
145                 150                 155                 160

GCT GTA AGA CAT ATG AGA CAA GTT AAT TCA GAA GTT AGT CGA TTG ACT     528
Ala Val Arg His Met Arg Gln Val Asn Ser Glu Val Ser Arg Leu Thr
                 165                 170                 175

GTA ATG AAT GAT GAT GAG ATT ATG ACT TTT GCG AAA GAT ATC GGT GCG     576
Val Met Asn Asp Asp Glu Ile Met Thr Phe Ala Lys Asp Ile Gly Ala
             180                 185                 190

CCT TAT GAA ATT TTA AAA CAA ATT AAA GAC AAT GGT CGT TTA CCG GTA     624
Pro Tyr Glu Ile Leu Lys Gln Ile Lys Asp Asn Gly Arg Leu Pro Val
         195                 200                 205

GTT AAC TTT GCA GCT GGT GGC GTT GCG ACT CCT CAA GAT GCT GCT TTA     672
Val Asn Phe Ala Ala Gly Gly Val Ala Thr Pro Gln Asp Ala Ala Leu
     210                 215                 220

ATG ATG GAA TTA GGT GCT GAC GGT GTA TTC GTT GGA TCA GGT ATT TTT     720
Met Met Glu Leu Gly Ala Asp Gly Val Phe Val Gly Ser Gly Ile Phe
225                 230                 235                 240

AAA TCA GAA GAT CCA GAA AAA TTT GCT AAA GCA ATT GTT CAA GCA ACA     768
Lys Ser Glu Asp Pro Glu Lys Phe Ala Lys Ala Ile Val Gln Ala Thr
                 245                 250                 255

ACA CAT TAC CAA GAC TAT GAA CTA ATT GGA AGA TTA GCA AGT GAA CTT     816
Thr His Tyr Gln Asp Tyr Glu Leu Ile Gly Arg Leu Ala Ser Glu Leu
             260                 265                 270

GGC ACT GCT ATG AAA GGT TTA GAT ATC AAT CAA TTA TCA TTA GAA GAA     864
Gly Thr Ala Met Lys Gly Leu Asp Ile Asn Gln Leu Ser Leu Glu Glu
         275                 280                 285

CGT ATG CAA GAG CGT GGT TGG TAA GAT ATG AAA ATA GGT GTA TTA GCA     912
Arg Met Gln Glu Arg Gly Trp Xaa Asp Met Lys Ile Gly Val Leu Ala
     290                 295                 300

TTA CAA GGT GCA GTA CGT GAA CAT ATT AGA CAT ATT GAA TTA AGT GGT     960
Leu Gln Gly Ala Val Arg Glu His Ile Arg His Ile Glu Leu Ser Gly
305                 310                 315                 320

CAT GAA GGT ATT GCA GTT AAA AAA GTT GAA CAA TTA GAA GAA ATC GAG    1008
His Glu Gly Ile Ala Val Lys Lys Val Glu Gln Leu Glu Glu Ile Glu
                 325                 330                 335

GGC TTA ATA TTA CCT GGT GGC GAG TCT ACA ACG TTA CGT CGA TTA ATG    1056
Gly Leu Ile Leu Pro Gly Gly Glu Ser Thr Thr Leu Arg Arg Leu Met
             340                 345                 350

AAT TTA TAT GGA TTT AAA GAG GCT TTA CAA AAT TCA ACT TTA CCT ATG    1104
Asn Leu Tyr Gly Phe Lys Glu Ala Leu Gln Asn Ser Thr Leu Pro Met
```

```
                                                                      -continued Asn Leu Tyr Gly Phe Lys Glu Ala Leu Gln Asn Ser Thr Leu Pro Met
    355                 360                 365

TTT GGT ACA TGC GCA GGA TTA ATA GTT CTA GCG CAA GAT ATA GTT GGT       1152
Phe Gly Thr Cys Ala Gly Leu Ile Val Leu Ala Gln Asp Ile Val Gly
    370                 375                 380

GAA GAA GGA TAC CTT AAC AAG TTG AAT ATT ACT GTA CAA CGA AAC TCA       1200
Glu Glu Gly Tyr Leu Asn Lys Leu Asn Ile Thr Val Gln Arg Asn Ser
385                 390                 395                 400

TTC GGT AGA CAA GTT GAC AGC TTT GAA ACA GAA TTA GAT ATT AAA GGT       1248
Phe Gly Arg Gln Val Asp Ser Phe Glu Thr Glu Leu Asp Ile Lys Gly
                405                 410                 415

ATC GCT ACA GAT ATT GAA GGT GTC TTT ATA AGA GCC CCA CAT ATT GAA       1296
Ile Ala Thr Asp Ile Glu Gly Val Phe Ile Arg Ala Pro His Ile Glu
            420                 425                 430

AAA GTA GGT CAA GGC GTA GAT ATC CTA TGT AAG GTT AAT GAG AAA ATT       1344
Lys Val Gly Gln Gly Val Asp Ile Leu Cys Lys Val Asn Glu Lys Ile
        435                 440                 445

GTA GCT GTT CAG CAA GGT AAA TAT TTA GGC GTA TCA TTC CAT CCT GAA       1392
Val Ala Val Gln Gln Gly Lys Tyr Leu Gly Val Ser Phe His Pro Glu
    450                 455                 460

TTA ACA GAT GAC TAT AGA GTA ACT GAT TAC TTT ATT AAT CAT ATT GTA       1440
Leu Thr Asp Asp Tyr Arg Val Thr Asp Tyr Phe Ile Asn His Ile Val
465                 470                 475                 480

AAA AAA GCA TAG                                                       1452
Lys Lys Ala (2) INFORMATION FOR SEQ ID NO:51:

(i) SEQUENCE CHARACTERISTICS:
        (A) LENGTH: 483 amino acids
        (B) TYPE: amino acid
        (D) TOPOLOGY: linear (ii) MOLECULE TYPE: protein (xi) SEQUENCE DESCRIPTION: SEQ ID NO:51:

Met Ser Lys Ile Ile Gly Ser Asp Arg Val Lys Arg Gly Met Ala Glu
1               5                   10                  15

Met Gln Lys Gly Gly Val Ile Met Asp Val Val Asn Ala Glu Gln Ala
                20                  25                  30

Arg Ile Ala Glu Glu Ala Gly Ala Val Ala Val Met Ala Leu Glu Arg
            35                  40                  45

Val Pro Ser Asp Ile Arg Ala Ala Gly Gly Val Ala Arg Met Ala Asn
        50                  55                  60

Pro Lys Ile Val Glu Glu Val Met Asn Ala Val Ser Ile Pro Val Met
65                  70                  75                  80

Ala Lys Ala Arg Ile Gly His Ile Thr Glu Ala Arg Val Leu Glu Ala
                85                  90                  95

Met Gly Val Asp Tyr Ile Asp Glu Ser Glu Val Leu Thr Pro Ala Asp
                100                 105                 110

Glu Glu Tyr His Leu Arg Lys Asp Gln Phe Thr Val Pro Phe Val Cys
            115                 120                 125

Gly Cys Arg Asn Leu Gly Glu Xaa Ala Arg Arg Ile Gly Glu Gly Ala
        130                 135                 140

Ala Met Leu Arg Thr Lys Gly Glu Pro Gly Thr Gly Asn Ile Val Glu
145                 150                 155                 160

Ala Val Arg His Met Arg Gln Val Asn Ser Glu Val Ser Arg Leu Thr
                165                 170                 175
```

```
Val Met Asn Asp Asp Glu Ile Met Thr Phe Ala Lys Asp Ile Gly Ala
            180                 185                 190

Pro Tyr Glu Ile Leu Lys Gln Ile Lys Asp Asn Gly Arg Leu Pro Val
        195                 200                 205

Val Asn Phe Ala Ala Gly Gly Val Ala Thr Pro Gln Asp Ala Ala Leu
        210                 215                 220

Met Met Glu Leu Gly Ala Asp Gly Val Phe Val Gly Ser Gly Ile Phe
225                 230                 235                 240

Lys Ser Glu Asp Pro Glu Lys Phe Ala Lys Ala Ile Val Gln Ala Thr
                245                 250                 255

Thr His Tyr Gln Asp Tyr Glu Leu Ile Gly Arg Leu Ala Ser Glu Leu
            260                 265                 270

Gly Thr Ala Met Lys Gly Leu Asp Ile Asn Gln Leu Ser Leu Glu Glu
        275                 280                 285

Arg Met Gln Glu Arg Gly Trp Xaa Asp Met Lys Ile Gly Val Leu Ala
        290                 295                 300

Leu Gln Gly Ala Val Arg Glu His Ile Arg His Ile Glu Leu Ser Gly
305                 310                 315                 320

His Glu Gly Ile Ala Val Lys Lys Val Glu Gln Leu Glu Glu Ile Glu
                325                 330                 335

Gly Leu Ile Leu Pro Gly Gly Glu Ser Thr Thr Leu Arg Arg Leu Met
            340                 345                 350

Asn Leu Tyr Gly Phe Lys Glu Ala Leu Gln Asn Ser Thr Leu Pro Met
        355                 360                 365

Phe Gly Thr Cys Ala Gly Leu Ile Val Leu Ala Gln Asp Ile Val Gly
        370                 375                 380

Glu Glu Gly Tyr Leu Asn Lys Leu Asn Ile Thr Val Gln Arg Asn Ser
385                 390                 395                 400

Phe Gly Arg Gln Val Asp Ser Phe Glu Thr Glu Leu Asp Ile Lys Gly
                405                 410                 415

Ile Ala Thr Asp Ile Glu Gly Val Phe Ile Arg Ala Pro His Ile Glu
            420                 425                 430

Lys Val Gly Gln Gly Val Asp Ile Leu Cys Lys Val Asn Glu Lys Ile
        435                 440                 445

Val Ala Val Gln Gln Gly Lys Tyr Leu Gly Val Ser Phe His Pro Glu
        450                 455                 460

Leu Thr Asp Asp Tyr Arg Val Thr Asp Tyr Phe Ile Asn His Ile Val
465                 470                 475                 480

Lys Lys Ala (2) INFORMATION FOR SEQ ID NO:52:

(i) SEQUENCE CHARACTERISTICS:
        (A) LENGTH: 977 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p4c63)"
            Unknown = Xaa
            Unknown for codon no. 318 = TAG (stop codon)

(ix) FEATURE:
        (A) NAME/KEY: CDS
        (B) LOCATION: 1..975

(xi) SEQUENCE DESCRIPTION: SEQ ID NO:52:
```

```
AAC AAA GCC TTC CAA TTA TCT GCG TCG GTA GAA CAA GTA TTA GCA ACT      48
Asn Lys Ala Phe Gln Leu Ser Ala Ser Val Glu Gln Val Leu Ala Thr
 1               5                  10                  15

TTA TCA CCT ACG CTA AAC AGT CCT TAC GAT TTA TAC GGC ACG ACA AAA      96
Leu Ser Pro Thr Leu Asn Ser Pro Tyr Asp Leu Tyr Gly Thr Thr Lys
              20                  25                  30

ATG CTA GAT ATT ACA TTC GAT TCA TTT GAA CAT GAT GGT ACA ACG TAC    144
Met Leu Asp Ile Thr Phe Asp Ser Phe Glu His Asp Gly Thr Thr Tyr
          35                  40                  45

CCT GTC GAC TAT GCT ACG TTT GAA AAT GAT TAT GAA GAT AAT AAA GAT    192
Pro Val Asp Tyr Ala Thr Phe Glu Asn Asp Tyr Glu Asp Asn Lys Asp
      50                  55                  60

CCT GAG TTT AGA CGT AAA AGT TTC AAA TCG TTT AGC GAT GGG ATT CGA    240
Pro Glu Phe Arg Arg Lys Ser Phe Lys Ser Phe Ser Asp Gly Ile Arg
 65                  70                  75                  80

AAA TAT CAG CAT ACT ACC GCG GCT ACA TAT AAT ATG CAA GTA CAA CAA    288
Lys Tyr Gln His Thr Thr Ala Ala Thr Tyr Asn Met Gln Val Gln Gln
                  85                  90                  95

GAA AAA ATT GAA GCT GAT TTA CGT GGA TTT GAA TCA GTC ATC GAT TAT    336
Glu Lys Ile Glu Ala Asp Leu Arg Gly Phe Glu Ser Val Ile Asp Tyr
              100                 105                 110

TTA TTA CAT AGT CAA GAA GTA ACG CGT GAT ATG TTT GAC CGT CAA ATC    384
Leu Leu His Ser Gln Glu Val Thr Arg Asp Met Phe Asp Arg Gln Ile
          115                 120                 125

GAT ATG ATT ATG CGT GAC TTG GCA CCA GTT ATG CAG AAA TAT GCT AAA    432
Asp Met Ile Met Arg Asp Leu Ala Pro Val Met Gln Lys Tyr Ala Lys
130                 135                 140

CTT TTA CAA CGT ATT CAC GGA TTA GAT AAC ATG CGT TTT GAA GAC TTG    480
Leu Leu Gln Arg Ile His Gly Leu Asp Asn Met Arg Phe Glu Asp Leu
145                 150                 155                 160

AAG ATT TCT GTA GAC CCT GAT TAT GAA CCA GAG ATT TCA ATT GAA GAC    528
Lys Ile Ser Val Asp Pro Asp Tyr Glu Pro Glu Ile Ser Ile Glu Asp
                  165                 170                 175

TCA AAA AAT TAT ATT TTC GGT GCG TTA AGT GTT TTA GGT GAT GAC TAT    576
Ser Lys Asn Tyr Ile Phe Gly Ala Leu Ser Val Leu Gly Asp Asp Tyr
              180                 185                 190

ACA AAC ATG TTA CGT GAA GCA TAC GAT CAG CGA TGG ATT GAT TTT GCA    624
Thr Asn Met Leu Arg Glu Ala Tyr Asp Gln Arg Trp Ile Asp Phe Ala
          195                 200                 205

CAA AAT AAA GGT AAA GAT ACA GGC GCA TTT TGT GCA AGT CCA TAC TTT    672
Gln Asn Lys Gly Lys Asp Thr Gly Ala Phe Cys Ala Ser Pro Tyr Phe
      210                 215                 220

ACA CAT TCA TAT GTG TTT ATT TCT TGG ACT GGT AAA ATG GCT GAA GCA    720
Thr His Ser Tyr Val Phe Ile Ser Trp Thr Gly Lys Met Ala Glu Ala
225                 230                 235                 240

TTT GTC TTA GCA CAT GAA TTA GGT CAT GCA GGT CAT TTT ACA TTA GCT    768
Phe Val Leu Ala His Glu Leu Gly His Ala Gly His Phe Thr Leu Ala
                  245                 250                 255

CAA AAA CAT CAA CCA TAT CTT GAA TCA GAA GCA TCA ATG TAC TTT GTT    816
Gln Lys His Gln Pro Tyr Leu Glu Ser Glu Ala Ser Met Tyr Phe Val
              260                 265                 270

GAA GCC CCT TCT ACA ATG AAT GAA ATG TTG ATG GCC AAT TAT TTA TTT    864
Glu Ala Pro Ser Thr Met Asn Glu Met Leu Met Ala Asn Tyr Leu Phe
          275                 280                 285

AAC ACA AGT GAT AAT CCA AGA TTT AAG CGT TGG GTT ATT GGC TCA ATT    912
Asn Thr Ser Asp Asn Pro Arg Phe Lys Arg Trp Val Ile Gly Ser Ile
      290                 295                 300

TTA TCT AGA ACA TAT TAT CAT AAT ATG GTA CCC mTT TAT TAG AAG CnG    960
Leu Ser Arg Thr Tyr Tyr His Asn Met Val Pro Xaa Tyr Xaa Lys Xaa
305                 310                 315                 320
```

```
CTT ATC CAC GGG GAG TG                                                                      977
Leu Ile His Gly Glu
            325
```

(2) INFORMATION FOR SEQ ID NO:53:

(i) SEQUENCE CHARACTERISTICS:
        (A) LENGTH: 325 amino acids
        (B) TYPE: amino acid
        (D) TOPOLOGY: linear (ii) MOLECULE TYPE: protein (xi) SEQUENCE DESCRIPTION: SEQ ID NO:53:

```
Asn Lys Ala Phe Gln Leu Ser Ala Ser Val Glu Gln Val Leu Ala Thr
  1               5                  10                  15

Leu Ser Pro Thr Leu Asn Ser Pro Tyr Asp Leu Tyr Gly Thr Thr Lys
                 20                  25                  30

Met Leu Asp Ile Thr Phe Asp Ser Phe Glu His Asp Gly Thr Thr Tyr
             35                  40                  45

Pro Val Asp Tyr Ala Thr Phe Glu Asn Asp Tyr Glu Asp Asn Lys Asp
 50                  55                  60

Pro Glu Phe Arg Arg Lys Ser Phe Lys Ser Phe Ser Asp Gly Ile Arg
 65                  70                  75                  80

Lys Tyr Gln His Thr Thr Ala Ala Thr Tyr Asn Met Gln Val Gln Gln
                 85                  90                  95

Glu Lys Ile Glu Ala Asp Leu Arg Gly Phe Glu Ser Val Ile Asp Tyr
            100                 105                 110

Leu Leu His Ser Gln Glu Val Thr Arg Asp Met Phe Asp Arg Gln Ile
            115                 120                 125

Asp Met Ile Met Arg Asp Leu Ala Pro Val Met Gln Lys Tyr Ala Lys
130                 135                 140

Leu Leu Gln Arg Ile His Gly Leu Asp Asn Met Arg Phe Glu Asp Leu
145                 150                 155                 160

Lys Ile Ser Val Asp Pro Asp Tyr Glu Pro Glu Ile Ser Ile Glu Asp
                165                 170                 175

Ser Lys Asn Tyr Ile Phe Gly Ala Leu Ser Val Leu Gly Asp Asp Tyr
            180                 185                 190

Thr Asn Met Leu Arg Glu Ala Tyr Asp Gln Arg Trp Ile Asp Phe Ala
            195                 200                 205

Gln Asn Lys Gly Lys Asp Thr Gly Ala Phe Cys Ala Ser Pro Tyr Phe
210                 215                 220

Thr His Ser Tyr Val Phe Ile Ser Trp Thr Gly Lys Met Ala Glu Ala
225                 230                 235                 240

Phe Val Leu Ala His Glu Leu Gly His Ala Gly His Phe Thr Leu Ala
                245                 250                 255

Gln Lys His Gln Pro Tyr Leu Glu Ser Glu Ala Ser Met Tyr Phe Val
            260                 265                 270

Glu Ala Pro Ser Thr Met Asn Glu Met Leu Met Ala Asn Tyr Leu Phe
            275                 280                 285

Asn Thr Ser Asp Asn Pro Arg Phe Lys Arg Trp Val Ile Gly Ser Ile
290                 295                 300

Leu Ser Arg Thr Tyr Tyr His Asn Met Val Pro Xaa Tyr Xaa Lys Xaa
305                 310                 315                 320

Leu Ile His Gly Glu
            325
```

(2) INFORMATION FOR SEQ ID NO:54:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p5c3)"
            Unknown = Xaa
            Unknown for codon no. 110 = TAA (stop codon)
            Unknown for codon no. 113 = TAA (stop codon)

(ix) FEATURE:
        (A) NAME/KEY: CDS
        (B) LOCATION: 1..465

(xi) SEQUENCE DESCRIPTION: SEQ ID NO:54:

```
ATG TAT CAA CTA CAA TTT ATA AAT TTA GTT TAC GAC ACA ACC AAA CTC        48
Met Tyr Gln Leu Gln Phe Ile Asn Leu Val Tyr Asp Thr Thr Lys Leu
 1               5                  10                  15

ACA CAT CTA GAA CAA ACC AAT ATC AAT TTA TTC ATT GGT AAT TGG AGT        96
Thr His Leu Glu Gln Thr Asn Ile Asn Leu Phe Ile Gly Asn Trp Ser
                20                  25                  30

AAT CAT CAA TTA CAA AAA TCA ATT TGT ATA CGT CAT GGC GAT GAT ACA       144
Asn His Gln Leu Gln Lys Ser Ile Cys Ile Arg His Gly Asp Asp Thr
            35                  40                  45

AGT CAC AAT CAA TAT CAT ATT CTT TTT ATA GAT ACG GCA CAT CAA CGC       192
Ser His Asn Gln Tyr His Ile Leu Phe Ile Asp Thr Ala His Gln Arg
        50                  55                  60

ATT AAA TTT TCA TCT ATT GAT AAT GAA GAA ATC ATT TAT ATT CTT GAT       240
Ile Lys Phe Ser Ser Ile Asp Asn Glu Glu Ile Ile Tyr Ile Leu Asp
65                  70                  75                  80

TAT GAT GAT ACA CAG CAT ATC CTC ATG CAA ACG TCA TCC AAA CAA GGT       288
Tyr Asp Asp Thr Gln His Ile Leu Met Gln Thr Ser Ser Lys Gln Gly
                85                  90                  95

ATT GGC ACT TCG CGA CCA ATC GTT TAT GAG CGC TTA GTA TAA CTA ATT       336
Ile Gly Thr Ser Arg Pro Ile Val Tyr Glu Arg Leu Val Xaa Leu Ile
               100                 105                 110

TAA ATG ATT TCA CTT CAT AAA GCG GGT TGG CGA GAA TTC AAT TTC TCA       384
Xaa Met Ile Ser Leu His Lys Ala Gly Trp Arg Glu Phe Asn Phe Ser
           115                 120                 125

CCA GCT CGT TTT TTC ATT GTA ATA ATA ATC TTT AAC ATT TAT TCT TTC       432
Pro Ala Arg Phe Phe Ile Val Ile Ile Ile Phe Asn Ile Tyr Ser Phe
       130                 135                 140

TCT ATT AAT TTT TCT CAA ACT ATC TTA TCT TTA TGATAA                    471
Ser Ile Asn Phe Ser Gln Thr Ile Leu Ser Leu
145                 150                 155
```

(2) INFORMATION FOR SEQ ID NO:55:

(i) SEQUENCE CHARACTERISTICS:
        (A) LENGTH: 155 amino acids
        (B) TYPE: amino acid
        (D) TOPOLOGY: linear (ii) MOLECULE TYPE: protein (xi) SEQUENCE DESCRIPTION: SEQ ID NO:55:

```
Met Tyr Gln Leu Gln Phe Ile Asn Leu Val Tyr Asp Thr Thr Lys Leu
 1               5                  10                  15

Thr His Leu Glu Gln Thr Asn Ile Asn Leu Phe Ile Gly Asn Trp Ser
                20                  25                  30
```

```
Asn His Gln Leu Gln Lys Ser Ile Cys Ile Arg His Gly Asp Asp Thr
        35                  40                  45

Ser His Asn Gln Tyr His Ile Leu Phe Ile Asp Thr Ala His Gln Arg
    50                  55                  60

Ile Lys Phe Ser Ser Ile Asp Asn Glu Glu Ile Ile Tyr Ile Leu Asp
65                  70                  75                  80

Tyr Asp Asp Thr Gln His Ile Leu Met Gln Thr Ser Ser Lys Gln Gly
                85                  90                  95

Ile Gly Thr Ser Arg Pro Ile Val Tyr Glu Arg Leu Val Xaa Leu Ile
                100                 105                 110

Xaa Met Ile Ser Leu His Lys Ala Gly Trp Arg Glu Phe Asn Phe Ser
        115                 120                 125

Pro Ala Arg Phe Phe Ile Val Ile Ile Ile Phe Asn Ile Tyr Ser Phe
        130                 135                 140

Ser Ile Asn Phe Ser Gln Thr Ile Leu Ser Leu
145                 150                 155
```

(2) INFORMATION FOR SEQ ID NO:56:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p8d26)"
            Unknown = Xaa (ix) FEATURE:
        (A) NAME/KEY: CDS
        (B) LOCATION: 14..343

(xi) SEQUENCE DESCRIPTION: SEQ ID NO:56:

```
ATTTNTAGAA TAA TAT TTC CAT ATT GGA AAA AGG GAA GAA TTC GTT ATG         49
           Tyr Phe His Ile Gly Lys Arg Glu Glu Phe Val Met
            1               5                   10

AAA AGC TAT AAG TGT AAA GGT TCA TTC TTA ATA GAT AGT ATG GCT GGA        97
Lys Ser Tyr Lys Cys Lys Gly Ser Phe Leu Ile Asp Ser Met Ala Gly
        15                  20                  25

TTT TTG CTA ATT GGA TTG ATN ACA TTA CTA TTG ATA CCA ATG ATG AAT       145
Phe Leu Leu Ile Gly Leu Xaa Thr Leu Leu Leu Ile Pro Met Met Asn
    30                  35                  40

CAA ATG CAA GCG AGT ATA AAC CAT AAA CTA CAA ACA ATT GAT GCT TCT       193
Gln Met Gln Ala Ser Ile Asn His Lys Leu Gln Thr Ile Asp Ala Ser
45                  50                  55                  60

AAA GTA ATT TTG ACG ACT GTA TCT AAA ATT AAT AAA GAA GAA CTT AAG       241
Lys Val Ile Leu Thr Thr Val Ser Lys Ile Asn Lys Glu Glu Leu Lys
            65                  70                  75

AAG GGG GTA ACT ATA GGG AAG TAT GAT ATT AAG CAA AGT GAC CAA CAA       289
Lys Gly Val Thr Ile Gly Lys Tyr Asp Ile Lys Gln Ser Asp Gln Gln
        80                  85                  90

ATT TGT GCT ATT TCA ANA AAT ACC ANT TCT TAT CAA AAG ACA TGT ATA       337
Ile Cys Ala Ile Ser Xaa Asn Thr Xaa Ser Tyr Gln Lys Thr Cys Ile
    95                  100                 105

CAG TAT    AAATGTCAAA GCTTTTTCGC TCATTGAAAT GTTAGTAGCG ATGATGGTTA     393
Gln Tyr
110

TAAGTATAAC TTTACTAATT GTTCCAGACT TAATTAGACT TAGTAAAACT TTTCTAATTG     453

AAAGTAGGGA TTTAACAACT GTAGATTTCG AATTTTTCTC AAGAGATATT CTAGATGATT     513
```

```
TTAAAGGAGT AGATAGAAAC GATATTGAAA TTAGGCAACA CCGTATCATT GTACATAAAG      573

GTGAATAAAA ATGGC                                                      588
```

(2) INFORMATION FOR SEQ ID NO:57:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO:57:

```
Tyr Phe His Ile Gly Lys Arg Glu Glu Phe Val Met Lys Ser Tyr Lys
 1               5                  10                  15

Cys Lys Gly Ser Phe Leu Ile Asp Ser Met Ala Gly Phe Leu Leu Ile
            20                  25                  30

Gly Leu Xaa Thr Leu Leu Ile Pro Met Met Asn Gln Met Gln Ala
            35                  40                  45

Ser Ile Asn His Lys Leu Gln Thr Ile Asp Ala Ser Lys Val Ile Leu
 50                  55                  60

Thr Thr Val Ser Lys Ile Asn Lys Glu Glu Leu Lys Lys Gly Val Thr
 65                  70                  75                  80

Ile Gly Lys Tyr Asp Ile Lys Gln Ser Asp Gln Gln Ile Cys Ala Ile
                85                  90                  95

Ser Xaa Asn Thr Xaa Ser Tyr Gln Lys Thr Cys Ile Gln Tyr
            100                 105                 110
```

(2) INFORMATION FOR SEQ ID NO:58:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p8d26)"
            Unknown = Xaa
            Unknown for codon no. 88 = TAA (stop codon)

(ix) FEATURE:
        (A) NAME/KEY: CDS
        (B) LOCATION: 318..587

(xi) SEQUENCE DESCRIPTION: SEQ ID NO:58:

```
ATTTATAGAA TAATATTTCC ATATTGGAAA AAGGGAAGAA TTCGTTATGA AAAGCTATAA       60

GTGTAAAGGT TCATTCTTAA TAGATAGTAT GGCTGGATTT TTGCTAATTG GATTGATAAC      120

ATTACTATTG ATACCAATGA TGAATCAAAT GCAAGCGAGT ATAAACCATA AACTACAAAC      180

AATTGATGCT TCTAAAGTAA TTTTGACGAC TGTATCTAAA ATTAATAAAG AAGAACTTAA      240

GAAGGGGTA ACTATAGGGA AGTATGATAT TAAGCAAAGT GACCAACAAA TTTGTGCTAT       300

TTCAAAAAAT ACCAATT CTT ATC AAA AGA CAT GTA TAC AGT ATA AAT GTC        350
                   Leu Ile Lys Arg His Val Tyr Ser Ile Asn Val
                     1               5                  10

AAA GCT TTT TCG CTC ATT GAA ATG TTA GTA GCG ATG ATG GTT ATA AGT       398
Lys Ala Phe Ser Leu Ile Glu Met Leu Val Ala Met Met Val Ile Ser
             15                  20                  25

ATA ACT TTA CTA ATT GTT CCA GAC TTA ATT AGA CTT AGT AAA ACT TTT       446
Ile Thr Leu Leu Ile Val Pro Asp Leu Ile Arg Leu Ser Lys Thr Phe
         30                  35                  40
```

```
CTA ATT GAA AGT AGG GAT TTA ACA ACT GTA GAT TTC GAA TTT TTC TCA        494
Leu Ile Glu Ser Arg Asp Leu Thr Thr Val Asp Phe Glu Phe Phe Ser
        45                  50                  55

AGA GAT ATT CTA GAT GAT TTT AAA GGA GTA GAT AGA AAC GAT ATT GAA        542
Arg Asp Ile Leu Asp Asp Phe Lys Gly Val Asp Arg Asn Asp Ile Glu
 60                  65                  70                  75

ATT AGG CAA CAC CGT ATC ATT GTA CAT AAA GGT GNN TAA AAA TGG            587
Ile Arg Gln His Arg Ile Ile Val His Lys Gly Xaa Xaa Lys Trp
                 80                  85                  90

C                                                                      588

(2) INFORMATION FOR SEQ ID NO:59:

(i) SEQUENCE CHARACTERISTICS:
        (A) LENGTH: 90 amino acids
        (B) TYPE: amino acid
        (D) TOPOLOGY: linear (ii) MOLECULE TYPE: protein (xi) SEQUENCE DESCRIPTION: SEQ ID NO:59:

Leu Ile Lys Arg His Val Tyr Ser Ile Asn Val Lys Ala Phe Ser Leu
 1               5                  10                  15

Ile Glu Met Leu Val Ala Met Met Val Ile Ser Ile Thr Leu Leu Ile
                20                  25                  30

Val Pro Asp Leu Ile Arg Leu Ser Lys Thr Phe Leu Ile Glu Ser Arg
                35                  40                  45

Asp Leu Thr Thr Val Asp Phe Glu Phe Phe Ser Arg Asp Ile Leu Asp
 50                  55                  60

Asp Phe Lys Gly Val Asp Arg Asn Asp Ile Glu Ile Arg Gln His Arg
 65                  70                  75                  80

Ile Ile Val His Lys Gly Xaa Xaa Lys Trp
                 85                  90

(2) INFORMATION FOR SEQ ID NO:60:

(i) SEQUENCE CHARACTERISTICS:
        (A) LENGTH: 1338 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p9b65)"

(ix) FEATURE:
        (A) NAME/KEY: CDS
        (B) LOCATION: 1..1335

(xi) SEQUENCE DESCRIPTION: SEQ ID NO:60:

ATG ATC CGG CTT GTG ACG ATG GGG AAA AGT TCT GAG GCC GGG GTG TCT         48
Met Ile Arg Leu Val Thr Met Gly Lys Ser Ser Glu Ala Gly Val Ser
 1               5                  10                  15

TCT TTC CAG GCG TTG ACG ATG TCG TTG TCC GGC CGC ATC GGC GTC GGG         96
Ser Phe Gln Ala Leu Thr Met Ser Leu Ser Gly Arg Ile Gly Val Gly
                20                  25                  30

AAC GTG GCC GGG ACG GCG ACG GGG ATT GCG TAC GGG GGG CCG GGC GCG        144
Asn Val Ala Gly Thr Ala Thr Gly Ile Ala Tyr Gly Gly Pro Gly Ala
                35                  40                  45

GTC TTT TGG ATG TGG GTG ATC ACC TTT ATC GGA GCG GCG ACC GCG TAT        192
Val Phe Trp Met Trp Val Ile Thr Phe Ile Gly Ala Ala Thr Ala Tyr
 50                  55                  60
```

```
GTC GAG TCG ACG TGG CGC AAA TTT ATA AAG AGG AAC AAG ACG GAC AAT        240
Val Glu Ser Thr Trp Arg Lys Phe Ile Lys Arg Asn Lys Thr Asp Asn
 65                  70                  75                  80

ACC GTG GCG GTC CGG CGT TCT ACA TTG AAA AAG GCC TTG GCT GGA AAT        288
Thr Val Ala Val Arg Arg Ser Thr Leu Lys Lys Ala Leu Ala Gly Asn
                     85                  90                  95

GGT TTG CGG TGT AGT CGC GCG GCG ATC ATT CTC TCG ATG GCG GTG CTG        336
Gly Leu Arg Cys Ser Arg Ala Ala Ile Ile Leu Ser Met Ala Val Leu
                100                 105                 110

ATG CCG GGA ATT CAA GCA AAC TCG ATT GCC GAC AGC TTT TCG AAT GCG        384
Met Pro Gly Ile Gln Ala Asn Ser Ile Ala Asp Ser Phe Ser Asn Ala
            115                 120                 125

TTT GGC ATT CCG AAA TTG GTG ACG GGA ATT TTC GTG ATT GCC GTT CTT        432
Phe Gly Ile Pro Lys Leu Val Thr Gly Ile Phe Val Ile Ala Val Leu
        130                 135                 140

GGC TTT ACG ATT TTT GGC GGA GTG AAG CGG ATC GCG AAA ACG GCG GAA        480
Gly Phe Thr Ile Phe Gly Gly Val Lys Arg Ile Ala Lys Thr Ala Glu
145                 150                 155                 160

ATT GTC GTG CCG TTT ATG GCA GTT GGC TAT TTG TTC GTC GCG ATT GCC        528
Ile Val Val Pro Phe Met Ala Val Gly Tyr Leu Phe Val Ala Ile Ala
                165                 170                 175

ATT ATT GCG GCC AAT ATT GAA AAA GTC CCG GAT GTG TTT GGT TTG ATT        576
Ile Ile Ala Ala Asn Ile Glu Lys Val Pro Asp Val Phe Gly Leu Ile
            180                 185                 190

TTC AAA AGC GCG TTT GGC GCT GAT CAA GTG TTT GGC GGC ATT CTT GGT        624
Phe Lys Ser Ala Phe Gly Ala Asp Gln Val Phe Gly Gly Ile Leu Gly
        195                 200                 205

TCG GCG GTG ATG TGG GGG GTC AAA CGC GGC CTT TAT GCG AAT GAA GCG        672
Ser Ala Val Met Trp Gly Val Lys Arg Gly Leu Tyr Ala Asn Glu Ala
210                 215                 220

GGG CAA GGG ACG GGC GCC CAC CCG GCA GCG GCG GAA GTG TCC CAC            720
Gly Gln Gly Thr Gly Ala His Pro Ala Ala Ala Glu Val Ser His
225                 230                 235                 240

CCG GCG AAG CAG GGG CTT GTG CAG GCA TTT TCG ATC TAT TTG GAC GTG        768
Pro Ala Lys Gln Gly Leu Val Gln Ala Phe Ser Ile Tyr Leu Asp Val
                245                 250                 255

TTC TTG GTC GTG ACG GCG ACG GCG CTG ATG ATT TTG TTT ACG GGT CAA        816
Phe Leu Val Val Thr Ala Thr Ala Leu Met Ile Leu Phe Thr Gly Gln
            260                 265                 270

TAC AAT GTG ATC AAT GAA AAA ACG GGA GAG ACG ATT GTC GAG CAT TTG        864
Tyr Asn Val Ile Asn Glu Lys Thr Gly Glu Thr Ile Val Glu His Leu
        275                 280                 285

AAA GGG GTG GAA CCG GGC GCA GGG TAT ACG CAG GCG GCG GTG GAC ACG        912
Lys Gly Val Glu Pro Gly Ala Gly Tyr Thr Gln Ala Ala Val Asp Thr
290                 295                 300

CTC TTC CCG GGA TTC GGG TCG GCC TTT ATT GCG ATC GCT CTG TTC TTC        960
Leu Phe Pro Gly Phe Gly Ser Ala Phe Ile Ala Ile Ala Leu Phe Phe
305                 310                 315                 320

TTC GCG TTT ACG ACG ATG TAC GCG TAT TAC TAT ATT GCC GAG ACG AAC       1008
Phe Ala Phe Thr Thr Met Tyr Ala Tyr Tyr Tyr Ile Ala Glu Thr Asn
                325                 330                 335

CTC GCC TAT TTG GTG CGC AGT GAA AAG AGG GGA ACG GCC TTC TTT GCC       1056
Leu Ala Tyr Leu Val Arg Ser Glu Lys Arg Gly Thr Ala Phe Phe Ala
            340                 345                 350

TTG AAG CTC GTC TTT TTG GCG GCC ACG TTC TAT GGA ACG GTC AAA ACG       1104
Leu Lys Leu Val Phe Leu Ala Ala Thr Phe Tyr Gly Thr Val Lys Thr
        355                 360                 365

GCG ACG ACG GCG TGG GCG ATG GGC GAC ATC GGG CTT GGC ATC ATG GTG       1152
Ala Thr Thr Ala Trp Ala Met Gly Asp Ile Gly Leu Gly Ile Met Val
370                 375                 380
```

-continued

```
TGG CTC AAC TTG ATT GCG ATC TTG TTG TTG TTT AAA CCG GCC TAT ATG    1200
Trp Leu Asn Leu Ile Ala Ile Leu Leu Leu Phe Lys Pro Ala Tyr Met
385                 390                 395                 400

GCC TTG AAA GAT TAT GAA GAA CAG CTG AAG CAA GGG AAA GAT CCG GAG    1248
Ala Leu Lys Asp Tyr Glu Glu Gln Leu Lys Gln Gly Lys Asp Pro Glu
                405                 410                 415

TTC AAC GCG TCG AAA TAC GGA ATC AAG AAC GCG AAA TTC TGG GAA AAT    1296
Phe Asn Ala Ser Lys Tyr Gly Ile Lys Asn Ala Lys Phe Trp Glu Asn
            420                 425                 430

GGA TAT AAG AGA TGG GAA GAA AAG AAA GGG AAG GCA TTG TAA            1338
Gly Tyr Lys Arg Trp Glu Glu Lys Lys Gly Lys Ala Leu
        435                 440                 445
```

(2) INFORMATION FOR SEQ ID NO:61:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO:61:

```
Met Ile Arg Leu Val Thr Met Gly Lys Ser Ser Glu Ala Gly Val Ser
 1               5                  10                  15

Ser Phe Gln Ala Leu Thr Met Ser Leu Ser Gly Arg Ile Gly Val Gly
                20                  25                  30

Asn Val Ala Gly Thr Ala Thr Gly Ile Ala Tyr Gly Gly Pro Gly Ala
            35                  40                  45

Val Phe Trp Met Trp Val Ile Thr Phe Ile Gly Ala Ala Thr Ala Tyr
        50                  55                  60

Val Glu Ser Thr Trp Arg Lys Phe Ile Lys Arg Asn Lys Thr Asp Asn
65                  70                  75                  80

Thr Val Ala Val Arg Arg Ser Thr Leu Lys Lys Ala Leu Ala Gly Asn
                85                  90                  95

Gly Leu Arg Cys Ser Arg Ala Ala Ile Ile Leu Ser Met Ala Val Leu
                100                 105                 110

Met Pro Gly Ile Gln Ala Asn Ser Ile Ala Asp Ser Phe Ser Asn Ala
            115                 120                 125

Phe Gly Ile Pro Lys Leu Val Thr Gly Ile Phe Val Ile Ala Val Leu
        130                 135                 140

Gly Phe Thr Ile Phe Gly Gly Val Lys Arg Ile Ala Lys Thr Ala Glu
145                 150                 155                 160

Ile Val Val Pro Phe Met Ala Val Gly Tyr Leu Phe Val Ala Ile Ala
                165                 170                 175

Ile Ile Ala Ala Asn Ile Glu Lys Val Pro Asp Val Phe Gly Leu Ile
            180                 185                 190

Phe Lys Ser Ala Phe Gly Ala Asp Gln Val Phe Gly Gly Ile Leu Gly
        195                 200                 205

Ser Ala Val Met Trp Gly Val Lys Arg Gly Leu Tyr Ala Asn Glu Ala
210                 215                 220

Gly Gln Gly Thr Gly Ala His Pro Ala Ala Ala Glu Val Ser His
225                 230                 235                 240

Pro Ala Lys Gln Gly Leu Val Gln Ala Phe Ser Ile Tyr Leu Asp Val
                245                 250                 255

Phe Leu Val Val Thr Ala Thr Ala Leu Met Ile Leu Phe Thr Gly Gln
            260                 265                 270
```

```
Tyr Asn Val Ile Asn Glu Lys Thr Gly Glu Thr Ile Val Glu His Leu
            275                 280                 285

Lys Gly Val Glu Pro Gly Ala Gly Tyr Thr Gln Ala Ala Val Asp Thr
    290                 295                 300

Leu Phe Pro Gly Phe Gly Ser Ala Phe Ile Ala Ile Ala Leu Phe Phe
305                 310                 315                 320

Phe Ala Phe Thr Thr Met Tyr Ala Tyr Tyr Ile Ala Glu Thr Asn
                325                 330                 335

Leu Ala Tyr Leu Val Arg Ser Glu Lys Arg Gly Thr Ala Phe Phe Ala
            340                 345                 350

Leu Lys Leu Val Phe Leu Ala Ala Thr Phe Tyr Gly Thr Val Lys Thr
            355                 360                 365

Ala Thr Thr Ala Trp Ala Met Gly Asp Ile Gly Leu Gly Ile Met Val
            370                 375                 380

Trp Leu Asn Leu Ile Ala Ile Leu Leu Leu Phe Lys Pro Ala Tyr Met
385                 390                 395                 400

Ala Leu Lys Asp Tyr Glu Glu Gln Leu Lys Gln Gly Lys Asp Pro Glu
                405                 410                 415

Phe Asn Ala Ser Lys Tyr Gly Ile Lys Asn Ala Lys Phe Trp Glu Asn
                420                 425                 430

Gly Tyr Lys Arg Trp Glu Glu Lys Lys Gly Lys Ala Leu
            435                 440                 445

(2) INFORMATION FOR SEQ ID NO:62:

(i) SEQUENCE CHARACTERISTICS:
        (A) LENGTH: 296 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA (genomic) (p10b32)"

(ix) FEATURE:
         (A) NAME/KEY: CDS
         (B) LOCATION: 1..294

(xi) SEQUENCE DESCRIPTION: SEQ ID NO:62:

ATG CAA ATA GAA CTT ACT GAT GCA GCA GTA ACT TGG TTT AAA AAT GAA      48
Met Gln Ile Glu Leu Thr Asp Ala Ala Val Thr Trp Phe Lys Asn Glu
  1               5                  10                  15

CTT GAG TTG CCT GAA AAT AAT AAA GTG CTC GTG TTT TTT GTA AGA TAT      96
Leu Glu Leu Pro Glu Asn Asn Lys Val Leu Val Phe Phe Val Arg Tyr
                 20                  25                  30

GGT GGC GAA TTC CAA CTC AAG CAA GGA TTT AGT CCT GCT TTT ACA GTT     144
Gly Gly Glu Phe Gln Leu Lys Gln Gly Phe Ser Pro Ala Phe Thr Val
             35                  40                  45

GAA CCA AAG GAA GAT GTT GAT ATT GGC TAT GAA CAA CAA TAT GAC GAT     192
Glu Pro Lys Glu Asp Val Asp Ile Gly Tyr Glu Gln Gln Tyr Asp Asp
         50                  55                  60

TTA AAT GTT GTC GTA GCG GAA AAA GAT TTG TGG TAC TTT GAA GAT GAC     240
Leu Asn Val Val Val Ala Glu Lys Asp Leu Trp Tyr Phe Glu Asp Asp
 65                  70                  75                  80

CAC ATT ATT GTA AAT GTA GTT GTC ACG AAG ATG AAT TTC TTA TTC CAC     288
His Ile Ile Val Asn Val Val Val Thr Lys Met Asn Phe Leu Phe His
                     85                  90                  95

CAA ATA AC                                                          296
Gln Ile
```

(2) INFORMATION FOR SEQ ID NO:63:

(i) SEQUENCE CHARACTERISTICS:
        (A) LENGTH: 98 amino acids
        (B) TYPE: amino acid
        (D) TOPOLOGY: linear (ii) MOLECULE TYPE: protein (xi) SEQUENCE DESCRIPTION: SEQ ID NO:63:

```
Met Gln Ile Glu Leu Thr Asp Ala Ala Val Thr Trp Phe Lys Asn Glu
 1               5                  10                  15

Leu Glu Leu Pro Glu Asn Asn Lys Val Leu Val Phe Phe Val Arg Tyr
             20                  25                  30

Gly Gly Glu Phe Gln Leu Lys Gln Gly Phe Ser Pro Ala Phe Thr Val
         35                  40                  45

Glu Pro Lys Glu Asp Val Asp Ile Gly Tyr Glu Gln Gln Tyr Asp Asp
     50                  55                  60

Leu Asn Val Val Val Ala Glu Lys Asp Leu Trp Tyr Phe Glu Asp Asp
 65                  70                  75                  80

His Ile Ile Val Asn Val Val Val Thr Lys Met Asn Phe Leu Phe His
                 85                  90                  95

Gln Ile
```

(2) INFORMATION FOR SEQ ID NO:64:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA(genomic) (p10b85)"

(xi) SEQUENCE DESCRIPTION: SEQ ID NO:64:

```
GNAACACTNC TNTTTCATTT GTAATAATT  TCACAATTAT TTTATCCTTT GGTTATGAAT      60

ATGTAAATAC CATTAATTAA TTATTCATAT TTTATCTATA ATTTGTTAAT AAATATTTAA     120

TATATTATNN TTATNCTTAA ATATTANGNG CAATTATACC ACTATATTTA TTTCTTATAC     180

TCCATTTGAT TTATAGTTGT ATTAATACAT TGACTCAAAA ACTAATTAAT CAAATATGTT     240

TTTTAGATTN ATAAAGTTGT AACTGTACTA TTTNGTAGTG TANGGTAATT TATTNGGATG     300

AAATATAATT CNNNNTACTC TATNGATTAA TCAAATATGT ATCTATCAAA ATTCGGCTTA     360

TTTATNCACT CTGACATATC CANATACGCA AAAAGACTAT NNCTACCTTG TATCGANAGA     420

AATAGTCTTT TTA                                                         433
```

(2) INFORMATION FOR SEQ ID NO:65:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p10b89)"
            Unknown = Xaa (ix) FEATURE:
        (A) NAME/KEY: CDS
        (B) LOCATION: 1..207

(xi) SEQUENCE DESCRIPTION: SEQ ID NO:65:

| | | | | | | | | | | | | | | | | |
|---|---|---|---|---|---|---|---|---|---|---|---|---|---|---|---|---|
| TAC | TAT | AAA | AGC | ACC | CAC | TCA | GTC | ACT | AGT | TTG | GGC | AGT | TAT | TGT | ATG | 48 |
| Tyr | Tyr | Lys | Ser | Thr | His | Ser | Val | Thr | Ser | Leu | Gly | Ser | Tyr | Cys | Met | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| CCT | ATT | GAA | CTC | AAT | GCG | TAT | ATT | ACA | ATA | CCT | TTT | TCG | CAT | ATT | CAT | 96 |
| Pro | Ile | Glu | Leu | Asn | Ala | Tyr | Ile | Thr | Ile | Pro | Phe | Ser | His | Ile | His | |
| | | | 20 | | | | | 25 | | | | | 30 | | | |

| | | | | | | | | | | | | | | | | |
|---|---|---|---|---|---|---|---|---|---|---|---|---|---|---|---|---|
| ATA | AGA | TCT | TTG | CAT | TCN | TTA | AGC | TTA | AAT | TTT | CTA | TTC | TTC | NTT | CTC | 144 |
| Ile | Arg | Ser | Leu | His | Ser | Leu | Ser | Leu | Asn | Phe | Leu | Phe | Phe | Xaa | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| TAC | GGC | GGC | ATA | GCA | TTA | ATA | TTA | CCG | GAA | CTA | ATC | CCA | GTA | NCN | GTA | 192 |
| Tyr | Gly | Gly | Ile | Ala | Leu | Ile | Leu | Pro | Glu | Leu | Ile | Pro | Val | Xaa | Val | |
| | 50 | | | | | 55 | | | | | 60 | | | | | |

| | | | | | |
|---|---|---|---|---|---|
| TTA | ATT | GGA | TAC | CCG | G | 208 |
| Leu | Ile | Gly | Tyr | Pro | | |
| 65 | | | | | | |

(2) INFORMATION FOR SEQ ID NO:66:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO:66:

Tyr Tyr Lys Ser Thr His Ser Val Thr Ser Leu Gly Ser Tyr Cys Met
1               5                   10                  15

Pro Ile Glu Leu Asn Ala Tyr Ile Thr Ile Pro Phe Ser His Ile His
            20                  25                  30

Ile Arg Ser Leu His Ser Leu Ser Leu Asn Phe Leu Phe Phe Xaa Leu
        35                  40                  45

Tyr Gly Gly Ile Ala Leu Ile Leu Pro Glu Leu Ile Pro Val Xaa Val
    50                  55                  60

Leu Ile Gly Tyr Pro
65

(2) INFORMATION FOR SEQ ID NO:67:

(i) SEQUENCE CHARACTERISTICS:
        (A) LENGTH: 1041 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p10c30)"
           Unknown = Xaa (ix) FEATURE:
        (A) NAME/KEY: CDS
        (B) LOCATION: 1..1038

(xi) SEQUENCE DESCRIPTION: SEQ ID NO:67:

| | | | | | | | | | | | | | | | | |
|---|---|---|---|---|---|---|---|---|---|---|---|---|---|---|---|---|
| AGA | AGT | CAA | ATC | ATT | ANT | GGC | GTC | NTA | TCG | AGT | ATA | CTA | TTA | ACT | TCA | 48 |
| Arg | Ser | Gln | Ile | Ile | Xaa | Gly | Val | Xaa | Ser | Ile | Leu | Leu | Thr | Ser | | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ACT | ATT | TTA | GCA | ATT | GCA | TAT | ATT | TTA | ATG | TGG | TTT | AAC | GGC | CAT | ATG | 96 |
| Thr | Ile | Leu | Ala | Ile | Ala | Tyr | Ile | Leu | Met | Trp | Phe | Asn | Gly | His | Met | |
| | | | 20 | | | | | 25 | | | | | 30 | | | |

| | | | | | | | | | | | | | | | | |
|---|---|---|---|---|---|---|---|---|---|---|---|---|---|---|---|---|
| ACA | CTA | ACT | TTG | ACC | TTA | ACG | ACA | ATA | ATT | ACA | AGC | TGT | TTA | ACC | TTA | 144 |
| Thr | Leu | Thr | Leu | Thr | Leu | Thr | Thr | Ile | Ile | Thr | Ser | Cys | Leu | Thr | Leu | |
| | | 35 | | | | | 40 | | | | | 45 | | | | |

```
TTA ATA TGT AGT ATT TTT ATT AAT CCA CTT ATA CAA AAA ATT AAG CAG        192
Leu Ile Cys Ser Ile Phe Ile Asn Pro Leu Ile Gln Lys Ile Lys Gln
    50                  55                  60

TTT AAT ATA AAA ACT AAG CAA TTT GCT AAC GGA AAT TAC GCA AGC AAT        240
Phe Asn Ile Lys Thr Lys Gln Phe Ala Asn Gly Asn Tyr Ala Ser Asn
65                  70                  75                  80

GAT AAA ACG TTT AAT TCA CCA AAA GAA ATT TAT GAA TTA AAT CAA TCT        288
Asp Lys Thr Phe Asn Ser Pro Lys Glu Ile Tyr Glu Leu Asn Gln Ser
                85                  90                  95

TTT AAT AAA ATG GCT TCT GAA ATT ACG CAA CAA ATG AAT CAA ATT AAA        336
Phe Asn Lys Met Ala Ser Glu Ile Thr Gln Gln Met Asn Gln Ile Lys
            100                 105                 110

TCC GAA CAA CAA GAA AAA ACA GAA CTG ATT CAA AAC TTA GCC CAT GAT        384
Ser Glu Gln Gln Glu Lys Thr Glu Leu Ile Gln Asn Leu Ala His Asp
        115                 120                 125

TTA AAA ACA CCT TTA GCA AGC ATT ATT TCA TAT TCT GAA GGA CTA CGT        432
Leu Lys Thr Pro Leu Ala Ser Ile Ile Ser Tyr Ser Glu Gly Leu Arg
    130                 135                 140

GAT GGT ATA ATC ACT AAG GAT CAT GAG ATT AAA GAG TCA TAC GAC ATA        480
Asp Gly Ile Ile Thr Lys Asp His Glu Ile Lys Glu Ser Tyr Asp Ile
145                 150                 155                 160

TTA ATT AAA CAA GCA AAC AGA TTA TCA ACA TTA TTT GAT GAT ATG ACT        528
Leu Ile Lys Gln Ala Asn Arg Leu Ser Thr Leu Phe Asp Asp Met Thr
                165                 170                 175

CAT ATT ATC ACT TTA AAT ACA GGT AAA ACA TAT CCC CCA GAA TTA ATA        576
His Ile Ile Thr Leu Asn Thr Gly Lys Thr Tyr Pro Pro Glu Leu Ile
            180                 185                 190

CAA CTA GAC CAA TTA CTT GTA TCA ATA TTG CAA CCA TAT GAG CAA CGT        624
Gln Leu Asp Gln Leu Leu Val Ser Ile Leu Gln Pro Tyr Glu Gln Arg
        195                 200                 205

ATC AAA CAT GAA AAC CGC ACA TTA GAA GTG AAT TTC TGT AAC GAA ATT        672
Ile Lys His Glu Asn Arg Thr Leu Glu Val Asn Phe Cys Asn Glu Ile
    210                 215                 220

GAT GCA TTT TAT CAA TAT CGA ACG CCA CTT GAG CGT ATT TTA ACA AAC        720
Asp Ala Phe Tyr Gln Tyr Arg Thr Pro Leu Glu Arg Ile Leu Thr Asn
225                 230                 235                 240

TTA CTT GAT AAT GCG CTA AAA TTT TCA AAT GTT GGT AGT CGC ATT GAT        768
Leu Leu Asp Asn Ala Leu Lys Phe Ser Asn Val Gly Ser Arg Ile Asp
                245                 250                 255

ATT AAT ATT AGT GAA AAC GAA GAT CAA GAT ACT ATC GAC ATT GCT ATT        816
Ile Asn Ile Ser Glu Asn Glu Asp Gln Asp Thr Ile Asp Ile Ala Ile
            260                 265                 270

AGC GAT GAA GGT ATT GGC ATT ATA CCA GAA CTA CAA GAA CGT ATA TTC        864
Ser Asp Glu Gly Ile Gly Ile Ile Pro Glu Leu Gln Glu Arg Ile Phe
        275                 280                 285

GAA CGT ACA TTC AGA GTA GAA AAC TCT CGT AAT ACA AAA ACG GGT GGT        912
Glu Arg Thr Phe Arg Val Glu Asn Ser Arg Asn Thr Lys Thr Gly Gly
    290                 295                 300

TCT GGA TTA GGC TTA TAT ATA GCT AAT GAA CTC GCG CAA CAA AAT AAC        960
Ser Gly Leu Gly Leu Tyr Ile Ala Asn Glu Leu Ala Gln Gln Asn Asn
305                 310                 315                 320

GCA AAA ATC AGT GTA AGC AGT GAT ATA GAT GTA GGA ACT ACG ATG ACT       1008
Ala Lys Ile Ser Val Ser Ser Asp Ile Asp Val Gly Thr Thr Met Thr
                325                 330                 335

GTA ACA TTA CAC AAA TTA GAC ATT ACG TCA TAA                           1041
Val Thr Leu His Lys Leu Asp Ile Thr Ser
            340                 345
```

(2) INFORMATION FOR SEQ ID NO:68:

(i) SEQUENCE CHARACTERISTICS:
        (A) LENGTH: 346 amino acids
        (B) TYPE: amino acid
        (D) TOPOLOGY: linear (ii) MOLECULE TYPE: protein (xi) SEQUENCE DESCRIPTION: SEQ ID NO:68:

Arg Ser Gln Ile Ile Xaa Gly Val Xaa Ser Ser Ile Leu Leu Thr Ser
 1               5                  10                  15

Thr Ile Leu Ala Ile Ala Tyr Ile Leu Met Trp Phe Asn Gly His Met
             20                  25                  30

Thr Leu Thr Leu Thr Leu Thr Thr Ile Ile Thr Ser Cys Leu Thr Leu
         35                  40                  45

Leu Ile Cys Ser Ile Phe Ile Asn Pro Leu Ile Gln Lys Ile Lys Gln
     50                  55                  60

Phe Asn Ile Lys Thr Lys Gln Phe Ala Asn Gly Asn Tyr Ala Ser Asn
 65                  70                  75                  80

Asp Lys Thr Phe Asn Ser Pro Lys Glu Ile Tyr Glu Leu Asn Gln Ser
                 85                  90                  95

Phe Asn Lys Met Ala Ser Glu Ile Thr Gln Gln Met Asn Gln Ile Lys
             100                 105                 110

Ser Glu Gln Gln Glu Lys Thr Glu Leu Ile Gln Asn Leu Ala His Asp
         115                 120                 125

Leu Lys Thr Pro Leu Ala Ser Ile Ile Ser Tyr Ser Glu Gly Leu Arg
     130                 135                 140

Asp Gly Ile Ile Thr Lys Asp His Glu Ile Lys Glu Ser Tyr Asp Ile
145                 150                 155                 160

Leu Ile Lys Gln Ala Asn Arg Leu Ser Thr Leu Phe Asp Asp Met Thr
                 165                 170                 175

His Ile Ile Thr Leu Asn Thr Gly Lys Thr Tyr Pro Pro Glu Leu Ile
             180                 185                 190

Gln Leu Asp Gln Leu Leu Val Ser Ile Leu Gln Pro Tyr Glu Gln Arg
         195                 200                 205

Ile Lys His Glu Asn Arg Thr Leu Glu Val Asn Phe Cys Asn Glu Ile
     210                 215                 220

Asp Ala Phe Tyr Gln Tyr Arg Thr Pro Leu Glu Arg Ile Leu Thr Asn
225                 230                 235                 240

Leu Leu Asp Asn Ala Leu Lys Phe Ser Asn Val Gly Ser Arg Ile Asp
                 245                 250                 255

Ile Asn Ile Ser Glu Asn Glu Asp Gln Asp Thr Ile Asp Ile Ala Ile
             260                 265                 270

Ser Asp Glu Gly Ile Gly Ile Ile Pro Glu Leu Gln Glu Arg Ile Phe
         275                 280                 285

Glu Arg Thr Phe Arg Val Glu Asn Ser Arg Asn Thr Lys Thr Gly Gly
     290                 295                 300

Ser Gly Leu Gly Leu Tyr Ile Ala Asn Glu Leu Ala Gln Gln Asn Asn
305                 310                 315                 320

Ala Lys Ile Ser Val Ser Ser Asp Ile Asp Val Gly Thr Thr Met Thr
                 325                 330                 335

Val Thr Leu His Lys Leu Asp Ile Thr Ser
             340                 345

(2) INFORMATION FOR SEQ ID NO:69:

(i) SEQUENCE CHARACTERISTICS:
    (A) LENGTH: 392 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "DNA (genomic) (p10c52)"
        Unknown = Xaa
        Unknown for codon no. 125 = TGA (stop codon)

(ix) FEATURE:
    (A) NAME/KEY: CDS
    (B) LOCATION: 1..390

(xi) SEQUENCE DESCRIPTION: SEQ ID NO:69:

| | | | | | | | | | | | | | | | | |
|---|---|---|---|---|---|---|---|---|---|---|---|---|---|---|---|---|
| GTG | AAC | TAT | GAA | TAT | TTC | GAA | TAT | TCG | GTT | AAT | TTA | GGT | GGT | ACC | ACG | 48 |
| Val | Asn | Tyr | Glu | Tyr | Phe | Glu | Tyr | Ser | Val | Asn | Leu | Gly | Gly | Thr | Thr | |
| 1 | | | | 5 | | | | | 10 | | | | | 15 | | |
| yGT | CAC | GTC | CTT | TAT | ATT | GAT | AAG | GAT | GCT | GGC | GCT | TTT | TTG | AAA | GGA | 96 |
| Xaa | His | Val | Leu | Tyr | Ile | Asp | Lys | Asp | Ala | Gly | Ala | Phe | Leu | Lys | Gly | |
| | | | 20 | | | | | 25 | | | | | 30 | | | |
| GCG | TAT | AGA | ATG | GAT | ATA | TTT | TAT | AAA | AAA | ATA | AAA | GCA | AAT | GTA | ACG | 144 |
| Ala | Tyr | Arg | Met | Asp | Ile | Phe | Tyr | Lys | Lys | Ile | Lys | Ala | Asn | Val | Thr | |
| | | 35 | | | | | 40 | | | | | 45 | | | | |
| CCC | GAA | GTT | TTA | GCA | CAA | CTT | CAT | TCC | AAG | AAG | ATC | ATT | TTG | GAA | AGT | 192 |
| Pro | Glu | Val | Leu | Ala | Gln | Leu | His | Ser | Lys | Lys | Ile | Ile | Leu | Glu | Ser | |
| 50 | | | | | 55 | | | | | 60 | | | | | | |
| ACA | AAT | CAA | CAA | CAA | ACT | AAA | GGT | CGC | TAT | TCA | GTT | GTT | ATT | TTT | GAT | 240 |
| Thr | Asn | Gln | Gln | Gln | Thr | Lys | Gly | Arg | Tyr | Ser | Val | Val | Ile | Phe | Asp | |
| 65 | | | | | 70 | | | | | 75 | | | | | 80 | |
| ATT | TAT | GGC | ACT | TTA | ACT | TTA | GAT | AAT | GAT | GTA | TTA | TCA | GTA | AGT | ACT | 288 |
| Ile | Tyr | Gly | Thr | Leu | Thr | Leu | Asp | Asn | Asp | Val | Leu | Ser | Val | Ser | Thr | |
| | | | | 85 | | | | | 90 | | | | | 95 | | |
| TTA | AAA | GAA | TCG | TAT | CAA | ATC | ACT | GAA | AGA | CCG | TAC | CAT | TAT | TTA | ACG | 336 |
| Leu | Lys | Glu | Ser | Tyr | Gln | Ile | Thr | Glu | Arg | Pro | Tyr | His | Tyr | Leu | Thr | |
| | | | | 100 | | | | | 105 | | | | | 110 | | |
| ACT | AAn | ATA | AAT | GAA | GAC | TAC | CAT | AAT | ATT | CCA | AGA | TGA | GGC | AAC | TTA | 384 |
| Thr | Xaa | Ile | Asn | Glu | Asp | Tyr | His | Asn | Ile | Pro | Arg | Xaa | Gly | Asn | Leu | |
| | | 115 | | | | | 120 | | | | | 125 | | | | |
| AGT | CAT | TA | | | | | | | | | | | | | | 392 |
| Ser | His | | | | | | | | | | | | | | | |
| | 130 | | | | | | | | | | | | | | | |

(2) INFORMATION FOR SEQ ID NO:70:

(i) SEQUENCE CHARACTERISTICS:
    (A) LENGTH: 130 amino acids
    (B) TYPE: amino acid
    (D) TOPOLOGY: linear (ii) MOLECULE TYPE: protein (xi) SEQUENCE DESCRIPTION: SEQ ID NO:70:

| | | | | | | | | | | | | | | |
|---|---|---|---|---|---|---|---|---|---|---|---|---|---|---|
| Val | Asn | Tyr | Glu | Tyr | Phe | Glu | Tyr | Ser | Val | Asn | Leu | Gly | Gly | Thr | Thr |
| 1 | | | | 5 | | | | | 10 | | | | | 15 | |
| Xaa | His | Val | Leu | Tyr | Ile | Asp | Lys | Asp | Ala | Gly | Ala | Phe | Leu | Lys | Gly |
| | | | 20 | | | | | 25 | | | | | 30 | | |
| Ala | Tyr | Arg | Met | Asp | Ile | Phe | Tyr | Lys | Lys | Ile | Lys | Ala | Asn | Val | Thr |
| | | 35 | | | | | 40 | | | | | 45 | | | |
| Pro | Glu | Val | Leu | Ala | Gln | Leu | His | Ser | Lys | Lys | Ile | Ile | Leu | Glu | Ser |
| 50 | | | | | 55 | | | | | 60 | | | | | |
| Thr | Asn | Gln | Gln | Gln | Thr | Lys | Gly | Arg | Tyr | Ser | Val | Val | Ile | Phe | Asp |
| 65 | | | | | 70 | | | | | 75 | | | | | 80 |

```
Ile Tyr Gly Thr Leu Thr Leu Asp Asn Asp Val Leu Ser Val Ser Thr
                85                  90                  95

Leu Lys Glu Ser Tyr Gln Ile Thr Glu Arg Pro Tyr His Tyr Leu Thr
            100                 105                 110

Thr Xaa Ile Asn Glu Asp Tyr His Asn Ile Pro Arg Xaa Gly Asn Leu
        115                 120                 125

Ser His
    130
```

(2) INFORMATION FOR SEQ ID NO:71:

(i) SEQUENCE CHARACTERISTICS:
        (A) LENGTH: 1071 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p10d9)"

(ix) FEATURE:
        (A) NAME/KEY: CDS
        (B) LOCATION: 1..1068

(xi) SEQUENCE DESCRIPTION: SEQ ID NO:71:

```
ATG AAA ATG AGA ACA ATT GCT AAA ACC AGT TTA GCA CTA GGG CTT TTA        48
Met Lys Met Arg Thr Ile Ala Lys Thr Ser Leu Ala Leu Gly Leu Leu
 1               5                  10                  15

ACA ACA GGC GCA ATT ACA GTA ACG ACG CAA TCG GTC AAA GCA GAA AAA        96
Thr Thr Gly Ala Ile Thr Val Thr Thr Gln Ser Val Lys Ala Glu Lys
            20                  25                  30

ATA CAA TCA ACT AAA GTT GAC AAA GTA CCA ACG CTT AAA GCA GAG CGA       144
Ile Gln Ser Thr Lys Val Asp Lys Val Pro Thr Leu Lys Ala Glu Arg
        35                  40                  45

TTA GCA ATG ATA AAC ATA ACA GCA GGT GCA AAT TCA GCG ACA ACA CAA       192
Leu Ala Met Ile Asn Ile Thr Ala Gly Ala Asn Ser Ala Thr Thr Gln
    50                  55                  60

GCA GCT AAC ACA AGA CAA GAA CGC ACG CCT AAA CTC GAA AAG GCA CCA       240
Ala Ala Asn Thr Arg Gln Glu Arg Thr Pro Lys Leu Glu Lys Ala Pro
65                  70                  75                  80

AAT ACT AAT GAG GAA AAA ACC TCA GCT TCC AAA ATA GAA AAA ATA TCA       288
Asn Thr Asn Glu Glu Lys Thr Ser Ala Ser Lys Ile Glu Lys Ile Ser
                85                  90                  95

CAA CCT AAA CAA GAA GAG CAG AAA ACG CTT AAT ATA TCA GCA ACG CCA       336
Gln Pro Lys Gln Glu Glu Gln Lys Thr Leu Asn Ile Ser Ala Thr Pro
            100                 105                 110

GCG CCT AAA CAA GAA CAA TCA CAA ACG ACA ACC GAA TCC ACA ACG CCG       384
Ala Pro Lys Gln Glu Gln Ser Gln Thr Thr Thr Glu Ser Thr Thr Pro
        115                 120                 125

AAA ACT AAA GTG ACA ACA CCT CCA TCA ACA AAC ACG CCA CAA CCA ATG       432
Lys Thr Lys Val Thr Thr Pro Pro Ser Thr Asn Thr Pro Gln Pro Met
    130                 135                 140

CAA TCT ACT AAA TCA GAC ACA CCA CAA TCT CCA ACC ATA AAA CAA GCA       480
Gln Ser Thr Lys Ser Asp Thr Pro Gln Ser Pro Thr Ile Lys Gln Ala
145                 150                 155                 160

CAA ACA GAT ATG ACT CCT AAA TAT GAA GAT TTA AGA GCG TAT TAT ACA       528
Gln Thr Asp Met Thr Pro Lys Tyr Glu Asp Leu Arg Ala Tyr Tyr Thr
                165                 170                 175

AAA CCG AGT TTT GAA TTT GAA AAG CAG TTT GGA TTT ATG CTC AAA CCA       576
Lys Pro Ser Phe Glu Phe Glu Lys Gln Phe Gly Phe Met Leu Lys Pro
            180                 185                 190
```

```
TGG ACG ACG GTT AGG TTT ATG AAT GTT ATT CCA AAT AGG TTC ATC TAT      624
Trp Thr Thr Val Arg Phe Met Asn Val Ile Pro Asn Arg Phe Ile Tyr
            195                 200                 205

AAA ATA GCT TTA GTT GGA AAA GAT GAG AAA AAA TAT AAA GAT GGA CCT      672
Lys Ile Ala Leu Val Gly Lys Asp Glu Lys Lys Tyr Lys Asp Gly Pro
        210                 215                 220

TAC GAT AAT ATC GAT GTA TTT ATC GTT TTA GAA GAC AAT AAA TAT CAA      720
Tyr Asp Asn Ile Asp Val Phe Ile Val Leu Glu Asp Asn Lys Tyr Gln
225                 230                 235                 240

TTG AAA AAA TAT TCT GTC GGT GGC ATC ACG AAG ACT AAT AGT AAA AAA      768
Leu Lys Lys Tyr Ser Val Gly Gly Ile Thr Lys Thr Asn Ser Lys Lys
                245                 250                 255

GTT AAT CAC AAA GTA GAA TTA AGC ATT ACT AAA AAA GAT AAT CAA GGT      816
Val Asn His Lys Val Glu Leu Ser Ile Thr Lys Lys Asp Asn Gln Gly
            260                 265                 270

ATG ATT TCA CGC GAT GTT TCA GAA TAC ATG ATT ACT AAG GAA GAG ATT      864
Met Ile Ser Arg Asp Val Ser Glu Tyr Met Ile Thr Lys Glu Glu Ile
        275                 280                 285

TCC TTG AAA GAG CTT GAT TTT AAA TTG AGA AAA CAA CTT ATT GAA AAA      912
Ser Leu Lys Glu Leu Asp Phe Lys Leu Arg Lys Gln Leu Ile Glu Lys
    290                 295                 300

CAT AAT CTT TAC GGT AAC ATG GGT TCA GGA ACA ATC GTT ATT AAA ATG      960
His Asn Leu Tyr Gly Asn Met Gly Ser Gly Thr Ile Val Ile Lys Met
305                 310                 315                 320

AAA AAC GGT GGG AAA TAT ACG TTT GAA TTA CAC AAA AAA CTG CAA GAG     1008
Lys Asn Gly Gly Lys Tyr Thr Phe Glu Leu His Lys Lys Leu Gln Glu
                325                 330                 335

CAT CGT ATG GCA GAC GTC ATA GAT GGC ACT AAT ATT GAT AAC ATT GAA     1056
His Arg Met Ala Asp Val Ile Asp Gly Thr Asn Ile Asp Asn Ile Glu
            340                 345                 350

GTG AAT ATA AAA TAA                                                  1071
Val Asn Ile Lys
        355
```

(2) INFORMATION FOR SEQ ID NO:72:

(i) SEQUENCE CHARACTERISTICS:
        (A) LENGTH: 356 amino acids
        (B) TYPE: amino acid
        (D) TOPOLOGY: linear (ii) MOLECULE TYPE: protein (xi) SEQUENCE DESCRIPTION: SEQ ID NO:72:

```
Met Lys Met Arg Thr Ile Ala Lys Thr Ser Leu Ala Leu Gly Leu Leu
 1               5                  10                  15

Thr Thr Gly Ala Ile Thr Val Thr Thr Gln Ser Val Lys Ala Glu Lys
                20                  25                  30

Ile Gln Ser Thr Lys Val Asp Lys Val Pro Thr Leu Lys Ala Glu Arg
        35                  40                  45

Leu Ala Met Ile Asn Ile Thr Ala Gly Ala Asn Ser Ala Thr Thr Gln
    50                  55                  60

Ala Ala Asn Thr Arg Gln Glu Arg Thr Pro Lys Leu Glu Lys Ala Pro
65                  70                  75                  80

Asn Thr Asn Glu Glu Lys Thr Ser Ala Ser Lys Ile Glu Lys Ile Ser
                85                  90                  95

Gln Pro Lys Gln Glu Glu Gln Lys Thr Leu Asn Ile Ser Ala Thr Pro
            100                 105                 110

Ala Pro Lys Gln Glu Gln Ser Gln Thr Thr Thr Glu Ser Thr Thr Pro
        115                 120                 125
```

```
Lys Thr Lys Val Thr Thr Pro Pro Ser Thr Asn Thr Pro Gln Pro Met
    130                 135                 140

Gln Ser Thr Lys Ser Asp Thr Pro Gln Ser Pro Thr Ile Lys Gln Ala
145                 150                 155                 160

Gln Thr Asp Met Thr Pro Lys Tyr Glu Asp Leu Arg Ala Tyr Tyr Thr
                165                 170                 175

Lys Pro Ser Phe Glu Phe Glu Lys Gln Phe Gly Phe Met Leu Lys Pro
                180                 185                 190

Trp Thr Thr Val Arg Phe Met Asn Val Ile Pro Asn Arg Phe Ile Tyr
                195                 200                 205

Lys Ile Ala Leu Val Gly Lys Asp Glu Lys Tyr Lys Asp Gly Pro
210                 215                 220

Tyr Asp Asn Ile Asp Val Phe Ile Val Leu Glu Asp Asn Lys Tyr Gln
225                 230                 235                 240

Leu Lys Lys Tyr Ser Val Gly Gly Ile Thr Lys Thr Asn Ser Lys Lys
                245                 250                 255

Val Asn His Lys Val Glu Leu Ser Ile Thr Lys Lys Asp Asn Gln Gly
                260                 265                 270

Met Ile Ser Arg Asp Val Ser Glu Tyr Met Ile Thr Lys Glu Glu Ile
                275                 280                 285

Ser Leu Lys Glu Leu Asp Phe Lys Leu Arg Lys Gln Leu Ile Glu Lys
290                 295                 300

His Asn Leu Tyr Gly Asn Met Gly Ser Gly Thr Ile Val Ile Lys Met
305                 310                 315                 320

Lys Asn Gly Gly Lys Tyr Thr Phe Glu Leu His Lys Lys Leu Gln Glu
                325                 330                 335

His Arg Met Ala Asp Val Ile Asp Gly Thr Asn Ile Asp Asn Ile Glu
                340                 345                 350

Val Asn Ile Lys
        355

(2) INFORMATION FOR SEQ ID NO:73:

(i) SEQUENCE CHARACTERISTICS:
        (A) LENGTH: 1590 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p11c12)"

(ix) FEATURE:
        (A) NAME/KEY: CDS
        (B) LOCATION: 1..1587

(xi) SEQUENCE DESCRIPTION: SEQ ID NO:73:

AGA GCA AAC CCT AGA AAA GGA GGT GTT TGT GTG AAT TTA TTA AGC CTC      48
Arg Ala Asn Pro Arg Lys Gly Gly Val Cys Val Asn Leu Leu Ser Leu
  1               5                  10                  15

CTA CTC ATT TTG CTG GGG ATC ATT CTA GGA GTT GTT GGA GGG TAT GTT      96
Leu Leu Ile Leu Leu Gly Ile Ile Leu Gly Val Val Gly Gly Tyr Val
             20                  25                  30

GTT GCC CGA AAT TTG TTG CTT CAA AAG CAA TCA CAA GCT AGA CAA ACT     144
Val Ala Arg Asn Leu Leu Leu Gln Lys Gln Ser Gln Ala Arg Gln Thr
         35                  40                  45

GCC GAA GAT ATT GTA AAT CAA GCA CAT AAA GAA GCT GAC AAT ATC AAA     192
Ala Glu Asp Ile Val Asn Gln Ala His Lys Glu Ala Asp Asn Ile Lys
 50                  55                  60
```

-continued

```
AAA GAG AAA TTA CTT GAG GCA AAA GAA GAA AAC CAA ATC CTA AGA GAA      240
Lys Glu Lys Leu Leu Glu Ala Lys Glu Glu Asn Gln Ile Leu Arg Glu
 65              70                  75                  80

CAA ACT GAA GCA GAA CTA CGA GAA AGA CGT AGC GAA CTT CAA AGA CAA      288
Gln Thr Glu Ala Glu Leu Arg Glu Arg Arg Ser Glu Leu Gln Arg Gln
                 85                  90                  95

GAA ACC CGA CTT CTT CAA AAA GAA GAA AAC TTA GAG CGC AAA TCT GAT      336
Glu Thr Arg Leu Leu Gln Lys Glu Glu Asn Leu Glu Arg Lys Ser Asp
            100                 105                 110

CTA TTA GAT AAA AAA GAT GAG ATT TTA GAG CAA AAA GAA TCA AAA ATT      384
Leu Leu Asp Lys Lys Asp Glu Ile Leu Glu Gln Lys Glu Ser Lys Ile
        115                 120                 125

GAA GAA AAA CAA CAA CAA GTA GAT GCA AAA GAG AGT AGT GTT CAA ACG      432
Glu Glu Lys Gln Gln Gln Val Asp Ala Lys Glu Ser Ser Val Gln Thr
130                 135                 140

TTA ATA ATG AAG CAT GAA CAA GAA TTA GAA CGC ATC TCC GGT CTC ACT      480
Leu Ile Met Lys His Glu Gln Glu Leu Glu Arg Ile Ser Gly Leu Thr
145                 150                 155                 160

CAA GAA GAA GCT ATT AAT GAG CAA CTT CAA AGA GTA GAG GAA GAA CTG      528
Gln Glu Glu Ala Ile Asn Glu Gln Leu Gln Arg Val Glu Glu Glu Leu
                165                 170                 175

TCA CAA GAT ATT GCA GTA CTT GTT AAA GAA AAA GAA AAA GAA GCT AAA      576
Ser Gln Asp Ile Ala Val Leu Val Lys Glu Lys Glu Lys Glu Ala Lys
            180                 185                 190

GAA AAA GTT GAT AAA ACA GCA AAA GAA TTA TTA GCT ACA GCA GTA CAA      624
Glu Lys Val Asp Lys Thr Ala Lys Glu Leu Leu Ala Thr Ala Val Gln
        195                 200                 205

AGA TTA GCA GCA GAT CAC ACA AGT GAA TCA ACG GTA TCA GTA GTT AAC      672
Arg Leu Ala Ala Asp His Thr Ser Glu Ser Thr Val Ser Val Val Asn
210                 215                 220

TTA CCT AAT GAT GAG ATG AAA GGT CGA ATC ATT GGA CGA GAA GGA CGA      720
Leu Pro Asn Asp Glu Met Lys Gly Arg Ile Ile Gly Arg Glu Gly Arg
225                 230                 235                 240

AAC ATC CGC ACA CTT GAA ACT TTA ACT GGC ATT GAT TTA ATT ATT GAT      768
Asn Ile Arg Thr Leu Glu Thr Leu Thr Gly Ile Asp Leu Ile Ile Asp
                245                 250                 255

GAC ACA CCA GAA GCG GTT ATA TTA TCT GGT TTT GAT CCA ATA AGA AGA      816
Asp Thr Pro Glu Ala Val Ile Leu Ser Gly Phe Asp Pro Ile Arg Arg
            260                 265                 270

GAA ATT GCT AGA ACA GCA CTT GTT AAC TTA GTA TCT GAT GGA CGT ATT      864
Glu Ile Ala Arg Thr Ala Leu Val Asn Leu Val Ser Asp Gly Arg Ile
        275                 280                 285

CAT CCA GGT AGA ATT GAA GAT ATG GTC GAA AAA GCT AGA AAA GAA GTA      912
His Pro Gly Arg Ile Glu Asp Met Val Glu Lys Ala Arg Lys Glu Val
290                 295                 300

GAC GAT ATT ATT AGA GAA GCA GGT GAA CAA GCT ACA TTT GAA GTG AAC      960
Asp Asp Ile Ile Arg Glu Ala Gly Glu Gln Ala Thr Phe Glu Val Asn
305                 310                 315                 320

GCA CAT AAT ATG CAT CCT GAC TTA GTA AAA ATT GTA GGG CGT TTA AAC     1008
Ala His Asn Met His Pro Asp Leu Val Lys Ile Val Gly Arg Leu Asn
                325                 330                 335

TAT CGT ACG AGT TAC GGT CAA AAT GTA CTT AAA CAT TCA ATT GAA GTT     1056
Tyr Arg Thr Ser Tyr Gly Gln Asn Val Leu Lys His Ser Ile Glu Val
            340                 345                 350

GCG CAT CTT GCT AGT ATG TTA GCT GCT GAG CTA GGC GAA GAT GAG ACA     1104
Ala His Leu Ala Ser Met Leu Ala Ala Glu Leu Gly Glu Asp Glu Thr
        355                 360                 365

TTA GCG AAA CGA GCT GGA CTT TTA CAT GAT GTT GGT AAA GCA ATT GAT     1152
Leu Ala Lys Arg Ala Gly Leu Leu His Asp Val Gly Lys Ala Ile Asp
```

-continued

```
                 370                 375                 380
CAT GAA GTA GAA GGT AGT CAT GTT GAA ATC GGT GTA GAA TTA GCG AAA         1200
His Glu Val Glu Gly Ser His Val Glu Ile Gly Val Glu Leu Ala Lys
385                     390                 395                 400

AAA TAT GGT GAA AAT GAA ACA GTT ATT AAT GCA ATC CAT TCT CAT CAT         1248
Lys Tyr Gly Glu Asn Glu Thr Val Ile Asn Ala Ile His Ser His His
                    405                 410                 415

GGT GAT GTT GAA CCT ACA TCT ATT ATA TCT ATC CTT GTT GCT GCT GCA         1296
Gly Asp Val Glu Pro Thr Ser Ile Ile Ser Ile Leu Val Ala Ala Ala
                420                 425                 430

GAT GCA TTG TCT GCG GCT CGT CCA GGT GCA AGA AAA GAA ACA TTA GAG         1344
Asp Ala Leu Ser Ala Ala Arg Pro Gly Ala Arg Lys Glu Thr Leu Glu
            435                 440                 445

AAT TAT ATT CGT CGA TTA GAA CGT TTA GAA ACG TTA TCA GAA AGT TAT         1392
Asn Tyr Ile Arg Arg Leu Glu Arg Leu Glu Thr Leu Ser Glu Ser Tyr
        450                 455                 460

GAT GGT GTA GAA AAA GCA TTT GCG ATT CAG GCA GGT AGA GAA ATC CGA         1440
Asp Gly Val Glu Lys Ala Phe Ala Ile Gln Ala Gly Arg Glu Ile Arg
465                 470                 475                 480

GTG ATT GTA TCT CCT GAA GAA ATT GAT GAT TTA AAA TCT TAT CGA TTG         1488
Val Ile Val Ser Pro Glu Glu Ile Asp Asp Leu Lys Ser Tyr Arg Leu
                485                 490                 495

GCT AGA GAT ATT AAA AAT CAG ATT GAA GAT GAA TTA CAA TAT CCT GGT         1536
Ala Arg Asp Ile Lys Asn Gln Ile Glu Asp Glu Leu Gln Tyr Pro Gly
            500                 505                 510

CAT ATC AAG GTG ACA GTT GTT CGA GAG ACT AGA GCA GTA GAA TAT GCG         1584
His Ile Lys Val Thr Val Val Arg Glu Thr Arg Ala Val Glu Tyr Ala
        515                 520                 525

AAA TAA                                                                 1590
Lys
```

(2) INFORMATION FOR SEQ ID NO:74:

(i) SEQUENCE CHARACTERISTICS:
        (A) LENGTH: 529 amino acids
        (B) TYPE: amino acid
        (D) TOPOLOGY: linear (ii) MOLECULE TYPE: protein (xi) SEQUENCE DESCRIPTION: SEQ ID NO:74:

```
Arg Ala Asn Pro Arg Lys Gly Gly Val Cys Val Asn Leu Leu Ser Leu
1               5                   10                  15

Leu Leu Ile Leu Leu Gly Ile Ile Leu Gly Val Val Gly Gly Tyr Val
            20                  25                  30

Val Ala Arg Asn Leu Leu Leu Gln Lys Gln Ser Gln Ala Arg Gln Thr
        35                  40                  45

Ala Glu Asp Ile Val Asn Gln Ala His Lys Glu Ala Asp Asn Ile Lys
    50                  55                  60

Lys Glu Lys Leu Leu Glu Ala Lys Glu Glu Asn Gln Ile Leu Arg Glu
65              70                  75                  80

Gln Thr Glu Ala Glu Leu Arg Glu Arg Arg Ser Glu Leu Gln Arg Gln
                85                  90                  95

Glu Thr Arg Leu Leu Gln Lys Glu Glu Asn Leu Glu Arg Lys Ser Asp
            100                 105                 110

Leu Leu Asp Lys Lys Asp Glu Ile Leu Glu Gln Lys Glu Ser Lys Ile
        115                 120                 125

Glu Glu Lys Gln Gln Gln Val Asp Ala Lys Glu Ser Ser Val Gln Thr
    130                 135                 140
```

```
Leu Ile Met Lys His Glu Gln Glu Leu Glu Arg Ile Ser Gly Leu Thr
145                 150                 155                 160

Gln Glu Glu Ala Ile Asn Glu Gln Leu Gln Arg Val Glu Glu Glu Leu
            165                 170                 175

Ser Gln Asp Ile Ala Val Leu Val Lys Glu Lys Glu Lys Glu Ala Lys
            180                 185                 190

Glu Lys Val Asp Lys Thr Ala Lys Glu Leu Leu Ala Thr Ala Val Gln
        195                 200                 205

Arg Leu Ala Ala Asp His Thr Ser Glu Ser Thr Val Ser Val Val Asn
    210                 215                 220

Leu Pro Asn Asp Glu Met Lys Gly Arg Ile Ile Gly Arg Glu Gly Arg
225                 230                 235                 240

Asn Ile Arg Thr Leu Glu Thr Leu Thr Gly Ile Asp Leu Ile Ile Asp
                245                 250                 255

Asp Thr Pro Glu Ala Val Ile Leu Ser Gly Phe Asp Pro Ile Arg Arg
            260                 265                 270

Glu Ile Ala Arg Thr Ala Leu Val Asn Leu Val Ser Asp Gly Arg Ile
        275                 280                 285

His Pro Gly Arg Ile Glu Asp Met Val Glu Lys Ala Arg Lys Glu Val
    290                 295                 300

Asp Asp Ile Ile Arg Glu Ala Gly Glu Gln Ala Thr Phe Glu Val Asn
305                 310                 315                 320

Ala His Asn Met His Pro Asp Leu Val Lys Ile Val Gly Arg Leu Asn
                325                 330                 335

Tyr Arg Thr Ser Tyr Gly Gln Asn Val Leu Lys His Ser Ile Glu Val
            340                 345                 350

Ala His Leu Ala Ser Met Leu Ala Ala Glu Leu Gly Glu Asp Glu Thr
        355                 360                 365

Leu Ala Lys Arg Ala Gly Leu Leu His Asp Val Gly Lys Ala Ile Asp
    370                 375                 380

His Glu Val Glu Gly Ser His Val Glu Ile Gly Val Glu Leu Ala Lys
385                 390                 395                 400

Lys Tyr Gly Glu Asn Glu Thr Val Ile Asn Ala Ile His Ser His His
                405                 410                 415

Gly Asp Val Glu Pro Thr Ser Ile Ile Ser Ile Leu Val Ala Ala Ala
            420                 425                 430

Asp Ala Leu Ser Ala Ala Arg Pro Gly Ala Arg Lys Glu Thr Leu Glu
        435                 440                 445

Asn Tyr Ile Arg Arg Leu Glu Arg Leu Glu Thr Leu Ser Glu Ser Tyr
    450                 455                 460

Asp Gly Val Glu Lys Ala Phe Ala Ile Gln Ala Gly Arg Glu Ile Arg
465                 470                 475                 480

Val Ile Val Ser Pro Glu Ile Asp Asp Leu Lys Ser Tyr Arg Leu
                485                 490                 495

Ala Arg Asp Ile Lys Asn Gln Ile Glu Asp Glu Leu Gln Tyr Pro Gly
            500                 505                 510

His Ile Lys Val Thr Val Val Arg Glu Thr Arg Ala Val Glu Tyr Ala
        515                 520                 525

Lys
```

(2) INFORMATION FOR SEQ ID NO:75:

(i) SEQUENCE CHARACTERISTICS:

```
        (A) LENGTH: 799 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p11c66)"
            Unknown = Xaa (ix) FEATURE:
        (A) NAME/KEY: CDS
        (B) LOCATION: 1..384

(xi) SEQUENCE DESCRIPTION: SEQ ID NO:75:

TCA TGG TAT TAT ATT GTT TGG AGT GAT TTG ATG AGA TTT GTC TTT GAT      48
Ser Trp Tyr Tyr Ile Val Trp Ser Asp Leu Met Arg Phe Val Phe Asp
 1               5                  10                  15

ATT GAT GGT ACG CTT TGT TTT GAC GGC CGA TTA ATT GAC CAG ACT ATT      96
Ile Asp Gly Thr Leu Cys Phe Asp Gly Arg Leu Ile Asp Gln Thr Ile
                20                  25                  30

ATT GAT ACA TTG TTA CAA TTA CAA CAT GAT GGT CAT GAA CTT ATA TTT     144
Ile Asp Thr Leu Leu Gln Leu Gln His Asp Gly His Glu Leu Ile Phe
             35                  40                  45

GCA TCA GCA CGT CCG ATT CGT GAT TTG TTG CCA GTT TTA CCA TCA GTA     192
Ala Ser Ala Arg Pro Ile Arg Asp Leu Leu Pro Val Leu Pro Ser Val
     50                  55                  60

TTT CAT CAG CAC ACA TTA ATT GGC GCA AAT GGT GCT ATG ATT TCA CAG     240
Phe His Gln His Thr Leu Ile Gly Ala Asn Gly Ala Met Ile Ser Gln
 65                  70                  75                  80

CAA TCA AAG ATT TCT GTT ATC AAA CCA ATT CAT ACT GAT ACA TAT CAT     288
Gln Ser Lys Ile Ser Val Ile Lys Pro Ile His Thr Asp Thr Tyr His
                 85                  90                  95

CAT ATC TTC AAA ATA ATT CAA AAG TAT GAG TTA GAT TAT ATT ATT GAT     336
His Ile Phe Lys Ile Ile Gln Lys Tyr Glu Leu Asp Tyr Ile Ile Asp
            100                 105                 110

GAT GAT TGG AAT TAT GCT GCA CAA CTT GAC GCT GnA GAA CGC GAT TTT     384
Asp Asp Trp Asn Tyr Ala Ala Gln Leu Asp Ala Xaa Glu Arg Asp Phe
        115                 120                 125

TGAGCGTTTA GATCCACATA AGCTGGCCAG TTGTATTGAT GTTGCAAATA TCGACACGCC    444

AATCAAGAkT ATTTTATTAA ATATAGACCC GGCACAAATT ACAACTATAT TAGACGAGCT    504

AGATAAATAC CATCAAGAAT TGGAAATGAT TCACCATTCA AATGAGTATA ACATTGATAT    564

AACAGCGCAA AATATTAACA AATATACTGC ATTACAATAT ATATTTGATG CAGATGTTAA    624

ATATATAGCA TTTGGTAATG ACCACAATGA TATTGTCATG TTACAACATG CTAGTAGTGG    684

CTATATTATA GGACCATCAG AAGCATACAC ACACGCAATA TTGAAACTTG ATAAAATCAA    744

ACACATCAAT AATAATGCAC AAGCTATTTG CAAAGTCTTA AAATCATATA AATAA         799

(2) INFORMATION FOR SEQ ID NO:76:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:76:

Ser Trp Tyr Tyr Ile Val Trp Ser Asp Leu Met Arg Phe Val Phe Asp
 1               5                  10                  15

Ile Asp Gly Thr Leu Cys Phe Asp Gly Arg Leu Ile Asp Gln Thr Ile
                20                  25                  30
```

```
Ile Asp Thr Leu Leu Gln Leu Gln His Asp Gly His Glu Leu Ile Phe
         35                  40                  45

Ala Ser Ala Arg Pro Ile Arg Asp Leu Leu Pro Val Leu Pro Ser Val
 50                  55                  60

Phe His Gln His Thr Leu Ile Gly Ala Asn Gly Ala Met Ile Ser Gln
 65                  70                  75                  80

Gln Ser Lys Ile Ser Val Ile Lys Pro Ile His Thr Asp Thr Tyr His
                 85                  90                  95

His Ile Phe Lys Ile Ile Gln Lys Tyr Glu Leu Asp Tyr Ile Ile Asp
             100                 105                 110

Asp Asp Trp Asn Tyr Ala Ala Gln Leu Asp Ala Xaa Glu Arg Asp Phe
         115                 120                 125
```

(2) INFORMATION FOR SEQ ID NO:77:

(i) SEQUENCE CHARACTERISTICS:
      (A) LENGTH: 799 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "DNA (genomic) (p11c66)"
          Unknown = Xaa (ix) FEATURE:
      (A) NAME/KEY: CDS
      (B) LOCATION: 335..796

(xi) SEQUENCE DESCRIPTION: SEQ ID NO:77:

```
TCATGGTATT ATATTGTTTG GAGTGATTTG ATGAGATTTG TCTTTGATAT TGATGGTACG      60

CTTTGTTTTG ACGGCCGATT AATTGACCAG ACTATTATTG ATACATTGTT ACAATTACAA     120

CATGATGGTC ATGAACTTAT ATTTGCATCA GCACGTCCGA TTCGTGATTT GTTGCCAGTT     180

TTACCATCAG TATTTCATCA GCACACATTA ATTGGCGCAA ATGGTGCTAT GATTTCACAG     240

CAATCAAAGA TTTCTGTTAT CAAACCAATT CATACTGATA CATATCATCA TATCTTCAAA     300

ATAATTCAAA AGTATGAGTT AGATTATATT ATTG ATG ATG ATT GGA ATT ATG          352
                                      Met Met Ile Gly Ile Met
                                       1               5

CTG CAC AAC TTG ACG CTG nAG AAC GCG ATT TTT GAG CGT TTA GAT CCA        400
Leu His Asn Leu Thr Leu Xaa Asn Ala Ile Phe Glu Arg Leu Asp Pro
             10                  15                  20

CAT AAG CTG GCC AGT TGT ATT GAT GTT GCA AAT ATC GAC ACG CCA ATC        448
His Lys Leu Ala Ser Cys Ile Asp Val Ala Asn Ile Asp Thr Pro Ile
         25                  30                  35

AAG AkT ATT TTA TTA AAT ATA GAC CCG GCA CAA ATT ACA ACT ATA TTA        496
Lys Xaa Ile Leu Leu Asn Ile Asp Pro Ala Gln Ile Thr Thr Ile Leu
 40                  45                  50

GAC GAG CTA GAT AAA TAC CAT CAA GAA TTG GAA ATG ATT CAC CAT TCA        544
Asp Glu Leu Asp Lys Tyr His Gln Glu Leu Glu Met Ile His His Ser
 55                  60                  65                  70

AAT GAG TAT AAC ATT GAT ATA ACA GCG CAA AAT ATT AAC AAA TAT ACT        592
Asn Glu Tyr Asn Ile Asp Ile Thr Ala Gln Asn Ile Asn Lys Tyr Thr
                 75                  80                  85

GCA TTA CAA TAT ATA TTT GAT GCA GAT GTT AAA TAT ATA GCA TTT GGT        640
Ala Leu Gln Tyr Ile Phe Asp Ala Asp Val Lys Tyr Ile Ala Phe Gly
             90                  95                 100

AAT GAC CAC AAT GAT ATT GTC ATG TTA CAA CAT GCT AGT AGT GGC TAT        688
Asn Asp His Asn Asp Ile Val Met Leu Gln His Ala Ser Ser Gly Tyr
         105                 110                 115
```

```
ATT ATA GGA CCA TCA GAA GCA TAC ACA CAC GCA ATA TTG AAA CTT GAT        736
Ile Ile Gly Pro Ser Glu Ala Tyr Thr His Ala Ile Leu Lys Leu Asp
120                 125                 130

AAA ATC AAA CAC ATC AAT AAT AAT GCA CAA GCT ATT TGC AAA GTC TTA        784
Lys Ile Lys His Ile Asn Asn Asn Ala Gln Ala Ile Cys Lys Val Leu
135                 140                 145                 150

AAA TCA TAT AAA TAA                                                    799
Lys Ser Tyr Lys
```

(2) INFORMATION FOR SEQ ID NO:78:

(i) SEQUENCE CHARACTERISTICS:
        (A) LENGTH: 154 amino acids
        (B) TYPE: amino acid
        (D) TOPOLOGY: linear (ii) MOLECULE TYPE: protein (xi) SEQUENCE DESCRIPTION: SEQ ID NO:78:

```
Met Met Ile Gly Ile Met Leu His Asn Leu Thr Leu Xaa Asn Ala Ile
1               5                   10                  15

Phe Glu Arg Leu Asp Pro His Lys Leu Ala Ser Cys Ile Asp Val Ala
                20                  25                  30

Asn Ile Asp Thr Pro Ile Lys Xaa Ile Leu Leu Asn Ile Asp Pro Ala
            35                  40                  45

Gln Ile Thr Thr Ile Leu Asp Glu Leu Asp Lys Tyr His Gln Glu Leu
        50                  55                  60

Glu Met Ile His His Ser Asn Glu Tyr Asn Ile Asp Ile Thr Ala Gln
65                  70                  75                  80

Asn Ile Asn Lys Tyr Thr Ala Leu Gln Tyr Ile Phe Asp Ala Asp Val
                85                  90                  95

Lys Tyr Ile Ala Phe Gly Asn Asp His Asn Asp Ile Val Met Leu Gln
                100                 105                 110

His Ala Ser Ser Gly Tyr Ile Ile Gly Pro Ser Glu Ala Tyr Thr His
            115                 120                 125

Ala Ile Leu Lys Leu Asp Lys Ile Lys His Ile Asn Asn Asn Ala Gln
130                 135                 140

Ala Ile Cys Lys Val Leu Lys Ser Tyr Lys
145                 150
```

(2) INFORMATION FOR SEQ ID NO:79:

(i) SEQUENCE CHARACTERISTICS:
        (A) LENGTH: 1236 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) p5c34"

(ix) FEATURE:
        (A) NAME/KEY: CDS
        (B) LOCATION: 1..1233

(xi) SEQUENCE DESCRIPTION: SEQ ID NO:79:

```
AGC TCT ACG TTC AAC ATT TTT CCA TTG GGG ATT CCA TGC TTG GGC TGT         48
Ser Ser Thr Phe Asn Ile Phe Pro Leu Gly Ile Pro Cys Leu Gly Cys
1               5                   10                  15

TTA TGG TGT TGT TGC GTT ACG TTG GCA TAT TCG CAA TTC CGT AAA GGT         96
Leu Trp Cys Cys Cys Val Thr Leu Ala Tyr Ser Gln Phe Arg Lys Gly
                20                  25                  30
```

-continued

| | |
|---|---|
| GAA CCA GGT TTA TTA TCT AGA ACT TTA CGT CCT CTT TTA GGT GAT AAA<br>Glu Pro Gly Leu Leu Ser Arg Thr Leu Arg Pro Leu Leu Gly Asp Lys<br>          35                  40                    45 | 144 |
| GTA GAA GGT CCT ATT GGG ATT TTT ATT GAC GTT TTA TCT GTA TTT GCG<br>Val Glu Gly Pro Ile Gly Ile Phe Ile Asp Val Leu Ser Val Phe Ala<br>    50                  55                  60 | 192 |
| ACA ATC GTT GGG GTA GCC GTT TCG TTA GGT ATG GGT GCT CTA CAA ATT<br>Thr Ile Val Gly Val Ala Val Ser Leu Gly Met Gly Ala Leu Gln Ile<br>65                  70                  75                80 | 240 |
| AAT GGT GGT TTA CAT TAC TTG TTC AAT GTT CCA AAC AAT ACG TTT GTA<br>Asn Gly Gly Leu His Tyr Leu Phe Asn Val Pro Asn Asn Thr Phe Val<br>                  85                  90                95 | 288 |
| CAA GCG ATT ATC ATC ATT GTT GTT ACT ATC TTA TTT ATA GCA AGT GCA<br>Gln Ala Ile Ile Ile Ile Val Val Thr Ile Leu Phe Ile Ala Ser Ala<br>          100                  105               110 | 336 |
| TGG TCT GGA TTA AGT AAA GGT ATT CAA TAC TTA AGT AAC TTG AAC ATT<br>Trp Ser Gly Leu Ser Lys Gly Ile Gln Tyr Leu Ser Asn Leu Asn Ile<br>         115                  120               125 | 384 |
| GGT TTA GGT ACT ATT TTA ATG GTA GCT GCT TTA ATT GTT GGA CCA ACT<br>Gly Leu Gly Thr Ile Leu Met Val Ala Ala Leu Ile Val Gly Pro Thr<br>130                     135               140 | 432 |
| GTT CTT ATT TTA AAT ATG TTA ACT AGC TCT ACG GGT AGT TTA CTA AAC<br>Val Leu Ile Leu Asn Met Leu Thr Ser Ser Thr Gly Ser Leu Leu Asn<br>145                     150               155               160 | 480 |
| ACA TTC TTG TTT AAT AGT TTT GAT ACA GCA GCT TTA AAT CCT CAA AAA<br>Thr Phe Leu Phe Asn Ser Phe Asp Thr Ala Ala Leu Asn Pro Gln Lys<br>                  165               170               175 | 528 |
| CGT GAA TGG ATG TCT TCA TGG ACA CTT TAT TAC TGG GGT TGG TGG TTA<br>Arg Glu Trp Met Ser Ser Trp Thr Leu Tyr Tyr Trp Gly Trp Trp Leu<br>         180                  185               190 | 576 |
| AGT TGG AGT CCA TTC GTT GGA GTG TTT ATT GCA CGA GTT TCA AAA GGA<br>Ser Trp Ser Pro Phe Val Gly Val Phe Ile Ala Arg Val Ser Lys Gly<br>         195                  200               205 | 624 |
| CGT TCA ATT AGA GAG TTC ATT TCT GGT GTC TTG CTA GTT CCA GCA ATT<br>Arg Ser Ile Arg Glu Phe Ile Ser Gly Val Leu Leu Val Pro Ala Ile<br>         210                  215               220 | 672 |
| GTT AGT TTT GTT TGG TTT AGT GTC TTT GGT GTA TTA GGC ATC GAG ACA<br>Val Ser Phe Val Trp Phe Ser Val Phe Gly Val Leu Gly Ile Glu Thr<br>225                     230               235               240 | 720 |
| GGT AAG AAA CAC AAA GAA ATT TTT GAT ATG ACT CCT GAA ACA CAG CTA<br>Gly Lys Lys His Lys Glu Ile Phe Asp Met Thr Pro Glu Thr Gln Leu<br>         245                  250               255 | 768 |
| TTT GGA GTG TTT AAT CAT GTG CCA TTT GGC ATT GTT TTA TCG TTG ATT<br>Phe Gly Val Phe Asn His Val Pro Phe Gly Ile Val Leu Ser Leu Ile<br>         260                  265               270 | 816 |
| GCA TTA TTA TTA ATT GCA TCA TTC TTT ATT ACA TCT GCT GAC TCA GCA<br>Ala Leu Leu Leu Ile Ala Ser Phe Phe Ile Thr Ser Ala Asp Ser Ala<br>         275                  280               285 | 864 |
| ACA TTT GTA TTA GGA ATG CAA ACA ACA TTT GGT TCA TTA AAT CCA TCT<br>Thr Phe Val Leu Gly Met Gln Thr Thr Phe Gly Ser Leu Asn Pro Ser<br>         290                  295               300 | 912 |
| AGT ATG GTA AAA GTT GTT TGG GGA ATT TCA CAG GCC TTA ATA GCA TTT<br>Ser Met Val Lys Val Val Trp Gly Ile Ser Gln Ala Leu Ile Ala Phe<br>305                     310               315               320 | 960 |
| GTA CTT TTA TTA GCT GGT GGC GGT AAC GGC GCT GAA GCT TTA AAT GCG<br>Val Leu Leu Leu Ala Gly Gly Gly Asn Gly Ala Glu Ala Leu Asn Ala<br>         325                  330               335 | 1008 |
| ATT CAA AGT GCT GCA ATT ATA AGT GCA TTC CCA TTC TCC TTT GTC GTC<br>Ile Gln Ser Ala Ala Ile Ile Ser Ala Phe Pro Phe Ser Phe Val Val<br>         340                  345               350 | 1056 |

```
ATA CTC ATG ATG GTA AGT TTC TAC AAG GAT GCG AAC CAG GAA CGT AAA      1104
Ile Leu Met Met Val Ser Phe Tyr Lys Asp Ala Asn Gln Glu Arg Lys
            355                 360                 365

TTC CTA GGT TTA ACA TTG ACT CCG AAT AAA CAT CGC TTA CAA GAA TAT      1152
Phe Leu Gly Leu Thr Leu Thr Pro Asn Lys His Arg Leu Gln Glu Tyr
        370                 375                 380

ATC AAG AGT CAA CAA GAA GAT TAT GAA TCT GAC ATT CTT GAA AAG CGT      1200
Ile Lys Ser Gln Gln Glu Asp Tyr Glu Ser Asp Ile Leu Glu Lys Arg
385                 390                 395                 400

CAG TCA CGT AGA AAT ATA GAG AAA AAA GAT AAC TAA                      1236
Gln Ser Arg Arg Asn Ile Glu Lys Lys Asp Asn
                    405                 410
```

(2) INFORMATION FOR SEQ ID NO:80:

(i) SEQUENCE CHARACTERISTICS:
        (A) LENGTH: 411 amino acids
        (B) TYPE: amino acid
        (D) TOPOLOGY: linear (ii) MOLECULE TYPE: protein (xi) SEQUENCE DESCRIPTION: SEQ ID NO:80:

```
Ser Ser Thr Phe Asn Ile Phe Pro Leu Gly Ile Pro Cys Leu Gly Cys
 1               5                  10                  15

Leu Trp Cys Cys Cys Val Thr Leu Ala Tyr Ser Gln Phe Arg Lys Gly
             20                  25                  30

Glu Pro Gly Leu Leu Ser Arg Thr Leu Arg Pro Leu Leu Gly Asp Lys
         35                  40                  45

Val Glu Gly Pro Ile Gly Ile Phe Ile Asp Val Leu Ser Val Phe Ala
     50                  55                  60

Thr Ile Val Gly Val Ala Val Ser Leu Gly Met Gly Ala Leu Gln Ile
 65                  70                  75                  80

Asn Gly Gly Leu His Tyr Leu Phe Asn Val Pro Asn Asn Thr Phe Val
                 85                  90                  95

Gln Ala Ile Ile Ile Val Val Thr Ile Leu Phe Ile Ala Ser Ala
                100                 105                 110

Trp Ser Gly Leu Ser Lys Gly Ile Gln Tyr Leu Ser Asn Leu Asn Ile
         115                 120                 125

Gly Leu Gly Thr Ile Leu Met Val Ala Ala Leu Ile Val Gly Pro Thr
130                 135                 140

Val Leu Ile Leu Asn Met Leu Thr Ser Ser Thr Gly Ser Leu Leu Asn
145                 150                 155                 160

Thr Phe Leu Phe Asn Ser Phe Asp Thr Ala Ala Leu Asn Pro Gln Lys
                165                 170                 175

Arg Glu Trp Met Ser Ser Trp Thr Leu Tyr Tyr Trp Gly Trp Trp Leu
             180                 185                 190

Ser Trp Ser Pro Phe Val Gly Val Phe Ile Ala Arg Val Ser Lys Gly
         195                 200                 205

Arg Ser Ile Arg Glu Phe Ile Ser Gly Val Leu Val Pro Ala Ile
    210                 215                 220

Val Ser Phe Val Trp Phe Ser Val Phe Gly Val Leu Gly Ile Glu Thr
225                 230                 235                 240

Gly Lys Lys His Lys Glu Ile Phe Asp Met Thr Pro Glu Thr Gln Leu
                245                 250                 255

Phe Gly Val Phe Asn His Val Pro Phe Gly Ile Val Leu Ser Leu Ile
            260                 265                 270
```

```
Ala Leu Leu Leu Ile Ala Ser Phe Phe Ile Thr Ser Ala Asp Ser Ala
            275                 280                 285
Thr Phe Val Leu Gly Met Gln Thr Thr Phe Gly Ser Leu Asn Pro Ser
        290                 295                 300
Ser Met Val Lys Val Val Trp Gly Ile Ser Gln Ala Leu Ile Ala Phe
305                 310                 315                 320
Val Leu Leu Leu Ala Gly Gly Asn Gly Ala Glu Ala Leu Asn Ala
                325                 330                 335
Ile Gln Ser Ala Ala Ile Ile Ser Ala Phe Pro Phe Ser Phe Val Val
            340                 345                 350
Ile Leu Met Met Val Ser Phe Tyr Lys Asp Ala Asn Gln Glu Arg Lys
            355                 360                 365
Phe Leu Gly Leu Thr Leu Thr Pro Asn Lys His Arg Leu Gln Glu Tyr
        370                 375                 380
Ile Lys Ser Gln Gln Glu Asp Tyr Glu Ser Asp Ile Leu Glu Lys Arg
385                 390                 395                 400
Gln Ser Arg Arg Asn Ile Glu Lys Lys Asp Asn
                405                 410
```

(2) INFORMATION FOR SEQ ID NO:81:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p10c18)"
            Unknown = N (xi) SEQUENCE DESCRIPTION: SEQ ID NO:81:

```
ATTATAGAGT TTTTCCGCTG TTTCTAAAGT TAAATTATTC ACTTTTCTTT TCCCGCTTCT      60
TAATTCACTT ATACCACCAT AAGAAACATC AGTGTCTTGA TTAATTCTAT AATTAGATAT     120
TGATYTATCA TTTAGTARTT TTTCTATTGT ATTATNAATT TCTTTAARCT GGTTCWTAAT     180
TTTNGTCNAA ATGAAAGAAT AATTTATTTT NTCTCTANGT TATATTAATC AATNAANTAA     240
TATTANAGTT GCAANTTAAG NATAGAGAGT TNATTTTTTT CCTTTANATT CCTCCTTGGT     300
CNCTNAANAT TANCCANCCT NCCCCTTATT TTTAAATTTG GTGGGTNNAA AGGGGTTNTT     360
CTNGGCCCCN TTTTTNCCCT NTTTTTTTTN ANAAAGNANC CGNAATTCTG GATCCTAACT     420
TTTANTNTTN NCTTGGGAAC TCTAATTCAA GGGNCCTCNG CTCGNCNAGC NCTAATT        477
```

(2) INFORMATION FOR SEQ ID NO:82:

(i) SEQUENCE CHARACTERISTICS:
        (A) LENGTH: 1212 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p12c3)"
            Unknown = Xaa (ix) FEATURE:
        (A) NAME/KEY: CDS
        (B) LOCATION: 1..1209

(xi) SEQUENCE DESCRIPTION: SEQ ID NO:82:

```
GAA AGA AAG CGT TTT CAC ATA ACA AAG GGG GAG TTT CAA ATG AAA GTC      48
```

```
            Glu Arg Lys Arg Phe His Ile Thr Lys Gly Glu Phe Gln Met Lys Val
             1               5                  10                  15

GAA GTT TAT AAA GGA GCG CAA GGT AAA CAT AAC CTT AAA GAT TAT GAA       96
            Glu Val Tyr Lys Gly Ala Gln Gly Lys His Asn Leu Lys Asp Tyr Glu
                            20                  25                  30

GAA ACA TAT AAT ACT TTT GAT TGG AAA GAC GTA GAA CAA GCA TTT TCT      144
            Glu Thr Tyr Asn Thr Phe Asp Trp Lys Asp Val Glu Gln Ala Phe Ser
                        35                  40                  45

TGG AGT GAA ACT GGA AAA ATG AAC ATG GCA TAT GAA TGC ATA GAT CGC      192
            Trp Ser Glu Thr Gly Lys Met Asn Met Ala Tyr Glu Cys Ile Asp Arg
                    50                  55                  60

CAT GTA GAT CAA GGA TTA GGG GAT AAA ATA GCG TTA AAT TAC AAA GAT      240
            His Val Asp Gln Gly Leu Gly Asp Lys Ile Ala Leu Asn Tyr Lys Asp
             65                  70                  75                  80

GAG CAC AGA AAA GAA TCG TAT ACT TAT AAA GAT ATG CAA CGG TTA TCT      288
            Glu His Arg Lys Glu Ser Tyr Thr Tyr Lys Asp Met Gln Arg Leu Ser
                            85                  90                  95

AAT AAA GCA GCG AAT GTT TTG TCT GAA CAT GCA GAA GTT GAC AAA GGT      336
            Asn Lys Ala Ala Asn Val Leu Ser Glu His Ala Glu Val Asp Lys Gly
                        100                 105                 110

GAC AGA GTA TTT ATA TTT ATG TCG CGT ACA CCT GAA CTA TAT TTT GCG      384
            Asp Arg Val Phe Ile Phe Met Ser Arg Thr Pro Glu Leu Tyr Phe Ala
                    115                 120                 125

TTG TTA GGT GTT TTA AAA ATT GGT GCA ATT GTT GGG CCG TTA TTT GAA      432
            Leu Leu Gly Val Leu Lys Ile Gly Ala Ile Val Gly Pro Leu Phe Glu
            130                 135                 140

GCA TTT ATG GAA AAG GCA GTT GCG GAT AGA TTA GAG AAC AGT GAA GCT      480
            Ala Phe Met Glu Lys Ala Val Ala Asp Arg Leu Glu Asn Ser Glu Ala
            145                 150                 155                 160

AAA GTG TTA ATT ACT AAT AAG GCA TTG TTA CCT CGA GTA CCT GTA GAT      528
            Lys Val Leu Ile Thr Asn Lys Ala Leu Leu Pro Arg Val Pro Val Asp
                            165                 170                 175

AAA TTA CCA AAC TTG AAA AAA ATT GTT GTC GTA GAT GAG GAT GTA GAA      576
            Lys Leu Pro Asn Leu Lys Lys Ile Val Val Val Asp Glu Asp Val Glu
                        180                 185                 190

GAC AAT TAC ATA GAC TTC ATT AGT TTG ATG GAA ACT GCT AGC GAT GAA      624
            Asp Asn Tyr Ile Asp Phe Ile Ser Leu Met Glu Thr Ala Ser Asp Glu
                    195                 200                 205

TTT GAC ATT GAA TGG TTA AAG TCG GAT GAT GGT TTG ATT TTA CAT TAT      672
            Phe Asp Ile Glu Trp Leu Lys Ser Asp Asp Gly Leu Ile Leu His Tyr
            210                 215                 220

ACA TCA GGT TCT ACT GGG CAA CCT AAA GGT GTA TTG CAT GTT CAA CAA      720
            Thr Ser Gly Ser Thr Gly Gln Pro Lys Gly Val Leu His Val Gln Gln
            225                 230                 235                 240

GCA ATG TTA GTG CAC TAT ATT TCT GGr AAA TAT GTA TTA GAT TTA CAA      768
            Ala Met Leu Val His Tyr Ile Ser Gly Lys Tyr Val Leu Asp Leu Gln
                            245                 250                 255

GAA GAT GAT GTT TAT TGG TGT ACA GCA GAT CCA GGT TGG GTT ACA GGA      816
            Glu Asp Asp Val Tyr Trp Cys Thr Ala Asp Pro Gly Trp Val Thr Gly
                        260                 265                 270

ACA TCT TAT GGT ATT TTT GCA CCA TGG TTA AAT GGC GCT ACA AAT TGT      864
            Thr Ser Tyr Gly Ile Phe Ala Pro Trp Leu Asn Gly Ala Thr Asn Cys
                    275                 280                 285

ATA GCT GGT GGT CGC TTT TCG CCA GAA CAG TGG TAT AGT ATG ATT GAA      912
            Ile Ala Gly Gly Arg Phe Ser Pro Glu Gln Trp Tyr Ser Met Ile Glu
            290                 295                 300

GAT TTT AAA GTG ACG ATT TGG TAT ACG GCA CCA ACA GCT TTA AGA ATG      960
            Asp Phe Lys Val Thr Ile Trp Tyr Thr Ala Pro Thr Ala Leu Arg Met
            305                 310                 315                 320
```

```
TTA ATG AGT GCT GGT GAC GAT ATT GTT GAG AAA TAT GAC TTG TCA TCG      1008
Leu Met Ser Ala Gly Asp Asp Ile Val Glu Lys Tyr Asp Leu Ser Ser
            325                 330                 335

TTA CGT TCG ATT CTA TCA GTA GGT GAG CCT TTA AAT CCT GAA GTT ATA      1056
Leu Arg Ser Ile Leu Ser Val Gly Glu Pro Leu Asn Pro Glu Val Ile
            340                 345                 350

AAA TGG GCG AAA AAA GTA TAC GGT TTA ACG GTG TTA GAT ACT TGG TGG      1104
Lys Trp Ala Lys Lys Val Tyr Gly Leu Thr Val Leu Asp Thr Trp Trp
            355                 360                 365

ATG ACA GAA ACA GGT GGA CAT ATG ATT GTT AAC TAT CCA ACG ATG GAC      1152
Met Thr Glu Thr Gly Gly His Met Ile Val Asn Tyr Pro Thr Met Asp
    370                 375                 380

GTn CAA GCT TGG CTC mAT GGG CAA ACC ATT ACC TGG TAT TCA AGC TGC      1200
Val Gln Ala Trp Leu Xaa Gly Gln Thr Ile Thr Trp Tyr Ser Ser Cys
385             390                 395                 400

AAT TAT CGA TGA                                                       1212
Asn Tyr Arg
```

(2) INFORMATION FOR SEQ ID NO:83:

(i) SEQUENCE CHARACTERISTICS:
        (A) LENGTH: 403 amino acids
        (B) TYPE: amino acid
        (D) TOPOLOGY: linear (ii) MOLECULE TYPE: protein (xi) SEQUENCE DESCRIPTION: SEQ ID NO:83:

```
Glu Arg Lys Arg Phe His Ile Thr Lys Gly Glu Phe Gln Met Lys Val
 1               5                  10                  15

Glu Val Tyr Lys Gly Ala Gln Gly Lys His Asn Leu Lys Asp Tyr Glu
            20                  25                  30

Glu Thr Tyr Asn Thr Phe Asp Trp Lys Asp Val Glu Gln Ala Phe Ser
        35                  40                  45

Trp Ser Glu Thr Gly Lys Met Asn Met Ala Tyr Glu Cys Ile Asp Arg
    50                  55                  60

His Val Asp Gln Gly Leu Gly Asp Lys Ile Ala Leu Asn Tyr Lys Asp
65                  70                  75                  80

Glu His Arg Lys Glu Ser Tyr Thr Tyr Lys Asp Met Gln Arg Leu Ser
                85                  90                  95

Asn Lys Ala Ala Asn Val Leu Ser Glu His Ala Glu Val Asp Lys Gly
            100                 105                 110

Asp Arg Val Phe Ile Phe Met Ser Arg Thr Pro Glu Leu Tyr Phe Ala
        115                 120                 125

Leu Leu Gly Val Leu Lys Ile Gly Ala Ile Val Gly Pro Leu Phe Glu
    130                 135                 140

Ala Phe Met Glu Lys Ala Val Ala Asp Arg Leu Glu Asn Ser Glu Ala
145                 150                 155                 160

Lys Val Leu Ile Thr Asn Lys Ala Leu Leu Pro Arg Val Pro Val Asp
                165                 170                 175

Lys Leu Pro Asn Leu Lys Lys Ile Val Val Asp Glu Asp Val Glu
            180                 185                 190

Asp Asn Tyr Ile Asp Phe Ile Ser Leu Met Glu Thr Ala Ser Asp Glu
        195                 200                 205

Phe Asp Ile Glu Trp Leu Lys Ser Asp Gly Leu Ile Leu His Tyr
    210                 215                 220

Thr Ser Gly Ser Thr Gly Gln Pro Lys Gly Val Leu His Val Gln Gln
225                 230                 235                 240
```

```
Ala Met Leu Val His Tyr Ile Ser Gly Lys Tyr Val Leu Asp Leu Gln
            245                 250                 255

Glu Asp Asp Val Tyr Trp Cys Thr Ala Asp Pro Gly Trp Val Thr Gly
        260                 265                 270

Thr Ser Tyr Gly Ile Phe Ala Pro Trp Leu Asn Gly Ala Thr Asn Cys
        275                 280                 285

Ile Ala Gly Gly Arg Phe Ser Pro Glu Gln Trp Tyr Ser Met Ile Glu
    290                 295                 300

Asp Phe Lys Val Thr Ile Trp Tyr Thr Ala Pro Thr Ala Leu Arg Met
305                 310                 315                 320

Leu Met Ser Ala Gly Asp Asp Ile Val Glu Lys Tyr Asp Leu Ser Ser
                325                 330                 335

Leu Arg Ser Ile Leu Ser Val Gly Glu Pro Leu Asn Pro Glu Val Ile
                340                 345                 350

Lys Trp Ala Lys Lys Val Tyr Gly Leu Thr Val Leu Asp Thr Trp Trp
                355                 360                 365

Met Thr Glu Thr Gly Gly His Met Ile Val Asn Tyr Pro Thr Met Asp
            370                 375                 380

Val Gln Ala Trp Leu Xaa Gly Gln Thr Ile Thr Trp Tyr Ser Ser Cys
385                 390                 395                 400

Asn Tyr Arg
```

(2) INFORMATION FOR SEQ ID NO:84:

(i) SEQUENCE CHARACTERISTICS:
        (A) LENGTH: 3147 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p14b25)"

(ix) FEATURE:
        (A) NAME/KEY: CDS
        (B) LOCATION: 1..3144

(xi) SEQUENCE DESCRIPTION: SEQ ID NO:84:

```
ATG AAA ATT CTC AGC CTG CGC CTG AAA AAC CTG AAC TCA TTA AAA GGC      48
Met Lys Ile Leu Ser Leu Arg Leu Lys Asn Leu Asn Ser Leu Lys Gly
 1               5                  10                  15

GAA TGG AAG ATT GAT TTC ACC CGC GAG CCG TTC GCC AGC AAC GGG CTG      96
Glu Trp Lys Ile Asp Phe Thr Arg Glu Pro Phe Ala Ser Asn Gly Leu
                20                  25                  30

TTT GCT ATT ACC GGC CCA ACA GGT GCG GGG AAA ACC ACC CTG CTG GAC     144
Phe Ala Ile Thr Gly Pro Thr Gly Ala Gly Lys Thr Thr Leu Leu Asp
            35                  40                  45

GCC ATT TGT CTG GCG CTG TAT CAC GAA ACT CCG CGT CTC TCT AAC GTT     192
Ala Ile Cys Leu Ala Leu Tyr His Glu Thr Pro Arg Leu Ser Asn Val
 50                  55                  60

TCA CAA TCG CAA AAT GAT CTC ATG ACC CGC GAT ACC GCC GAA TGT CTG     240
Ser Gln Ser Gln Asn Asp Leu Met Thr Arg Asp Thr Ala Glu Cys Leu
65                  70                  75                  80

GCG GAG GTG GAG TTT GAA GTG AAA GGT GAA GCG TAC CGT GCA TTC TGG     288
Ala Glu Val Glu Phe Glu Val Lys Gly Glu Ala Tyr Arg Ala Phe Trp
                85                  90                  95

AGC CAG AAT CGG GCG CGT AAC CAA CCC GAC GGT AAT TTG CAG GTG CCA     336
Ser Gln Asn Arg Ala Arg Asn Gln Pro Asp Gly Asn Leu Gln Val Pro
                100                 105                 110
```

```
CGC GTA GAG CTG GCG CGC TGC GCC GAC GGC AAA ATT CTC GCC GAC AAA      384
Arg Val Glu Leu Ala Arg Cys Ala Asp Gly Lys Ile Leu Ala Asp Lys
        115                 120                 125

GTG AAA GAT AAG CTG GAA CTG ACA GCG ACG TTA ACC GGG CTG GAT TAC      432
Val Lys Asp Lys Leu Glu Leu Thr Ala Thr Leu Thr Gly Leu Asp Tyr
130                 135                 140

GGG CGC TTC ACC CGT TCG ATG CTG CTT TCG CAG GGG CAA TTT GCT GCC      480
Gly Arg Phe Thr Arg Ser Met Leu Leu Ser Gln Gly Gln Phe Ala Ala
145                 150                 155                 160

TTC CTG AAT GCC AAA CCC AAA GAA CGC GCG GAA TTG CTC GAG GAG TTA      528
Phe Leu Asn Ala Lys Pro Lys Glu Arg Ala Glu Leu Leu Glu Glu Leu
                165                 170                 175

ACC GGC ACT GAA ATC TAC GGG CAA ATC TCG GCG ATG GTT TTT GAG CAG      576
Thr Gly Thr Glu Ile Tyr Gly Gln Ile Ser Ala Met Val Phe Glu Gln
            180                 185                 190

CAC AAA TCG GCC CGC ACA GAG CTG GAG AAG CTG CAA GCG CAG GCC AGC      624
His Lys Ser Ala Arg Thr Glu Leu Glu Lys Leu Gln Ala Gln Ala Ser
        195                 200                 205

GGC GTC ACG TTG CTC ACG CCG GAA CAA GTG CAA TCG CTG ACA GCG AGT      672
Gly Val Thr Leu Leu Thr Pro Glu Gln Val Gln Ser Leu Thr Ala Ser
210                 215                 220

TTG CAG GTA CTT ACT GAC GAA GAA AAA CAG TTA ATT ACC GCG CAG CAG      720
Leu Gln Val Leu Thr Asp Glu Glu Lys Gln Leu Ile Thr Ala Gln Gln
225                 230                 235                 240

CAA GAA CAA CAA TCG CTA AAC TGG TTA ACG CGT CAG GAC GAA TTG CAG      768
Gln Glu Gln Gln Ser Leu Asn Trp Leu Thr Arg Gln Asp Glu Leu Gln
                245                 250                 255

CAA GAA GCC AGC CGC CGT CAG CAG GCC TTG CAA CAG GCG TTA GCC GAA      816
Gln Glu Ala Ser Arg Arg Gln Gln Ala Leu Gln Gln Ala Leu Ala Glu
            260                 265                 270

GAA GAA AAA GCG CAA CCT CAA CTG GCG GCG CTT AGT CTG GCA CAA CCG      864
Glu Glu Lys Ala Gln Pro Gln Leu Ala Ala Leu Ser Leu Ala Gln Pro
        275                 280                 285

GCA CGA AAT CTT CGT CCA CAC TGG GAA CGC ATC GCA GAA CAC AGC GCG      912
Ala Arg Asn Leu Arg Pro His Trp Glu Arg Ile Ala Glu His Ser Ala
290                 295                 300

GCG CTG GCG CAT ATT CGC CAG CAG ATT GAA GAA GTA AAT ACT CGC TTA      960
Ala Leu Ala His Ile Arg Gln Gln Ile Glu Glu Val Asn Thr Arg Leu
305                 310                 315                 320

CAG AGC ACA ATG GCG CTT CGC GCG AGC ATT CGC CAC CAC GCG GCG AAG     1008
Gln Ser Thr Met Ala Leu Arg Ala Ser Ile Arg His His Ala Ala Lys
                325                 330                 335

CAG TCA GCA GAA TTA CAG CAG CAG CAA CAA AGC CTG AAT ACC TGG TTA     1056
Gln Ser Ala Glu Leu Gln Gln Gln Gln Gln Ser Leu Asn Thr Trp Leu
            340                 345                 350

CAG GAA CAC GAC CGC TTC CGT CAG TGG AAC AAC GAA CCG GCG GGT TGG     1104
Gln Glu His Asp Arg Phe Arg Gln Trp Asn Asn Glu Pro Ala Gly Trp
        355                 360                 365

CGT GCG CAG TTC TCC CAA CAA ACC AGC GAT CGC GAG CAT CTG CGG CAA     1152
Arg Ala Gln Phe Ser Gln Gln Thr Ser Asp Arg Glu His Leu Arg Gln
370                 375                 380

TGG CAG CAA CAG TTA ACC CAT GCT GAG CAA AAA CTT AAT GCG CTT GCG     1200
Trp Gln Gln Gln Leu Thr His Ala Glu Gln Lys Leu Asn Ala Leu Ala
385                 390                 395                 400

GCG ATC ACG TTG ACG TTA ACC GCC GAT GAA GTT GCT ACC GCC CTG GCG     1248
Ala Ile Thr Leu Thr Leu Thr Ala Asp Glu Val Ala Thr Ala Leu Ala
                405                 410                 415

CAA CAT GCT GAG CAA CGC CCA CTG CGT CAG CAC CTG GTC GCG CTG CAT     1296
Gln His Ala Glu Gln Arg Pro Leu Arg Gln His Leu Val Ala Leu His
            420                 425                 430
```

```
GGA CAG ATT GTT CCC CAA CAA AAA CGT CTG GCG CAG TTA CAG GTC GCT      1344
Gly Gln Ile Val Pro Gln Gln Lys Arg Leu Ala Gln Leu Gln Val Ala
        435                 440                 445

ATC CAG AAT GTC ACG CAA GAA CAG ACG CAA CGT AAC GCC GCA CTT AAC      1392
Ile Gln Asn Val Thr Gln Glu Gln Thr Gln Arg Asn Ala Ala Leu Asn
        450                 455                 460

GAA ATG CGC CAG CGT TAT AAA GAA AAG ACG CAG CAA CTT GCC GAT GTG      1440
Glu Met Arg Gln Arg Tyr Lys Glu Lys Thr Gln Gln Leu Ala Asp Val
465                 470                 475                 480

AAA ACC ATT TGC GAG CAG GAA GCG CGC ATC AAA ACG CTG GAA GCT CAA      1488
Lys Thr Ile Cys Glu Gln Glu Ala Arg Ile Lys Thr Leu Glu Ala Gln
                485                 490                 495

CGT GCA CAG TTA CAG GCG GGT CAG CCT TGC CCA CTT TGT GGT TCC ACC      1536
Arg Ala Gln Leu Gln Ala Gly Gln Pro Cys Pro Leu Cys Gly Ser Thr
        500                 505                 510

AGC CAC CCG GCG GTC GAG GCG TAT CAG GCG CTG GAG CCT GGC GTT AAT      1584
Ser His Pro Ala Val Glu Ala Tyr Gln Ala Leu Glu Pro Gly Val Asn
        515                 520                 525

CAG TCT CGA TTA CTG GCG CTG GAA AAC GAA GTT AAA AAG CTC GGT GAA      1632
Gln Ser Arg Leu Leu Ala Leu Glu Asn Glu Val Lys Lys Leu Gly Glu
        530                 535                 540

GAA GGT GCG ACG CTA CGT GGG CAA CTG GAC GCC ATA ACA AAG CAG CTT      1680
Glu Gly Ala Thr Leu Arg Gly Gln Leu Asp Ala Ile Thr Lys Gln Leu
545                 550                 555                 560

CAG CGT GAT GAA AAC GAA GCG CAA AGC CTC CGA CAA GAT GAG CAA GCA      1728
Gln Arg Asp Glu Asn Glu Ala Gln Ser Leu Arg Gln Asp Glu Gln Ala
                565                 570                 575

CTT ACT CAA CAA TGG CAA GCC GTC ACG GCC AGC CTC AAT ATC ACC TTG      1776
Leu Thr Gln Gln Trp Gln Ala Val Thr Ala Ser Leu Asn Ile Thr Leu
        580                 585                 590

CAG CCA CTG GAC GAT ATT CAA CCG TGG CTG GAT GCA CAA GAT GAG CAC      1824
Gln Pro Leu Asp Asp Ile Gln Pro Trp Leu Asp Ala Gln Asp Glu His
        595                 600                 605

GAA CGC CAG CTG CGG TTA CTC AGC CAA CGG CAT GAA TTA CAA GGG CAG      1872
Glu Arg Gln Leu Arg Leu Leu Ser Gln Arg His Glu Leu Gln Gly Gln
        610                 615                 620

ATT GCC GCG CAT AAT CAG CAA ATT ATC CAG TAT CAA CAG CAA ATT GAA      1920
Ile Ala Ala His Asn Gln Gln Ile Ile Gln Tyr Gln Gln Gln Ile Glu
625                 630                 635                 640

CAA CGC CAG CAA CTA CTT TTA ACG ACA TTG ACG GGT TAT GCA CTG ACA      1968
Gln Arg Gln Gln Leu Leu Leu Thr Thr Leu Thr Gly Tyr Ala Leu Thr
                645                 650                 655

TTG CCA CAG GAA GAT GAA GAA GAG AGC TGG TTG GCG ACA CGT CAG CAA      2016
Leu Pro Gln Glu Asp Glu Glu Glu Ser Trp Leu Ala Thr Arg Gln Gln
        660                 665                 670

GAA GCG CAG AGC TGG CAG CAA CGC CAG AAC GAA TTA ACC GCG CTG CAA      2064
Glu Ala Gln Ser Trp Gln Gln Arg Gln Asn Glu Leu Thr Ala Leu Gln
        675                 680                 685

AAC CGT ATT CAG CAG CTG ACG CCG ATT CTG GAA ACG TTG CCG CAA AGT      2112
Asn Arg Ile Gln Gln Leu Thr Pro Ile Leu Glu Thr Leu Pro Gln Ser
        690                 695                 700

GAT GAA CTC CCG CAC TGC GAA GAA ACT GTG GTA TTG GAA AAC TGG CGG      2160
Asp Glu Leu Pro His Cys Glu Glu Thr Val Val Leu Glu Asn Trp Arg
705                 710                 715                 720

CAG GTA CAT GAA CAA TGT CTC GCA TTA CAC AGC CAG CAG CAG ACG TTA      2208
Gln Val His Glu Gln Cys Leu Ala Leu His Ser Gln Gln Gln Thr Leu
                725                 730                 735

CAG CAA CAG GAT GTT CTG GCG GCG CAA AGT CTG CAA AAA GCC CAG GCG      2256
Gln Gln Gln Asp Val Leu Ala Ala Gln Ser Leu Gln Lys Ala Gln Ala
```

```
                    740                     745                     750
CAG TTT GAC ACC GCG CTA CAG GCC AGC GTC TTT GAC GAT CAG CAG GCG              2304
Gln Phe Asp Thr Ala Leu Gln Ala Ser Val Phe Asp Asp Gln Gln Ala
        755                     760                     765

TTC CTT GCG GCG CTA ATG GAT GAA CAA ACA CTA ACG CAG CTG GAA CAG              2352
Phe Leu Ala Ala Leu Met Asp Glu Gln Thr Leu Thr Gln Leu Glu Gln
        770                     775                     780

CTC AAG CAG AAT CTG GAA AAC CAG CGC CGT CAG GCG CAA ACT CTG GTC              2400
Leu Lys Gln Asn Leu Glu Asn Gln Arg Arg Gln Ala Gln Thr Leu Val
785                     790                     795                     800

ACT CAG ACA GCA GAA ACG CTG GCA CAG CAT CAA CAA CAC CGA CCT GAC              2448
Thr Gln Thr Ala Glu Thr Leu Ala Gln His Gln Gln His Arg Pro Asp
                805                     810                     815

GAC GGG TTG GCT CTC ACT GTG ACG GTG GAG CAG ATT CAG CAA GAG TTA              2496
Asp Gly Leu Ala Leu Thr Val Thr Val Glu Gln Ile Gln Gln Glu Leu
                820                     825                     830

GCG CAA ACT CAC CAA AAG TTG CGT GAA AAC ACC ACG AGT CAA GGC GAG              2544
Ala Gln Thr His Gln Lys Leu Arg Glu Asn Thr Thr Ser Gln Gly Glu
                835                     840                     845

ATT CGC CAG CAG CTG AAG CAG GAT GCA GAT AAC CGT CAG CAA CAA CAA              2592
Ile Arg Gln Gln Leu Lys Gln Asp Ala Asp Asn Arg Gln Gln Gln Gln
        850                     855                     860

ACC TTA ATG CAG CAA ATT GCT CAA ATG ACG CAG CAG GTT GAG GAC TGG              2640
Thr Leu Met Gln Gln Ile Ala Gln Met Thr Gln Gln Val Glu Asp Trp
865                     870                     875                     880

GGA TAT CTG AAT TCG CTA ATA GGT TCC AAA GAG GGC GAT AAA TTC CGC              2688
Gly Tyr Leu Asn Ser Leu Ile Gly Ser Lys Glu Gly Asp Lys Phe Arg
                885                     890                     895

AAG TTT GCC CAG GGG CTG ACG CTG GAT AAT TTA GTC CAT CTC GCT AAT              2736
Lys Phe Ala Gln Gly Leu Thr Leu Asp Asn Leu Val His Leu Ala Asn
                900                     905                     910

CAG CAA CTT ACC CGG CTG CAC GGG CGC TAT CTG TTA CAG CGC AAA GCC              2784
Gln Gln Leu Thr Arg Leu His Gly Arg Tyr Leu Leu Gln Arg Lys Ala
                915                     920                     925

AGC GAG GCG CTG GAA GTC GAG GTT GTT GAT ACC TGG CAG GCA GAT GCG              2832
Ser Glu Ala Leu Glu Val Glu Val Val Asp Thr Trp Gln Ala Asp Ala
        930                     935                     940

GTA CGC GAT ACC CGT ACC CTT TCC GGC GGC GAA AGT TTC CTC GTT AGT              2880
Val Arg Asp Thr Arg Thr Leu Ser Gly Gly Glu Ser Phe Leu Val Ser
945                     950                     955                     960

CTG GCG CTG GCG CTG GCG CTT TCG GAT CTG GTC AGC CAT AAA ACA CGT              2928
Leu Ala Leu Ala Leu Ala Leu Ser Asp Leu Val Ser His Lys Thr Arg
                965                     970                     975

ATT GAC TCG CTG TTC CTT GAT GAA GGT TTT GGC ACG CTG GAT AGC GAA              2976
Ile Asp Ser Leu Phe Leu Asp Glu Gly Phe Gly Thr Leu Asp Ser Glu
                980                     985                     990

ACG CTG GAT ACC GCC CTT GAT GCG CTG GAT GCC CTG AAC GCC AGT GGC              3024
Thr Leu Asp Thr Ala Leu Asp Ala Leu Asp Ala Leu Asn Ala Ser Gly
                995                     1000                    1005

AAA ACC ATC GGT GTG ATT AGC CAC GTA GAA GCG ATG AAA GAG CGT ATT              3072
Lys Thr Ile Gly Val Ile Ser His Val Glu Ala Met Lys Glu Arg Ile
        1010                    1015                    1020

CCG GTG CAG ATC AAA GTG AAA AAG ATC AAC GGC CTG GGC TAC AGC AAA              3120
Pro Val Gln Ile Lys Val Lys Lys Ile Asn Gly Leu Gly Tyr Ser Lys
1025                    1030                    1035                    1040

CTG GAA AGT ACG TTT GCA GTG AAA TAA                                          3147
Leu Glu Ser Thr Phe Ala Val Lys
                1045
```

(2) INFORMATION FOR SEQ ID NO:85:

(i) SEQUENCE CHARACTERISTICS:
        (A) LENGTH: 1048 amino acids
        (B) TYPE: amino acid
        (D) TOPOLOGY: linear (ii) MOLECULE TYPE: protein (xi) SEQUENCE DESCRIPTION: SEQ ID NO:85:

```
Met Lys Ile Leu Ser Leu Arg Leu Lys Asn Leu Asn Ser Leu Lys Gly
 1               5                   10                  15

Glu Trp Lys Ile Asp Phe Thr Arg Glu Pro Phe Ala Ser Asn Gly Leu
            20                  25                  30

Phe Ala Ile Thr Gly Pro Thr Gly Ala Gly Lys Thr Thr Leu Leu Asp
        35                  40                  45

Ala Ile Cys Leu Ala Leu Tyr His Glu Thr Pro Arg Leu Ser Asn Val
    50                  55                  60

Ser Gln Ser Gln Asn Asp Leu Met Thr Arg Asp Thr Ala Glu Cys Leu
65                  70                  75                  80

Ala Glu Val Glu Phe Glu Val Lys Gly Glu Ala Tyr Arg Ala Phe Trp
                85                  90                  95

Ser Gln Asn Arg Ala Arg Asn Gln Pro Asp Gly Asn Leu Gln Val Pro
            100                 105                 110

Arg Val Glu Leu Ala Arg Cys Ala Asp Gly Lys Ile Leu Ala Asp Lys
        115                 120                 125

Val Lys Asp Lys Leu Glu Leu Thr Ala Thr Leu Thr Gly Leu Asp Tyr
    130                 135                 140

Gly Arg Phe Thr Arg Ser Met Leu Leu Ser Gln Gly Gln Phe Ala Ala
145                 150                 155                 160

Phe Leu Asn Ala Lys Pro Lys Glu Arg Ala Glu Leu Leu Glu Glu Leu
                165                 170                 175

Thr Gly Thr Glu Ile Tyr Gly Gln Ile Ser Ala Met Val Phe Glu Gln
            180                 185                 190

His Lys Ser Ala Arg Thr Glu Leu Glu Lys Leu Gln Ala Gln Ala Ser
        195                 200                 205

Gly Val Thr Leu Leu Thr Pro Glu Gln Val Gln Ser Leu Thr Ala Ser
    210                 215                 220

Leu Gln Val Leu Thr Asp Glu Glu Lys Gln Leu Ile Thr Ala Gln Gln
225                 230                 235                 240

Gln Glu Gln Gln Ser Leu Asn Trp Leu Thr Arg Gln Asp Glu Leu Gln
                245                 250                 255

Gln Glu Ala Ser Arg Arg Gln Gln Ala Leu Gln Gln Ala Leu Ala Glu
            260                 265                 270

Glu Glu Lys Ala Gln Pro Gln Leu Ala Ala Leu Ser Leu Ala Gln Pro
        275                 280                 285

Ala Arg Asn Leu Arg Pro His Trp Glu Arg Ile Ala Glu His Ser Ala
    290                 295                 300

Ala Leu Ala His Ile Arg Gln Gln Ile Glu Glu Val Asn Thr Arg Leu
305                 310                 315                 320

Gln Ser Thr Met Ala Leu Arg Ala Ser Ile Arg His His Ala Ala Lys
                325                 330                 335

Gln Ser Ala Glu Leu Gln Gln Gln Gln Ser Leu Asn Thr Trp Leu
            340                 345                 350

Gln Glu His Asp Arg Phe Arg Gln Trp Asn Asn Glu Pro Ala Gly Trp
        355                 360                 365
```

```
Arg Ala Gln Phe Ser Gln Gln Thr Ser Asp Arg Glu His Leu Arg Gln
    370                 375                 380

Trp Gln Gln Gln Leu Thr His Ala Glu Gln Lys Leu Asn Ala Leu Ala
385                 390                 395                 400

Ala Ile Thr Leu Thr Leu Thr Ala Asp Glu Val Ala Thr Ala Leu Ala
                405                 410                 415

Gln His Ala Glu Gln Arg Pro Leu Arg Gln His Leu Val Ala Leu His
                420                 425                 430

Gly Gln Ile Val Pro Gln Lys Arg Leu Ala Gln Leu Gln Val Ala
            435                 440                 445

Ile Gln Asn Val Thr Gln Glu Gln Thr Gln Arg Asn Ala Ala Leu Asn
450                 455                 460

Glu Met Arg Gln Arg Tyr Lys Glu Lys Thr Gln Gln Leu Ala Asp Val
465                 470                 475                 480

Lys Thr Ile Cys Glu Gln Glu Ala Arg Ile Lys Thr Leu Glu Ala Gln
                485                 490                 495

Arg Ala Gln Leu Gln Ala Gly Gln Pro Cys Pro Leu Cys Gly Ser Thr
                500                 505                 510

Ser His Pro Ala Val Glu Ala Tyr Gln Ala Leu Glu Pro Gly Val Asn
            515                 520                 525

Gln Ser Arg Leu Leu Ala Leu Glu Asn Glu Val Lys Lys Leu Gly Glu
    530                 535                 540

Glu Gly Ala Thr Leu Arg Gly Gln Leu Asp Ala Ile Thr Lys Gln Leu
545                 550                 555                 560

Gln Arg Asp Glu Asn Glu Ala Gln Ser Leu Arg Gln Asp Glu Gln Ala
                565                 570                 575

Leu Thr Gln Gln Trp Gln Ala Val Thr Ala Ser Leu Asn Ile Thr Leu
                580                 585                 590

Gln Pro Leu Asp Asp Ile Gln Pro Trp Leu Asp Ala Gln Asp Glu His
            595                 600                 605

Glu Arg Gln Leu Arg Leu Leu Ser Gln Arg His Glu Leu Gln Gly Gln
    610                 615                 620

Ile Ala Ala His Asn Gln Gln Ile Ile Gln Tyr Gln Gln Gln Ile Glu
625                 630                 635                 640

Gln Arg Gln Gln Leu Leu Leu Thr Thr Leu Thr Gly Tyr Ala Leu Thr
                645                 650                 655

Leu Pro Gln Glu Asp Glu Glu Ser Trp Leu Ala Thr Arg Gln Gln
                660                 665                 670

Glu Ala Gln Ser Trp Gln Gln Arg Gln Asn Glu Leu Thr Ala Leu Gln
            675                 680                 685

Asn Arg Ile Gln Gln Leu Thr Pro Ile Leu Glu Thr Leu Pro Gln Ser
    690                 695                 700

Asp Glu Leu Pro His Cys Glu Glu Thr Val Val Leu Glu Asn Trp Arg
705                 710                 715                 720

Gln Val His Glu Gln Cys Leu Ala Leu His Ser Gln Gln Thr Leu
                725                 730                 735

Gln Gln Gln Asp Val Leu Ala Ala Gln Ser Leu Gln Lys Ala Gln Ala
                740                 745                 750

Gln Phe Asp Thr Ala Leu Gln Ala Ser Val Phe Asp Asp Gln Gln Ala
            755                 760                 765

Phe Leu Ala Ala Leu Met Asp Glu Gln Thr Leu Thr Gln Leu Glu Gln
770                 775                 780
```

```
Leu Lys Gln Asn Leu Glu Asn Gln Arg Arg Gln Ala Gln Thr Leu Val
785                 790                 795                 800

Thr Gln Thr Ala Glu Thr Leu Ala Gln His Gln Gln His Arg Pro Asp
            805                 810                 815

Asp Gly Leu Ala Leu Thr Val Thr Val Glu Gln Ile Gln Gln Glu Leu
            820                 825                 830

Ala Gln Thr His Gln Lys Leu Arg Glu Asn Thr Thr Ser Gln Gly Glu
            835                 840                 845

Ile Arg Gln Gln Leu Lys Gln Asp Ala Asp Asn Arg Gln Gln Gln Gln
850                 855                 860

Thr Leu Met Gln Gln Ile Ala Gln Met Thr Gln Gln Val Glu Asp Trp
865                 870                 875                 880

Gly Tyr Leu Asn Ser Leu Ile Gly Ser Lys Glu Gly Asp Lys Phe Arg
            885                 890                 895

Lys Phe Ala Gln Gly Leu Thr Leu Asp Asn Leu Val His Leu Ala Asn
            900                 905                 910

Gln Gln Leu Thr Arg Leu His Gly Arg Tyr Leu Leu Gln Arg Lys Ala
            915                 920                 925

Ser Glu Ala Leu Glu Val Glu Val Val Asp Thr Trp Gln Ala Asp Ala
930                 935                 940

Val Arg Asp Thr Arg Thr Leu Ser Gly Gly Glu Ser Phe Leu Val Ser
945                 950                 955                 960

Leu Ala Leu Ala Leu Ala Leu Ser Asp Leu Val Ser His Lys Thr Arg
            965                 970                 975

Ile Asp Ser Leu Phe Leu Asp Glu Gly Phe Gly Thr Leu Asp Ser Glu
            980                 985                 990

Thr Leu Asp Thr Ala Leu Asp Ala Leu Asp Ala Leu Asn Ala Ser Gly
            995                 1000                1005

Lys Thr Ile Gly Val Ile Ser His Val Glu Ala Met Lys Glu Arg Ile
            1010                1015                1020

Pro Val Gln Ile Lys Val Lys Lys Ile Asn Gly Leu Gly Tyr Ser Lys
1025                1030                1035                1040

Leu Glu Ser Thr Phe Ala Val Lys
            1045

(2) INFORMATION FOR SEQ ID NO:86:

(i) SEQUENCE CHARACTERISTICS:
        (A) LENGTH: 1239 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p14b74)"

(ix) FEATURE:
        (A) NAME/KEY: CDS
        (B) LOCATION: 1..1236

(xi) SEQUENCE DESCRIPTION: SEQ ID NO:86:

ATG ATG AAA GAA AAA GTG ATT TTT CTC GTT GAC ATG CAA TCG TTT TAT      48
Met Met Lys Glu Lys Val Ile Phe Leu Val Asp Met Gln Ser Phe Tyr
1               5                   10                  15

GCA TCT GTA GAG AAA GCG GAA AAT CCA CAT TTG AAA AAT AGG CCC GTC      96
Ala Ser Val Glu Lys Ala Glu Asn Pro His Leu Lys Asn Arg Pro Val
                20                  25                  30

ATT GTT TCG GGT GAC CCT GAA AAA AGG GGC GGA GTC GTA TTG GCT GCC     144
Ile Val Ser Gly Asp Pro Glu Lys Arg Gly Gly Val Val Leu Ala Ala
```

```
              35                  40                  45
TGC CCG CTG GCG AAA CAA AAG GGT GTG GTG AAT GCT TCA CGG CTG TGG     192
Cys Pro Leu Ala Lys Gln Lys Gly Val Val Asn Ala Ser Arg Leu Trp
        50                  55                  60

GAG GCG CAG GAA AAG TGT CCT GAG GCT GTT GTG CTC CGG CCG CGT ATG     240
Glu Ala Gln Glu Lys Cys Pro Glu Ala Val Val Leu Arg Pro Arg Met
65                  70                  75                  80

CAG CGG TAT ATT GAT GTA TCA CTG CAA ATT ACG GCC ATT CTC GAG GAG     288
Gln Arg Tyr Ile Asp Val Ser Leu Gln Ile Thr Ala Ile Leu Glu Glu
                85                  90                  95

TAT ACA GAC CTT GTG GAG CCG TAT TCC ATC GAT GAA CAG TTC ATG GAC     336
Tyr Thr Asp Leu Val Glu Pro Tyr Ser Ile Asp Glu Gln Phe Met Asp
            100                 105                 110

ATT ACA GGC AGC CAG AAG CTG TTT GGG ACG CCG ATG GAG ATC GCG AAA     384
Ile Thr Gly Ser Gln Lys Leu Phe Gly Thr Pro Met Glu Ile Ala Lys
        115                 120                 125

AGC ATT CAG GGC AGA ATC ATG CGG GAG ATC GGC GTT TAT GCA CGG GTC     432
Ser Ile Gln Gly Arg Ile Met Arg Glu Ile Gly Val Tyr Ala Arg Val
    130                 135                 140

GGA ATC GGC CCT AAC AAA GCG CTG GCC AAA ATT GCG TGT GAC AAT TTT     480
Gly Ile Gly Pro Asn Lys Ala Leu Ala Lys Ile Ala Cys Asp Asn Phe
145                 150                 155                 160

GCC AAA AAG AAT AAG AAC GGT ATT TTT ACC TTA ACG AAA GAA AAT ATG     528
Ala Lys Lys Asn Lys Asn Gly Ile Phe Thr Leu Thr Lys Glu Asn Met
                165                 170                 175

AAA ACC GAA ATG TGG CCG CTC CCG GTG GGC AGC ATG TTT GGC GTC GGG     576
Lys Thr Glu Met Trp Pro Leu Pro Val Gly Ser Met Phe Gly Val Gly
            180                 185                 190

AGC CGC ATG AAG CAT CAT TTA AAT CGA ATG GGC ATC AGC ACG ATC GGC     624
Ser Arg Met Lys His His Leu Asn Arg Met Gly Ile Ser Thr Ile Gly
        195                 200                 205

GGG CTC GCG GCT TTT CCG CTC GAT CTT TTA AAA AAG AAA TGG GGC ATT     672
Gly Leu Ala Ala Phe Pro Leu Asp Leu Leu Lys Lys Lys Trp Gly Ile
    210                 215                 220

AAC GGC CAC GTG CTG TGG ATG ACG GCA AAC GGA ATC GAC TAT TCC CCT     720
Asn Gly His Val Leu Trp Met Thr Ala Asn Gly Ile Asp Tyr Ser Pro
225                 230                 235                 240

GTG TCA ACT TCG TCT CTG GAC GGG CAA AAG GCG ATA GGT CAT GGA ATG     768
Val Ser Thr Ser Ser Leu Asp Gly Gln Lys Ala Ile Gly His Gly Met
                245                 250                 255

ACT CTC CCG AGA GAC TAC GAA CAC TTT GAC AAA GAA ATC AAG GTC GTA     816
Thr Leu Pro Arg Asp Tyr Glu His Phe Asp Lys Glu Ile Lys Val Val
            260                 265                 270

TTG CTT GAG CTG AGT GAA GAG GTG TGC AGG CGA AGC CGA AAC GCC GGG     864
Leu Leu Glu Leu Ser Glu Glu Val Cys Arg Arg Ser Arg Asn Ala Gly
        275                 280                 285

GTC ATG GGG CAG ACA GTG TCA GTG AGC TGC CGG GGT GCT GAT TTT GAT     912
Val Met Gly Gln Thr Val Ser Val Ser Cys Arg Gly Ala Asp Phe Asp
    290                 295                 300

TGG CCG ACG GGC TTC AAC CGG CAA GTG AAG CTG GCA GAG CCG ACT AAT     960
Trp Pro Thr Gly Phe Asn Arg Gln Val Lys Leu Ala Glu Pro Thr Asn
305                 310                 315                 320

TCT ACG CAG GAT GTA TAT GAG GCT GTA CGA CGG CTG TTT CTT ACA TTT    1008
Ser Thr Gln Asp Val Tyr Glu Ala Val Arg Arg Leu Phe Leu Thr Phe
                325                 330                 335

TGG GAC GGG AAA CCC GTC CGC CGC CTC GGT GTC AAT CTG TCT CAG CTC    1056
Trp Asp Gly Lys Pro Val Arg Arg Leu Gly Val Asn Leu Ser Gln Leu
            340                 345                 350

TCA TCT GAT GAC ATA TGG CAG CTC AAT TTA TTT CAG GAT TAT GCA AAG    1104
```

```
Ser Ser Asp Asp Ile Trp Gln Leu Asn Leu Phe Gln Asp Tyr Ala Lys
    355                 360                 365

AAA ATG AGC CTA GGC TAT GTG ATG GAT GGC ATT AAA AAT CGA TTC GGC      1152
Lys Met Ser Leu Gly Tyr Val Met Asp Gly Ile Lys Asn Arg Phe Gly
370                 375                 380

GAT ACA GCA ATC ATC AGG GCG GCG TCA CTG ACA GCG GCA GGC CAG GCA      1200
Asp Thr Ala Ile Ile Arg Ala Ala Ser Leu Thr Ala Ala Gly Gln Ala
385                 390                 395                 400

TTT GAA CGT GCG GCT AAA ATA GGG GGG CAT TAT AAA TGA                  1239
Phe Glu Arg Ala Ala Lys Ile Gly Gly His Tyr Lys
                405                 410
```

(2) INFORMATION FOR SEQ ID NO:87:

(i) SEQUENCE CHARACTERISTICS:
        (A) LENGTH: 412 amino acids
        (B) TYPE: amino acid
        (D) TOPOLOGY: linear (ii) MOLECULE TYPE: protein (xi) SEQUENCE DESCRIPTION: SEQ ID NO:87:

```
Met Met Lys Glu Lys Val Ile Phe Leu Val Asp Met Gln Ser Phe Tyr
1               5                   10                  15

Ala Ser Val Glu Lys Ala Glu Asn Pro His Leu Lys Asn Arg Pro Val
                20                  25                  30

Ile Val Ser Gly Asp Pro Glu Lys Arg Gly Val Val Leu Ala Ala
                35                  40                  45

Cys Pro Leu Ala Lys Gln Lys Gly Val Val Asn Ala Ser Arg Leu Trp
        50                  55                  60

Glu Ala Gln Glu Lys Cys Pro Glu Ala Val Val Leu Arg Pro Arg Met
65                  70                  75                  80

Gln Arg Tyr Ile Asp Val Ser Leu Gln Ile Thr Ala Ile Leu Glu Glu
                85                  90                  95

Tyr Thr Asp Leu Val Glu Pro Tyr Ser Ile Asp Glu Gln Phe Met Asp
                100                 105                 110

Ile Thr Gly Ser Gln Lys Leu Phe Gly Thr Pro Met Glu Ile Ala Lys
                115                 120                 125

Ser Ile Gln Gly Arg Ile Met Arg Glu Ile Gly Val Tyr Ala Arg Val
        130                 135                 140

Gly Ile Gly Pro Asn Lys Ala Leu Ala Lys Ile Ala Cys Asp Asn Phe
145                 150                 155                 160

Ala Lys Lys Asn Lys Asn Gly Ile Phe Thr Leu Thr Lys Glu Asn Met
                165                 170                 175

Lys Thr Glu Met Trp Pro Leu Pro Val Gly Ser Met Phe Gly Val Gly
                180                 185                 190

Ser Arg Met Lys His His Leu Asn Arg Met Gly Ile Ser Thr Ile Gly
        195                 200                 205

Gly Leu Ala Ala Phe Pro Leu Asp Leu Leu Lys Lys Trp Gly Ile
        210                 215                 220

Asn Gly His Val Leu Trp Met Thr Ala Asn Gly Ile Asp Tyr Ser Pro
225                 230                 235                 240

Val Ser Thr Ser Ser Leu Asp Gly Gln Lys Ala Ile Gly His Gly Met
                245                 250                 255

Thr Leu Pro Arg Asp Tyr Glu His Phe Asp Lys Glu Ile Lys Val Val
                260                 265                 270

Leu Leu Glu Leu Ser Glu Glu Val Cys Arg Arg Ser Arg Asn Ala Gly
```

```
                275                 280                 285
Val Met Gly Gln Thr Val Ser Val Ser Cys Arg Gly Ala Asp Phe Asp
    290                 295                 300

Trp Pro Thr Gly Phe Asn Arg Gln Val Lys Leu Ala Glu Pro Thr Asn
305                 310                 315                 320

Ser Thr Gln Asp Val Tyr Glu Ala Val Arg Arg Leu Phe Leu Thr Phe
                325                 330                 335

Trp Asp Gly Lys Pro Val Arg Arg Leu Gly Val Asn Leu Ser Gln Leu
                340                 345                 350

Ser Ser Asp Asp Ile Trp Gln Leu Asn Leu Phe Gln Asp Tyr Ala Lys
                355                 360                 365

Lys Met Ser Leu Gly Tyr Val Met Asp Gly Ile Lys Asn Arg Phe Gly
370                 375                 380

Asp Thr Ala Ile Ile Arg Ala Ala Ser Leu Thr Ala Ala Gly Gln Ala
385                 390                 395                 400

Phe Glu Arg Ala Ala Lys Ile Gly Gly His Tyr Lys
                405                 410
```

(2) INFORMATION FOR SEQ ID NO:88:

(i) SEQUENCE CHARACTERISTICS:
        (A) LENGTH: 441 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p14c13)"

(xi) SEQUENCE DESCRIPTION: SEQ ID NO:88:

```
TAAGGGGACT TATATAACTG TATGTTTGTG TAGTGTTTAT GTCAGTAAGC TAAATTTACA     60
TTCATGTTAT GTYTCATTAA ACCAATTACT CACGTTTTGG TGCATATTAA ATCTTTTATA    120
TCGATCATAC ATCTATCATC ATTTTTATTT CTAAAATACA AACTGAATAC TTTGCTAGAA    180
TTTGTTACAG CAATCATTGC TCATGCATTT TATAAATTAC AATTAGACAA ATATGACATT    240
TGATATCACA CACTTCAAAC ACACACATAT ATAATCAGAC ATAAATTGTT ATGCTAAGGG    300
TTTATTCACC AAAAATATAA TACATATGGG CTTGTTTTGA GTCCATATTG AATGAATTAA    360
AAAGTATACT CCACTCAATC ATTTACAAAT AGGTGGTGCC ACTCCNAATT TATTTTATGG    420
CCAACCCCAA ATATGAGAAC A                                              441
```

(2) INFORMATION FOR SEQ ID NO:89:

(i) SEQUENCE CHARACTERISTICS:
        (A) LENGTH: 909 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p15b9)"

(ix) FEATURE:
        (A) NAME/KEY: CDS
        (B) LOCATION: 1..906

(xi) SEQUENCE DESCRIPTION: SEQ ID NO:89:

```
ATG AAC CAA AAA GGC AGA GGG CTT GAG ATC CTC ATC AAT GAA AAA CAG      48
Met Asn Gln Lys Gly Arg Gly Leu Glu Ile Leu Ile Asn Glu Lys Gln
  1               5                  10                  15

GAC GGC CAA TGG CTG TTT TCC GTA CTC AAA ACA GCG CTC AAA GCT TCT      96
```

```
Asp Gly Gln Trp Leu Phe Ser Val Leu Lys Thr Ala Leu Lys Ala Ser
         20                  25                  30

AAA CCA GTG ATA CAA GAC TGG ATG TCC CAT CAA CAG ATA AAG GTC AAT         144
Lys Pro Val Ile Gln Asp Trp Met Ser His Gln Gln Ile Lys Val Asn
             35                  40                  45

CAC GAA TCC GTC TTA AAC AAT ATG ATT GTA AAA AAG GGA GAC CGC GTG         192
His Glu Ser Val Leu Asn Asn Met Ile Val Lys Lys Gly Asp Arg Val
 50                  55                  60

TTC ATT GAT CTT CAG GAA AGT GAA GCA TCT TCG GTC ATT CCG GAG TAT         240
Phe Ile Asp Leu Gln Glu Ser Glu Ala Ser Ser Val Ile Pro Glu Tyr
 65                  70                  75                  80

GGC GAG CTT GAT ATT TTA TTT GAG GAC AAT CAT ATG CTC ATC ATC AAT         288
Gly Glu Leu Asp Ile Leu Phe Glu Asp Asn His Met Leu Ile Ile Asn
                 85                  90                  95

AAA CCC GCT GGC ATC GCG ACG CAT CCG AAT GAG GAT GGG CAA ACC GGC         336
Lys Pro Ala Gly Ile Ala Thr His Pro Asn Glu Asp Gly Gln Thr Gly
            100                 105                 110

ACA CTG GCT AAT TTG ATC GCG TAT CAT TAT CAG ATA AAT GGC GAA ACA         384
Thr Leu Ala Asn Leu Ile Ala Tyr His Tyr Gln Ile Asn Gly Glu Thr
        115                 120                 125

TGT AAG GTG CGC CAC GTC CAT CGT CTT GAT CAG GAT ACA TCT GGC GCT         432
Cys Lys Val Arg His Val His Arg Leu Asp Gln Asp Thr Ser Gly Ala
130                 135                 140

ATC GTT TTT GCC AAG CAT CGT TTG GCA CAC GCC ATC TTA GAC CAG CAG         480
Ile Val Phe Ala Lys His Arg Leu Ala His Ala Ile Leu Asp Gln Gln
145                 150                 155                 160

TTA GAG AAA AAG ACG CTG AAG CGT ACG TAT ACC GCT ATC GCT GAA GGT         528
Leu Glu Lys Lys Thr Leu Lys Arg Thr Tyr Thr Ala Ile Ala Glu Gly
                165                 170                 175

AAG CTA CGG ACG AAA AAA GGG ACA ATT AAT CCA CCG ATC GGC AGA GAC         576
Lys Leu Arg Thr Lys Lys Gly Thr Ile Asn Pro Pro Ile Gly Arg Asp
            180                 185                 190

CGC TCA CAC CCG ACA AGA CGC CGG GTT TCA CCA GGC GGG CAA ACA GCC         624
Arg Ser His Pro Thr Arg Arg Arg Val Ser Pro Gly Gly Gln Thr Ala
        195                 200                 205

GTC ACT CAT TTC AAG GTA ATG GCC AGC AAT GCG AAA GAA CGG CTG TCG         672
Val Thr His Phe Lys Val Met Ala Ser Asn Ala Lys Glu Arg Leu Ser
    210                 215                 220

CTC GTT GAA TTA GAG CTG GAA ACA GGC AGA ACA CAC CAA ATC CGT GTT         720
Leu Val Glu Leu Glu Leu Glu Thr Gly Arg Thr His Gln Ile Arg Val
225                 230                 235                 240

CAT CTG GCG AGC CTC GGC CAT CCG TTG ACA GGA GAC TCG CTT TAC GGA         768
His Leu Ala Ser Leu Gly His Pro Leu Thr Gly Asp Ser Leu Tyr Gly
                245                 250                 255

GGC GGG AGC AAG CTG CTA AAC AGG CAG GCA CTG CAC GCC AAT AAA GTA         816
Gly Gly Ser Lys Leu Leu Asn Arg Gln Ala Leu His Ala Asn Lys Val
            260                 265                 270

CAA GCG GTT CAC CCG ATA ACA GAC GAG CTC ATA GTT GCT GAA GCC CCT         864
Gln Ala Val His Pro Ile Thr Asp Glu Leu Ile Val Ala Glu Ala Pro
        275                 280                 285

TTC CCT GCT GAT ATG AAA AAC CTT TGC CGC ACA TAT TTT TCA                 906
Phe Pro Ala Asp Met Lys Asn Leu Cys Arg Thr Tyr Phe Ser
    290                 295                 300

TGA                                                                     909
```

(2) INFORMATION FOR SEQ ID NO:90:

(i) SEQUENCE CHARACTERISTICS:
        (A) LENGTH: 302 amino acids
        (B) TYPE: amino acid (D) TOPOLOGY: linear (ii) MOLECULE TYPE: protein (xi) SEQUENCE DESCRIPTION: SEQ ID NO:90:

Met Asn Gln Lys Gly Arg Gly Leu Glu Ile Leu Ile Asn Glu Lys Gln
 1               5                   10                  15

Asp Gly Gln Trp Leu Phe Ser Val Leu Lys Thr Ala Leu Lys Ala Ser
                20                  25                  30

Lys Pro Val Ile Gln Asp Trp Met Ser His Gln Ile Lys Val Asn
            35                  40                  45

His Glu Ser Val Leu Asn Asn Met Ile Val Lys Lys Gly Asp Arg Val
        50                  55                  60

Phe Ile Asp Leu Gln Glu Ser Glu Ala Ser Ser Val Ile Pro Glu Tyr
65                  70                  75                  80

Gly Glu Leu Asp Ile Leu Phe Glu Asp Asn His Met Leu Ile Ile Asn
                85                  90                  95

Lys Pro Ala Gly Ile Ala Thr His Pro Asn Glu Asp Gly Gln Thr Gly
                100                 105                 110

Thr Leu Ala Asn Leu Ile Ala Tyr His Tyr Gln Ile Asn Gly Glu Thr
            115                 120                 125

Cys Lys Val Arg His Val His Arg Leu Asp Gln Asp Thr Ser Gly Ala
130                 135                 140

Ile Val Phe Ala Lys His Arg Leu Ala His Ala Ile Leu Asp Gln Gln
145                 150                 155                 160

Leu Glu Lys Lys Thr Leu Lys Arg Thr Tyr Thr Ala Ile Ala Glu Gly
                165                 170                 175

Lys Leu Arg Thr Lys Lys Gly Thr Ile Asn Pro Pro Ile Gly Arg Asp
            180                 185                 190

Arg Ser His Pro Thr Arg Arg Val Ser Pro Gly Gly Gln Thr Ala
        195                 200                 205

Val Thr His Phe Lys Val Met Ala Ser Asn Ala Lys Glu Arg Leu Ser
210                 215                 220

Leu Val Glu Leu Glu Leu Glu Thr Gly Arg Thr His Gln Ile Arg Val
225                 230                 235                 240

His Leu Ala Ser Leu Gly His Pro Leu Thr Gly Asp Ser Leu Tyr Gly
                245                 250                 255

Gly Gly Ser Lys Leu Leu Asn Arg Gln Ala Leu His Ala Asn Lys Val
            260                 265                 270

Gln Ala Val His Pro Ile Thr Asp Glu Leu Ile Val Ala Glu Ala Pro
        275                 280                 285

Phe Pro Ala Asp Met Lys Asn Leu Cys Arg Thr Tyr Phe Ser
290                 295                 300

(2) INFORMATION FOR SEQ ID NO:91:

(i) SEQUENCE CHARACTERISTICS:
        (A) LENGTH: 471 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p15b32)"

(ix) FEATURE:
        (A) NAME/KEY: CDS
        (B) LOCATION: 1..468

(xi) SEQUENCE DESCRIPTION: SEQ ID NO:91:

```
ATG GAT GAG TTG CAG CAG GTC TCC GAT GGC TGG CTT GCG CAC CAC AAT      48
Met Asp Glu Leu Gln Gln Val Ser Asp Gly Trp Leu Ala His His Asn
 1               5                  10                  15

ACG CGG GAA AAG CGC TTC TCG CTT GGC GCT TTC GAA CCG GAC TAT ATT      96
Thr Arg Glu Lys Arg Phe Ser Leu Gly Ala Phe Glu Pro Asp Tyr Ile
                20                  25                  30

CTG TCG CAA CCC GTC GCC GTG CTG CGC AAG GAT GGA AAA ATC ACC GCC     144
Leu Ser Gln Pro Val Ala Val Leu Arg Lys Asp Gly Lys Ile Thr Ala
         35                  40                  45

TTC GCC AAT CTG ATG GTG ACG GAG ACG AAA AAG GAA GCC ACC ATC GAC     192
Phe Ala Asn Leu Met Val Thr Glu Thr Lys Lys Glu Ala Thr Ile Asp
     50                  55                  60

CTC ATG CGC TTT TCG GCG GAT GCG CGC GCG GCT CGA TGG ATT TCC TCT     240
Leu Met Arg Phe Ser Ala Asp Ala Arg Ala Ala Arg Trp Ile Ser Ser
 65                  70                  75                  80

TCG TCA GCA TCA TGC AGC ATC TGC GCG AGG CGG GAT ATG AAA GCT TCA     288
Ser Ser Ala Ser Cys Ser Ile Cys Ala Arg Arg Asp Met Lys Ala Ser
                 85                  90                  95

ATC TCG GCA TGG CGC CCA TGT CCG GCA TGT CGA AGC GCG ATG CCG CGC     336
Ile Ser Ala Trp Arg Pro Cys Pro Ala Cys Arg Ser Ala Met Pro Arg
            100                 105                 110

CGG TCT GGG ACC GTA TCG GCA GCA CGC TGT TCG AGC ACG GCG AAC GTT     384
Arg Ser Gly Thr Val Ser Ala Ala Arg Cys Ser Ser Thr Ala Asn Val
        115                 120                 125

TCT ACA ACT TCA AGG GAC TTC GCG CCT TCA AGG CAA AGT TCC ACC CGA     432
Ser Thr Thr Ser Arg Asp Phe Ala Pro Ser Arg Gln Ser Ser Thr Arg
    130                 135                 140

AAT GGG AAC CCC GTT ACC TTG CTG TGC AGA ACG GCG TGA                  471
Asn Gly Asn Pro Val Thr Leu Leu Cys Arg Thr Ala
145                 150                 155
```

(2) INFORMATION FOR SEQ ID NO:92:

(i) SEQUENCE CHARACTERISTICS:
        (A) LENGTH: 156 amino acids
        (B) TYPE: amino acid
        (D) TOPOLOGY: linear (ii) MOLECULE TYPE: protein (xi) SEQUENCE DESCRIPTION: SEQ ID NO:92:

```
Met Asp Glu Leu Gln Gln Val Ser Asp Gly Trp Leu Ala His His Asn
 1               5                  10                  15

Thr Arg Glu Lys Arg Phe Ser Leu Gly Ala Phe Glu Pro Asp Tyr Ile
                20                  25                  30

Leu Ser Gln Pro Val Ala Val Leu Arg Lys Asp Gly Lys Ile Thr Ala
         35                  40                  45

Phe Ala Asn Leu Met Val Thr Glu Thr Lys Lys Glu Ala Thr Ile Asp
     50                  55                  60

Leu Met Arg Phe Ser Ala Asp Ala Arg Ala Ala Arg Trp Ile Ser Ser
 65                  70                  75                  80

Ser Ser Ala Ser Cys Ser Ile Cys Ala Arg Arg Asp Met Lys Ala Ser
                 85                  90                  95

Ile Ser Ala Trp Arg Pro Cys Pro Ala Cys Arg Ser Ala Met Pro Arg
            100                 105                 110

Arg Ser Gly Thr Val Ser Ala Ala Arg Cys Ser Ser Thr Ala Asn Val
        115                 120                 125

Ser Thr Thr Ser Arg Asp Phe Ala Pro Ser Arg Gln Ser Ser Thr Arg
```

```
                130                 135                 140
Asn Gly Asn Pro Val Thr Leu Leu Cys Arg Thr Ala
145                 150                 155
```

(2) INFORMATION FOR SEQ ID NO:93:

(i) SEQUENCE CHARACTERISTICS:
        (A) LENGTH: 192 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA (genomic) (p15c4)"

(ix) FEATURE:
        (A) NAME/KEY: CDS
        (B) LOCATION: 1..189

(xi) SEQUENCE DESCRIPTION: SEQ ID NO:93:

```
ATG CCT ATT GCC CAG ATC CAC ATC CTT GAA GGC CGC AGC GAC GAG CAG      48
Met Pro Ile Ala Gln Ile His Ile Leu Glu Gly Arg Ser Asp Glu Gln
 1               5                  10                  15

AAG GAA ACC CTG ATT CGG GAA GTC AGT GAG GCC ATC TCG CGC TCC CTG      96
Lys Glu Thr Leu Ile Arg Glu Val Ser Glu Ala Ile Ser Arg Ser Leu
            20                  25                  30

GAT GCG CCG CTG ACC AGC GTG CGA GTG ATT ATC ACG GAG ATG GCC AAG     144
Asp Ala Pro Leu Thr Ser Val Arg Val Ile Ile Thr Glu Met Ala Lys
        35                  40                  45

GGC CAC TTC GGC ATC GGC GGC GAA CTG GCC AGC AAG GTC AGA CGC         189
Gly His Phe Gly Ile Gly Gly Glu Leu Ala Ser Lys Val Arg Arg
    50                  55                  60

TGA                                                                 192
```

(2) INFORMATION FOR SEQ ID NO:94:

(i) SEQUENCE CHARACTERISTICS:
        (A) LENGTH: 63 amino acids
        (B) TYPE: amino acid
        (D) TOPOLOGY: linear (ii) MOLECULE TYPE: protein (xi) SEQUENCE DESCRIPTION: SEQ ID NO:94:

```
Met Pro Ile Ala Gln Ile His Ile Leu Glu Gly Arg Ser Asp Glu Gln
 1               5                  10                  15

Lys Glu Thr Leu Ile Arg Glu Val Ser Glu Ala Ile Ser Arg Ser Leu
            20                  25                  30

Asp Ala Pro Leu Thr Ser Val Arg Val Ile Ile Thr Glu Met Ala Lys
        35                  40                  45

Gly His Phe Gly Ile Gly Gly Glu Leu Ala Ser Lys Val Arg Arg
    50                  55                  60
```

(2) INFORMATION FOR SEQ ID NO:95:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:95:

```
GGAGCTCACT AGTCGGAGGC ATCAGTGACC                              30
```

(2) INFORMATION FOR SEQ ID NO:96:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:96:

```
GGGATCCCAT GAGAATTCTT GAAGACG                                 27
```

(2) INFORMATION FOR SEQ ID NO:97:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:97:

```
CTAGGTACCT ACAACCTCAA GCTTNKNKNK NKNKNKNKNK NKNKNKNKNK         60
NKNKAAGCTT GGTTAGAATG GGTACCATG                               89
```

(2) INFORMATION FOR SEQ ID NO:98:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:98:

```
CTAGAATTCT ACAACCTCAA GCTT                                    24
```

(2) INFORMATION FOR SEQ ID NO:99:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:99:

```
AAGCTTGGTT AGAATGGAAT TCATG                                   25
```

(2) INFORMATION FOR SEQ ID NO:100:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:100:

GAATTCCATT CTAAC                                                15

(2) INFORMATION FOR SEQ ID NO:101:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:101:

ATTCCATTCT AACCAAGC                                             18

(2) INFORMATION FOR SEQ ID NO:102:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:102:

TGAACTGCCA CTGTAGAGAG A                                         21

(2) INFORMATION FOR SEQ ID NO:103:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:103:

GGCCATCGAT AATGAAATTA ATTAACGAGA GACAAATAGG                     40

(2) INFORMATION FOR SEQ ID NO:104:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:104:

GGCCGGATCC CTAGTGATGG TGATGGTGAT GAAAAATTCT GTCTTTAACT TTTTT     55

(2) INFORMATION FOR SEQ ID NO:105:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid -continued

```
    (A) DESCRIPTION: /desc = "primer"

(xi) SEQUENCE DESCRIPTION: SEQ ID NO:105:

GGCCGGTACC AAATTAATTA ACGAGAGACA AATAGG                              36

(2) INFORMATION FOR SEQ ID NO:106:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:106:

GGCCGGATCC CTAGTGATGG TGATGGTGAT GAAAAATTCT GTCTTTAACT TTTTT         55
```